United States Patent
Danishefsky et al.

(10) Patent No.: US 7,854,934 B2
(45) Date of Patent: *Dec. 21, 2010

(54) GLYCOCONJUGATES, GLYCOAMINO ACIDS, INTERMEDIATES THERETO, AND USES THEREOF

(75) Inventors: Samuel J. Danishefsky, Englewood, NJ (US); Don M. Coltart, New York, NY (US); Stacy J. Keding, New York, NY (US); Kaustav Biswas, Thousand Oaks, CA (US); Philip O. Livingston, New York, NY (US); Govindaswami Ragupathi, New York, NY (US); Jennifer R. Allen, Indianapolis, IN (US); Lawrence Williams, Edison, NJ (US)

(73) Assignee: Sloan-Kettering Institute For Cancer Research, New York, NY (US)

( * ) Notice: Subject to any disclaimer, the term of this patent is extended or adjusted under 35 U.S.C. 154(b) by 667 days.

This patent is subject to a terminal disclaimer.

(21) Appl. No.: 10/209,618

(22) Filed: Jul. 31, 2002

(65) Prior Publication Data

US 2003/0153492 A1 Aug. 14, 2003

Related U.S. Application Data

(63) Continuation-in-part of application No. 09/641,742, filed on Aug. 18, 2000.

(60) Provisional application No. 60/150,088, filed on Aug. 20, 1999.

(51) Int. Cl.
*A01N 43/04* (2006.01)
*A61K 39/385* (2006.01)
*A61K 31/70* (2006.01)
*A61K 31/715* (2006.01)

(52) U.S. Cl. .................. 424/193.1; 514/8; 514/23; 514/25; 514/42; 514/53; 514/54; 514/62; 530/322; 536/123.1

(58) Field of Classification Search .................. None
See application file for complete search history.

(56) References Cited

U.S. PATENT DOCUMENTS

| 5,053,489 A | 10/1991 | Kufe et al. ................ 530/350 |
| 5,212,298 A | 5/1993 | Rademacher et al. ...... 536/55.2 |
| 5,229,289 A | 7/1993 | Kjeldsen et al. ......... 435/240.27 |
| 5,280,113 A | 1/1994 | Rademacher et al. ...... 536/55.2 |
| 5,376,531 A | 12/1994 | Anderson et al. ........ 435/240.24 |
| 5,421,733 A | 6/1995 | Nudelman et al. ............ 435/105 |
| 5,491,088 A | 2/1996 | Hellerstrom et al. ..... 435/240.24 |
| 5,625,030 A | 4/1997 | Williams et al. ............. 528/361 |
| 5,660,834 A | 8/1997 | Kjeldsen et al. .......... 424/277.1 |
| 5,679,769 A | 10/1997 | Danishefsky ............... 530/322 |
| 5,683,674 A | 11/1997 | Taylor-Papadimitriou et al. ................ 424/1.49 |
| 5,747,048 A | 5/1998 | Kjeldsen et al. .......... 424/277.1 |
| 5,798,090 A | 8/1998 | Longenecker et al. ..... 424/279.1 |
| 5,807,559 A | 9/1998 | Jondal et al. .............. 424/278.1 |
| 5,858,994 A | 1/1999 | Kretzschmar et al. .......... 514/62 |
| 5,871,990 A | 2/1999 | Clausen et al. .............. 435/193 |
| 5,977,081 A | 11/1999 | Marciani |
| 6,013,779 A | 1/2000 | Wong et al. ................ 536/18.6 |
| 6,080,725 A | 6/2000 | Marciani |
| 6,090,789 A | 7/2000 | Danishefsky et al. ......... 514/25 |
| 6,222,020 B1 | 4/2001 | Taylor-Papadimitriou et al. ..... 530/395 |
| 6,238,668 B1 | 5/2001 | Danishefsky et al. .... 424/184.1 |
| 6,355,639 B1 | 3/2002 | Chou et al. |
| RE38,046 E | 3/2003 | Longenecker et al. .... 424/279.1 |
| 6,544,952 B1 | 4/2003 | Danishefsky et al. ......... 514/23 |
| 6,548,661 B1 | 4/2003 | Danishefsky et al. |
| 6,660,714 B1 | 12/2003 | Danishefsky et al. |
| 7,018,637 B2 | 3/2006 | Chong et al. |
| 7,160,856 B2 | 1/2007 | Danishefsky et al. |
| 7,531,181 B2 | 5/2009 | Danishefsky et al. |
| 7,550,146 B2 | 6/2009 | Danishefsky et al. |
| 7,635,750 B2 | 12/2009 | Danishefsky et al. |
| 7,645,454 B2 | 1/2010 | Danishefsky et al. |
| 2002/0006900 A1 | 1/2002 | Danishefsky et al. .......... 514/8 |
| 2002/0038017 A1 | 3/2002 | Danishefsky et al. ......... 536/53 |
| 2003/0153492 A1 | 8/2003 | Danishefsky et al. |

(Continued)

FOREIGN PATENT DOCUMENTS

EP 315153 * 5/1989

(Continued)

OTHER PUBLICATIONS

Abstract of Severin et al, Biokhimiya (Moscow), 1973, vol. 38, pp. 583-588.*

(Continued)

*Primary Examiner*—Karen A Canella
(74) *Attorney, Agent, or Firm*—Choate, Hall & Stewart LLP; Brenda Herschbach Jarrell; John P. Rearick

(57) ABSTRACT

The present invention provides novel glycosides and glycoconjugates, glycoamino acids, and methods for the synthesis thereof. In another aspect, the present invention provides novel clustered glycopeptides and methods for the synthesis thereof. In still another aspect, the present invention provides methods for the treatment of cancer, preferably for the prevention of recurrence of cancer, and methods for inducing antibodies in a subject, comprising administering to a subject in need, an effective amount of any of the inventive glycopeptides as disclosed herein, either in conjugated form or unconjugated and in combination with a suitable immunogenic carrier.

76 Claims, 26 Drawing Sheets

U.S. PATENT DOCUMENTS

| | | | |
|---|---|---|---|
| 2004/0208884 | A1 | 10/2004 | Danishefsky et al. |
| 2010/0081786 | A1 | 4/2010 | Danishefsky et al. |

FOREIGN PATENT DOCUMENTS

| | | | |
|---|---|---|---|
| EP | 315153 | A2 | 5/1989 |
| EP | 341252 | | 11/1997 |
| JP | 8-319300 | | 12/1996 |
| WO | WO 96/34005 | | 10/1996 |
| WO | WO 96/40198 | | 12/1996 |
| WO | WO 97/03995 | | 2/1997 |
| WO | WO 98/30190 | | 7/1998 |
| WO | WO 98/46246 | | 10/1998 |
| WO | WO 98/52573 | * | 11/1998 |
| WO | WO-9852573 | A1 | 11/1998 |
| WO | WO 99/15201 | | 4/1999 |
| WO | WO-9915201 | A1 | 4/1999 |
| WO | WO 99/48515 | | 9/1999 |
| WO | WO-9948515 | A1 | 9/1999 |
| WO | WO 01/14395 | | 3/2001 |
| WO | WO 01/14395 | A2 | 3/2001 |
| WO | WO 01/14395 | A3 | 3/2001 |
| WO | WO-01065261 | A1 | 9/2001 |
| WO | WO-2004011476 | A1 | 2/2004 |
| WO | WO-2004050711 | A2 | 6/2004 |
| WO | WO-200460915 | A2 | 7/2004 |
| WO | WO-2010006343 | A2 | 1/2010 |

OTHER PUBLICATIONS

Abstract of Grazi et al, Biochemical and Biophysical Research Communications, 1960, vol. 2, pp. 121-125).*
Ferezou et al (Nutrition, 2001, vol. 17, pp. 930-933).*
Abstract of Bischoff et al (International Archives of Allergy and Applied Immunology, 1984, vol. 75, pp. 20-26).*
Warren et al, 'Synthetic Glycopeptide-Based Vaccines', In: Topics in Current Chemistry, 2007, vol. 267, pp. 109-141.*
Ragupathi et al, Cancer Immunol lmmunother, 2003, vol. 52, pp. 608-616.*
Orlandi et al, Clinical Cancer Research, 2007, vol. 13, pp. 6195-6203.*
Gatza et al, Journal of Immunology, 2002, vol. 169, pp. 5227-5235.*
Kedar and Klien, 'Cancer Immunotherapy', In: Advances in Cancer Research, 1992, vol. 59, pp. 245-322.*
Keding and Danishefsky, PNAS, 2004, vol. 101, pp. 11937-11942.*
Efferson et al (Anticancer research, 2005, vol. 25, pp. 715-724).*
Bachman et al (Journal of Immunology, 2005, vol. 175, pp. 4677-4685).*
Allen et al (JACS, 2001, vol. 123, pp. 1890-1897).*
Gilewski et al (PNAS, Mar. 31, 2001, vol. 98, pp. 3270-3275).*
Kim et al (Vaccine, 2001, vol. 19, pp. 530-537).*
Chen et al., "Exploration of Modalities in Building a α-O-Linked Systems Through Glycal Assembly: A Total Synthesis of the Mucin-Related Flα Antigen" *J. Am. Chem. Soc.*, 120, 7760-7769, 1998.
Kudryashov et al. "Immunogenicity of Synthetic Conjugates of Lewis$^y$Oligosaccharide with Proteins in Mice: Towards the Design of Anticancer Vaccines," *Cancer Immunol Immunother*, 45, 281-286, 1998.
Kuduk et al. "Synthetic and Immunological Studies on Clustered Modes of Mucin-Related Tn and TF O-Linked Antigens: The Preparation of a Glycopeptide-Based Vaccine for Clinical Trials against Prostate Cancer," *J. Am. Chem. Soc.*, 120, 12474-12485, 1998.
Liu et al., "Structurally Defined Synthetic Cancer Vaccines: Analysis of Structure, Glycosylation and Recognition of cancer Associated Mucin, MUC-1 Derived Peptides," *Glycoconjugate Journal*, 12, 607-617.
Paulsen et al., "Sysnthesis of the Glycosyl Amino Acids . . . ," *Carbohydrate Research*, 268, 17-34, 1995.
Qiu et al., "Mucin Type Glycopeptides: Synthesis of Core 2, Core 6 and Fl-α Building Blocks and Unexpected Reactions," *Tetrahedron Letters*, 38(1), 45-48, 1997.

Sames et al., "Convergent Total Synthesis of a Tumor-Associated Mucin Motif," *Nature*, 389, 587-591, 1997.
Toyokuni et al., "Synthetic Vaccines: Synthesis of a Dimeric Tn Antigen-Lipopeptide Conjugate that Elicits Immune Responses Against Tn-Expressing Glycoproteins," *J. Am. Chem. Soc.*, 116, 395-396, 1994.
Zhang, et al., "Selection of Tumor Agents as Targets for Immune Attack Using Immunohistochemistry: II. Blood Group Related Antigens," *Int. J. Cancer*, 73, 50-56, 1997.
Allen et al., "Pursuit of optimal carbohydrate-based anticancer vaccines: preparation of a multiantigenic unimolecular glycopeptide containing the Tn, MBr1, and Lewis$^y$ antigens", *J. Am. Chem. Soc.*, 123:1890-1897, 2001.
Allen et al., "A second generation synthesis of the MBr1 (Globo-H) breast tumor antigen: new application of the n-pentenyl glycoside method for achieving complex carbohydrate protein linkages", *Chem. Eur. J.*, 6(8):1366-1375, 2000.
Biswas et al., "Construction of carbohydrate-based antitumor vaccines: synthesis of glycosyl amino acids by olefin cross-metathesis", *Tetrahedron Letters*, 43:6107-6110, 2002.
Blackwell et al., "New approaches to olefin cross-metathesis", *J. Am. Chem. Soc.*, 122:58-71, 2000.
Bosse et al., "Linear synthesis of the tumor-associated carbohydrate antigens Globo-H, SSEA-3, and Gb3", *J. Org. Chem.*, 67:6659-6670, 2002.
Keding et al., "Hydroxynorleucine as a glycosyl acceptor is an efficient means for introducing amino acid functionality into complex carbohydrates", *Tetrahedron Letters*, 44:3413-3416, 2003.
Kim et al., "Effect of immunological adjuvant combinations on the antibody and T-cell response to vaccination with MUC1-KLH and GD3-KLH conjugates", *Vaccine*, 19:530-537, 2001.
Kudryashov et al., "Toward optimized carbohydrate-based anticancer vaccines: Epitope clustering, carrier structure, and adjuvant all influence antibody responses to lewis$^y$ conjugates in mice", *Proc. Natl. Acad. Sci. USA*, 98:3264-3269, 2001.
Nicolaou et al., "A practical and enantioselective synthesis of glycosphingolipids and related compounds. Total synthesis of Globotriasosylceramide (Gb$_3$)", *J. Am. Chem. Soc.*, 110:7910-7912, 1988.
Ragupathi etal., "A Fully synthetic Globo H carbohydrate vaccine induces a focused humoral response in prostate cancer patients: a proof of principle", *Angew. Chem. Int. Ed.*, 38(4):563-566, 1999.
Ragupathi et al., "On the power of chemical synthesis: Immunological evaluation of models for multiantigenic carbohydrate-based cancer vaccines", *Proc. Natl. Acad. Sci. USA*, 99(21):13699-13704, 2002.
Slovin et al., "Carbohydrate vaccines in cancer: Immunogenicity of a fully Globo H hexasaccharide conjugate in man", *Proc. Natl. Acad. Sci. USA*, 96:5710-5715, 1999.
Williams et al., "In pursuit of an anticancer vaccine: a monomolecular construct containing multiple carbohydrate antigens", *Tetrahedron Letters*, 41:9505-9508, 2000.
Database BIOSIS 'Online! Biosciences Information Service, Philadelphia, PA, US; Mar. 22, 2002, Kovbasnjuk Olga et al., "Glycosphingolipid Gb3 as biomarker for invasive colon carcinoma cells", FASEB Journal, 16(5):A1200, 2002, Annual Meeting of Professional Research Scientists on Experimental Biology; New Orleans, LA, USA, Apr. 20-24, 2002.
International Search Report issued for PCT application PCT/US03/22657.
U.S. Appl. No. 08/457,485, filed Jun. 1, 1995, Taylor-Papadimitriou et al.
* Allen, et al., "A Second Generation Synthesis of the MBr1(Globo-H) Breast Tumor Antigen: New Application of the N-Pentenyl Glycoside Method for Achieving Complex Carbohydrate Protein Linkages", Chem. Eur. J., 6(8): 1366-1375, 2000.
* Balcom, B.J. and Petersen, N. O., "Synthesis and Surfactant Behavior of an Unusual Cyclic Triester Based on a *cis, cis*-1, 3, 5-Cyclohexanetriol Headgroup," *Langmuir*, 7:2425-2427, 1991.
* Bayle, et al., "O-(3-Butenyl) A Stable Blocking Group Removable by Ozonolysis", *Carbohydrate Research*, 232: 375-380, 1992.

* Bencomo et al., "Synthesis of glycopeptides having clusters of O-glycosylic disaccharide chains...," *Carbohydrate Research*, 116, C9-C12, 1983.
* Bilodeau M.T., "Total Synthesis of a Human Breast Tumro Associated Antigen", *J. Am. Chem. Soc.*, 117:7840-7841, 1995.
* Boehm T. et al., "Development of a Novel Silyl Ether Linker for Solid-Phase Organic Synthesis" *J. Org. Chem.*, 61:6498-6499, 1996.
* Boon, T., "Toward a Genetic Analysis of Tumor Rejection Antigens," *Adv. Can. Res.*, 58:177-211, 1992.
* Broddefalk, et al., "Preparation of a Glycopeptide Analogue of Type II Collagen—Use of Acid Labile Protective Groups for Carbohydrate Moieties in Solid Phase Synthesis of O-Linked Glycopeptides", *Tetrahedron Letters, NL, Elsevier Science*, 37(17): 3011-3014, 1996.
* Cabaret, et al., "Amphiphilic Liposaccharides. Synthesis and Reductive Cleavage of C-Allyl, O-Allyl, and O-Butenyl Glycosyl Derivatives", *Carbohydrate Research*, 189: 341-348, 1989.
* Chan et al., "Polymer-anchored Organosilyl Protecting Group in Organic Synthesis," *J. Chem. Soc., Chem. Commun.*, 909-911, 1985.
* Collins and Ferrier Monosaccharides: Their Chemistry and Their Roles in Natural Products, Publ. by John Wiley & Sons, Ltd., p. 4, 1995.
* Commissions on Nomenclature of Organic Chemistry and Physical Organic Chemistry, IUPAC, *Pure and Applied Chemistry*, 67, 1325 and 1334, 1995.
* Danishefsky et al. "Glycals in Organic Synthesis: The Evolution of Comprehensive Strategies for the Assembly of Oligosaccharides and Glycoconjugates of Biological Consequence" *Angew. Chem. Int. Ed. Engl.*, 35:1380-1419, 1996.
* Danishefsky et al. "From the Laboratory to the Clinic: A Retrospective on Fully Synthetic Carbohydrate-Based Anticancer Vaccines" *Angew. Chem. Int. Ed Engl.*, 39:836-863, 2000.
* Dermer, G.B., "Another Anniversary for the War on Cancer," *Bio/Technology*, 12, 320, 1994.
* Deshpande et al., "Strategy in Oligosaccharide Synthesis: An Application to a Concise Total Synthesis of the KH-1 (Adenocarcinoma) Antigen," *J. Am. Chem. Soc.*, 120, 1600-1614, 1998.
* Elofsson and Kihlberg, "Synthesis of Tn and Sialyl Tn Building Blocks for Solid Phase Glycopeptide Synthesis," *Tetrahedron Letters*, 36, 7499-7502, 1995.
* Elofsson et al., "Preparation of Tn and Sialyl Tn Building Blocks...," *Tetrahedron*, 53, 369-390, 1997.
* Ezzell, "Cancer "Vaccines": An Idea Whose Time Has Come?" J. NIH Res, 7, 46-49, 1995.
* Finn et al., "MUC-1 Epithelial Tumor Mucin-based Immunity and Cancer Vaccines" *Immunol. Rev.*, 145, 61-89, 1995.
* Freshney, R.I., Culture of Animal Cells, A Manual of Basic Techniques, Alan R. Liss, Inc., New York, p. 3-4, 1983.
* Fung et al., "Active Specific Immunotherapy of Murine Mammary...," *Cancer Research*, 50, 4308-4314, 1990.
* Garg et al., "Developments in the Synthesis of Glycopeptides Containing Glycosyl L-Asparagine, L-Serine, and L-Threonine" *Adv. Carb. Chem. Biochem.*, 50, 277-310, 1994.
* Gleiter et al., "Synthesis and Properties of Eight-and Ten-Membered Selenaradialenes," *Tetrahedron Letters*, 35, 8779-8782, 1994.
* Grice et al., "Tuning and Reactivity of Glycosides: Efficient One-pot Oligosaccharide Synthesis," *Synlett*, 781-784, 1995.
* Iijima, H. And Ogawa, T. "Synthesis of Mucin-type O-Glycosylated Amino Acid β-Gal-(1-3)-[α-Neu5Ac-2→6)]-GalNAc-(1→3)-Ser" *Carbohydr. Res.*, 186, 95-106, 1989.
* Kaizu et al., "Novel Fucolipids of Human Adenocarcinoma: Monoclonal Antibody Specific for Trifucosyl $Le^y(III^3FucV^3FucVI^2FucnLc_6)$ and a Possible Three-dimensional Epitope Structure," *J. Biol. Chem.* 261, 11254-11258, 1986.
* Kameyama et al., "Total Synthesis of Sialyl Lewis X*," *Carbohydrate Research*, 209, c1-c4, 1991.
* Kim et al., "Expression of $Le^Y$ and Extended $Le^Y$ Blood Group-related Antigens in Human Malignant, Premalignant, and Nonmaligmant Colonic Tissues," *Cancer Res.*, 46, 5985-5992, 1986.
* Koganty et al., "Glycopeptide- and Carbohydrate-based Synthetic Vaccines for the Immunotherapy of Cancer," *Drug Discovery Today*, 5, 190-198, 1996.

* Kondo et al.,"In vitro Action of Human and Porcine α-amylases...," *Carbohydrate Research*, 204, 207-213, 1990.
* Kunz, H. And Bimbach, S., "Synthesis of O-Glycopeitides of the Tumor-Associated $T_N$...," *Angew. Chem. Int Ed. Engl.*, 25, 360-362, 1986.
* Lassaletta, et al., "Glycosyl Imidates. Synthesis of the Hexasaccharide Moiety of Globo H (Human Breast Cancer) Antigen", *Liebigs Ann.* 9: 1417-1423, 1996.
* Lay L. et al., "Oligosaccharides Related to Tumor-Associated Antigens", *Helv. Chim. Acta*, 77:509-514, 1994.
* Liebe, B. and Kunz, H., "Solid Phase Synthesis of a Tumor-Associated Sialyl-$T_N$ Antigen Glycopeitde-..." *Angew. Chem. Int. Ed. Engl.* 33, 618-621, 1997.
* Lönn, H. "Synthesis of a Tri- and a Hepta-saccharide..." *Carbohydrate Research*, 139, 105-113, 1985.
* Nicolaou et al., "Stereocontrolled Synthesis of Sialyl $Le^x$...," *J. Chem. Soc., Chem. Commun.*, 870-872, 1991.
* Nudelman et al., Novel Fucolipids of Human Adenocarcinoma: Characterization of the Major $Le^y$ Antigen of Human Adenocarcinoma as Trifucosylnonaosyl $Le^y$ Lycolipid $(III^3FucV^3FucnVI2FucnLc_6)$, *J. Biol. Chem.*, 261, 11247-11253, 1986.
* Park, et al., "Total Synthesis and Proof of Structure of a Human Breast Tumor (Globo-H) Antigen", *J. Am. Chem. Soc.*, 118(46): 11488-11500, 1996.
* Paulsen et al., "Glycosidierung mit Thioglycosiden von Oligosacchariden zu Segmenten von O-Glycoproteinen" *Liebigs Ann. Chem.*, 75-86, 1988.
* Ragupathi et al., "Immunization of Mice with a Fully Synthetic Globo H Antigen Results in Antibodies Against Human Cancer Cells: A Combined Chemical Immunological Approach to the Fashioning of an Anticancer Vaccine" *Angew. Chem. Int. Ed. Engl.* 36, 125-128, 1997.
* Ragupathi, et al., "A Fully Synthetic Globo H Carbohydrate Vaccine Induces a Focused Humoral Response in Prostate Cancer Patients: A Proof of Principle", *Angew. Chem., Int. Ed.*, 38(4): 563-566, 1999.
* Ragupathi, G. "Carbohydrate Antigens as Targets for Active Specific Immunotherapy" *Cancer Immunol. Immunther.*, 43, 152-157, 1996.
* Randolph J.T. et al., "An Interactive Strategy for the Assembly of Complex, Branched Oligosaccharide Domains on a Solid Support: A Concise Synthesis of the $Lewis^b$ Domain in Bioconjugatable Form", *Angew. Chem. Int. Ed/ Engl.*, 33(14):1470-1473, 1994.
* Randolph et al., "Major Simplifications in Oligosaccharide Syntheses Arising from a Solid-Phase Based Method: An Application to the Synthesis of the Lewis b Antigen," *J. Amer. Chem. Soc.*,117, 5712-5719, 1995.
* Reid, et al., "N-Pentenyl Glycosides in Organic Chemistry: A Contemporary Example of Serendipity", *Synlett*, 927-942, 1992.
* Roberge et al., "A Strategy for a Convergent Synthesis of N-Linked Glycopeptides on a Solid Support," *Science* (Washington, D.C.), 269, 202-204, 1995.
* Schultheiss-Riemann, P. and Kunz, H., "O-Glycopeptide Synthesis...," *Angew. Chem. Int. Ed. Engl.*, 22, 62-63, 1983.
* Seeberger et al., "Synthesis of Biologically Important Oligosaccharides and Other Glycoconjugates by the Glycal Assembly Method," *Aldrichimica Acta*, 30(3), 75-92, 1997.
* Slovin et al., "Carbohydrate Vaccines in Cancer: Immunogenicity of Fully Synthetic Globo H Hexasaccharide Conjugate in Man" *Proc. Natl. Acad. Sci. USA*, 96, 5710-5715, 1999.
* Spitler, "Cancer Vaccines: The Interferon Analogy," *Cancer Biotherapy*, 10, 1-3, 1995.
* Tao, M. and Levy, R. "Idiotype/Granulocyte-macrophage Colony-simulating Factor Fusion Protein as a Vaccine for B-cell Lymphoma," *Nature*, 362, 755-758, 1993.
* Tokoyuni et al., "Synthetic Vaccines: I. Synthesis of Multivalent Tn Antigen Cluster-Lysyllysine Conjugates," *Tetrahedron Lett.*, 31, 2673-2676, 1990.
* Tokoyuni, T. and Singhal, A.K., "Synthetic Carbohydrate...," *Chem. Soc. Rev.*, 24, 231-242, 1995.

* Toyokuni et al., "Synthetic Carbohydrate Vaccines: Synthesis and Immunogenicity of Tn Antigen Conjugates", *Bioorg. Med. Chem.*, 2, 1119-1132, 1994.
* Udodong, et al., "A Ready, Convergent Synthesis of the Heptasaccharide GPI Membrane Anchor of Rat Brain Thy-1 Glycoprotein" *J. Am. Chem. Soc.*, 115: 7886-7887, 1993.
* Waldmann et al. "New Enzymatic Protecting Group Techniques for the Construction of Peptides and Glycopeptides" *Biomed. Biochim. Acta.* 50 (10/11) S243-S248, 1991.
* Yura et al., "Preparation of oligosaccharide-linked polystyrene and method for immobilization of lectin and base materials for cells", abstract, Jpn. Kokai Tokkyo Koho (Japan), Dec. 3, 1996.
* Zhang et al., "Immune Sera and Monoclonal Antibodies Define Two Configurations for the Sialyl Tn Tumor Antigen", *Cancer Res.*, 55, 3364-3368, 1995.
Hashimoto et al. "Armed-Disarmed" Glycosidation Strategy Based on Glycosyl Donors and Acceptors Carrying Phosphoroamidate as a Leaving Group: A Convergent Synthesis of Globotriaosylceramide. Tetrahedon Letters, vol. 38, No. 52, pp. 8969-8972, 1997.
Farkas-Himsley, et al. The bacterial colicin active against tumor cells in vitro and in vivo is verotoxin 1. Proc. Natl. Acad. Sci. vol. 92, pp. 6996-7000, Jul. 1995.
Furstner, A. Olefin Metathesis and Beyond. Angew. Chem. Int. Ed. 2000, 39, 3012-3043.
U.S. Appl. No. 09/276,595.
U.S. Appl. No. 09/641,742.
U.S. Appl. No. 09/083,776.
Allen et al. "Pursuit of optimal carbohydrate-based anticancer vaccines: preparation of a multiantigenic unimolecular glycopeptide containing the Tn, MBr1, and Lewis$^y$antigens", J. Am. Chem. Soc., 123:1890-1897, 2001.
Anderson, P. (1983) Infection & Immunity 39, 233-238.
Bachman, et al. Journal of Immunology, 2005, vol. 175, pp. 4677-4685.
Barington, T. et al. (1993) Infect. Immun. 61, 432-438.
Barington, T. et al. (1994) Infection & Immunity 62, 9-14.
Bilodeau et al. J. Am. Chem. Soc. 1995, 117, 7840-7841.
Bischoff, et al. International Archives of Allergy and Applied Immunology, 1984, vol. 75, pp. 20-26 (abstract only).
Biswas et al. "Construction of carbohydrate-based antitumor vaccines: synthesis of glycosyl amino acids by olefin cross-metathesis", Tetrahedron Letters, 43:6107-6110, 2002.
Blackwell et al. "New approaches to olefin cross-metathesis", J. Am. Chem. Soc., 122:58-71, 2000.
Bosse et al. "Linear synthesis of the tumor-associated carbohydrate antigens Globo-H, SSEA-3, and Gb3", J. Org. Chem., 67:6659-6670, 2002.
Brezicka et al. Cancer Res. 1989, 49, 1300-1305.
Brocke, C. et al. Bioorg. & Med. Chem. 2002, 10, 3085-3112.
Burk et al. Accts. Chem. Res. 2000, 33, 363-372.
Burk et al. Pure & Appl. Chem. 1996, 68, 37-44.
Catelani et al. Carb. Res. 1988, 182, 297-300.
Chappell et al. Tetrahedron 1997, 53, 11109-11120.
Chen et al. J. Am. Chem. Soc. 1998, 120, 7760-7769.
Cross, A. M. et al. (1994) Journal of Infectious Diseases 170, 834-840.
D. M. Coltart et al. "Principles of Mucin Architecture: Structural Studies on Synthetic Glycopeptides Bearing Clustered Mono-, Di-, Tri- and Hexasaccharide Glycodomains" J. Am. Chem. Soc. (2002) 124, 9833-9844.
Danishefsky et al. J. Am. Chem. Soc. 1995, 117, 5701-5711.
Danishefsky, S. J. et al. Angew. Chem., Int. Ed. Engl. 1996, 35, 1380-1419.
Dasgupta et al. Carbohydr. Res. 1994, 264, 155-160.
Database BIOSIS'Online! Biosciences Information Service, Philadelphia, PA, US; Mar. 22, 2002, Kovbasnjuk Olga et al., "Glycosphingolipid Gb3 as biomarker for invasive colon carcinoma cells", FASEB Journal, 16(5):A1200, 2002, Annual Meeting of Professional Research Scientists on Experimental Biology; New Orleans, LA, USA, Apr. 20-24, 2002.
David et al. J. Chem. Soc. Perkin Trans. I 1981, 1796-1801.
Dranoff et al. Proc. Natl. Acad. Sci, USA 1993, 90, 3539-3543.
Efferson, et al. Anticancer Research, 2005, vol. 25, pp. 715-724.

Fattom, A. et al. (1999) Vaccine 17, 126-133.
Ferezou, et al. Nutrition, 2001, vol. 17, pp. 930-933.
Fraser-Reid et al. 1990, 55, 6068-6070.
Fung, P. et al. Cancer Res. 1990, 50, 4308-4314.
Furstner, A. Angew. Chem., Int. Ed. Engl. 2000, 39, 3013-3043.
Garegg, P.J. Pure Appl. Chem. 1984, 56, 845-858.
Gatza, et al. Journal of Immunology, 2002, vol. 169, pp. 5227-5235.
Gilewski, et al. PNAS, Mar. 31, 2001, vol. 98, pp. 3270-3275.
Glunz, P. W. et al. J. Am. Chem. Soc. 1999, 121, 10636-10637 and 14186.
Gordon et al. Carbohydrate Res. 1990, 206, 361-366.
Grazi, et al. Biochemical and Biophysical Research Communications, 1960, vol. 2, pp. 121-125 (abstract only).
Griffith et al. J. Am. Chem. Soc. 1990, 112, 5811-5819.
Griffith et al. J. Am. Chem. Soc. 1991, 113, 5863-5864.
Hakomori, S. Adv. Cancer Res. 1989, 52, 257-331.
Hakomori, S. et al. Chem. Biol. 1997, 4, 97-104.
Helling, F. et al. (1994) Cancer Research 54, 197-203.
Hellstrom, I. et al. (1990) Cancer Res. 50, 2183-2190.
International Search Report for PCT/US03/22657 mailed Dec. 10, 2003.
International Search Report for PCT/US2000/022894 mailed Apr. 10, 2001.
International Search Report for PCT/US2004/040253 mailed Oct. 18, 2005.
Jannson et al. J. Org. Chem. 1998, 53, 5629-5647.
Jones, I. G. et al. (1998) Vaccine 16, 109-113.
Kanra, G. et al. (2000) Vaccine 18, 947-954.
Kawai et al. Chem. Lett. 1990, 577-580.
Kedar and Klien, "Cancer Immunotherapy", in: Advances in Cancer Research, 1992, vol. 59, pp. 245-322.
Keding et al. "Hydroxynorleucine as a glycosyl acceptor is an efficient means for introducing amino acid functionality into complex carbohydrates", Tetrahedron Letters, 44:3413-3416, 2003.
Keding, S. J. et al. Tetrahedron 2003, 59, 7023-7031.
Kensil, C. R. et al. (1991) J. Immunol. 146, 431-437.
Kim et al. "Effect of immunological adjuvant combinations on the antibody and T-cell response to vaccination with MUC1-KLH and GD3-KLH conjugates", Vaccine, 19:530-537, 2001.
Kim et al. J. Org. Chem. 1995, 60, 7716-7717.
Kim, S. K. et al. (2000) Vaccine 18, 597-603.
Kjeldsen, T. B. et al. Cancer Res. 1988, 48, 2214-2220.
Koeman et al. Tetrahedron 1993, 49, 5291-5304.
Kudryashov et al. "Toward optimized carbohydrate-based anticancer vaccines: Epitope clustering, carrier structure, and adjuvant all influence antibody responses to lewis$^y$conjugates in mice", Proc. Natl. Acad. Sci. USA, 98:3264-3269, 2001.
Kudryashov et al. Cancer Immunol. Immunother. 1998, 45, 281-286.
Kudryashov, V. et al. (1998) Glycoconjugate Journal 15, 243-249.
Kuduk, S. D. et al. J. Am. Chem. Soc. 1998, 120, 12474-12485.
Kurikka, S. (1996) Vaccine 14, 1239-1242.
Kwon et al. J. Am. Chem. Soc. 1998, 120, 1588-1599.
Lanzavechis, Science, 1993, 260, 937-944.
Livingston et al. Curr. Opin. Immunol. 1992, 4, 624-629.
Livingston et al. J. Cancer Res. 1989, 49, 7045-7050.
Livingston et al. J. Clin. Oncol., 1994, 12, 1036-1044.
Livingston, P. O. et al. Cancer Immunol. Immunother. 1997, 45, 1-9.
Livingston, P. O. et al. Cancer Immunol. Immunother. 1997, 45, 10-19.
Lloyd et al. (1966) Biochemistry 5, 1489-1501.
Lloyd et al. Am. J. Clin. Path. 1987, 87, 129-139.
Lloyd et al. Cancer Biol. 1991, 2, 421-431.
Lo-Man, R. et al. Cancer Res., 1999, 59, 1520-1524.
Lonn, H. J. Carbohydr. Chem. 1987, 6, 301-306.
M.A. Bernstein et al. Carbohydr. Res. 1980, 78, C1-03.
Maranduba et al. Carbohydr. Res. 1986, 151, 105-119.
Mar., Advanced Organic Chemistry, 2nd edition, 1977, p. 867.
Marciani, D. J. et al. (2000) Vaccine 18, 3141-3151.
Melani et al. Cancer Res. 1991, 51, 2897-2901.
Merritt et al. J. Am. Chem. Soc. 1994, 116, 5551-5559.
Molrine, D. C. et al. (1995) Annals of International Medicine 123, 828-834.
Mootoo et al. J. Am. Chem. Soc. 1988, 110, 2662-2663.

Mootoo et al. J. Am. Chem. Soc. 1989, 111, 8540-8542.
Mukaiyama et al. Chem. Lett. 1981, 431-432.
Nicolaou et al. "A practical and enantioselective synthesis of glycosphingolipids and related compounds. Total synthesis of Globotriasosylceramide (Gb$_3$)", J. Am. Chem. Soc., 110:79107912, 1988.
Nicolaou et al. J. Am. Chem. Soc. 1990, 112, 3693-3695.
Nilsson et al. Cancer Res. 1986, 46, 1403-1407.
Nilsson et al. Glycoconjugate J. 1984, 1, 43-49.
Ogata, S. et al. (1994) Cancer Res. 54, 4036-4044.
Orlandi, et al. Clinical Cancer Research, 2007, vol. 13, pp. 6195-6203.
Pardoll et al. Curr. Opin. Immunol. 1993, 5, 719-725.
Peeters, C. C. et al. (1991) Infect. Immun. 59, 3504-3510.
Qiu et al. Liebigs Ann. Chem. 1992, 217-224.
R.U. Lemieux Chem. Soc. Rev. 1978, 7, 423-452.
Ragupathi et al. "On the power of chemical synthesis: Immunological evaluation of models for multiantigenic carbohydrate-based cancer vaccines", Proc. Natl. Acad. Sci. USA, 99(21):13699-13704, 2002.
Ragupathi G, et al. A novel and efficient method for synthetic carbohydrate conjugate vaccine preparation: Synthesis of sialyl Tn-KLH conjugate using a 4-(4-N-maleimidomethyl) cyclohexane-1-carboxyl hydrazide (MMCCH) linker arm. Glycoconjugate J., 15: 217-221, 1998.
Ragupathi, G. et al. Cancer Immunol Immunother 2003, 52, 608-616.
Reddish et al. Glycoconjugate J. 1997, 14, 549-560.
Reithal, Y. J. Am. Chem. Soc. 1952, 74, 4210-4211.

Riddles PW, Blackeley RL, Zerner B Ellman's reagent: 5,5'-dithiobis(2-nitrobenzoic acid)—a reexamination, Anal Biochem 94: 75-81, 1979.
Rodriguez et al. Aust. J. Chem. 1990, 43, 665-679.
Sabbatini et al. Int. J. Cancer 2000, 87, 79-85.
Sarnaik, S. et al. (1990) Pediatric Infectious Disease 9, 181-186.
Sarvas, H. et al. (1974) Scand. J. Immunol. 3, 455-460.
Schmidt et al. Synthesis 1984, 53-60.
Schmidt, R. R. Synthesis of Glycosides. In Comprehensive organic synthesis; selectivity, strategy and efficiency in modern organic chemistry, Trost, B. M., Fleming, I., Eds.; Pergamon Press: Elmsford, NY, 1991, vol. 6, pp. 33-64.
Schwarz, J. B. et al. J. Am. Chem. Soc. 1999 121, 2662-2673.
Seeberger, P. H. J. Carbohydr. Chem. 2002, 21, 613-643.
Severin et al. Biokhimiya (Moscow), 1973, vol. 38, pp. 583-588 (abstract only).
Sim et al. J. Am. Chem. Soc. 1993, 115, 2260-2267.
Springer, G. F. Science 1984, 224, 1198-1206.
T. Boon, Int. J. Cancer 1993, 54, 177-180.
Warren, et al. "Synthetic Glycopeptide-Based Vaccines", In: Topics in Current Chemistry, 2007, vol. 267, pp. 109-141.
Williams, L. et al. (2000) Tetrahedron Lett. 41, 9505-9508.
Yin et al. Int. J. Cancer, 1996, 65, 406-412.
Zhang, S. et al. (1996) Cancer Research 56, 3315-3319.
Zhang, S. et al. Int. J. Cancer 1997, 73, 42-49.
Zhang, S. et al. Int. J. Cancer 1997, 73, 50-56.

\* cited by examiner m = 20-600

GLYCOCONJUGATES, GLYCOAMINO ACIDS, INTERMEDIATES THERETO, AND USES THEREOF

PRIORITY INFORMATION

This application is a continuation-in-part of co-pending patent application Ser. No. 09/641,742 filed Aug. 18, 2000, which claims priority under § 119(e) of the United States Code to provisional application 60/150,088, filed Aug. 20, 1999, entitled "Synthesis and Bioconjugation of the n-Pentenyl Glycoside of the Tumor-Associated Antigen Fucosyl GM1", each of which is hereby incorporated by reference in its entirety.

GOVERNMENT SUPPORT

The present invention was supported by the National Institutes of Health Grant Numbers: AI16943 and CA28824. Therefore, the government has certain rights in the present invention.

BACKGROUND OF THE INVENTION

The improvement of existing therapeutics and the development of novel therapeutics to treat and/or prolong survival of cancer patients has been the subject of continuing research in the scientific community. Although certain of these efforts have been directed to "traditional" chemotherapeutics (e.g., Paclitaxel and other small molecule and/or natural product based therapies) that act by killing malignant cancer cells, it has also been a long-standing goal (Lanzavechis, *Science,* 260, 937-944; Pardoll et al., *Curr. Opin. Immunol.* 1993, 5, 719-725; Livingston et al., *Curr. Opin. Immunol.* 1992, 4, 2; Dranoff et al., *Proc. Natl. Acad. Sci, USA* 1993, 90, 3539; M. H. Taoet et al., *Nature,* 1993, 362, 755; T. Boon, *Int. J. Cancer* 1993, 54, 177) to develop an anti-cancer vaccine that will induce an anticancer immune response. Although cancer vaccines have thus far been perceived as a mode of treatment subsequent to the detection of the disease (for example, by providing an enhanced immunological response), it would be most desirable to develop a selective vaccine that would be able to provide enhanced protection against tumor recurrence and metastasis, for example when the tumor burden has been addressed through surgery, radiation or other chemotherapeutic treatment.

In general, tumor immunotherapy is based on the theory that tumors possess specific antigens that can be recognized when presented to or processed by a properly trained immune system. The goal for the development of an effective anticancer vaccine is to break the tolerance which the immune system has for these antigens expressed mainly or exclusively by the tumor. One approach researchers have taken has been to present glycoconjugate versions of the antigens, to induce an effective immune response. In an effort to achieve this goal, identified cancer carbohydrate antigens such as TF, Tn, sTN, KH-1, Le$^y$ and Globo-H have been carefully characterized as being over-expressed at the surface of malignant cells in a variety of cancers (breast, colon, prostate, ovarian, liver, small cell lung and adenocarcinomas). In addition, they have been immunocharacterized by monoclonal antibodies and therefore have relevant serological markers available for immunological studies. Such studies have suggested that patients immunized in an adjuvant setting with carbohydrate-based vaccines produce antibodies reactive with human cancer cells, and that the production of such antibodies prohibits tumor recurrence and correlates with a more favorable diagnosis (see, Livingston et al., *J. Cancer Res.* 1989, 49, 7045; Ragupathi, G. *Cancer Immunol. Immunother.* 1996, 43, 152). Additionally, the isolation and careful structural identification of specific carbohydrate antigens overexpressed in cancer cells has provided a framework for an attack using carbohydrate-based tumor immunotherapy (For reviews see (a) Hakomori, S.; Zhang, Y. *Chem. Biol.* 1997, 4, 97; (b) Toyokuni, T.; Singhal, A. K. *Chem. Soc. Rev.* 1995, 24, 23 and references therein).

A major drawback in using carbohydrate epitopes, however, is that they are generally not readily available by isolation from natural sources. For example, the immense difficulties associated with their purification from natural sources render them virtually nonavailable as homogeneous starting materials for a clinical program. Thus, the incorporation of these naturally occurring epitopes into carrier proteins or any favorable molecular context via conjugation for eliciting a therapeutically useful immunological response is inefficient at best, and often virtually impossible. Therefore, to effectively study these vaccines as therapeutic agents, sufficient material can only be obtained by chemical synthesis.

In an effort to remedy this problem, one of the continuing research efforts is the development of anti-cancer vaccines that incorporate fully synthetic carbohydrate moieties (For a review, see Danishefsky, S. J.; Allen, J. R. *Angew Chem. Int. Ed.* 2000, 39, 836-863). One strategy for the development of synthetic anti-cancer vaccines involves the total synthesis of the carbohydrate epitope and its subsequent covalent bioconjugation to carrier protein. The vaccine constructs are then subjected to appropriate mouse immunization studies, with the ultimate goal of advancing to human clinical trials. This strategy has resulted in several fully synthetic tumor associated carbohydrate-based vaccines which are at various stages of advanced pre-clinical and clinical processing. In fact, a Globo-H vaccine is undergoing clinical evaluation for the treatment of prostate and breast carcinomas at the phase II level (see, for example, Ragupathi et al., *Angew. Chem. Int. Ed. Engl.* 1997, 36, 125) while a Lewis$^y$ antigen-based vaccine, already tested in ovarian cancer, is awaiting more extensive follow-up evaluation (see, Kudryashov et al. *Cancer Immunol. Immunother.* 1998, 45, 281).

Although several synthetic constructs have been developed in recent years, as described above, and in other references described herein, there remains a need for the further investigation to develop novel constructs capable of eliciting a more sustained or effective (and preferably selective) immune response. Clearly, in an effort to achieve this goal, it would be useful to develop improved and/or novel synthetic methods to access heretofore synthetically unavailable antigenic components (e.g., more complex antigenic components such as fucosyl GM1, clustered epitopes and similar structures), or to access non-natural structures [derived from naturally occurring structures] for further immunologic and therapeutic studies.

SUMMARY OF THE INVENTION

In recognition of the need to further develop novel constructs and improved synthetic methods, the present invention, in one aspect, provides novel glycosides and glycoconjugates glycoamino acids, and methods for the synthesis and use thereof. In another aspect, the present invention provides novel clustered glycopeptides and methods for the synthesis and use thereof. In yet another aspect, the present invention provides pharmaceutical compositions comprising novel glycosides and novel clustered glycopeptides. In still another aspect, the present invention provides methods for the treatment of cancer, preferably for the prevention of recurrence of cancer, and methods for inducing antibodies in a subject comprising administering to a subject in need, an effective amount of any of the inventive glycoconjugates as disclosed herein.

In one aspect of the present invention, novel n-alkenyl glycosides and n-alkenyl glycoconjugates glycoamino acids are provided. In certain exemplary embodiments, a synthetic methodology disclosed herein relies on the realization that the incorporation of an n-alkenyl glycoside protecting group at the reducing end of a carbohydrate acceptor allows for increased coupling efficiencies and accessibility to complex carbohydrates. Thus, the present invention also provides the recognition that for certain protected carbohydrates, the n-alkenyl moieties can serve as useful precursors that can be utilized ultimately for the synthesis of complex glycopeptides.

Thus, in one aspect, the present invention provides novel synthetic methodologies for the synthesis of complex carbohydrates comprising (1) providing a carbohydrate acceptor having a reducing end alkenyl group; (2) providing a suitable donor compound and (3) coupling said donor and acceptor under conditions to generate an alkenyl glycoside. Using this method, complex antigenic alkenyl glycosides are provided, as described above, many of which never before have been provided, which can then be conjugated or further reacted, as described herein, to generate glycoconjugates and glycopeptide structures.

Among other things, the present invention provides novel compounds and/or conjugates having the general structure:

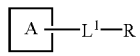

wherein $L^1$ is a substituted or unsubstituted, linear or branched, cyclic or acyclic, saturated or unsaturated aliphatic or heteroaliphatic moiety;

R is hydrogen; substituted or unsubstituted alkyl; alkenyl; aryl; —CH$_2$CH(CO$_2$R')(NHR''), wherein R' or R'' are each independently hydrogen, protecting group, substituted or unsubstituted alkyl, aryl, peptide, protein or lipid; R''' or NHR''', wherein R''' is an immunogenic carrier linked to $L^1$ or N either directly or through a crosslinker;

A is a carbohydrate determinant having the structure:

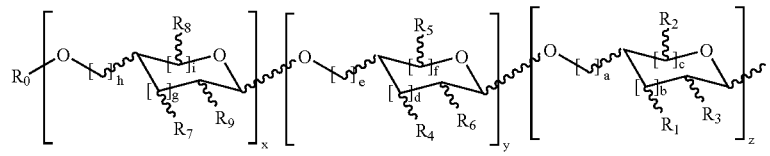

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, OR$^i$, NHR$^i$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

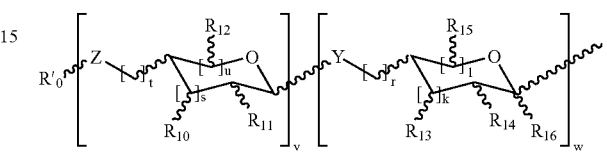

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, OR$^{iii}$, NHR$^{iii}$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, COOR$^{ii}$, CONHR$^{ii}$, a substituted or unsubstituted linear or branched chain alkyl or aryl group; wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group.

In certain embodiments, $L^1$ is —O—(CH$_2$)$_n$—, wherein n is 0-9, or a glycoside-containing moiety. In certain exemplary embodiments, $L^1$ comprises a mono saccharide. In certain preferred embodiments, R is allyl, n is 2 and thus the inventive compounds comprise an n-pentenyl moiety. In certain other embodiments, the immunogenic carrier is a protein, peptide or lipid. In certain other embodiments of the present invention, R is NHR''', and the carrier R''' is KLH or Bovine Serum Albumin. In yet other embodiments, the immunogenic carrier is conjugated to the glycoside construct through one of its amino groups (e.g., the carrier's amino groups). In still other embodiments of the present invention, R is NHR''', and the carrier R''' is a lipid having the structure:

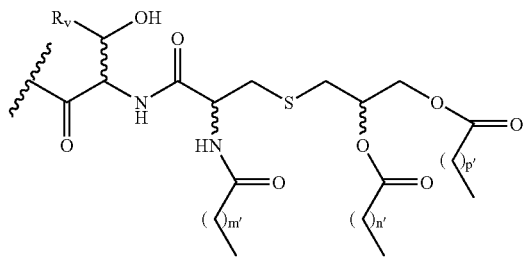

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys). It will be appreciated that the protein or lipid can be linked to N or $L^1$ either directly or through a crosslinker, and thus R''' incorporates proteins, peptides, and lipids, as well as (crosslinker-protein), (crosslinker-peptide) and (crosslinker-lipid) moieties.

In other embodiments, the inventive compound is a glycoamino acid and thus R is $CH_2CH(CO_2R')(NHR'')$, which compound has the structure

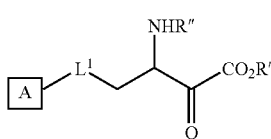

wherein $L^1$ is as defined above, and R' and R'' are suitable protecting groups.

In certain preferred embodiments, the glycoamino acids of the present invention are derived from n-pentenyl glycosides and thus $L^1$ is $-O(CH_2)_3-$. In certain other preferred embodiments, R' and R'' are each a protecting group independently selected from the group consisting of benzyl, t-butyl, TSE (2-(trimethylsilyl ethyl), Ac (acetyl), Boc (t-butoxycarbonyl), Cbz and Fmoc (9-fluoroenyl methoxy carbonyl).

In certain embodiments, $L^1$ is $-O(CH_2)_n-$ and the present invention provides novel compounds and/or conjugates having the general structure:

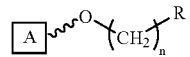

wherein n is an integer from 0-9;

R is hydrogen; substituted or unsubstituted alkyl; alkenyl; aryl; $-CH_2CH(CO_2R')(NHR'')$, wherein R' or R'' are each independently hydrogen, protecting group, substituted or unsubstituted alkyl, a linker, aryl, peptide, protein or lipid; R''' or NHR''', wherein R''' is an immunogenic carrier, peptide, protein or lipid linked to N or the alkyl linker either directly or through a crosslinker;

A is a carbohydrate domain having the structure:

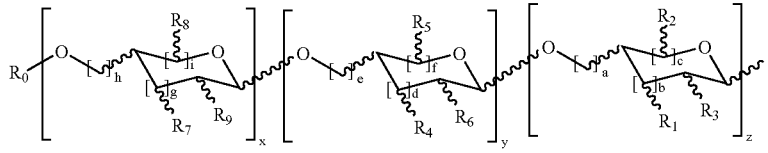

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

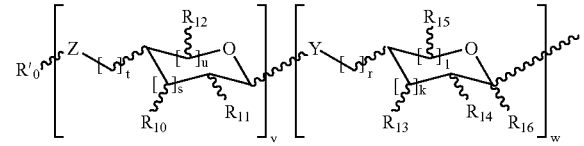

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, COOR$^{iv}$, or a substituted or unsubstituted linear or branched chain alkyl, acyl, arylalkyl or aryl group; and wherein each occurrence of $R^{iii}$ and $R^{iv}$ are each independently H, or a substituted or unsubstituted linear or branched chain alkyl, arylalkyl or aryl group.

In certain embodiments, if A is KH-1, N3, globo-H, glycophorin, Tn, TF, STN, (2,3)ST, 2,6-STn or Le$^y$, and A is α-O-linked, then n is at least 1. In certain other embodiments, A is α- or β-O-linked.

In certain preferred embodiments of the present invention, R is allyl, n is 2 and thus the inventive compound is a n-pentenyl moiety. In certain other embodiments, the immunogenic carrier is protein, peptide, or lipid. In certain other embodiments of the present invention, R is NHR''', and the carrier R''' is KLH or Bovine Serum Albumin. In yet other embodiments, the immunogenic carrier is conjugated to the glycoside construct through one of its amino groups (e.g., the carrier's amino groups). In still other embodiments of the present invention, R is NHR''', and the carrier R''' is a lipid having the structure:

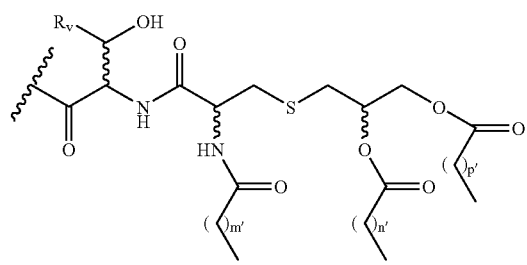

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys). It will be appreciated that the protein or lipid can be linked to N or the rest of the construct either directly or through a crosslinker, and thus R''' incorporates proteins, peptides, and lipids, as well as (crosslinker-protein), (crosslinker-peptide) and (crosslinker-lipid) moieties.

In other embodiments, the inventive compound is a glycoamino acid and thus R is CH$_2$CH(CO$_2$R')(NHR''), which compound has the structure:

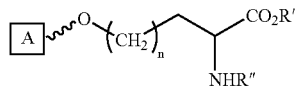

In certain preferred embodiments, the glycoamino acids of the present invention are derived from n-pentenyl glycosides and thus n is 3. In certain other preferred embodiments, R' and R'' are each a protecting group independently selected from the group consisting of benzyl, t-butyl, TSE (2-(trimethylsilyl ethyl), Ac (acetyl), Boc (t-butoxycarbonyl), Cbz and Fmoc (9-fluoroenyl methoxy carbonyl).

For each of the compounds described above, in certain preferred embodiments the carbohydrate determinant is selected from the group consisting of Globo-H, fucosyl GM1, KH-1, glycophorin, N3, Tn, TF, STN, (2,3)ST, 2,6-STn, Gb3 and Le$^y$. In other preferred embodiments, the carbohydrate determinant of the compound contains a Globo-H determinant or fucosyl GM1 determinant, as all or part of the carbohydrate determinant A.

In another aspect, the present invention provides methods for the synthesis of novel n-alkyl glycoamino acids, as described in more detail below for Globo-H and fucosyl GM1 and their subsequent use to generate novel glycopeptides and synthetic constructs thereof.

In certain embodiments, the inventive method for the production of these novel glycoaminoacids comprises: 1) providing an alkenyl glycosidic moiety, as described herein; 2) subjecting said alkenyl glycosidic moiety to oxidative conditions to generate an aldehyde; 3) subjecting said aldehyde to olefination conditions to generate an enamide ester; 4) subjecting said resulting enamide ester to conditions sufficient to hydrogenate said enamide ester to generate a protected glycoamino acid and 5) deprotecting said protected glycoamino acid under suitable conditions to generate a desired glycoamino acid.

In particular, a method for the synthesis of a glycoamino acid, the structure of which is set forth herein, is provided, which comprises steps of:

(a) providing an alkenyl glycoside having the structure:

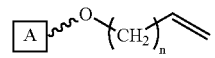

(b) reacting said alkenyl glycoside under suitable conditions to generate an enamide ester having the structure:

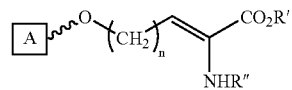

(c) reacting said enamide ester under suitable conditions to generate a glycoamino acid having the structure:

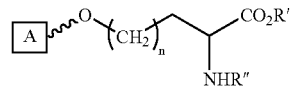

wherein, for each of the structures above, n is 0-8, wherein A is a carbohydrate domain having the structure:

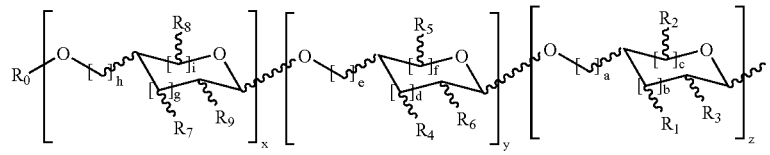

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

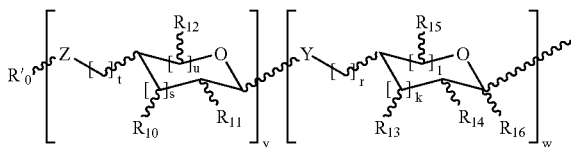

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;

and wherein for the glycoamino acid structure R' and R" are each independently hydrogen, protecting group, substituted or unsubstituted alkyl, linker, aryl, peptide, protein or lipid; R''' or NHR''' wherein R''' is an immunogenic carrier, linked to the glycoaminoacid moiety or N either directly or through a crosslinker. In preferred embodiments, R' and R" are each independently hydrogen or a protecting group. In particularly preferred embodiments R" is a nitrogen protecting group, including, but not limited to, acetyl, Fmoc, Cbz or Boc, and R' is an acid protecting group such as benzyl, t-butyl or TSE. In certain embodiments, the immunogenic carrier is a protein, peptide, or lipid. In certain preferred embodiments, the carbohydrate determinant is selected from the group consisting of Globo-H, fucosyl GM1, KH-1, glycophorin, STN, (2,3)ST, $Le^y$, N3, Tn, 2,6-STn, Gb3 and TF. In certain other preferred embodiments, the carbohydrate determinant of the compound contains a Globo-H determinant or a fucosyl GM1 determinant, as described herein, as all or part of the carbohydrate determinant A.

In certain preferred embodiments, the step of reacting an n-alkenyl glycoside under suitable conditions to generate an enamide ester comprises reacting an n-alkenyl glycoside first under oxidative conditions and second under olefination conditions in the presence of base (e.g., tetramethylguanidine) and phosphonate to generate an enamide ester.

In certain embodiments, the step of reacting said enamide ester under suitable conditions to generate a glycoamino acid comprises reacting said enamide ester under hydrogenation conditions.

In certain other embodiments, the inventive method for the production of these novel glycoaminoacids comprises: 1) providing an alkenyl glycosidic moiety, as described herein; 2) reacting said alkenyl glycosidic moiety with a suitable alkenylamino acid under suitable conditions in the presence of a suitable catalyst to generate an enamide ester; 4) subjecting said resulting enamide ester to conditions sufficient to hydrogenate said enamide ester to generate a protected glycoamino acid and 5) deprotecting said protected glycoamino acid under suitable conditions to generate a desired glycoamino acid. In certain embodiments, the alkenylamino acid is a suitably protected allylglycine.

For example, the present invention provides a method for the synthesis of a glycoamino acid, the structure of which is set forth herein, which method comprises steps of:

(a) providing an alkenyl glycoside having the structure:

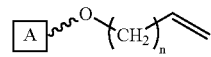

(b) reacting said alkenyl glycosidic moiety with a suitable alkenylglycine under suitable conditions in the presence of a suitable catalyst to generate an enamide ester having the structure:

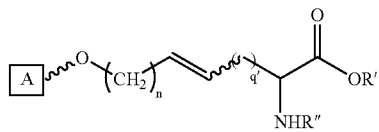

(c) reacting said enamide ester under suitable conditions to generate a glycoamino acid having the structure:

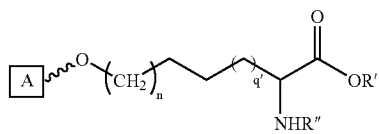

wherein, for each of the structures above, n is 0-8, q' is an integer from 0-8; wherein A is a carbohydrate domain having the structure:

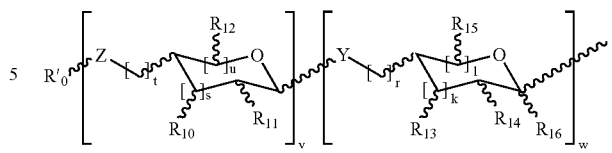

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

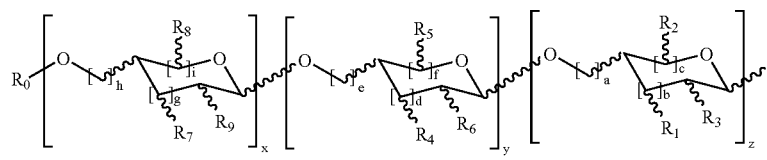

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;

and wherein for the glycoamino acid structure R' and R" are each independently hydrogen, protecting group, substituted or unsubstituted alkyl, linker, aryl, peptide, protein or lipid; R''' or NHR''', wherein R''' is an immunogenic carrier, linked to N or the glycoamino acid moiety either directly or through a crosslinker. In certain preferred embodiments, R' and R" are each independently hydrogen or a protecting group. In particularly preferred embodiments R" is a nitrogen protecting group, including, but not limited to, acetyl, Fmoc, Cbz or Boc, and R' is an acid protecting group such as benzyl, t-butyl or TSE. In certain embodiments, the immunogenic carrier is a protein, peptide, or lipid. In certain preferred embodiments, the carbohydrate determinant is selected from the group consisting of Globo-H, fucosyl GM1, KH-1, glycophorin, STN, (2,3)ST, $Le^y$, N3, Tn, 2,6-STn, Gb3 and TF. In certain other preferred embodiments, the carbohydrate determinant of the compound contains a Globo-H determinant or a fucosyl GM1 determinant, as described herein, as all or part of the carbohydrate determinant A.

In certain preferred embodiments, the step of reacting an n-alkenyl glycoside under suitable conditions to generate an enamide ester comprises reacting an n-alkenyl glycoside with a suitably protected alkenylglycine in the presence of a suitable catalyst. In certain exemplary embodiments, the protected alkenylglycine is a protected allylglycine having the structure:

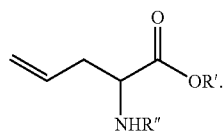

In certain preferred embodiments, the protected allylglycine has the structure:

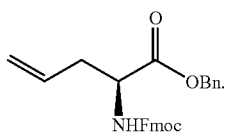

In certain other preferred embodiments, the catalyst is selected from the group consisting of:

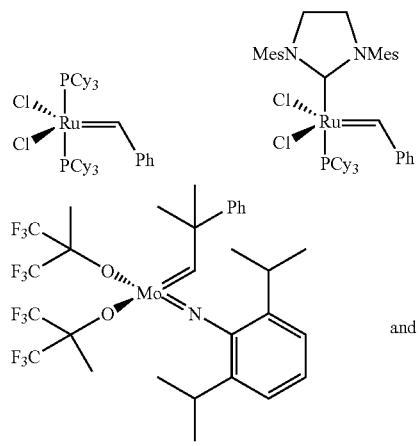

and

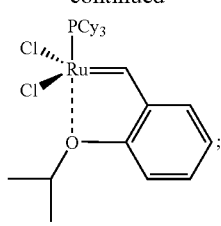

wherein Cy represents a cyclohexyl moiety.

Additionally, in certain embodiments, the step of reacting said enamide ester under suitable conditions to generate a glycoamino acid comprises reacting said enamide ester under hydrogenation conditions.

In another aspect, the invention provides multi-antigenic glycopeptides comprising a peptidic backbone made up of two or more amino acids, wherein one or more of said amino acids is/are independently substituted with a glycosidic moiety having the structure:

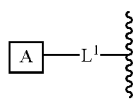

wherein $L^1$ is a substituted or unsubstituted, linear or branched, cyclic or acyclic, saturated or unsaturated aliphatic or heteroaliphatic moiety;

each occurrence of A is independently a carbohydrate determinant having the structure:

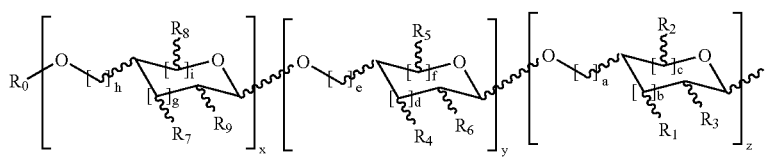

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

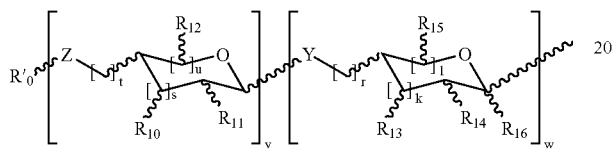

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group.

In certain embodiments, if each occurrence of $L^1$ is a moiety having the structure —$O(CH_2)_n$—, wherein each occurrence of n is independently 0-9, and if for each occurrence of n, n=0, then at least one occurrence of A has a different structure from other occurrences of A. In certain embodiments, the n-alkyl glycosidic moiety is either α- or β-linked to an amino acid residue of the backbone. In certain embodiments, at least one occurrence of $L^1$ is independently a glycoside-containing moiety. In certain exemplary embodiments, at least one occurrence of $L^1$ independently comprises a monosaccharide. It will be appreciated that these inventive clustered glycopeptides are not limited to n-alkyl where n is greater than or equal to 1; rather multi-antigenic clustered glycopeptides can be linked via the traditional direct linkage (n=0), via n-alkyl (such as pentyl) or via a glycoside moiety or any combination thereof. In other embodiments, each occurrence of A may be the same, however, n-alkenyl (n greater than 1) linkages or glycoside-containing linkages are then utilized. In preferred embodiments, each occurrence of A is independently selected from the group consisting of Globo-H, fucosyl GM1, KH-1, glycophorin, STN, (2,3)ST, $Le^y$, N3, Tn, 2,6-STn, Gb3 and TF.

In certain embodiments, multi-antigenic glycopeptides are provided comprising a peptidic backbone made up of at least three glycoamino acids, wherein one or more of said amino acids is/are substituted with an n-alkyl glycosidic moiety having the structure:

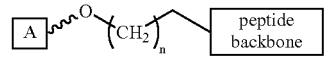

wherein each occurrence of A is independently a carbohydrate determinant having the structure:

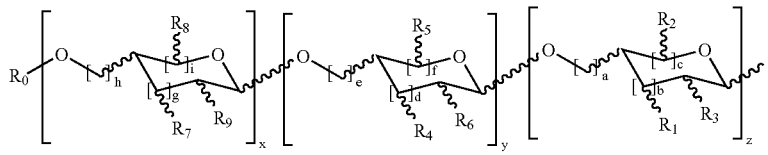

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

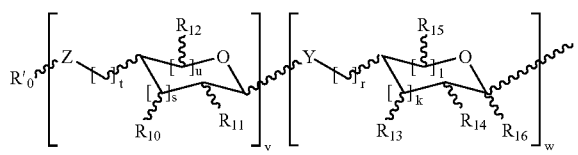

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;

wherein each occurrence of n is independently 0-8. In certain embodiments, if for each occurrence of n, n=0, at least one occurrence of A has a different structure from other occurrences of A. In certain other embodiments, each occurrence of the n-alkyl glycosidic moiety is independently either α- or β-linked to an amino acid residue of the backbone. It will be appreciated that these inventive clustered glycopeptides are not limited to n-alkyl where n is greater than or equal to 1; rather multi-antigenic clustered glycopeptides can be linked via the traditional direct linkage (n=0) or via n-alkyl (such as pentyl) or any combination thereof. In other embodiments, each occurrence of A may be the same, however, n-alkenyl (n greater than 1) linkages are then utilized. In preferred embodiments, each occurrence of A is independently selected from the group consisting of Globo-H, fucosyl GM1, KH-1, glycophorin, STN, (2,3)ST, Le$^y$, N3, Tn, 2,6-STn, Gb3 and TF.

In certain embodiments, the inventive glycopeptide is a construct having the structure:

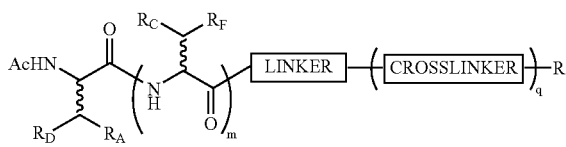

wherein q is 0 or 1;
m is an integer from 1-20;
R is hydrogen or an immunogenic carrier;
the linker is either a free carboxylic acid, —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;

each occurrence of $R_A$ and $R_C$ is independently hydrogen, a substituted or unsubstituted, linear or branched, cyclic or acyclic, saturated or unsaturated alkyl, aliphatic or heteroaliphatic moiety or a substituted or unsubstituted aryl or heteroaryl moiety; and wherein each occurrence of $R_D$ and $R_F$ is independently a glycosidic moiety having the structure:

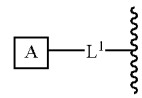

wherein $L^1$ is a substituted or unsubstituted aliphatic or heteroaliphatic moiety;

each occurrence of A is independently a carbohydrate domain having the structure:

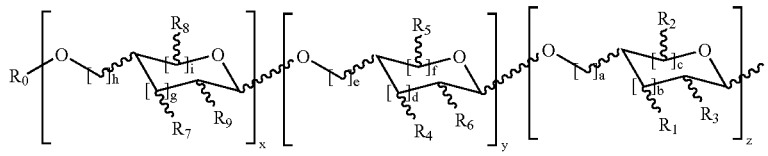

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

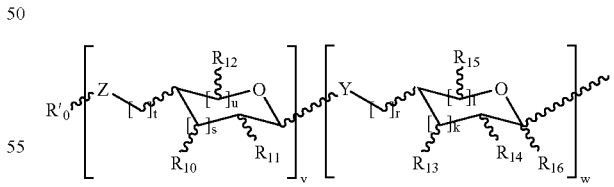

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R$_{16}$ is hydrogen, COOH, COOR$^{ii}$, CONHR$^{ii}$, a substituted or unsubstituted linear or branched chain alkyl or aryl group; wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group; and wherein each occurrence of n is independently 0-8; and wherein each glycosidic moiety is either α- or β-linked to an amino acid. In certain embodiments, each occurrence of L$^1$ is independently a moiety having the structure —O(CH$_2$)$_n$— wherein n is an integer from 0-9. In certain embodiments, each occurrence of R$_A$ and R$_C$ is independently hydrogen or methyl. In certain embodiments, the glycopeptide is attached to a suitable immunogenic carrier via a linker and the glycopeptide has the structure:

or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester; wherein each occurrence of R$_A$, R$_B$ and R$_C$ is independently hydrogen, a substituted o runsubstituted, linear or branched, cyclic or acyclic, saturated or unsaturated moiety, or a substituted or unsubstituted aryl or heteroaryl moiety; and wherein each occurrence of R$_D$, R$_E$ and R$_F$ is independently a glycosidic moiety having the structure:

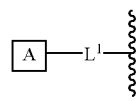

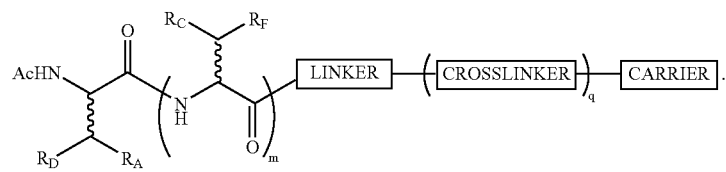

In certain embodiments, multi-antigenic clusters having three or more antigens are desirable and thus the present invention also provides constructs having the following structure:

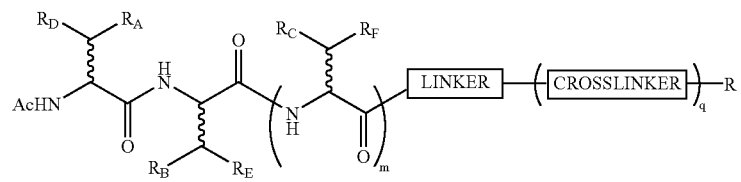

wherein q is 0 or 1;
m is an integer from 1-19;
R is hydrogen or an immunogenic carrier;
the linker is either a free carboxylic acid, —O—, (carboxamido)alkyl carboxamide, MBS, primary carboxamide, mono- or dialkyl carboxamide, mono- or diarylcarboxamide, linear or branched chain (carboxy)alkyl carboxamide, linear wherein each occurrence of L$^1$ is independently a substituted or unsubstituted aliphatic or heteroaliphatic moiety;
each occurrence of A is independently a carbohydrate domain having the structure:

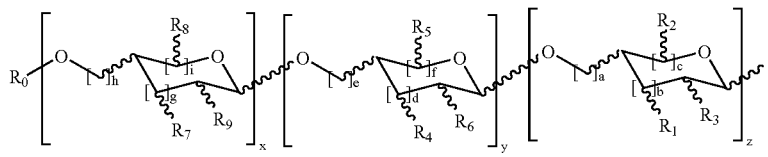

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

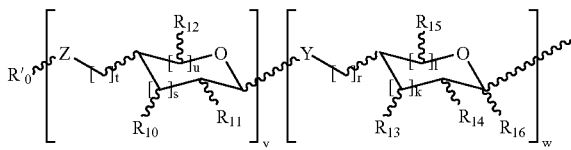

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group.

In certain embodiments, if each occurrence of $L^1$ is a moiety having the structure $-O(CH_2)_n-$, wherein each occurrence of n is independently 0-9, and if for each occurrence of n, n=0, then at least one occurrence of A has a different structure from other occurrences of A. In certain other embodiments, each occurrence of the n-alkyl glycosidic moiety is independently either α- or β-linked to an amino acid residue of the backbone. In certain embodiments, each occurrence of $L^1$ is independently a moiety having the structure $-O(CH_2)_n-$, wherein each occurrence of n is independently 0-9. In certain embodiments, at least one occurrence of $L^1$ is independently a glycoside-containing moiety. In certain exemplary embodiments, at least one occurrence of $L^1$ independently comprises a monosaccharide. In certain embodiments, the immunogenic carrier is a protein, peptide or lipid. It will be appreciated that these inventive clustered glycopeptides are not limited to n-alkyl where n is greater than or equal to 1; rather multi-antigenic clustered glycopeptides can be linked via the traditional direct linkage (n=0), via n-alkyl (such as pentyl) or via a glycoside moiety or any combination thereof. In other embodiments, each occurrence of A may be the same, however, n-alkenyl (n greater than 1) linkages or glycoside-containing linkages are then utilized. In preferred embodiments, each occurrence of A is independently selected from the group consisting of Globo-H, fucosyl GM1, KH-1, glycophorin, STN, (2,3)ST, $Le^y$, N3, Tn, 2,6-STn, Gb3 and TF. In certain other embodiments, each occurrence of $R_A$, $R_B$ and $R_C$ is independently hydrogen or methyl.

In certain embodiments, each occurrence of $L^1$ is independently a moiety having the structure $-O(CH_2)_n-$ and the multi-antigenic glycopeptide has the following structure:

wherein q is 0 or 1;

m is an integer from 1-19;

R is hydrogen or an immunogenic carrier;

the linker is either a free carboxylic acid, $-O-$, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;

each occurrence of $R_A$, $R_B$ and $R_C$ is independently hydrogen, a substituted or unsubstituted, linear or branched, cyclic or acyclic, saturated or unsaturated aliphatic or heteroaliphatic moiety or a substituted or unsubstituted aryl or heteroaryl moiety; and wherein each occurrence of $R_D$, $R_E$ and $R_F$ is independently an alkyl glycosidic moiety having the structure:

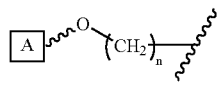

wherein each occurrence of A is independently a carbohydrate domain having the structure:

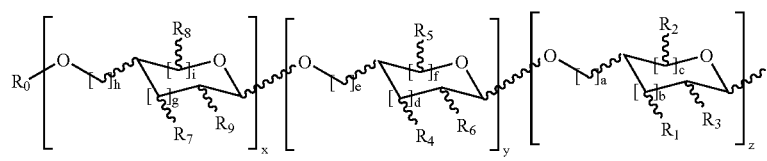

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

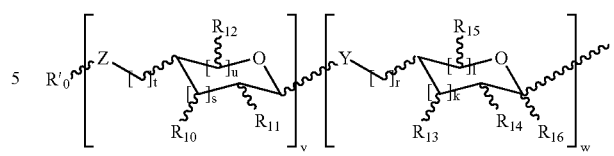

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group; and wherein each occurrence of n is independently 0-9. In certain embodiments, if for each occurrence of n, n=0, at least one occurrence of A has a different structure from other occurrences of A. In certain other embodiments, each occurrence of the n-alkyl glycosidic moiety is independently either α- or β-linked to an amino acid residue of the backbone. In certain embodiments, each occurrence of $R_A$, $R_B$ and $R_C$ is independently hydrogen or methyl. In yet other embodiments, the immunogenic carrier is a protein, peptide or lipid.

In certain embodiments, the glycopeptide is attached to a suitable immunogenic carrier via a linker and the glycopeptide has the structure:

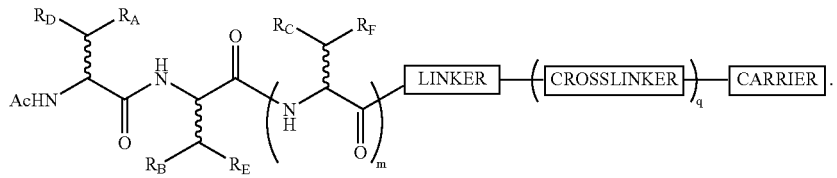

In preferred embodiments, each occurrence of A is selected from the group consisting of Globo-H, fucosyl GM1, KH-1, glycophorin, STN, (2,3)ST, Le$^y$, N3, Tn, 2,6 STn, Gb3 and TF. In but one preferred example, the present invention provides a novel trimeric antigenic glycopeptide incorporating globo-H, Le$^y$ and Tn, to generate a novel trimeric antigenic compound. In certain other exemplary embodiments, the present invention provides a novel trimeric antigenic glycopeptide incorporating TF, Le$^y$ and Tn, to generate a novel trimeric antigenic compound. In yet other exemplary embodiments, the present invention provides a novel pentameric antigenic glycopeptide incorporating Globo-H, STn, TF, Le$^y$ and Tn, to generate a novel pentameric antigenic compound.

As detailed herein, in another aspect of the present invention, any of the inventive compounds may be conjugated to generate a glycoconjugate, and may be administered alone, with an immunogenic carrier (for example, a carrier protein, peptide or lipid), or with an immunological adjuvant or any combination thereof for the treatment of cancer and/or for preventing the recurrence of cancer, or may be administered alone or with an immunological adjuvant to induce antibodies in a subject. In certain exemplary embodiments, when the glycopeptide is a multi-antigenic glycopeptide (e.g., one that comprises at least two different antigenic carbohydrate antigens on the peptide backbone), the antibodies induced recognize the carbohydrate antigens present on the peptidic backbone. In certain embodiments, the carbohydrate antigens present on the peptidic backbone comprise a carbohydrate domain, or truncated or elongated version thereof, that is present on tumor cells.

DEFINITIONS

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position unless otherwise indicated. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of cancer, or in the inducement of antibodies, as described herein. The term "stable", as used herein, preferably refers to compounds which possess stability sufficient to allow manufacture and which maintain the integrity of the compound for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes both straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups.

The term "alkylamino" refers to a group having the structure —NHR' wherein R' is alkyl, as defined herein. Examples of alkylamino include, but are not limited to, methylamino, ethylamino, iso-propylamino and the like.

Some examples of substituents of the above-described aliphatic (and other) moieties of compounds of the invention include, but are not limited to: F, Cl, Br, I, OH, NO$_2$, CN, C(O)—C$_1$-C$_6$-alkyl, C(O)-aryl, C(O)-heteroaryl, CO$_2$-alkyl, CO$_2$-aryl, CO$_2$-heteroaryl, CONH$_2$, CONH—C$_1$-C$_6$-alkyl, CONH-aryl, CONH-heteroaryl, OC(O)—C$_1$-C$_6$-alkyl, OC(O)-aryl, OC(O)-heteroaryl, OCO$_2$-alkyl, OCO$_2$-aryl, OCO$_2$-heteroaryl, OCONH$_2$, OCONH—C$_1$-C$_6$-alkyl, OCONH-aryl, OCONH-heteroaryl, NHC(O)—C$_1$-C$_6$-alkyl, NHC(O)-aryl, NHC(O)-heteroaryl, NHCO$_2$-alkyl, NHCO$_2$-aryl, NHCONH-heteroaryl, SO$_2$—C$_1$-C$_6$-alkyl, SO$_2$-aryl, C$_3$-C$_6$-cycloalkyl, CF$_3$, CH$_2$CF$_3$, CHCl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, C$_1$-C$_6$-alkoxy, methoxymethoxy, methoxyethoxy, amino, benzylamino, arylamino, heteroarylamino, C$_1$-C$_3$-alkyl-amino, thio, aryl-thio, heteroarylthio, benzylthio, C$_1$-C$_6$-alkyl-thio, or methylthiomethyl. Additional examples of generally applicable substituents are illustrated by the specific embodiments shown in the Examples which are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, NHCONH-heteroaryl, $SO_2$—$C_1$-$C_6$-alkyl, $SO_2$-aryl, $C_3$-$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl. Additional examples of generally applicable substitutents are illustrated by the specific embodiments shown in the Examples which are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted. F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, NHCONH-heteroaryl, $SO_2$—$C_1$-$C_6$-alkyl, $SO_2$-aryl, $C_3$-$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl. Additional examples of generally applicable substitutents are illustrated by the specific embodiments shown in the Examples which are described herein.

The terms "halo" and "halogen" as used herein refer to an atom selected from fluorine, chlorine, bromine and iodine.

It will be appreciated that additional examples of generally applicable substitutents are illustrated by the specific embodiments shown in the Examples which are described herein, but are not limited to these Examples.

DETAILED DESCRIPTION OF CERTAIN PREFERRED EMBODIMENTS OF THE INVENTION

Figure 1:
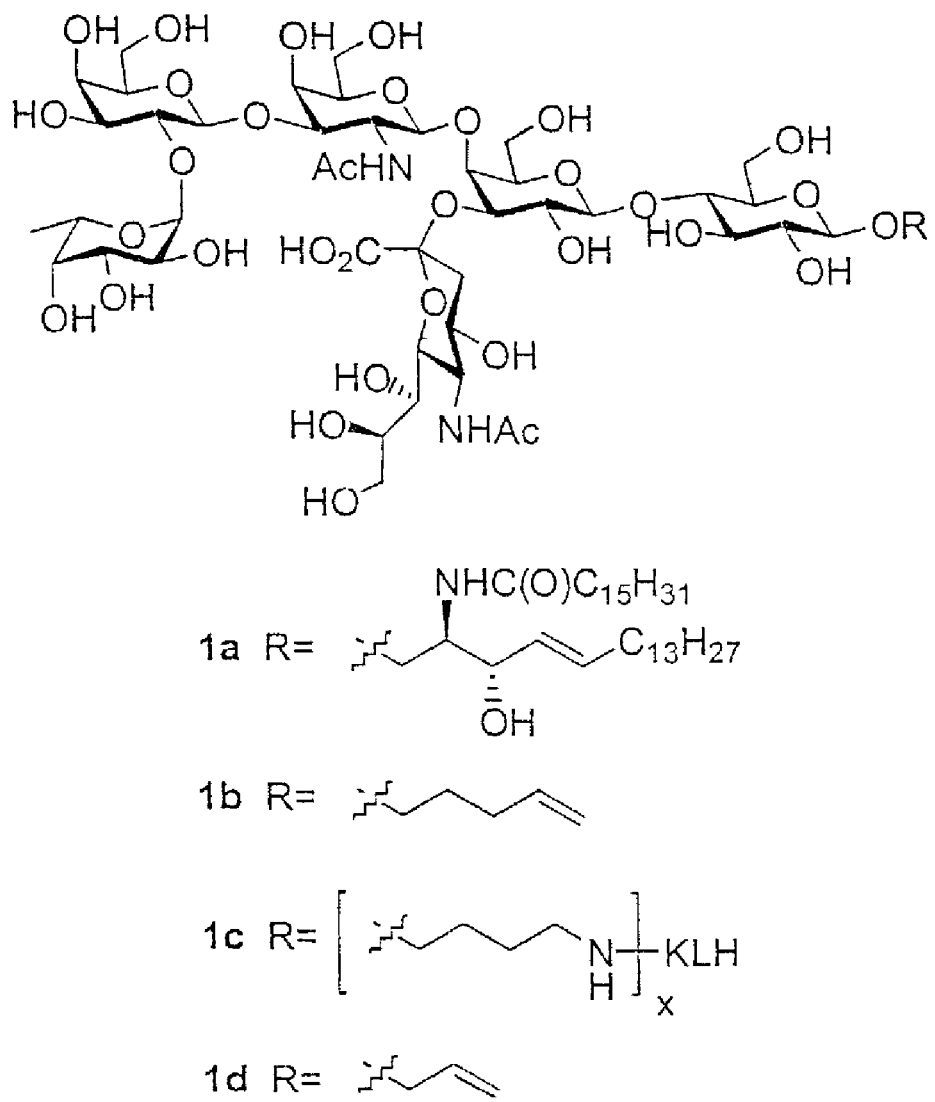
FIG. 1 depicts Fucosyl GM1, derivatives and constructs thereof.

As discussed above, the desire to develop improved methods for the preparation of synthetic vaccines has led to increased research efforts directed toward the synthesis of naturally occurring complex carbohydrate antigens, as well as novel complex structures (e.g., glycopeptides) incorporating these antigenic structures. As is often the case during the course of any such large synthetic undertaking, improved synthetic methods are often developed that can be applied universally. In particular, synthetic studies of naturally occurring antigenic structures has led to the development of novel methodologies enabling the development of heretofore unavailable synthetic carbohydrate-based vaccines. For a review, see Danishefsky, S. J.; Allen, J. R., *Angew. Chem. Int. Ed. Engl.* 2000, 39, 836-863, and references cited therein.

Significantly, the present invention provides improved methodologies for the synthesis of complex carbohydrates and related therapeutic compounds (e.g., glycoconjugates and/or glycopeptides). In particular, in the context of synthetic studies developed for the total syntheses of fucosyl GM1 and the n-pentenyl glycoside of Globo-H, generalized methodologies were developed for the improved synthesis of complex carbohydrate structures. This general synthetic method encompasses the realization that the incorporation of an n-alkenyl glycoside protecting group at the reducing end of a carbohydrate acceptor allows for increased coupling efficiencies and accessibility to complex carbohydrates. In yet another aspect, the present invention also provides the recognition that for certain protected carbohydrates, the n-alkenyl moieties can serve as useful precursors that can be utilized ultimately for the synthesis of complex glycopeptides.

Furthermore, the present invention also provides the recognition that the presence of the n-alkenyl moiety, whether or not in the context of an antigenic n-pentenyl glycoside or glycopeptide, is advantageous for the development of improved carbohydrate based therapeutics (e.g., synthetic vaccines) because more efficient syntheses of conjugation precursors can be prepared (and ultimately conjugated), and the n-alkenyl carbohydrate also serves as a precursor for the synthesis of novel n-alkyl glycoamino acids, as described herein. The ability to easily access these glycoamino acids allows for the ultimate synthesis of complex clustered glycopeptides. Significantly, the methodologies provided by the present invention, as described above and in more detail herein, allow the efficient preparation of complex glycopeptide structures having more than one type of carbohydrate determinant.

Specific examples, particularly with respect to the total synthesis of fucosyl GM1 and a novel synthetic scheme for the synthesis of the n-pentenyl glycoside of Globo-H are described in more detail below, along with certain general methodologies developed during the course of these syntheses. It will be appreciated by one of ordinary skill in the art that these examples are not intended to be limiting; rather all equivalents are intended to be incorporated into the scope of the present invention.

Inventive Compounds and Methods for the Synthesis Thereof

As mentioned above, the total synthesis of complex antigenic structures has led to significant development in methodologies for complex carbohydrate synthesis. Of particular recent interest is the naturally occurring antigenic structure, fucosylated GM1 ganglioside as shown in FIG. 1 (1a) which heretofore had not yet been synthesized. Nilsson et al. identified fucosyl GM1 as a specific marker associated with small lung cancer (SCLC) cells (Nilsson et al., *Glycoconjugate J.* 1984, 1, 43; Brezicka et al., *Cancer Res.* 1989, 49, 1300). These workers isolated the glycosphingolipid fucosyl GM1 (1a) as the major ganglioside component contained in human SCLC tissue. Furthermore, monoclonal antibodies (F12) to the antigen serve to detect fucosyl GM1 in tissues and serum of SCLC patients (Nilsson et al., *Cancer Res.* 1986, 46, 1403; Vangsted et al., *Cancer Res.* 1991, 51, 2897). Immunohistochemistry studies have suggested that, due to its highly restricted distribution in normal tissues, fucosyl GM1 could be an excellent target for immune attack against SCLC. Remarkably, fucosyl GM1 has thus far not been found on any other human cancer cell lines, indicating that it is very SCLC tumor specific (Zhang et al., *Int. J. Cancer* 1997, 73, 42).

The structural assignment of the carbohydrate moiety of the SCLC antigen was based on a combination of enzymatic and chemical degradations (Nilsson et al., *Glycoconjugate J.* 1984, 1, 43). While there was no particular reason to question this assignment, the development of a carbohydrate based attack on SCLC could benefit from a definitive assignment of the linkage modes of the various monosaccharides, including the stereochemistry at each glycosidic attachment. Furthermore, no syntheses of this carbohydrate sector have appeared in the literature. In a preferred embodiment, a synthetic scheme would allow for presentation of the hexasaccharide epitope independent of the ceramide to the F12 mAb to ensure that all specificity is directed at the carbohydrate sector. In other preferred embodiments, the construct should be so functionalized as to anticipate the need for its conjugation to a carrier protein in anticipation of building an effective anti-tumor vaccine. As detailed herein, the ability to generate an n-alkenyl glycoside enables for the efficient synthesis of this epitope and allows for its effective modification and/or conjugation to build an effective anti-tumor vaccine.

Thus, in one aspect of the present invention, the synthesis of the complex fucosyl GM1 carbohydrate sector has been achieved and a compound having the structure as shown below is provided:

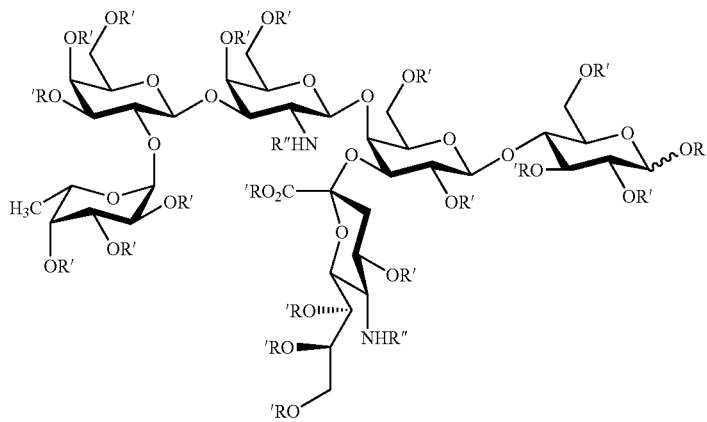

wherein each occurrence of R' is independently hydrogen or a protecting group; wherein each occurrence of R" is independently hydrogen or a nitrogen protecting group; wherein R is hydrogen, substituted or unsubstitued alkyl alkenyl, —NHR''', wherein R''' is a protein, peptide or lipid linked to N or the rest of the construct either directly or through a crosslinker, an amino acyl moiety, an amino acyl residue of a peptide, an amino acyl residue of a protein, which amino acyl moiety or residue, or —NHR''' is linked to O via a polymethylene chain having the structure —$(CH_2)_r$-, where r is an integer between 1 and 9, or wherein R is substituted with a moiety having the structure:

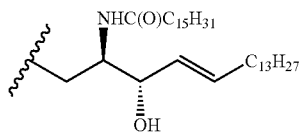

In certain preferred embodiments, each occurrence of R' is hydrogen. In certain other preferred embodiments of the present invention, R is n-alkenyl, including, but not limited to allyl, propenyl, butenyl and pentenyl. In a particularly preferred embodiment, R is n-pentenyl. In certain other preferred embodiments, R is —NHR''', an amino acyl moiety, an amino acyl residue of a peptide, or an amino acyl residue of a protein, as described above, wherein r is preferably 4. In still other preferred embodiments, a compound as described above is provided, with the proviso that the compound is not the glycosphingolipid structure.

In another aspect of the present invention, a method for the synthesis of fucosyl GM1 glycoside is provided, said method comprising steps of:

(a) providing a thioethyl donor having the structure:

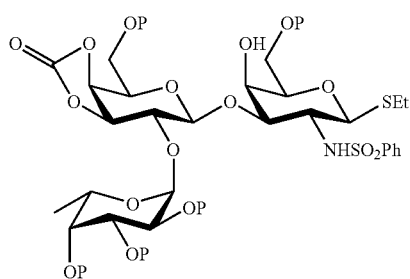

wherein P is a protecting group;

(b) providing a trisaccharide acceptor having the structure:

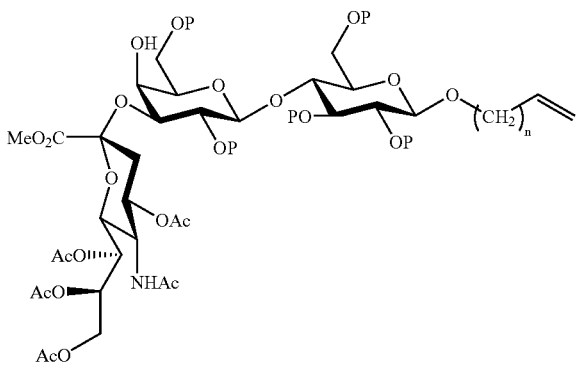

wherein n is 0-8, and wherein P is a protecting group; and (c) reacting said thioethyl donor and said trisaccharide acceptor under conditions to generate a protected hexasaccharide and subsequently deprotecting the protected hexasaccharide under suitable conditions to generate n-alkenyl fucosyl GM 1 glycoside.

In yet another aspect of the present invention, novel derivatives of Globo-H are provided and a novel general synthetic methodology for the synthesis thereof. The derivatives of Globo-H are depicted below:

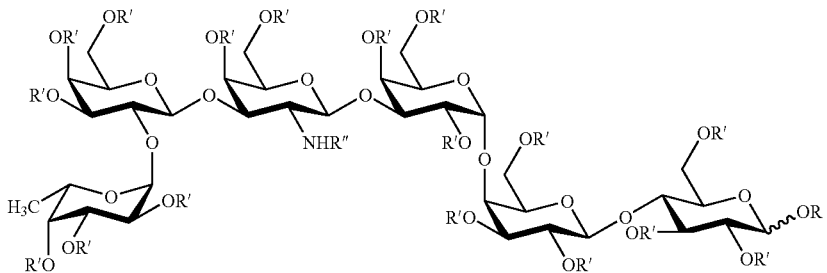

wherein each occurrence of R' is hydrogen or a protecting group, wherein R" is hydrogen or a nitrogen protecting group; wherein R is hydrogen, substituted or unsubstitued alkyl or alkenyl, wherein the alkenyl moiety has four or more carbons; —NHR''', wherein R''' is a protein, peptide or lipid linked to N or the rest of the construct either directly or through a crosslinker; an amino acyl moiety; an amino acyl residue of a peptide; an amino acyl residue of a protein; which amino acyl moiety or residue or —NHR''' is linked to O via a polymethylene chain having the structure —$(CH_2)_r$, where, if said carbohydrate moiety is linked to O via an α-linkage, r is an integer between 2 and 9, or, alternatively, if said carbohydrate moiety is linked to O via a β-linkage, r is an integer between 1 and 9; or wherein R is substituted with a moiety having the structure:

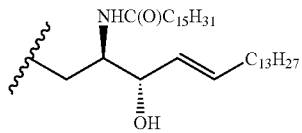

In certain preferred embodiments, each occurrence of R' is hydrogen. In certain other preferred embodiments of the present invention, R is n-alkenyl, including, but not limited to allyl, propenyl, butenyl and pentenyl. In a particularly preferred embodiment, R is n-pentenyl. In certain other preferred embodiments, R is an amino acyl moiety, an amino acyl residue of a peptide, or an amino acyl residue of a protein, as described above, wherein r is preferably 4. In still other preferred embodiments, a compound as described above is provided, with the proviso that the compound is not the glycosphingolipid structure.

As described in more detail herein in Example 2, a similar methodology to that described for fucosyl GM1 is employed for the synthesis of Globo-H and derivatives thereof. Thus, in another aspect of the present invention, a method for the improved synthesis of Globo-H, and derivatives thereof, said method comprising steps of:

(a) providing a thioethyl donor having the structure:

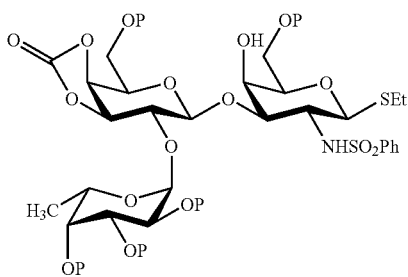

wherein P is a protecting group; and (b) providing a trisaccharide acceptor having the structure:

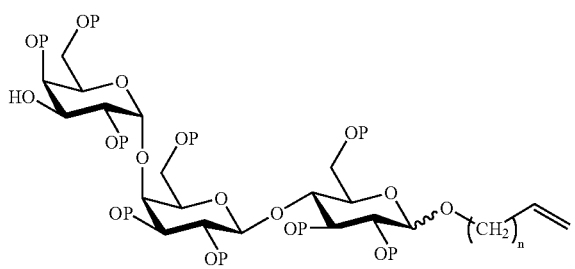

wherein n is 0-8, and wherein P is a suitable protecting group; and (c) reacting said thioethyl donor and said trisaccharide acceptor under conditions to generate a protected hexasaccharide and subsequently deprotecting the protected hexasaccharide under suitable conditions to generate n-alkenyl Globo-H.

In yet another aspect of the present invention, novel derivatives of Gb3 are provided and a novel general synthetic methodology for the synthesis thereof is described herein. Gb3 is a glycosphingolipid which is structurally related to Globo-H, in that, the trisaccharide portion of Gb3 is identical to the trisaccharide portion at the reducing end of Globo-H. Gb3 has recently been shown to be over expressed in Burkitt lymphoma cell-lines, human ovarian cancer, human teratocarcinoma, human embryonal carcinoma, and other types of tumor cells (See Hashimoto, S.; Sakamoto, H.; Honda, T.; Abe, H.; Nakamura, S.; Ikegami, S. Tetrahedron Lett. 1997, 38, 8969-8972, and references cited therein). Consequently, Gb3 emerged as an ideal target from the point of view of preparing novel vaccine constructs.

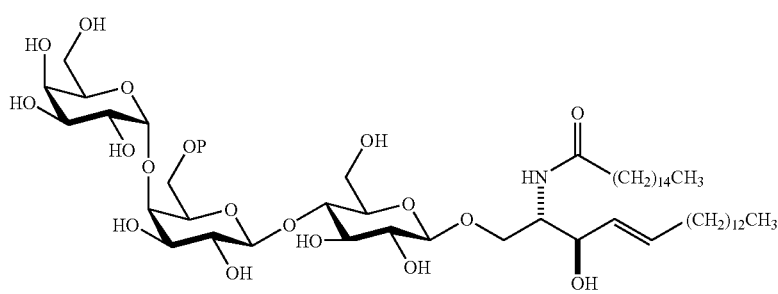

Gb3

Derivatives of Gb3 provided in the present invention are depicted below:

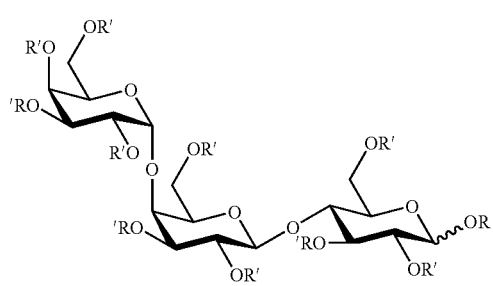

wherein each occurrence of R' is hydrogen or a protecting group; wherein R is hydrogen, substituted or unsubstitued alkyl or alkenyl; a glycoside-containing moiety; a glycoside-linker moiety; R'''; —NHR'''; -(glycoside-linker)-R'''; wherein R''' is an immunogenic carrier linked to the rest of the construct either directly or through a crosslinker; an amino acyl moiety; an amino acyl residue of a peptide; an amino acyl residue of a protein; which amino acyl moiety or residue or —NHR''' is linked to O via a polymethylene chain having the structure —(CH$_2$)$_r$, where, if said carbohydrate moiety is linked to O via an α-linkage, r is an integer between 2 and 9, or, alternatively, if said carbohydrate moiety is linked to O via a β-linkage, r is an integer between 1 and 9; or wherein R is a moiety having the structure:

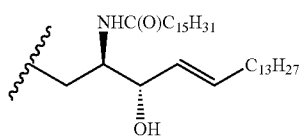

In certain preferred embodiments, each occurrence of R' is hydrogen. In certain other preferred embodiments of the present invention, R is n-alkenyl, including, but not limited to allyl, propenyl, butenyl and pentenyl. In certain exemplary embodiments, the immunogenic carrier is a protein, peptide or lipid. In a particularly preferred embodiment, R is n-pentenyl. In certain other preferred embodiments, R is an amino acyl moiety, an amino acyl residue of a peptide, or an amino acyl residue of a protein, as described above, wherein r is preferably 4. In certain preferred embodiments, R is a glycoside. In particularly preferred embodiments, R is a monosaccharide. In still other preferred embodiments, a compound as described above is provided, with the proviso that the compound is not the glycosphingolipid structure.

In another aspect, the invention provides Gb3 n-alkenyl, glycoamino acid, derivatives and conjugates thereof.

In another aspect of the present invention, a method for the synthesis of Gb3, and derivatives thereof is provided, said method comprising steps of:

(a) providing a fluoromonosaccharide donor having the structure:

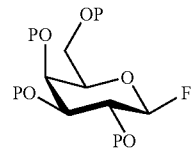

wherein each occurrence of P is independently a suitable protecting group; and (b) providing a disaccharide acceptor having the structure:

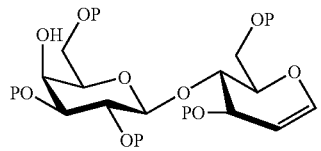

wherein each occurrence of P is independently a suitable protecting group;

(c) reacting said fluoromonosaccharide donor and said disaccharide acceptor under conditions to generate a protected trisaccharide having the structure:

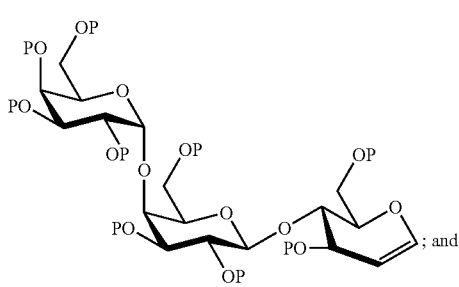

; and (d) reacting said protected trisaccharide with an alkenol under suitable conditions and subsequently deprotecting the protected hexasaccharide under suitable conditions to generate n-alkenyl Gb3.

In another aspect of the present invention, a method for the synthesis of a Gb3 glycoamino acid, and derivatives thereof is provided, said method comprising steps of:

(a) providing an alkenyl trisaccharide having the structure:

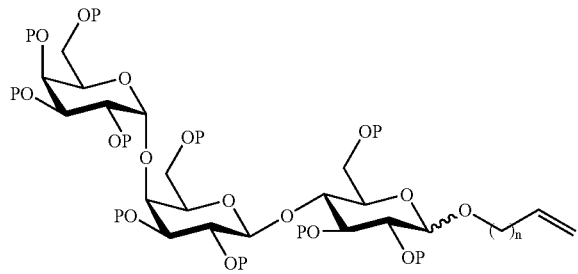

wherein each occurrence of P is independently a suitable protecting group; and n is 1-8;

(b) providing a suitably protected alkenylglycine having the structure:

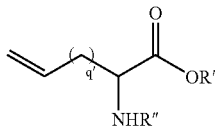

wherein R' and R" are suitable protecting groups; and q' is 0-8;

(c) reacting said alkenyl trisaccharide and said alkenylglycine under suitable conditions in the presence of a suitable catalyst to generate an enamide ester having the structure:

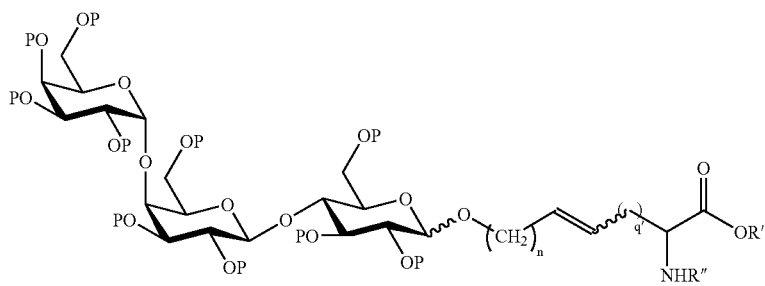

(c) reacting said enamide ester under suitable conditions to generate a glycoamino acid having the structure:

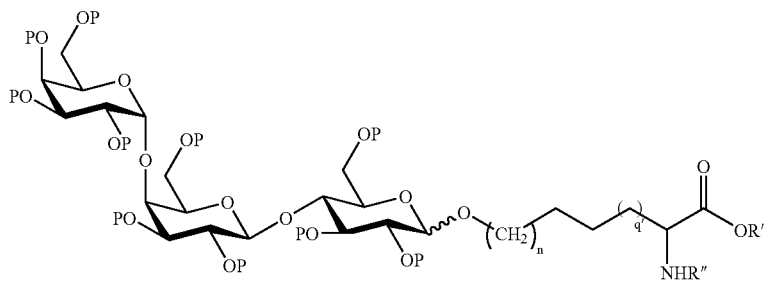

wherein, for each of the structures above, n is 0-8, q' is an integer from 0-8, and each occurrence of P, R' and R" is independently a suitable protecting group.

It will be appreciated that for each of the methods as detailed herein, the full arsenal of protecting groups known in the art of organic synthesis can be utilized, for example, as set forth in "Activating Agents and Protecting Groups: Handbook of Reagents for Organic Synthesis" Roush, W. R. and Pearson, A. J., Eds., John Wiley & Sons: 1999; and "Protective Groups in Organic Synthesis" Greene, T. W. and Wuts, P. G., John Wiley & Sons, New York: 1999, the entire contents of which are hereby incorporated by reference. In but a few examples, suitable protecting groups utilized herein include, but are not limited to, Bn (benzyl), TIPS (triisopropylsilyl), and Ac (acetate). In a preferred embodiment of the present invention, said thioethyl donor and said trisaccharide acceptor are reacted under MeOTf promotion, as described herein. It will be appreciated by one of ordinary skill in the art however, that a variety of conditions known in the art of organic synthesis can be utilized to effect coupling of these moieties.

It will also be appreciated that the novel n-alkenyl moieties provided herein can be subsequently modified to generate useful compounds (e.g., alkyl derivatives and glycoamino acids) or constructs thereof (e.g., glycopeptides and conjugated derivatives).

In addition to providing the first synthesis of fucosyl GM1, a synthesis of Gb3 and improved synthetic methodologies for Globo-H, as described above, in a more general aspect, the present invention provides novel synthetic methodologies for the synthesis of complex carbohydrates comprising (1) providing a carbohydrate acceptor having a reducing end alkenyl group; (2) providing a suitable donor compound and (3) coupling said donor and acceptor under conditions to generate an alkenyl glycoside. Using this method, complex antigenic alkenyl glycosides are provided, as described above, many of which never before have been provided, which can then be conjugated or further reacted, as described herein, to generate glycoconjugates and glycopeptide structures.

Thus, in one aspect, the present invention provides novel compounds and/or conjugates having the general structure:

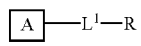

wherein $L^1$ is a substituted or unsubstituted, linear or branched, cyclic or acyclic, saturated or unsaturated aliphatic or heteroaliphatic moiety;

R is hydrogen; substituted or unsubstituted alkyl; alkenyl; aryl; —CH$_2$CH(CO$_2$R')(NHR"), wherein R' or R" are each independently hydrogen, protecting group, substituted or unsubstituted alkyl, a linker, aryl, peptide, protein or lipid; R'" or NHR'", wherein R'" is an immunogenic carrier, peptide, protein or lipid linked to N or the rest of the construct either directly or through a crosslinker;

A is a carbohydrate determinant having the structure:

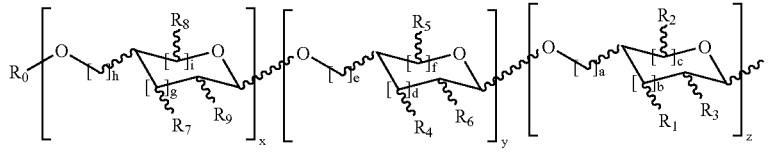

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, OR$^i$, NHR$^i$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

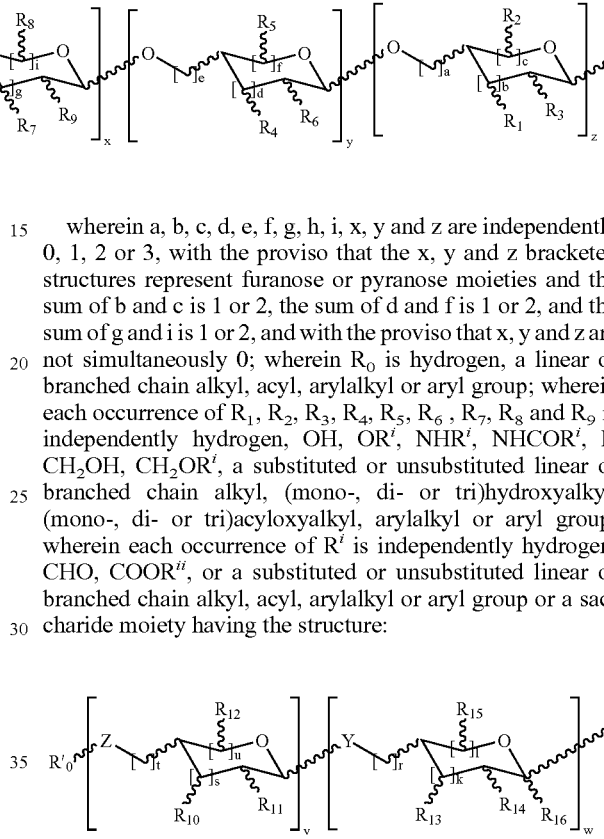

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein R'$_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, OR$^{iii}$, NHR$^{iii}$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, COOR$^{ii}$, CONHR$^{ii}$, a substituted or unsubstituted linear or branched chain alkyl or aryl group; wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group.

In certain embodiments, if each occurrence of $L^1$ is a moiety having the structure —O(CH$_2$)$_n$— and if for each occurrence of n, n=0, then at least one occurrence of A has a different structure from other occurrences of A. In certain embodiments, each occurrence of $L^1$ is independently —O—(CH$_2$)$_n$—, wherein n is 0-9, or a glycoside-containing moiety (e.g., mono saccharide). In certain preferred embodiments, R is allyl, n is 2 and thus the inventive compounds comprise an n-pentenyl moiety. In certain other embodiments, the immunogenic carrier is a protein, peptide, or lipid. In certain other embodiments of the present invention, R is NHR''', and the carrier R''' is KLH or Bovine Serum Albumin. In still other embodiments of the present invention, R is NHR''', and the carrier R''' is a lipid having the structure:

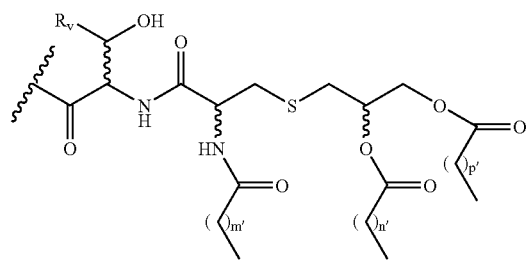

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys). It will be appreciated that the carrier can be linked to the rest of the construct directly or through a crosslinker, and thus R''' incorporates proteins, peptides, and lipids, as well as (crosslinker-protein), (crosslinker-peptide) and (crosslinker-lipid) moieties.

In other embodiments, the inventive compound is a glycoamino acid and thus R is CH$_2$CH(CO$_2$R')(NHR''), which compound has the structure:

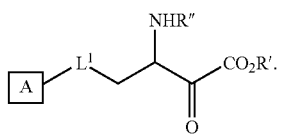

In certain preferred embodiments, the glycoamino acids of the present invention are derived from n-pentenyl glycosides and thus L$^1$ is —O(CH$_2$)$_3$—. In certain other preferred embodiments, R' and R'' are each a protecting group independently selected from the group consisting of benzyl, t-butyl, TSE (2-(trimethylsilyl ethyl), Ac (acetyl), Boc (t-butoxycarbonyl), Cbz and Fmoc (9-fluoroenyl methoxy carbonyl).

In certain embodiments, the present invention provides novel compounds and/or conjugates having the general structure:

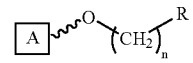

wherein R is hydrogen; substituted or unsubstituted alkyl; alkenyl; aryl; —CH$_2$CH(CO$_2$R')(NHR''), wherein R' or R'' are each independently hydrogen, protecting group, substituted or unsubstituted alkyl, a linker, aryl, protein, peptide or lipid; R''' or NHR''', wherein R''' is an immunogenic carrier, protein, peptide, or lipid, linked to N or the rest of the construct either directly or through a crosslinker; wherein n is 0-9; wherein A is a carbohydrate domain having the structure:

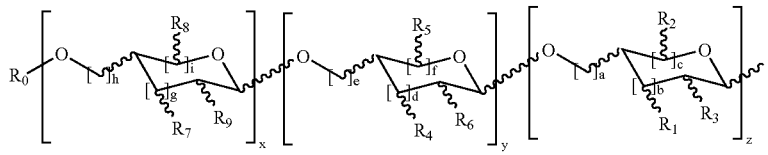

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein R$_0$ is hydrogen, a linear or branched chain alkyl, acyl, arylalkyl or aryl group; wherein each occurrence of R$_1$, R$_2$, R$_3$, R$_4$, R$_5$, R$_6$, R$_7$, R$_8$ and R$_9$ is independently hydrogen, OH, OR$^i$, NHR$^i$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

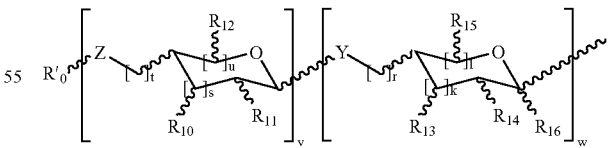

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein R'$_0$ is hydrogen, a linear or branched chain alkyl, acyl, arylalkyl or aryl group; wherein each occurrence of R$_{10}$, R$_{11}$, R$_{12}$, R$_{13}$, R$_{14}$ and R$_{15}$ is independently hydrogen, OH, OR$^{iii}$, NHR$^{iii}$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R$_{16}$ is hydrogen, COOH, COOR$^{ii}$, CONHR$^{ii}$, a substituted or unsubstituted linear or branched chain alkyl or aryl group; wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group.

In certain exemplary embodiments, if A is KH-1, N3, globo-H, glycophorin, Tn, TF, STN, (2,3-ST), 2,6-STn or Le$^y$, and A is α-O-linked, then n is at least 1. In certain embodiments, A is α- or β-O-linked. In certain preferred embodiments of the present invention, R is allyl, n is 2 and thus the inventive compound is an n-pentenyl moiety. In certain embodiments, the immunogenic carrier is a protein, peptide, or lipid. In certain other embodiments of the present invention, R is NHR''', and the carrier R''' is KLH or Bovine Serum Albumin. In still other embodiments of the present invention, R is NHR''', and the carrier R''' is a lipid having the structure:

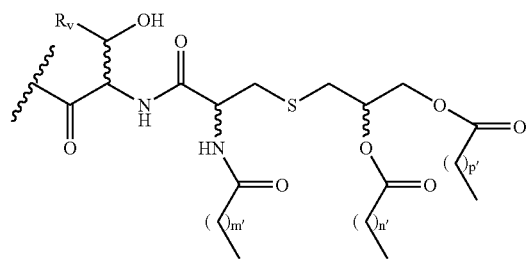

wherein m', n' and p' are each independently integers between about 8 and 20; and R$_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys). It will be appreciated that the protein or lipid can be linked to N or the rest of the construct either directly or through a crosslinker and thus R''' incorporates proteins, peptides and lipids, as well as (crosslinker-protein), (crosslinker-peptide) and (crosslinker-lipid) moieties. In certain preferred embodiments, the crosslinker is MMCCH (4-(maleimidomethyl) cyclohexane-1-carboxyl hydrazide).

In still other embodiments, the inventive compound is a glycoamino acid and thus R is CH$_2$CH(CO$_2$R')(NHR''), which compound has the structure:

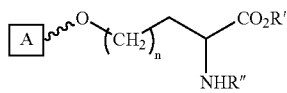

In certain preferred embodiments, the glycoamino acids of the present invention are derived from n-pentenyl glycosides and thus n is 3. In certain other preferred embodiments, R' and R'' are a protecting group, each independently selected from the group consisting of benzyl, t-butyl, TSE, Boc, Fmoc, Cbz and acetyl.

For each of the compounds described above, in certain preferred embodiments the carbohydrate determinant is selected from the group consisting of Globo-H, fucosyl GM1, KH-1, N3, glycophorin, Tn, TF, STN, (2,3)ST, 2,6-STn, Gb3 and Le$^y$. In other preferred embodiments, the carbohydrate determinant of the compound contains a Globo-H determinant or fucosyl GM1 determinant as all of part of the carbohydrate determinant A.

Crosslinkers suited to the invention are widely known in the art (see, for example, 1994 Pierce Technical Handbook: cross-linking available at http://www.piercenet.com/resources/browse.cfm?fldID=184), including bromoacetic NHS ester, 6-(iodoacetamido)caproic acid NHS ester, maleimidoacetic acid NHS ester, maleimidobenzoic acide NHS ester, etc. In certain preferred embodiments, the crosslinker is MMCCH (4-(maleimidomethyl)cyclohexane-1-carboxyl hydrazide). In certain other preferred embodiments, the crosslinker is MBS (m-maleimidobenzoyl acid N-Hydroxysuccinimidyl ester).

As described above, specifically in the context of the second generation synthesis of the MBr1 antigen (GloboH) and the total synthesis of the fucosylated ganglioside of GM1 (fucosyl GM1) and Gb3, incorporating the reducing end n-alkenyl moiety (specifically n-pentenyl) offers certain benefits. First, the anomeric n-pentenyl glycoside linkage serves as an effective linker for immunoconjugation to carrier protein KLH and also provides some advantages in terms of synthetic convergency. In the context of protected carbohydrates, the n-alkenyl moieties are also capable of acting as donors for glycosylation (see, for example, Fraser-Reid et al., SynLett, 1992, 927).

In this context, the present invention additionally provides methods for the synthesis of n-alkyl glycoamino acids, as described in more detail below for Globo-H and fucosyl GM1 and their subsequent use to generate glycopeptides and synthetic constructs thereof.

In certain embodiments, the inventive method for the production of these novel glycoaminoacids comprises: 1) providing an alkenyl glycosidic moiety, as described herein; 2) subjecting said alkenyl glycosidic moiety to oxidative conditions to generate an aldehyde; 3) subjecting said aldehyde to olefination conditions to generate an enamide ester; 4) subjecting said resulting enamide ester to conditions sufficient to hydrogenate said enamide ester to generate a protected glycoamino acid and 5) deprotecting said protected glycoamino acid under suitable conditions to generate a desired glycoamino acid.

In particular, a method for the synthesis of a glycoamino acid, the structure of which is set forth herein, is provided, which comprises steps of:

(a) providing an alkenyl glycoside having the structure:

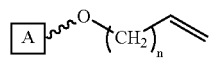

(b) reacting said alkenyl glycoside under suitable conditions to generate an enamide ester having the structure:

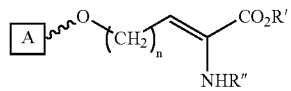

(c) reacting said enamide ester under suitable conditions to generate a glycoamino acid having the structure:

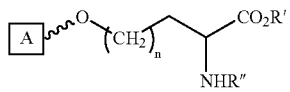

wherein, for each of the structures above, n is 0-8, wherein A is a carbohydrate domain having the structure:

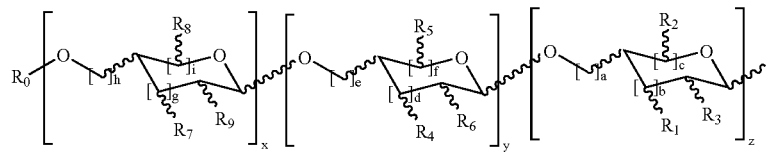

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

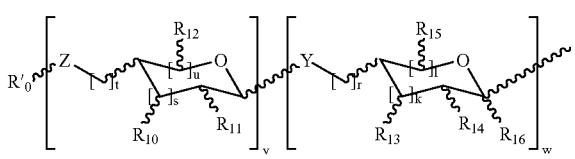

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;

and wherein for the glycoamino acid structure R' and R" are each independently hydrogen, protecting group, substituted or unsubstituted alkyl, linker, aryl, peptide, protein or lipid; R'" or NHR'", wherein R'" is an immunogenic carrier, protein, peptide, or lipid, linked to N or the rest of the construct either directly or through a crosslinker. In preferred embodiments, R' and R" are each independently hydrogen or a protecting group. In particularly preferred embodiments R" is a nitrogen protecting group, including, but not limited to, acetyl, Fmoc, Cbz or Boc, and R' is an acid protecting group such as benzyl, t-butyl or TSE. It will be appreciated, however, that a variety of protecting groups known in the art of organic synthesis can be employed, as referenced herein.

In certain preferred embodiments, the carbohydrate determinant is selected from the group consisting of Globo-H, fucosyl GM1, KH-1, glycophorin, STN, (2,3)ST, Le$^y$, N3, Tn, 2,6-STn, Gb3 and TF. In certain other preferred embodiments, the carbohydrate determinant of the compound contains a Globo-H determinant or a fucosyl GM1 determinant, as described herein, as all or part of the carbohydrate determinant A.

In general, in preferred embodiments, the step of reacting an n-alkenyl glycoside under suitable conditions to generate an enamide ester comprises reacting an n-alkenyl glycoside first under oxidative conditions and second under olefination conditions in the presence of base (e.g., tetramethylguanidine) and phosphonate to generate an enamide ester. It will be appreciated that other oxidative conditions known in the art of organic synthesis can be employed, including, but not limited to $OsO_4$ and periodate, or $OsO_4$ and $Pb(OAc)_4$. Additionally, other well-known bases can be utilized in the present invention, including, but not limited to, lithium t-butoxide or lithium hexamethyl disilylazide.

In certain exemplary embodiments, reacting said enamide ester under suitable conditions to generate a glycoamino acid comprises reacting said enamide ester under hydrogenation conditions and subsequent reaction under deprotection conditions to generate a glycoamino acid. It is particularly preferred that the hydrogenation conditions employed are asymmetric hydrogenation conditions. In a preferred embodiment, asymmetric hydrogenation can be achieved by utilizing an ethyl DuPHOS catalyst precursor, as described in more detail herein (see, Burk et al. *Accts. Chem. Res.* 2000, 33, 3631; Burk et al. *Pure & Appl. Chem.* 1996, 68, 37).

In certain other embodiments, the inventive method for the production of these novel glycoaminoacids comprises: (i) providing a suitable alkenyl glycoside; (ii) providing a suitably protected alkenylamino acid; (iii) reacting the alkenyl glycoside with the alkenylamino acid under suitable conditions in the presence of a suitable catalyst to generate a glycoenamide ester; and (iv) subjecting the glycoenamide ester to suitable conditions to generate a glycoamino acid.

In preferred embodiments, the step of reacting an alkenyl glycoside under suitable conditions to generate an enamide ester comprises reacting an n-alkenyl glycoside with a suitably protected alkenylamino acid under cross-metathesis conditions in the presence of a suitable catalyst. In certain exemplary embodiments, the protected alkenylamino acid is an allylglycine having the structure:

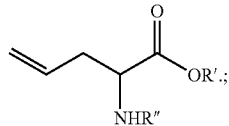

wherein R' and R" are each independently hydrogen or a protecting group. In certain embodiments, the step of reacting said glycoenamide ester under suitable conditions to generate a glycoamino acid comprises reacting said enamide ester under hydrogenation conditions and subsequent reaction under deprotection conditions to generate a glycoamino acid. In certain exemplary embodiments, the method for the synthesis of a glycoamino acid comprises steps of:

(a) providing an alkenyl glycoside having the structure:

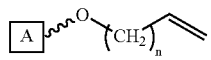

(b) reacting said alkenyl glycosidic moiety with a suitable alkenylglycine under suitable conditions in the presence of a suitable catalyst to generate an enamide ester having the structure:

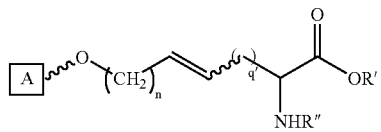

(c) reacting said enamide ester under suitable conditions to generate a glycoamino acid having the structure:

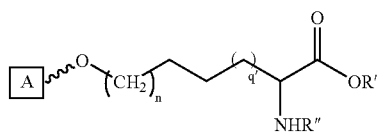

wherein, for each of the structures above, n is 0-8; q' is an integer from 0-8; A is a carbohydrate domain having the structure:

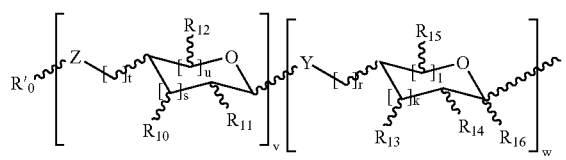

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;

and wherein for the glycoamino acid structure R' and R" are each independently hydrogen, protecting group, substituted or unsubstituted alkyl, linker, aryl, peptide, protein or lipid; R''' or NHR''', wherein R''' is an immunogenic carrier, protein, peptide, or lipid, linked to the rest of the construct directly or through a crosslinker. In preferred embodiments, R' and R" are each independently hydrogen or a protecting group. In particularly preferred embodiments R" is a nitrogen protecting group, including, but not limited to, acetyl, Fmoc, Cbz or Boc, and R' is an acid protecting group such as benzyl, t-butyl or TSE. In certain preferred embodiments, the carbohydrate determinant is selected from the group consisting of Globo-H, fucosyl GM1, KH-1, glycophorin, STN, (2,3)ST, Le$^y$, N3, Tn, 2,6-STn, Gb3 and TF. In certain other preferred embodiments, the carbohydrate determinant of the compound contains a Globo-H determinant or a fucosyl GM1 determinant, as described herein, as all or part of the carbohydrate determinant A.

In certain preferred embodiments, the protected alkenylglycine has the structure:

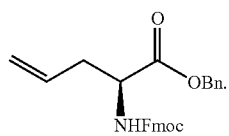

In certain other embodiments, the catalyst is selected from the group consisting of:

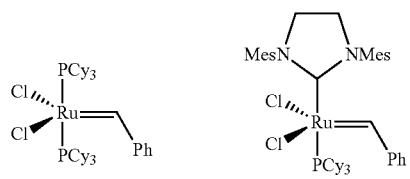

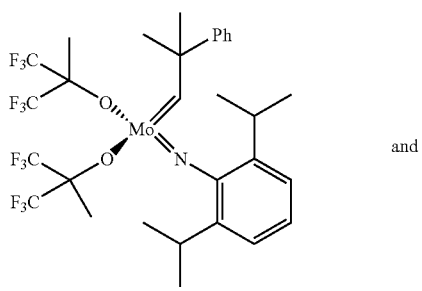

and

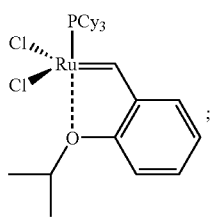

wherein Cy represents a cyclohexyl moiety. (see, for example, Furstner, A. *Angew. Chem., Int. Ed. Engl.* 2000, 39, 3013-3043).

In certain exemplary embodiments, the catalysts is bis (tricyclohexyl phosphine) ruthenium Grubbs catalyst:

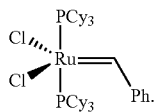

Additionally, in certain embodiments, the step of subjecting the glycoenamide ester to suitable conditions to generate a glycoamino acid comprises catalytic hydrogenation. In certain exemplary embodiments, the hydrogenation reaction concomitantly removes the nitrogen protecting group on the amino acid moiety, thus generating a glycoamino acid unit suitable for incorporation into a peptide construct.

It will be appreciated that the ability to generate the glycoamino acids, as described herein, ultimately enables the synthesis of novel clustered glycopeptides, a motif commonly found on the surface of cancer cells (mucin-like structures) which are desirable for the uses described herein as anticancer vaccines. For example, immunological studies indicate that, in general, the clustering of antigens in glycopeptides results in a more therapeutically immune response than with singly glycosylated peptides (see, Lo-Man, R. et al., *Cancer Res.*, 1999, 59, 1520; Reddish et al., *Glycoconjugate J.* 1997, 14, 549).

To date, the clustering of α-O-linked antigens has been accomplished with the same antigen across the peptide backbone via the traditional allyl linkage, as described in pending U.S. patent Ser. Nos. 09/083,776 and 09/276,595, the entire contents of which are hereby incorporated by reference. However, the present invention efficiently provides peptides having different antigens simultaneously in a clustered format. Thus, in one aspect, the present invention provides multi-antigenic glycopeptides comprising a peptidic backbone made up of two or more amino acids, wherein one or more of said amino acids is/are independently substituted with a glycosidic moiety having the structure:

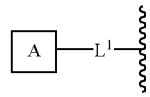

wherein each occurrence of $L^1$ is independently a substituted or unsubstituted, linear or branched, cyclic or acyclic, saturated or unsaturated aliphatic or heteroaliphatic moiety;

each occurrence of A is independently a carbohydrate determinant having the structure:

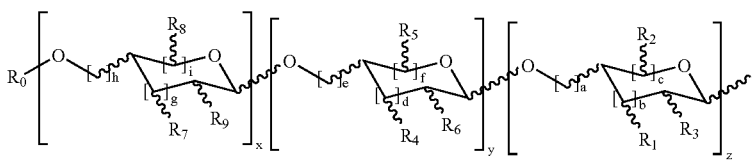

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

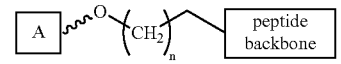

wherein each occurrence of A is independently a carbohydrate determinant having the structure:

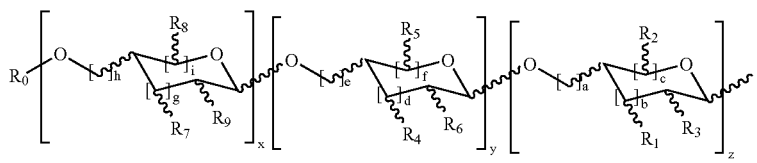

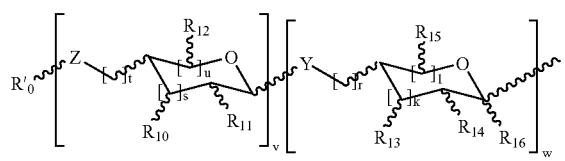

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein R'$_0$ is hydrogen, a linear or branched chain alkyl, acyl, arylalkyl or aryl group; wherein each occurrence of R$_{10}$, R$_{11}$, R$_{12}$, R$_{13}$, R$_{14}$ and R$_{15}$ is independently hydrogen, OH, OR$^{iii}$, NHR$^{iii}$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R$_{16}$ is hydrogen, COOH, COOR$^{ii}$, CONHR$^{ii}$, a substituted or unsubstituted linear or branched chain alkyl or aryl group; wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group.

In certain embodiments, if each occurrence of L$^1$ is a moiety having the structure —O(CH$_2$)$_n$— and if for each occurrence of n, n=0, then at least one occurrence of A has a different structure from other occurrences of A. In certain embodiments, each occurrence of L$^1$ is independently —O— (CH$_2$)$_n$—, wherein n is 0-9, or a glycoside-containing moiety (e.g mono- or poly-saccharide).

It will also be appreciated from the structures as set forth above, that, in addition to providing multi-antigenic structures, the present invention additionally provides clustered structures having one or more saccharide linkages. Thus, in yet another aspect of the present invention, saccharide linked clustered glycopeptides are provided, which glycopeptides may incorporate multiple antigenic structures or may also incorporate all of the same antigenic structures.

In certain embodiments, multi-antigenic glycopeptides are provided comprising a peptidic backbone made up of at least three glycoamino acids, wherein one or more of said amino acids is/are substituted with an n-alkyl glycosidic moiety having the structure:

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein R$_0$ is hydrogen, a linear or branched chain alkyl, acyl, arylalkyl or aryl group; wherein each occurrence of R$_1$, R$_2$, R$_3$, R$_4$, R$_5$, R$_6$, R$_7$, R$_8$ and R$_9$ is independently hydrogen, OH, OR$^i$, NHR$^i$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

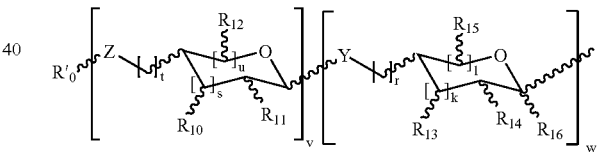

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein R'$_0$ is hydrogen, a linear or branched chain alkyl, acyl, arylalkyl or aryl group; wherein each occurrence of R$_{10}$, R$_{11}$, R$_{12}$, R$_{13}$, R$_{14}$ and R$_{15}$ is independently hydrogen, OH, OR$^{iii}$, NHR$^{iii}$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R$_{16}$ is hydrogen, COOH, COOR$^{ii}$, CONHR$^{ii}$, a substituted or unsubstituted linear or branched chain alkyl or aryl group; wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group;

wherein each occurrence of n is independently 0-8. In certain embodiments, if for each occurrence of n, n=0, at least one occurrence of A has a different structure from other occurrences of A. In certain other embodiments, each occurrence of the n-alkyl glycosidic moiety is independently either α- or β-linked to an amino acid residue of the backbone. It will be appreciated that these inventive clustered glycopeptides are not limited to n-alkyl where n is greater than or equal to 1; rather multi-antigenic clustered glycopeptides can be linked via the traditional direct linkage (n=0) or via n-alkyl (such as pentyl) or any combination thereof. In preferred embodiments, each occurrence of A is independently selected from the group consisting of Globo-H, fucosyl GM1, KH-1, glycophorin, STN, (2,3)ST, Le$^y$, N3, Tn, 2,6-STn, Gb3 and TF.

It will also be appreciated from the structures as set forth above, that, in addition to providing multi-antigenic structures, the present invention additionally provides clustered structures having n-alkyl linkages. Thus, in yet another aspect of the present invention, n-alkyl linked (where n is greater than or equal to 1) clustered glycopeptides are provided, which glycopeptides may incorporate multiple antigenic structures or may also incorporate all of the same antigenic structures.

It will also be appreciated from the structures as set forth above, that the present invention additionally provides clustered structures having n-alkyl linkages or glycoside-containing linkages, or any combination thereof. Thus, in yet another aspect of the present invention, n-alkyl linked (where n is greater than or equal to 1) and/or monosaccharide linked clustered glycopeptides are provided, which glycopeptides may incorporate multiple antigenic structures or may also incorporate all of the same antigenic structures.

In certain preferred embodiments, the generation of the inventive glycopeptides comprises treating a first glycoamino acid with a deprotecting agent to reveal the corresponding carboxylic acid and then coupling said carboxylic acid under suitable conditions with a spacer moiety and a protecting group to generate a protected amide. A second glycoamino acid can then be coupled under standard conditions (e.g., BOP promoter or other known coupling reagents known in the art of peptide couplings) these couplings can be continued until a peptide of desired length is obtained. It will also be appreciated that solid phase methods of peptide synthesis known in the art can also be employed in the method of the present invention to generate the inventive glycopeptides.

In certain embodiments, the inventive glycopeptide is a construct having the structure:

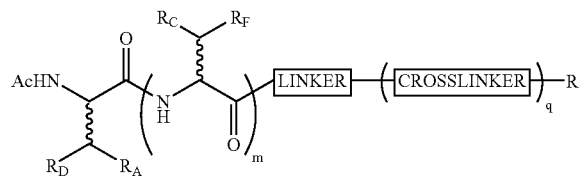

wherein q is 0 or 1;
m is an integer from 1-20;
R is hydrogen or an immunogenic carrier;
the linker is either a free carboxylic acid, —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;

each occurrence of $R_A$ and $R_C$ is independently hydrogen, a subsituted or unsubstituted, linear or branched, cyclic or acyclic, saturated or unsaturated alkyl, aliphatic or heteroaliphatic moiety or a substituted or unsubstituted aryl or heteroaryl moiety; and wherein each occurrence of $R_D$ and $R_F$ is independently a glycosidic moiety having the structure:

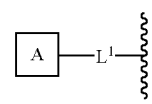

wherein each occurrence of $L^1$ is independently a substituted or unsubstituted aliphatic or heteroaliphatic moiety;

each occurrence of A is independently a carbohydrate domain having the structure:

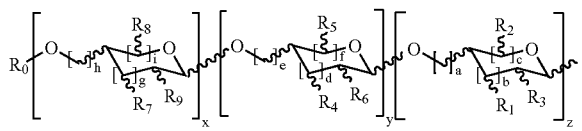

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, OR$^i$, NHR$^i$, NHCOR$^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

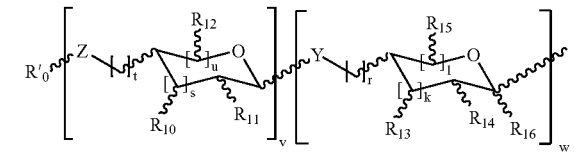

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein R'$_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group; and wherein each occurrence of n is independently 0-8; and wherein each glycosidic moiety is either α- or β-linked to an amino acid. In certain embodiments, each occurrence of $L^1$ is independently a moiety having the structure $-O(CH_2)_n-$ wherein n is an integer from 0-9. In certain embodiments, each occurrence of $R_A$ and $R_C$ is independently hydrogen or methyl. In still other embodiments, the immunogenic carrier is a protein, peptide or lipid.

In certain embodiments, the glycopeptide is attached to a suitable immunogenic carrier via a linker and the glycopeptide has the structure:

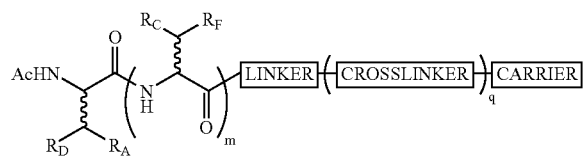

In certain embodiments, for the above two constructs, m is at least 4. In certain other embodiments, m is at least 5. In yet other embodiments, m is at least 6.

While the glycopeptide of the present invention is not intended to be limited in size, in certain preferred embodiments, multi-antigenic clusters having three or more antigens are desirable and thus the present invention also provides constructs having the following structure:

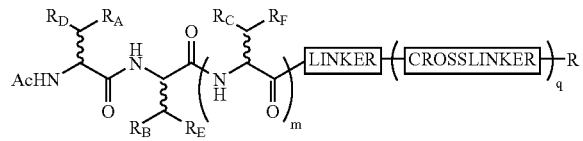

wherein q is 0 or 1;

m is an integer from 1-19;

R is hydrogen or an immunogenic carrier;

the linker is either a free carboxylic acid, —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;

wherein each occurrence of $R_A$, $R_B$ and $R_C$ is independently hydrogen, a subsituted or unsubstituted, linear or branched, cyclic or acyclic, saturated or unsaturated alkyl, aliphatic or heteroaliphatic moiety or a substituted or unsubstituted aryl or heteroaryl moiety; and wherein each occurrence of $R_D$, $R_E$ and $R_F$ is independently a glycosidic moiety having the structure:

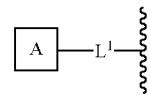

wherein each occurrence of $L^1$ is independently a substituted or unsubstituted aliphatic or heteroaliphatic moiety;

each occurrence of A is independently a carbohydrate domain having the structure:

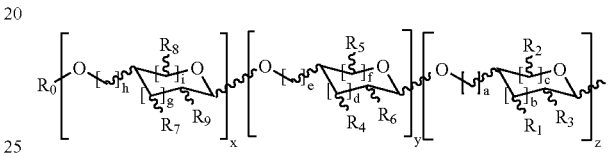

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

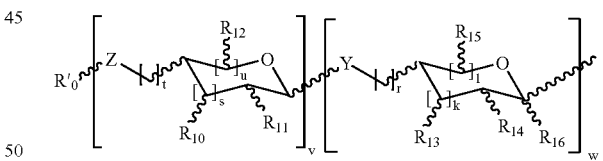

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, COOR$^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group.

In certain embodiments, if each occurrence of $L^1$ is independently a moiety having the structure —O(CH$_2$)$_n$—, wherein each occurrence of n is independently 0-9, and if for each occurrence of n, n=0, then at least one occurrence of A has a different structure from other occurrences of A. In certain other embodiments, the glycosidic moiety is either α- or β-linked to an amino acid residue of the backbone. In certain embodiments, each occurrence of $L^1$ is independently a moiety having the structure —O(CH$_2$)$_n$—, wherein each occurrence of n is independently 0-, or a glycoside-containing moiety. In certain exemplary embodiments, at one occurrence of $L^1$ comprises a monosaccharide. It will be appreciated that these inventive clustered glycopeptides are not limited to n-alkyl where n is greater than or equal to 1; rather multi-antigenic clustered glycopeptides can be linked via the traditional direct linkage (n=0), via n-alkyl (such as pentyl) or via a glycoside moiety or any combination thereof. In other embodiments, each occurrence of A may be the same, however, n-alkenyl (n greater than 1) linkages or glycoside-containing linkages are then utilized. In preferred embodiments, each occurrence of A is independently selected from the group consisting of Globo-H, fucosyl GM1, KH-1, glycophorin, STN, (2,3)ST, Le$^y$, N3, Tn, 2,6-STn, Gb3 and TF. In certain other embodiments, each occurrence of $R_A$, $R_B$ and $R_C$ is independently hydrogen or methyl. In still other embodiments, the immunogenic carrier is a protein, peptide or lipid.

In certain embodiments, each occurrence of $L^1$ is independently a moiety having the structure —O(CH$_2$)$_n$— and the multi-antigenic glycopeptide has the following structure:

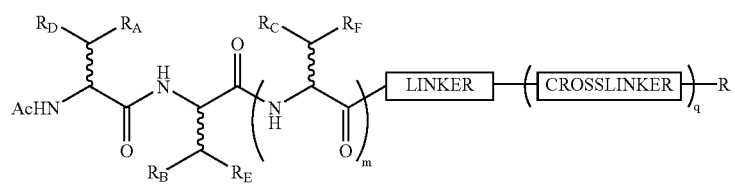

wherein q is 0 or 1;
m is an integer from 1-19;
R is hydrogen or an immunogenic carrier;
the linker is either a free carboxylic acid, —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;

each occurrence of $R_A$, $R_B$ and $R_C$ is independently hydrogen, a substituted or unsubstituted, linear or branched, cyclic or acyclic, saturated or unsaturated aliphatic or heteroaliphatic moiety or a substituted or unsubstituted aryl or heteroaryl moiety; and wherein each occurrence of $R_D$, $R_E$ and $R_F$ is independently an alkyl glycosidic moiety having the structure:

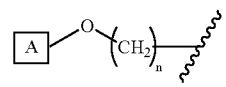

wherein each occurrence of A is independently a carbohydrate domain having the structure:

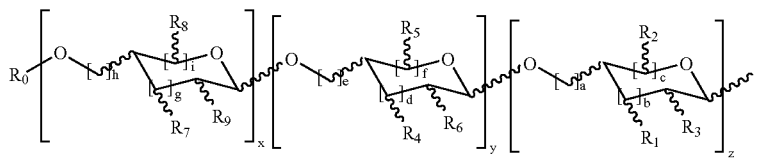

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, OR$^i$, NHR$^i$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

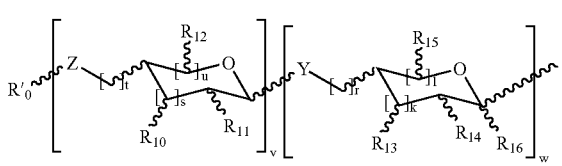

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group; and wherein acyl residues, a peptidic fragment comprising from 2 to about 20 amino acyl residues, or a linear or branched chain alkyl or aryl carboxylic ester;

the carrier is an immunogenic carrier;

each occurrence of $R_A$, $R_B$ and $R_C$ is independently hydrogen, a substituted or unsubstituted, linear or branched, cyclic or acyclic, saturated or unsaturated aliphatic or heteroaliphatic moiety or a substituted or unsubstituted aryl or heteroaryl moiety; and wherein each occurrence of $R_D$, $R_E$ and $R_F$ is independently an alkyl glycosidic moiety having the structure:

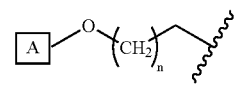

wherein each occurrence of A is independently a carbohydrate domain having the structure:

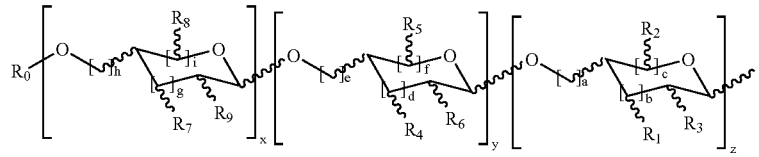

each occurrence of n is independently 0-8. In certain embodiments, if for each occurrence of n, n=0, at least one occurrence of A has a different structure from other occurrences of A. In certain other embodiments, each occurrence of the n-alkyl glycosidic moiety is independently either α- or β-linked to an amino acid residue of the backbone. In certain embodiments, each occurrence of $R_A$, $R_B$ and $R_C$ is independently hydrogen or methyl. In still other embodiments, the immunogenic carrier is a protein, peptide or lipid.

In certain embodiments, the glycopeptide is attached to a suitable immunogenic carrier via a linker and the glycopeptide has the following structure:

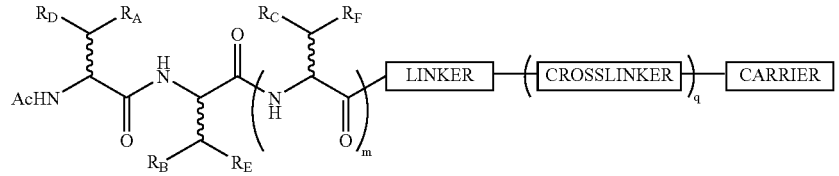

wherein q is 0 or 1;

m is an integer from 1-19;

the linker is either a free carboxylic acid, —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group;

wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

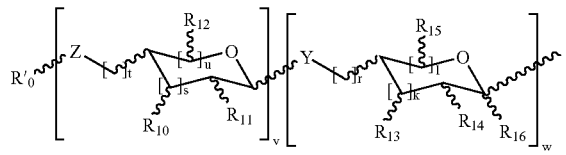

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group; and wherein each occurrence of n is independently 0-8. In certain embodiments, if for each occurrence of n, n=0, at least one occurrence of A has a different structure from other occurrences of A. In certain other embodiments, each occurrence of the n-alkyl glycosidic moiety is independently either α- or β-linked to an amino acid residue of the backbone. In certain embodiments, each occurrence of $R_A$, $R_B$ and $R_C$ is independently hydrogen or methyl. In still other embodiments, the immunogenic carrier is a protein, peptide or lipid.

In certain embodiments, for the above three constructs, m is at least 3. In certain other embodiments, m is at least 4. In yet other embodiments, m is at least 5. In yet other embodiments, m is at least 6.

In certain embodiments, for the above five constructs, q is 1 and the crosslinker is a fragment having the structure:

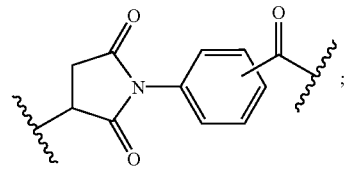

whereby said structure is generated upon conjugation of a maleimidobenzoic acid N-hydroxy succinimide ester with a linker.

In certain embodiments, for the above five constructs, the linker is —O—, —$NR_G$—, —$NR_G$(aliphatic)$NR_J$—, —$NR_G$(heteroaliphatic)$NR_J$—, -(aliphatic)$NR_J$—, —O(het-eroaliphatic)$NR_J$—, —O(aliphatic)$NR_J$—, —O(het-eroaliphatic)$NR_J$—, —$NR_G$(aliphatic)$NR_J(C=O)(CR_HR_I)_k$S—, —$NR_G$(heteroaliphatic)$NR_J(C=O)(CR_HR_I)_k$S—, —(aliphatic)$NR_J(C=O)(CR_HR_I)_k$S—, —(heteroaliphatic)$NR_J(C=O)(CR_HR_I)_k$S—, —O(aliphatic)$NR_J(C=O)(CR_HR_I)_k$S—, —O(heteroaliphatic)$NR_J(C=O)(CR_HR_I)_k$S—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5; wherein each occurrence of $R_G$, $R_H$, $R_I$ or $R_J$ is independently hydrogen, a linear or branched, substituted or unsubstituted, cyclic or acyclic moiety, or a substituted or unsubstituted aryl moiety, and wherein each aliphatic or heteroaliphatic moiety is independently substituted or unsubstituted, linear or branched, cyclic or acyclic.

In certain embodiments, for the above five constructs, the linker is —O—, —$NR_G(CR_HR_I)_kNR_J$—, —$NR_G(CR_HR_I)_kNR_J(C=O)(CR_HR_I)_k$S—, —$NR_G$—, —$(CR_HR_I)_kNR_J$—, —$O(CR_HR_I)_kNR_J$, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5, wherein each occurrence of $R_G$, $R_H$, $R_I$ or $R_J$ is independently hydrogen, a linear or branched, substituted or unsubstituted, cyclic or acyclic moiety, or a substituted or unsubstituted aryl moiety.

In certain embodiments, for the above five constructs, each occurrence of A is independently selected from the group consisting of Globo-H, fucosyl GM1, KH-1, glycophorin, STN, (2,3)-ST, Le$^y$, N3, Tn, 2,6-STn, Gb3 and TF.

In certain exemplary embodiments, the present invention provides a novel trimeric antigenic glycopeptide incorporating three occurrences of Gb3, to generate a novel trimeric antigenic compound having the structure:

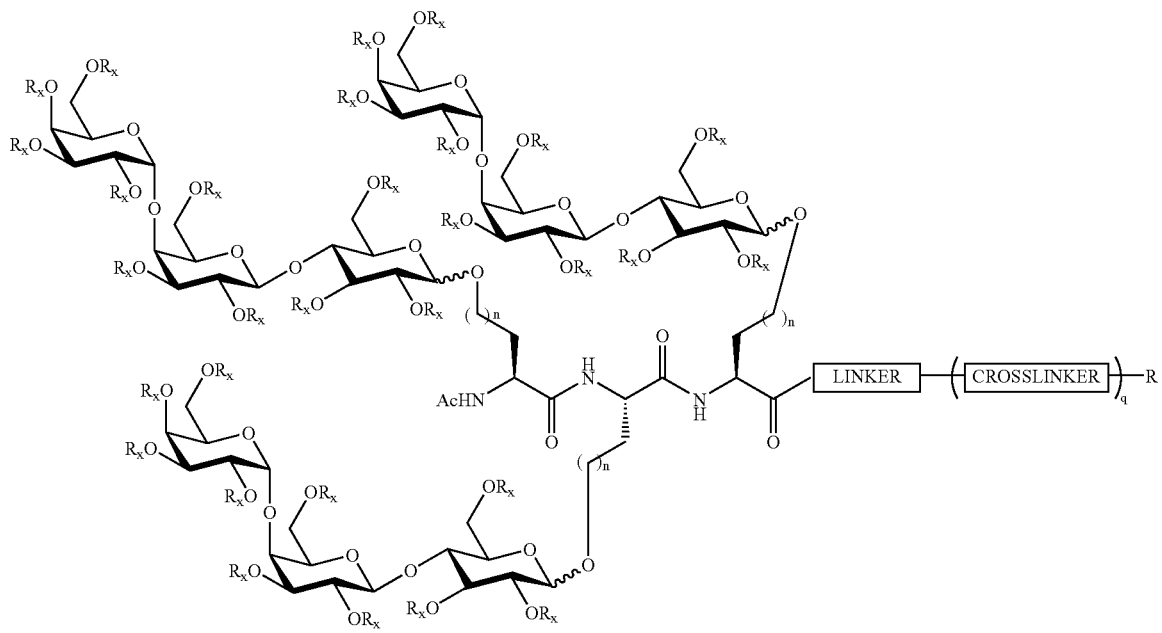

wherein each occurrence of $R_x$ is independently hydrogen or a protecting group; q is 0 or 1; each occurrence of n is independently an integer from 0-9; R is hydrogen or an immunogenic carrier. In certain exemplary embodiments, the immunogenic carrier is a protein, peptide or lipid. In certain embodiments, each occurrence of n is 3. In certain other embodiments, q is 0. In still other embodiments, R is KLH, Bovine Serum Albumin or polylysine. In yet other embodiments, the linker is a moiety having the structure —NH(CH$_2$)$_t$NHC(=O)(CH$_2$)$_v$S— wherein t and v are each integers from 1-6. In certain embodiments, t is 3 and v is 1. In certain exemplary embodiments, each occurrence of $R_x$ is hydrogen. In certain exemplary embodiments, n and q are each 0, R is KLH and the linker is a moiety having the structure —NH(CH$_2$)$_t$NHC(=O)(CH$_2$)$_v$S— wherein t and v are each integers from 1-6. In certain embodiments, one or more of the carbohydrate domains is/are α-linked to the peptide backbone.

In certain exemplary embodiments, the present invention provides a novel trimeric antigenic glycopeptide incorporating three occurrences of Gb3, to generate a novel trimeric antigenic compound having the structure:

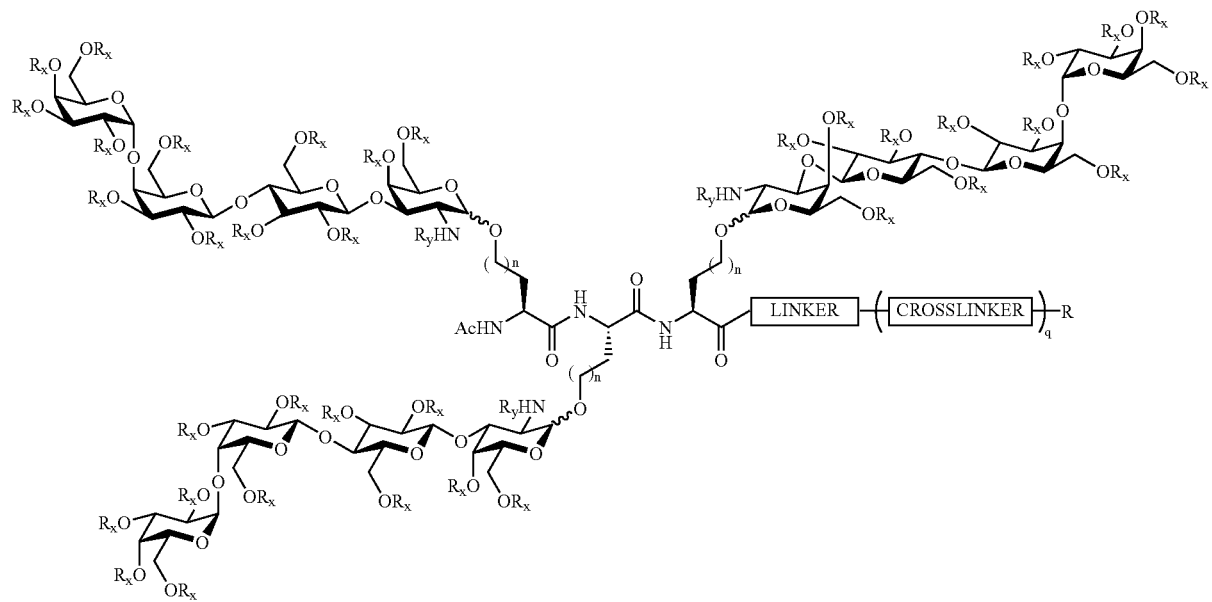

wherein each occurrence of $R_x$ and $R_y$ is independently hydrogen or a protecting group; q is 0 or 1; each occurrence of n is independently an integer from 0-9; R is hydrogen or an immunogenic carrier. In certain exemplary embodiments, the immunogenic carrier is a protein, peptide or lipid. In certain embodiments, each occurrence of n is 0. In certain other embodiments, q is 0. In still other embodiments, R is KLH, Bovine Serum Albumin or polylysine. In yet other embodiments, the linker is a moiety having the structure —NH(CH$_2$)$_t$NHC(=O)(CH$_2$)$_v$S— wherein t and v are each integers from 1-6. In certain exemplary embodiments, each occurrence of $R_x$ is hydrogen and each occurrence of $R_y$ is Ac. In certain exemplary embodiments, n and q are each 0, R is KLH and the linker is a moiety having the structure —NH(CH$_2$)$_t$NHC(=O)(CH$_2$)$_v$S— wherein t and v are each integers from 1-6. In certain embodiments, one or more of the carbohydrate domains is/are α-linked to the peptide backbone.

In certain exemplary embodiments, the present invention provides a novel trimeric antigenic glycopeptide incorporating TF, Le$^y$ and Tn, to generate a novel trimeric antigenic compound having the structure:

n is independently an integer from 0-9; R is hydrogen or an immunogenic carrier. In certain exemplary embodiments, the immunogenic carrier is a protein, peptide or lipid. In certain embodiments, each occurrence of n is 0. In certain other embodiments, q is 0. In still other embodiments, R is KLH, Bovine Serum Albumin or polylysine. In yet other embodiments, the linker is a moiety having the structure —NH(CH$_2$)$_t$NHC(=O)(CH$_2$)$_v$S— wherein t and v are each integers from 1-6. In certain embodiments, t is 3 and v is 1. In certain exemplary embodiments, each occurrence of $R_x$ is hydrogen and each occurrence of $R_y$ is Ac. In certain exemplary embodiments, n and q are each 0, R is KLH and the linker is a moiety having the structure —NH(CH$_2$)$_t$NHC(=O)(CH$_2$)$_v$S— wherein t and v are each integers from 1-6. In certain embodiments, one or more of the carbohydrate domains is/are α-linked to the peptide backbone.

In certain other exemplary embodiments, the present invention provides a novel trimeric antigenic glycopeptide incorporating globo-H, Le$^y$ and Tn, to generate a novel trimeric antigenic compound, as described in more detail below.

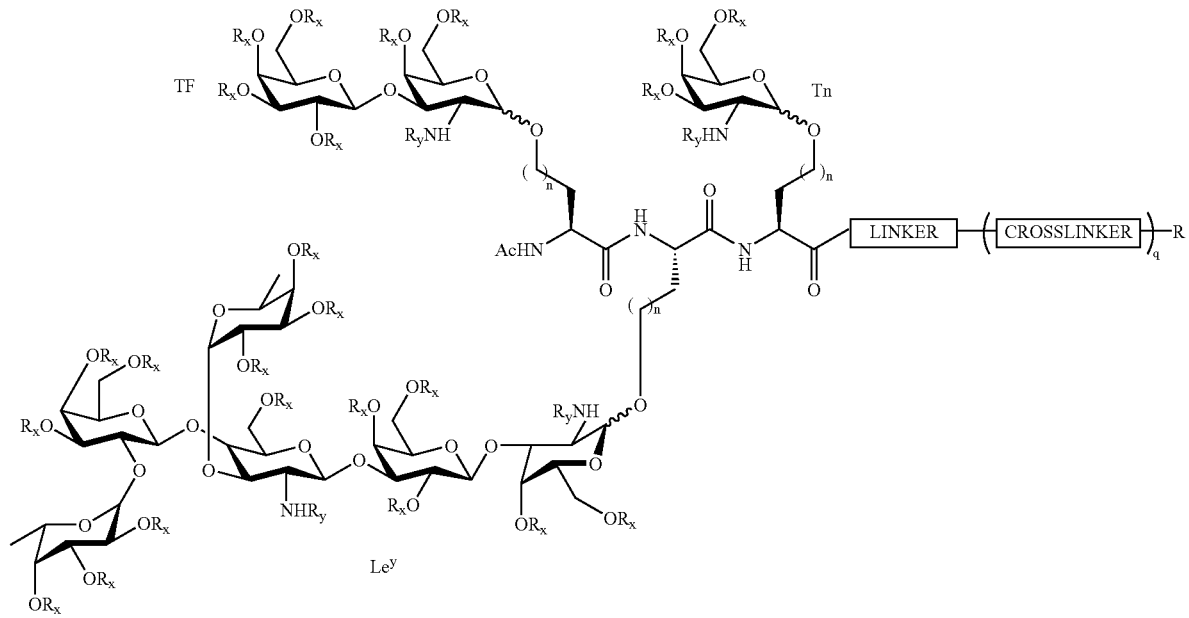

wherein each occurrence of $R_x$ and $R_y$ is independently hydrogen or a protecting group; q is 0 or 1; each occurrence of In certain other exemplary embodiments, the multi-antigenic glycopeptide has the structure:

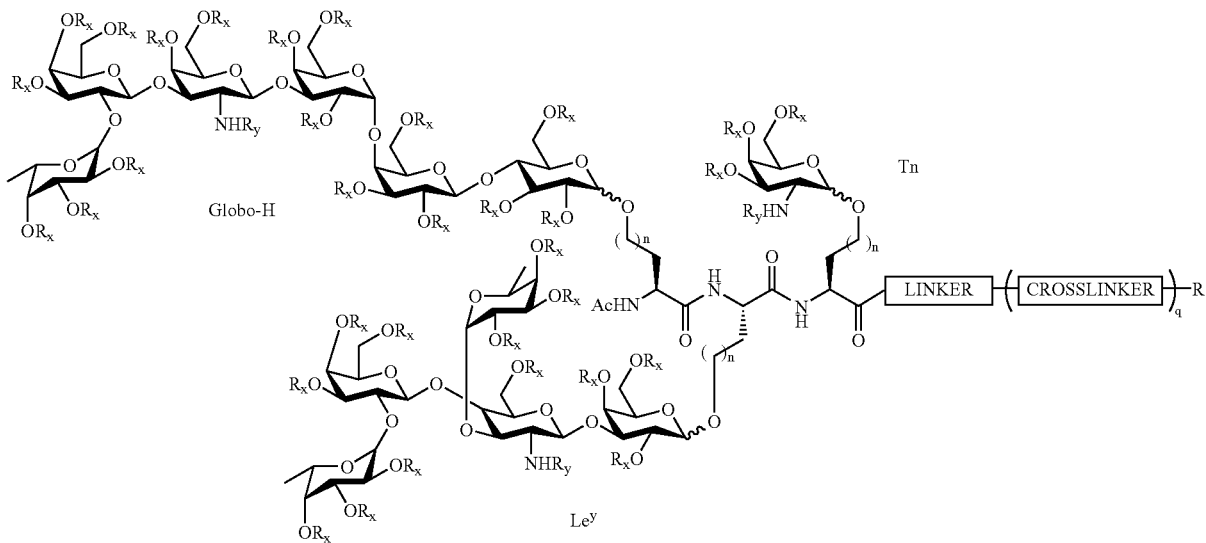

wherein each occurrence of $R_x$ and $R_y$ is independently hydrogen or a protecting group; q is 0 or 1; each occurrence of n is independently an integer from 0-9; R is hydrogen or an immunogenic carrier. In certain exemplary embodiments, the immunogenic carrier is a protein, peptide or lipid. In certain embodiments, each occurrence of n is 3. In certain other embodiments, q is 0. In still other embodiments, R is KLH, Bovine Serum Albumin or polylysine. In yet other embodiments, the linker is a moiety having the structure —NH(CH$_2$)$_t$NHC(=O)(CH$_2$)$_v$S— wherein t and v are each integers from 1-6. In certain embodiments, t is 3 and v is 1 In certain exemplary embodiments, each occurrence of $R_x$ is hydrogen and each occurrence of $R_y$ is Ac. In certain exemplary embodiments, n is 3, q is 0, R is KLH and the linker is a moiety having the structure —NH(CH$_2$)$_t$NHC(=O)(CH$_2$)$_v$S— wherein t and v are each integers from 1-6. In certain embodiments, one or more of the carbohydrate domains is/are α-linked to the peptide backbone.

In certain other exemplary embodiments, the present invention provides a novel pentameric antigenic glycopeptide incorporating globo-H, Le$^y$, STn, TF and Tn to generate a novel pentameric antigenic compound, as described in more detail below. In certain other exemplary embodiments, the multi-antigenic glycopeptide has the structure:

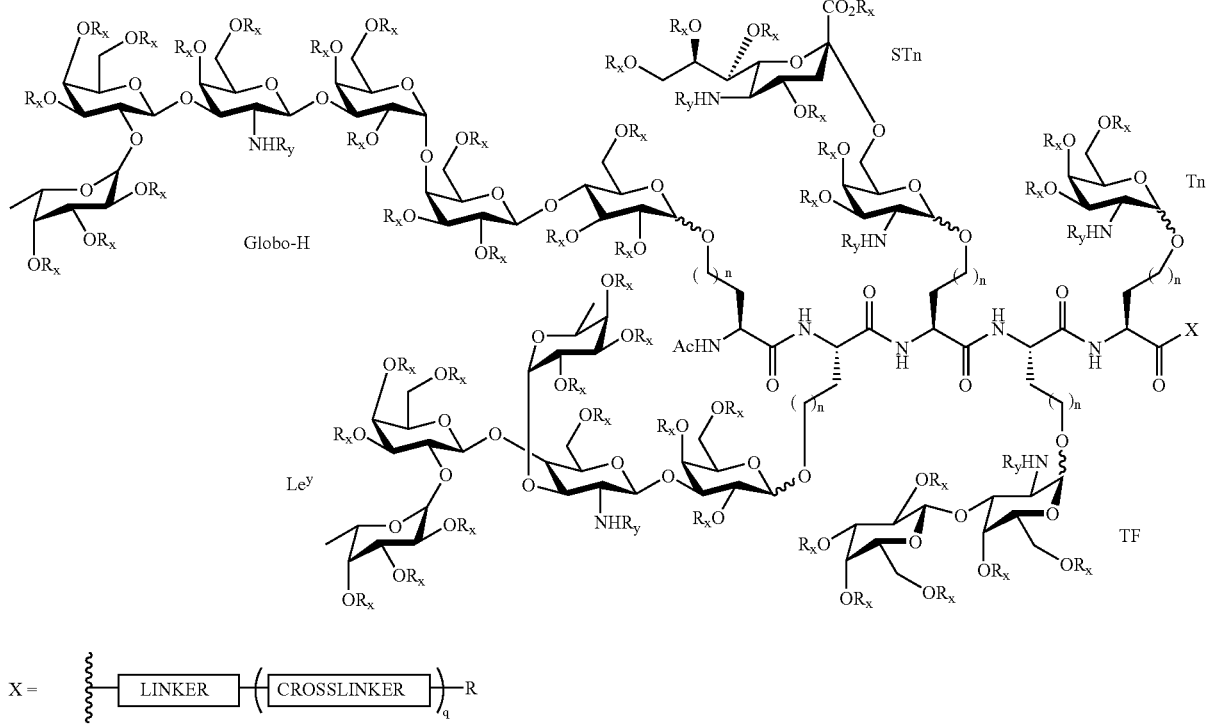

wherein each occurrence of $R_x$ and $R_y$ is independently hydrogen or a protecting group; q is 0 or 1; each occurrence of n is independently an integer from 0-9; R is hydrogen or an immunogenic carrier. In certain exemplary embodiments, the immunogenic carrier is a protein, peptide or lipid. In certain embodiments, each occurrence of n is 3. In certain other embodiments, q is 0. In still other embodiments, R is KLH, Bovine Serum Albumin or polylysine. In yet other embodiments, the linker is a moiety having the structure —NH(CH$_2$)$_t$NHC(=O)(CH$_2$)$_v$S— wherein t and v are each integers from 1-6. In certain embodiments, t is 3 and v is 1. In certain exemplary embodiments, each occurrence of $R_x$ is hydrogen and each occurrence of $R_y$ is Ac. In certain exemplary embodiments, n is 3, q is 0, R is KLH and the linker is a moiety having the structure —NH(CH$_2$)$_t$NHC(=O)(CH$_2$)$_v$S— wherein t and v are each integers from 1-6. In certain embodiments, one or more of the carbohydrate domains is/are α-linked to the peptide backbone.

In certain embodiments, for each of the above five constructs, the linker is —O—, —NR$_G$—, —NR$_G$(aliphatic)NR$_J$—, —NR$_G$(heteroaliphatic)NR$_J$—, —(aliphatic)NR$_J$—, —(heteroaliphatic)NR$_J$—, —O(aliphatic)NR$_J$—, —O(heteroaliphatic)NR$_J$—, —NR$_G$(aliphatic)NR$_J$(C=O)(CR$_H$R$_I$)$_k$S—, —NR$_G$(heteroaliphatic)NR$_J$(C=O)(CR$_H$R$_I$)$_k$S—, —(aliphatic)NR$_J$(C=O)(CR$_H$R$_I$)$_k$S—, -(heteroaliphatic)NR$_J$(C=O)(CR$_H$R$_I$)$_k$S—, —O(aliphatic)NR$_J$(C=O)(CR$_H$R$_I$)$_k$S—, —O(heteroaliphatic)NR$_J$(C=O)(CR$_H$R$_I$)$_k$S—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5; wherein each occurrence of $R_G$, $R_H$, $R_I$ or $R_J$ is independently hydrogen, a linear or branched, substituted or unsubstituted, cyclic or acyclic moiety, or a substituted or unsubstituted aryl moiety, and wherein each aliphatic or heteroaliphatic moiety is independently substituted or unsubstituted, linear or branched, cyclic or acyclic.

In certain embodiments, for each of the above five constructs, the linker is —O—, —NR$_G$(CR$_H$R$_I$)$_k$NR$_J$—, —NR$_G$(CR$_H$R$_I$)$_k$NR$_J$(C=O)(CR$_H$R$_I$)$_k$S—, —NR$_G$—, —(CR$_H$R$_I$)$_k$NR$_J$—, —O(CR$_H$R$_I$)$_k$NR$_J$, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5, wherein each occurrence of $R_G$, $R_H$, $R_I$ or $R_J$ is independently hydrogen, a linear or branched, substituted or unsubstituted, cyclic or acyclic moiety, or a substituted or unsubstituted aryl moiety.

In certain embodiments, for each of the above five constructs, q is 1 and the crosslinker is a fragment having the structure:

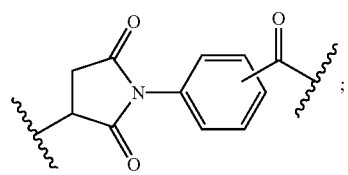

whereby said structure is generated upon conjugation of a maleimidobenzoic acid N-hydroxy succinimide ester with a linker.

Pharmaceutical Compositions, Constructs and Uses Thereof

As described above, the present invention provides compounds and synthetic methodologies useful in the development of novel therapeutic agents, particularly for fully synthetic cancer vaccines and/or therapeutics. In general, the compounds and glycopeptides prepared as disclosed herein can be conjugated to a protein carrier or a lipid to generate useful glycoconjugates for the treatment and/or prevention, (preferably the prevention of the recurrence), of cancer in a subject suffering therefrom. In addition, glycoconjugates prepared by processes disclosed herein are useful in adjuvant therapies as vaccines capable of inducing antibodies immunoreactive with various tumor cells. Such adjuvant therapies may reduce the rate of recurrence of certain cancers, and increase survival rates after surgery. Clinical trials on patients surgically treated for cancer who are then treated with vaccines prepared from a cell surface differentiation antigen found in patients lacking the antibody prior to immunization, a highly significant increase in disease-free interval may be observed. Cf. P.O. Livingston, et al., *J. Clin. Oncol.*, 1994, 12, 1036.

Thus, the present invention provides pharmaceutical compositions for treating cancer, preferably for preventing the recurrence of cancer, comprising any of the compounds of the present invention disclosed herein, as an active ingredient, optionally, though typically in combination with a pharmaceutically acceptable carrier. The pharmaceutical compositions of the present invention may further comprise other therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and antisickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

In certain embodiments, a method of treatment is provided comprising administering to the subject a therapeutically effective amount of any of the glycoconjugates disclosed herein, optionally in combination with a pharmaceutically acceptable carrier. The method may be applied wherein the cancer is a solid tumor or an epithelial tumor. As mentioned above, methods for the treatment of cancer (preferably for the prevention of recurrence of cancer) are provided, as well as methods for inducing antibodies in a human subject, wherein the antibodies are capable of specifically binding with human tumor cells, which comprises administering to the subject an amount of any of the glycoconjugates disclosed above effective to induce antibodies. In certain embodiments, the carbohydrate antigen is linked to an immunogenic carrier either directly or through a crosslinker, which carrier is a protein, peptide or lipid. In certain embodiments, the carrier is Bovine Serum Albumin, polylysine or KLH. In certain other embodiments, the carrier is a lipid having the structure:

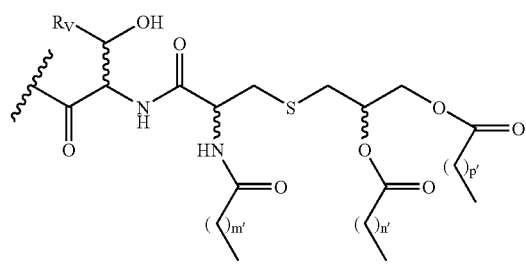

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys).

In certain other embodiments, the method comprises administering to the subject a therapeutically effective amount of any of the compounds and/or glycopeptides disclosed herein, in combination with an immunogenic carrier, optionally in combination with a pharmaceutically acceptable carrier. Specifically, in certain exemplary embodiments, the method comprises administering a carbohydrate antigen conjugated to an immunogenic carrier. In certain embodiments, the method comprises administering a carbohydrate antigen and an immunogenic carrier that have not been conjugated. Rather, they are administered concurrently, or successively, as separate entities. In certain other exemplary embodiments, the method comprises administering a glycopeptide of the invention conjugated to an immunogenic carrier. In certain embodiments, the method comprises administering an inventive glycopeptide that has not been conjugated to an immunogenic carrier. Rather, the glycopeptide and the immunogenic carrier are administered concurrently, or successively, as separate entities. In certain embodiments, the immunogenic carrier is a protein, pepitde or lipid. In certain exemplary embodiments, the carrier is Bovine Serum Albumin, polylysine or KLH. In certain other embodiments, the carrier is PamCys. For the purpose of the invention, a compound/glycopeptide and a carrier are said to be administrered concurrently when they are administered (i) as a single composition containing the compound/glycopeptide and the carrier, (ii) as two separate compositions or (iii) are delivered by separate routes within a short enough period of time that the effective result is equivalent to that obatined when both compound/glycopeptide and carrier are administered as a single composition.

In still other embodiments, the present invention provides the related method of inducing antibodies which further comprises co-administering an immunological adjuvant, or a combination of immunological adjuvants. Specifically, when a multi-antigenic glycopeptide comprising at least two different antigenic carbohydrate domains is used, it is possible to induce at least two different types of antibodies. In certain embodiments, each carbohydrate antigen present on the peptide backbone elicits an antibody type specific to that carbohydrate antigen. In certain other embodiments, the antibodies produced are those that recognize at least one carbohydrate antigen present on the glycopeptide. In certain embodiments, an inventive multi-antigenic glycopeptide, when administered to a subject, produces antibodies to a subset of the carbohydate antigens present on the glycopeptide backbone. In certain embodiments, some of the antibodies produced recognize two or more carbohydrate antigens of the glycopeptide. In certain exemplary embodiements, the inventive glycopeptides comprise carbohydrate domains, or truncated or elongated versions thereof, that are found on tumor cells.

In certain exemplary embodiments, the multi-antigenic glycopeptide is a trimeric construct having the structure:

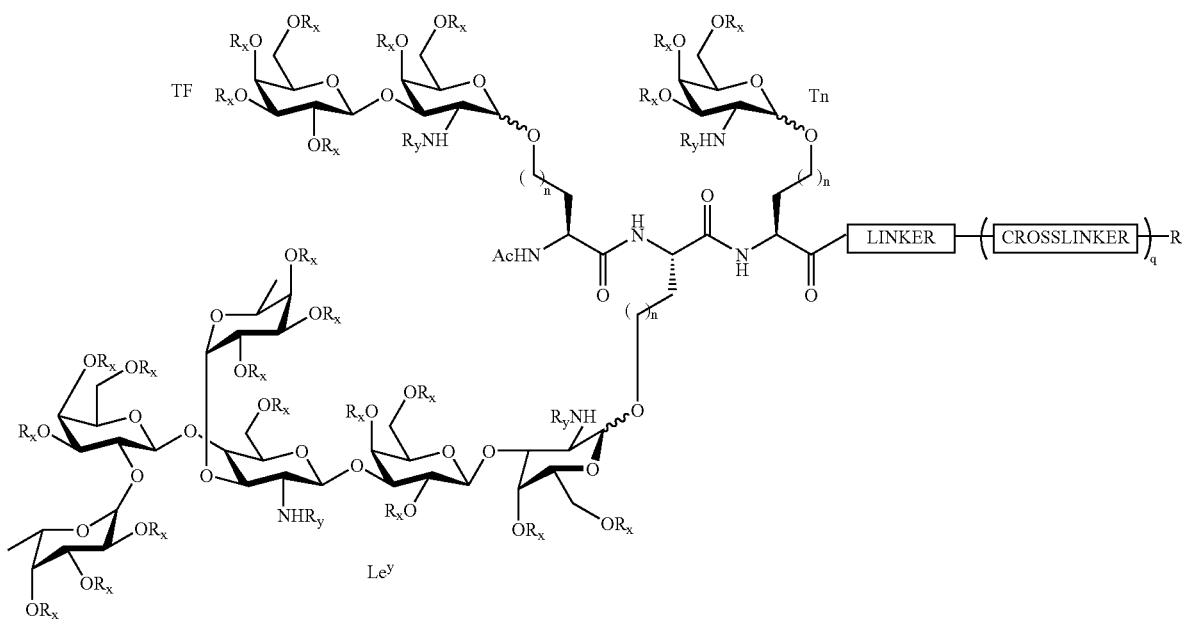

wherein each occurrence of $R_x$ and $R_y$ is independently hydrogen or a protecting group; q is 0 or 1; each occurrence of n is independently an integer from 0-9; R is hydrogen or an immunogenic carrier. In certain exemplary embodiments, the immunogenic carrier is a protein, peptide or lipid. In certain embodiments, each occurrence of n is 0. In certain other embodiments, q is 0. In still other embodiments, R is KLH, Bovine Serum Albumin or polylysine. In yet other embodiments, the linker is a moiety having the structure —NH(CH$_2$)$_t$NHC(=O)(CH$_2$)$_v$S— wherein t and v are each integers from 1-6. In certain embodiments, t is 3 and v is 1. In certain exemplary embodiments, each occurrence of $R_x$ is hydrogen and each occurrence of $R_y$ is Ac. In certain exemplary embodiments, n and q are each 0, R is KLH and the linker is a moiety having the structure —NH(CH$_2$)$_t$NHC(=O)(CH$_2$)$_v$S— wherein t and v are each integers from 1-6. In certain embodiments, one or more of the carbohydrate domains is/are α-linked to the peptide backbone.

In certain other exemplary embodiments, the multi-antigenic glycopeptide has the structure:

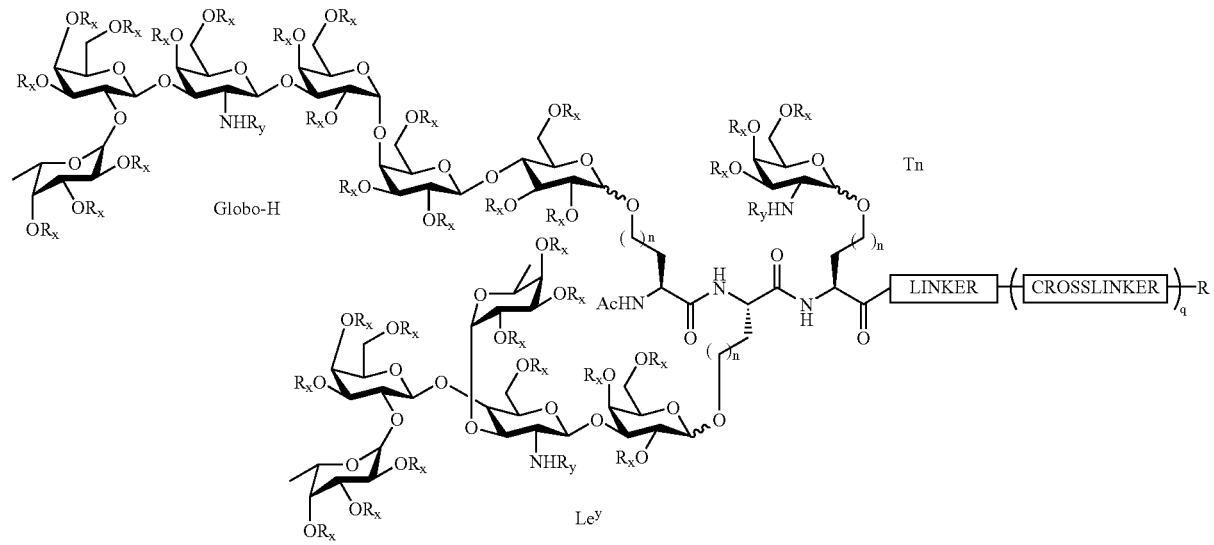

wherein each occurrence of $R_x$ and $R_y$ is independently hydrogen or a protecting group; q is 0 or 1; each occurrence of n is independently an integer from 0-9; R is hydrogen or an immunogenic carrier. In certain exemplary embodiments, the immunogenic carrier is a protein, peptide or lipid. In certain embodiments, each occurrence of n is 3. In certain other embodiments, q is 0. In still other embodiments, R is KLH, Bovine Serum Albumin or polylysine. In yet other embodiments, the linker is a moiety having the structure —NH(CH$_2$)$_t$NHC(=O)(CH$_2$)$_v$S— wherein t and v are each integers from 1-6. In certain embodiments, t is 3 and v is 1 In certain exemplary embodiments, each occurrence of $R_x$ is hydrogen and each occurrence of $R_y$ is Ac. In certain exemplary embodiments, n is 3, q is 0, R is KLH and the linker is a moiety having the structure —NH(CH$_2$)$_t$NHC(=O)(CH$_2$)$_v$S— wherein t and v are each integers from 1-6. In certain embodiments, one or more of the carbohydrate domains is/are α-linked to the peptide backbone.

In certain other exemplary embodiments, the multi-antigenic glycopeptide has the structure:

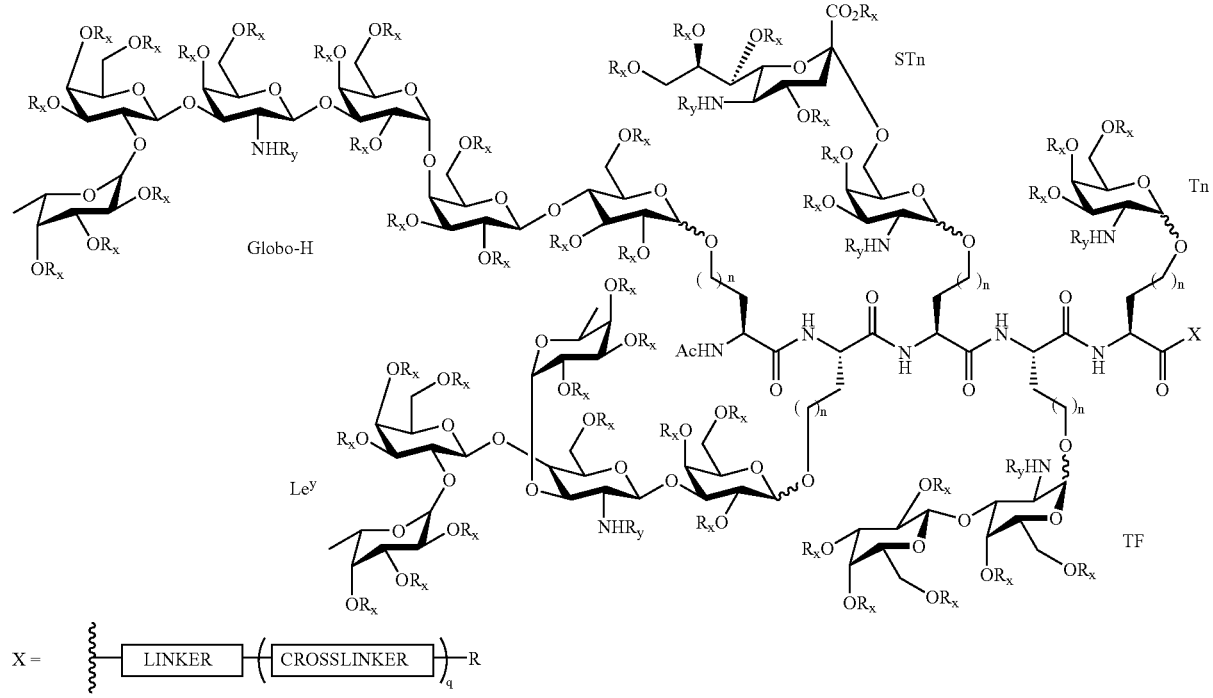

wherein each occurrence of $R_x$ and $R_y$ is independently hydrogen or a protecting group; q is 0 or 1; each occurrence of n is independently an integer from 0-9; R is hydrogen or an immunogenic carrier. In certain exemplary embodiments, the immunogenic carrier is a protein, peptide or lipid. In certain embodiments, each occurrence of n is 3. In certain other embodiments, q is 0. In still other embodiments, R is KLH, Bovine Serum Albumin or polylysine. In yet other embodiments, the linker is a moiety having the structure —NH(CH$_2$)$_t$NHC(=O)(CH$_2$)$_v$S— wherein t and v are each integers from 1-6. In certain embodiments, t is 3 and v is 1. In certain exemplary embodiments, each occurrence of $R_x$ is hydrogen and each occurrence of $R_y$ is Ac. In certain exemplary embodiments, n is 3, q is 0, R is KLH and the linker is a moiety having the structure —NH(CH$_2$)$_t$NHC(=O)(CH$_2$)$_v$S— wherein t and v are each integers from 1-6. In certain embodiments, one or more of the carbohydrate domains is/are α-linked to the peptide backbone.

In certain embodiments, for each of the above three constructs, the linker is —O—, —NR$_G$—, —NR$_G$(aliphatic)NR$_J$—, —NR$_G$(heteroaliphatic)NR$_J$—, -(aliphatic)NR$_J$—, —(heteroaliphatic)NR$_J$—, —O(aliphatic)NR$_J$—, —O(heteroaliphatic)NR$_J$—, —NR$_G$(aliphatic)NR$_J$(C=O)(CR$_H$R$_I$)$_k$S—, —NR$_G$(heteroaliphatic)NR$_J$(C=O)(CR$_H$R$_I$)$_k$S—, —(aliphatic)NR$_J$(C=O)(CR$_H$R$_I$)$_k$S—, —(heteroaliphatic)NR$_J$(C=O)(CR$_H$R$_I$)$_k$S—, —O(aliphatic)NR$_J$(C=O)(CR$_H$R$_I$)$_k$S—, —O(heteroaliphatic)NR$_J$(C=O)(CR$_H$R$_I$)$_k$S—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5; wherein each occurrence of $R_G$, $R_H$, $R_I$ or $R_J$ is independently hydrogen, a linear or branched, substituted or unsubstituted, cyclic or acyclic moiety, or a substituted or unsubstituted aryl moiety, and wherein each aliphatic or heteroaliphatic moiety is independently substituted or unsubstituted, linear or branched, cyclic or acyclic.

In certain embodiments, for each of the above three constructs, the linker is —O—, —NR$_G$(CR$_H$R$_I$)$_k$NR$_J$—, —NR$_G$(CR$_H$R$_I$)$_k$NR$_J$(C=O)(CR$_H$R$_I$)$_k$S—, —NR$_G$—, —(CR$_H$R$_I$)$_k$NR$_J$—, —O(CR$_H$R$_I$)$_k$NR$_J$, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5, wherein each occurrence of $R_G$, $R_H$, $R_I$ or $R_J$ is independently hydrogen, a linear or branched, substituted or unsubstituted, cyclic or acyclic moiety, or a substituted or unsubstituted aryl moiety.

In certain embodiments, for each of the above three constructs, q is 1 and the crosslinker is a fragment having the structure:

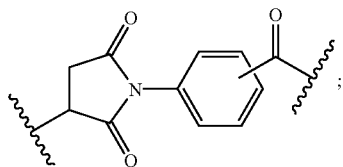

whereby said structure is generated upon conjugation of a maleimidobenzoic acid N-hydroxy succinimide ester with a linker.

In certain embodiments, the adjuvant is a saponin adjuvant (see, e.g., Marciani et al., *Vaccine*, 2000, 18, 3141, U.S. Pat. Nos. 6,080,725 and 5,977,081, the entire contents of which are hereby incorporated by reference). One example of a preferred saponin adjuvant includes, but is not limited to, GPI-0100, (Galenica Pharmaceuticals, Inc., Frederick, Md.) which is a semi-synthetic adjuvant derived by modifying selected natural saponins.

GPI-0100

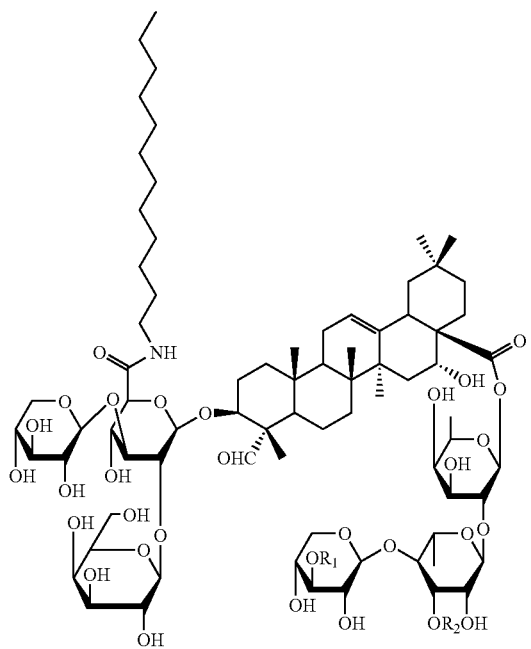

Saponins isolated from *Quillaja soponaria* Molina contain two acyl moieties, a normonoterpene carboxylic acid and a normonoterpene carboxylic acid glycoside, which are linked linearly to a fucosyl residue attached at position C-28. It has been hypothesized that these lipophilic acyl groups may be responsible for these saponins' toxicity and their ability to stimulate cytotoxic T cells against exogenous antigens. The linkage between the fucosyl residue and the acyl group is unstable and hydrolyzes under mild conditions (pH≧6) with concomitant loss of saponins capability to stimulate cell-mediated immune response. Unlike their saponin precursors, GPI-0100 adjuvants comprise a stable non-toxic lipophilic moiety in the saponin's glucuronic residue. Methods for preparing these semi-synthetic adjuvants are well-known in the art. For example, GPI-0100 adjuvants may be prepared by hydrolizing *quillaja saponins* (which are commercially available) under basic conditions to yield the corresponding deacylated product. The deacylated intermediate may then be reacted with a suitable amine reagent using standard carboxylic acid moiety activation methodology to give the desired compounds. A wide variety of procedures are effective for extrating saponin compounds. They are generalized as follows: (i) defatting of the organic matter with a hydrophobic organic solvent such as petroleum ether; (ii) extraction with a suitable alcohol (e.g., methanol or ethanol) or alcohol-water mixture; (iii) evaporation of the carinol solvent; and (iv) partitioning of the dried alcohol extract between water and n-butanol saturated with water, followed by precipitation of the crude saponins from the n-butanol/water with a suitable organic solvent (e.g., diethyl ether). Purification of the saponin extract may require multiple separation steps. For example, preliminary fractionation may be carried out using conventional open column chromatography or flash chromatography on silica gel, in combination with a more sophisticated chromatographic technique such as High Pressure Liquid Chromatography (HPLC), droplet counter-current liquid chromatography (DCCC) or centrifugal Liquid Chromatography (RLCC). The integration of these techniques with preparative TLC typically affords separated and purified saponins.

In certain other preferred embodiments, the adjuvant is bacteria or liposomes. In certain examples, the adjuvant includes but is not limited to, *Salmonella minnesota* cells, bacille Calmette-Guerin or QS21.

It will be appreciated that the magnitude of the therapeutic dose of the compounds of the invention will vary with the nature and severity of the condition to be treated and with the particular compound and its route of administration. In general, the daily dose range for anticancer activity lies in the range of 0.0001 to 1.0 mg/kg of body weight in a mammal, although the present invention is not intended to be limited by this range.

Any suitable route of administration may be employed for providing a mammal, especially a human, with an effective dosage of a compound disclosed herein. For example, oral, rectal, topical, parenteral, ocular, pulmonary, nasal, etc. routes may be employed. Dosage forms include tablets, troches, dispersions, suspensions, solutions, capsules, creams, ointments, aerosols, etc. In preferred embodiments, the effective dosage is employed using a syringe injection.

The inventive compositions include those suitable for oral, rectal, topical (including transdermal devices, aerosols, creams, ointments, lotions and dusting powders), parenteral (including subcutaneous, intramuscular, and intravenous), ocular (opthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disinterating agents, etc., in the case of oral solid preparations are preferred over liquid oral preparations such as powders, capsules and tablets. If desired, capsules may be coated by standard aqueous or nonaqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as a powder or granule optionally mixed with a binder, lubricant, inert diluent or surface active or dispersing agent. Molded tablets may be made by molding in a suitable machine, a mixture of the powdered compound moistened with an inert liquid diluent.

It will be appreciated by one of ordinary skill in the art, however, that the most suitable route for administration will depend largely on the nature and severity of the condition being treated and on the nature of the active ingredient. As discussed above, the inventive therapeutics may be conveniently presented in unit dosage form and prepared by any of the methods well known in the art of pharmacy.

As discussed above, in one embodiment of the present invention, the inventive n-alkenyl glycosides can be conjugated either directly or through a crosslinker to an appropriate carrier (e.g., KLH) to generate a synthetic tumor antigen. In general, a typical conjugation strategy that can be employed involves a reductive coupling of a glycoside which terminates in a glycoaldehyde, with the intended protein carrier, or lipid, presumably at the ε-amino acid residues of exposed lysines. (M. A. Bernstein; L. D. Hall, *Carbohydr. Res.* 1980, 78, C1; R. V. Lemieux *Chem. Soc. Rev.* 1978, 7, 423).

Thus, in another aspect, the present invention provides synthetic constructs, whereby novel antigenic structures, as described herein, are conjugated to immunogenic carriers (e.g., proteins, peptides or lipids). It will also be appreciated by one of ordinary skill in the art that, in the generation of a synthetic construct, more than one n-alkenyl moiety or glycopeptide moiety can ultimately be conjugated to a carrier protein to generate the synthetic vaccine. Thus, in addition to the conjugated glycopeptide structures as provided herein, constructs having the general structure as depicted below are also provided:

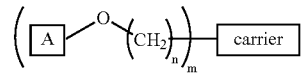

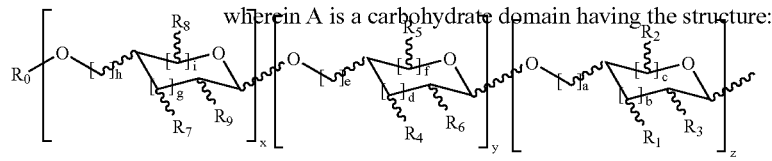

wherein A is a carbohydrate domain having the structure:

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

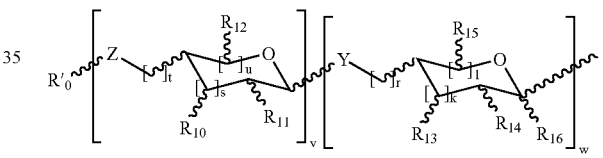

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;

wherein n is 0-8; wherein the carrier is an immunogenic carrier, wherein said carrier is linked directly or though a crosslinker; and wherein t' is at least 1. In certain preferred embodiments, n is 4. In certain embodiments, the immunogenic carrier is a protein, peptide or lipid, including, but not limited to Bovine Serum Albumin, KLH and PamCys. In certain exemplary embodiments, t' is in tha range 20-600. In still other preferred embodiments, the carbohydrate determinant is selected from the group consisting of Globo-H, KH-1, glycophorin, STN, (2,3)ST, N3, Tn, TF, 2,6-STn, Gb3 and Le$^y$. In yet other preferred embodiments, the carbohydrate determinant is fucosyl GM1, which has the structure as depicted above, and as shown in FIG. 1. In certain embodiments, one or more of the alkylglycoside moieties is/are attached to the carrier via an —NH— moiety present on the carrier.

It will be appreciated that because certain of the inventive compounds produced terminate in an alkenyl linkage, in a typical protocol according to the present invention, conversion to an aldehyde is first required. Thus, in but one exemplary embodiment, an inventive synthetic globo-H tumor antigen is prepared from an n-alkenyl globo-H glycoside. As described in Example 2, this procedure involves exposing the n-alkenyl globo-H glycoside to oxidative conditions, in this case ozonolysis, followed by reductive work-up to yield an aldehyde intermediate to generate a vaccine glycoconjugate. Subsequent hydrolytic carbohydrate analysis reveals approximately 350 carbohydrate residues/molecule of carrier protein, as described in Example 2.

In yet another example, a fucosyl GM1-KLH glycoconjugate is generated according to the method of the present invention, as discussed in Example 1. Notably, prior to conjugation studies, synthetic n-pentenyl fucosyl GM1 was shown to bind to monoclonal antibody F12 in ELISA and immune thin layer chromatography assays. Inhibition studies revealed that preincubation of F 12 with antibody completely inhibits reactivity of natural fucosyl GM1, with the antibody. Clearly, the synthetic fucosyl GM1 pentenyl glycoside provides the antigenic epitope with which F12 reacts on SCLC cells.

Additionally, once a synthetic vaccine has been derivatized and characterized, mouse immunological studies can be performed to assess the potency and/or specificity of the novel tumor vaccines, as described in Example 6 herein.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent those skilled in the art from the full contents of this document, including the examples which follow and the references to the scientific and patent literature cited herein. In but one illustrative example, protecting groups play an important role in the synthesis of the carbohydrate domains and synthetic conjugates, as described herein; however it will be appreciated by one of ordinary skill in the art that the present invention encompasses the use of various alternate protecting groups known in the art. Those protecting groups used in the disclosure including the Examples below are merely illustrative.

It should further be appreciated that the contents of those cited references are incorporated herein by reference to help illustrate the state of the art. The following examples contain important additional information, exemplification and guidance which can be adapted to the practice of this invention in its various embodiments and the equivalents thereof.

EXEMPLIFICATION

A. Example 1

Synthesis of Fucosyl GM1 Pentenyl Glycoside

Figure 2:
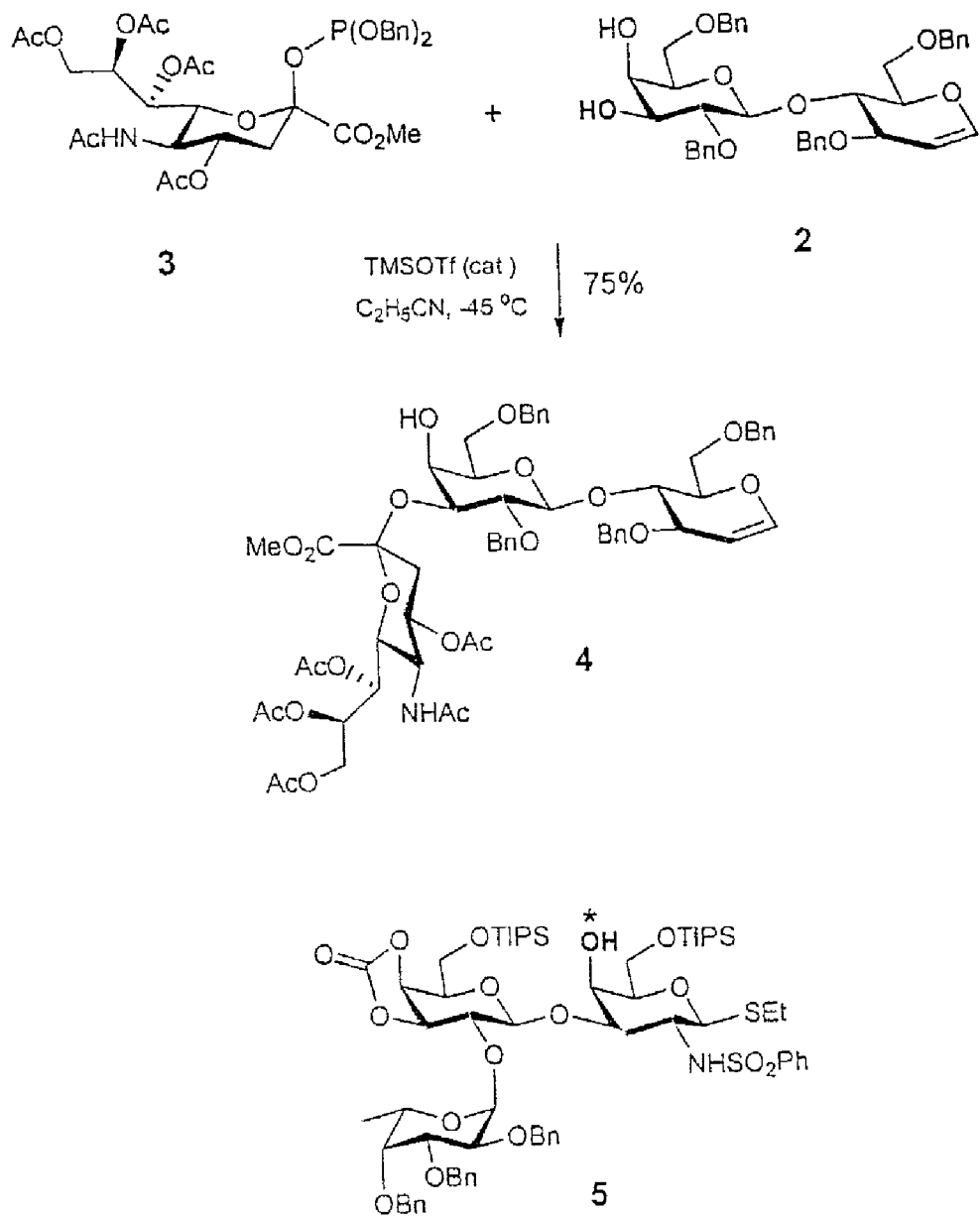
FIG. 2 depicts synthesis of the ABC trisaccharide 4 and depicts the thioethyl donor 5.
Figure 3:
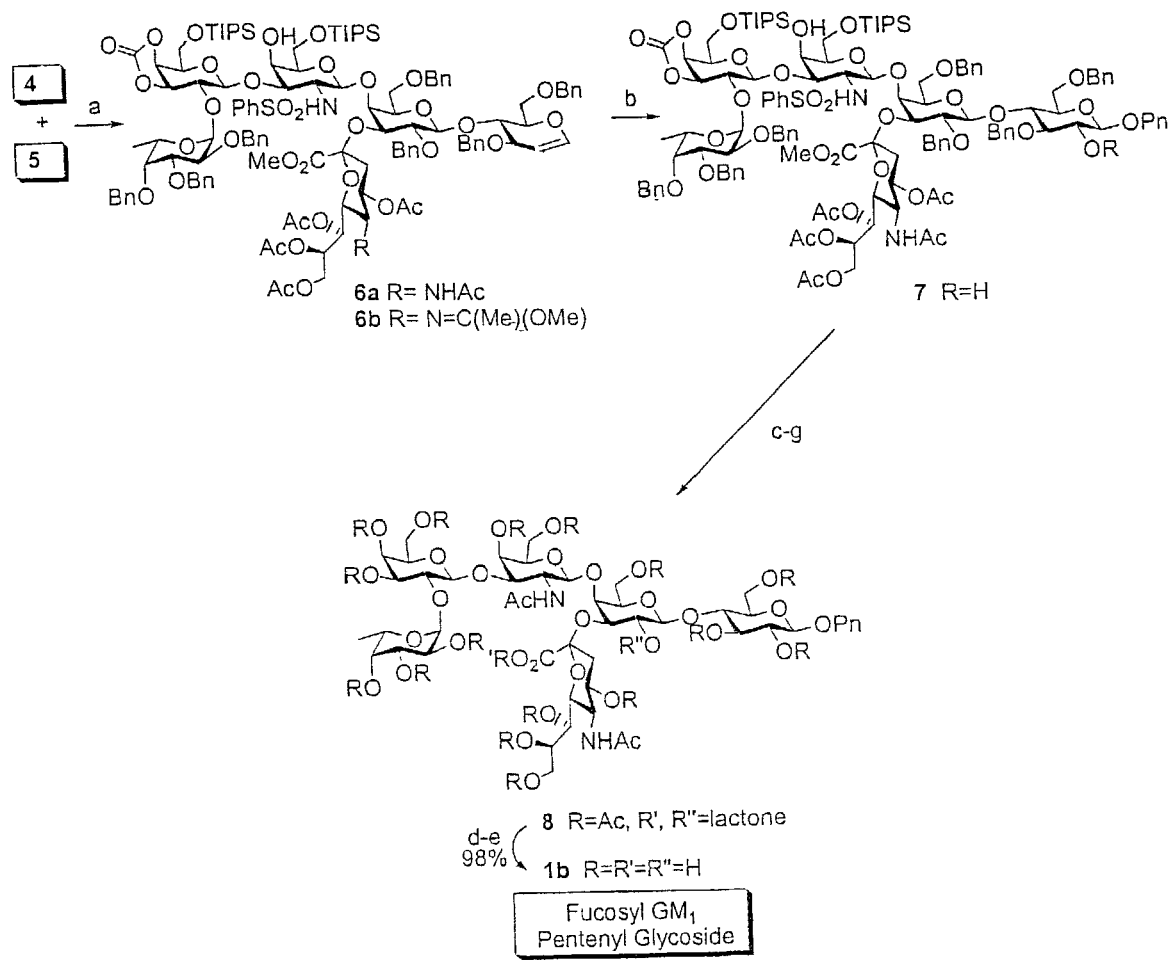
FIG. 3 depicts the synthesis of hexasaccharide 6a and the synthesis of Fucosyl $GM_1$ pentenyl glycoside 1b. Reagents: (a) MeOTf, $CH_2Cl_2$:$Et_2O$ (2:1), 0° C., 23%; (b) (i) DMDO, $CH_2Cl_2$; (ii) PnOH, $ZnCl_2$, –78° C., 65%; (c) TBAF, AcOH, THF; (d) NaOMe, MeOH; (e) NaOH, THF; (f) Na/$NH_3$, THF –78° C., then MeOH; (g) $Ac_2O$, pyridine, DMAP, $CH_2Cl_2$, 46% 5 steps.

1) Discussion of Synthesis:

As discussed above, in one aspect of the invention, the synthesis of fucosyl GM1 pentenyl glycoside is provided. In one embodiment of the present invention, this was achieved similarly to the methodology employed in the synthesis of MBr1 antigen, Globo-H (see, Park et al., *J. Am. Chem. Soc.* 1996, 118, 11488). For example, as shown in FIG. 2, the synthesis of the ABC trisaccharide starting from the known protected lactal derivative 2, was first undertaken (Kwon, O.; Danishefsky. S. J. *J. Am. Chem. Soc.* 1998, 120, 1588). Selective sialylation of the C3' equatorial hydroxyl in 2 proceeded smoothly with phosphite donor 3 (Sim et al., *J. Am. Chem. Soc.* 1993, 115, 2260; Chappell et al., *Tetrahedron* 1997, 53, 11109) to yield the glycal 4 as the only observable isomer in 75% yield. In addition, propionitrile was employed as the solvent because of the necessity to perform the reaction at low temperatures. Use of elevated temperatures in acetonitrile as the solvent resulted in diminished anomeric selectivity, regioselectivity and lower chemical yields. The key DEF trisaccharide was synthesized as previously described in the Globo-H synthesis (Park et al. *J. Am. Chem. Soc.* 1996, 118, 11488). The requisite thioethyl donor 5 is shown in FIG. 2. Based on previous experience, it was expected that this specific donor would favor β-glycosidation via sulfonamido participation under the close guidance of the "proximal hydroxyl" directing effect (see asterisk) (see also, Park et al. *J. Am. Chem. Soc.* 1996, 118, 11488; Kwon et al. *J. Am. Chem. Soc.* 1998, 120, 1588), and the results confirmed this expectation. In an experiment directed at "proof of principle", reaction of 5 with 5.0 equivalents of MeOTf (Lonn, H. *Carbo. Res.* 1985, 134, 105; Lonn, H. *J. Carbohydr. Chem.* 1987, 6, 301) in the presence of 4 gave the desired hexasaccharide 6 in 23% yield, as shown in FIG. 3. Although direct deprotection of this compound was not achieved to yield the desired compound, in an effort to find a hexasaccharide which was suitable for global deprotection, replacement of the reducing end glycal was considered. Such a replacement would also be potentially useful as a linker capable of being modified to allow for conjugation to a protein carrier or lipid.

In but one example, the use of a n-pentenyl glycoside was considered (For a review of n-pentenyl glycosides, see Fraser-Reid et al., *Synlett,* 1992, 927; Udodong et al. *J. Am. Chem. Soc.* 1993, 115, 7886; Merritt et al. *J. Am. Chem. Soc.* 1994, 116, 8334; Fraser-Reid et al. 1990, 55, 6068; Mootoo et al. *J. Am. Chem. Soc.* 1988, 110, 2662; Mootoo et al. *J. Am. Chem. Soc.* 1989, 111, 8540 and references therein). N-pentenyl glycosides are stable to a range of reaction conditions and reagents, but are readily activated for glycosidation reactions by treatment with a halogen oxidant. As a result of their stability and the neutral conditions required for their activation, pentenyl glycosides have been demonstrated to be valuable linkages for mechanistic and synthetic studies. Additionally, a terminal pentenyl group, or more generally a terminal alkenyl group, could also provide a handle for bioconjugation. Thus, in one embodiment, glycal 6a was subjected to epoxidation under standard procedures with 3,3-dimethyldioxirane (FIG. 3). Reaction with pentenyl alcohol and anhydrous zinc chloride (Gordon et al. *Carbohydrate Res.* 1990, 206, 361) afforded the glycoside 7 in 65% yield. Indeed, with the pentenyl glycoside in place, global deprotection of 7 was possible. The sequence shown in FIG. 3 furnished the peracetylated hexasaccharide lactone 8 in 46% yield (5 steps). Removal of the acetates with sodium methoxide followed by saponification of the resulting methyl ester yielded the target, fucosyl GM1 pentenyl glycoside, 1b. The assignment of structure 1b was based on $^1$H and $^{13}$C NMR analysis of 1b, in conjunction with characterization of intermediates en route to the final structure, and is supported by high resolution mass spectrometry.

Figure 4:
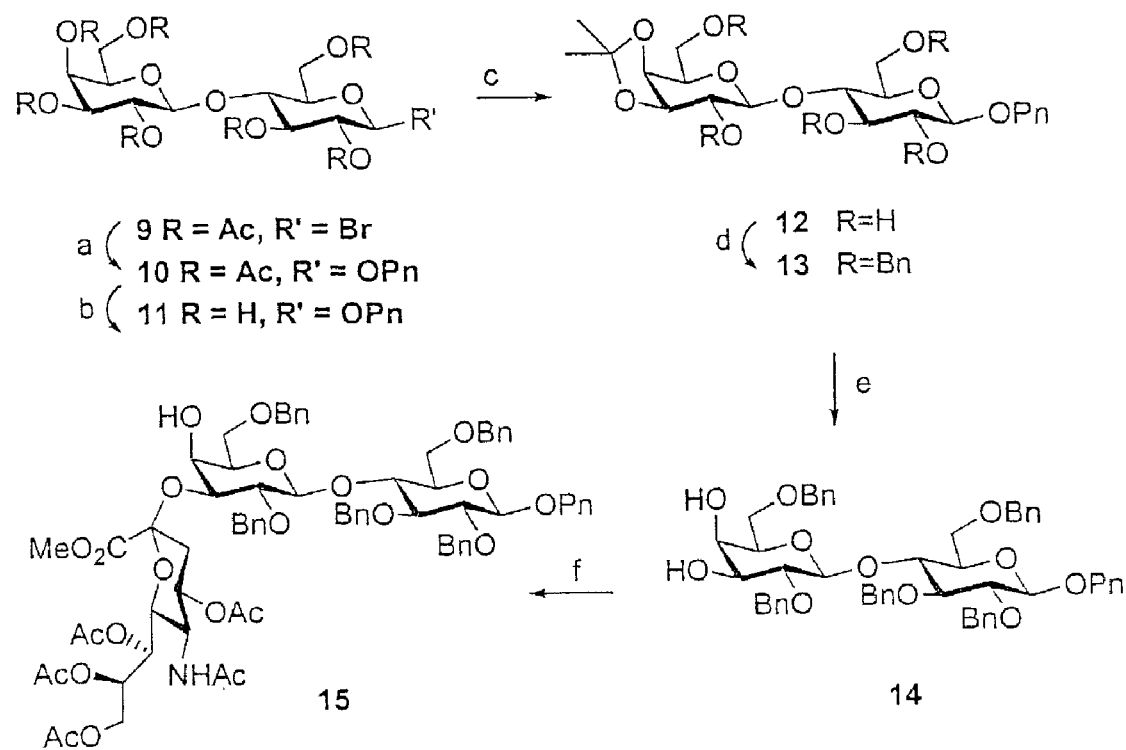
FIG. 4 depicts the synthesis of trisaccharide acceptor 15. Reagents: (a) $Ag_2CO_3$, cat. $I_2$, PnOH, $CH_2Cl_2$, 75%; (b) NaOMe, MeOH; (c) Acetone, cat. PPTS, 44% 2 steps; (d) BnBr, NaH, DMF; 84%; (e) 80% AcOH: $H_2O$, 90%; (f) 3, TMSOTf, EtCN, molecular sieves, –40° C., 77%.

In yet another embodiment, in an effort to produce significant quantities of this epitope for pre-clinical, and eventually clinical evaluation, a more efficient synthetic route was developed utilizing a glycoside at the reducing end at the acceptor, rather than a glycal. As shown in FIG. 4, pentenyl lactoside was first investigated. For this purpose, lactose octaacetate was converted to the known bromide 9 (Reithal, Y. *J. Am. Chem. Soc.* 1952, 74, 4210; Dasgupta et al. *Carbohydr. Res.* 1994, 264, 155). Reaction of this compound with pentenyl alcohol under promotion by silver carbonate delivered the desired pentenyl glycoside, 10, on 100 g scale (Rodriguez, et al. *Aust. J. Chem.* 1990, 43, 665). An analogous coupling to produce 9 using silver triflate as promoter resulted in only a 17% yield of the desired product. Removal of the acetates yielded lactoside 11. Again, the C3' and C4' hydroxyl groups were engaged, this time as the dimethyl ketal 12. This reaction, as currently conducted, was accompanied by formation of minor amounts of 4,6-acetonide (Catelani et al. *Carb. Res.* 1988, 182, 297). Perbenzylation of 12 to give 13 followed by acetonide removal with aqueous acetic acid yielded the desired AB acceptor 14. Sialylation using phosphite donor 3 (FIG. 2) proceeded in comparable yield to give trisaccharide acceptor, 15.

Figure 5:
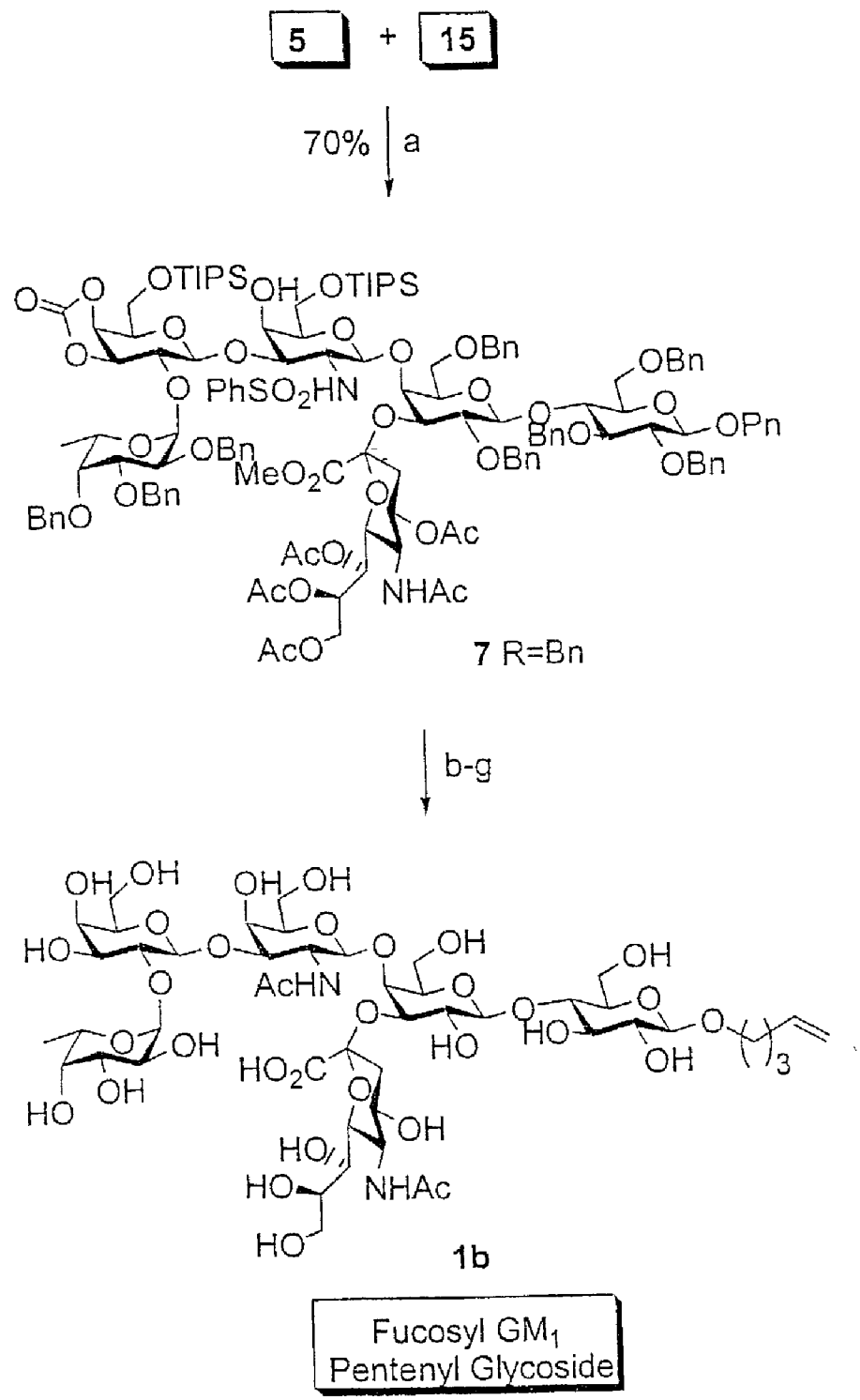
FIG. 5 depicts the synthesis of Fucosyl $GM_1$ Pentenyl Glycoside. Reagents: (a) MeOTf, $CH_2Cl_2$:$Et_2O$, 0° C., 70%; (b) TBAF, AcOH, THF; (c) NaOMe, MeOH; (d) NaOH, THF; (e) Na/$NH_3$, THF, –78° C., then MeOH; (i) $Ac_2O$, pyridine, DMAP, $CH_2Cl_2$, 45% 5 steps, (g) steps c-d, 96%.

Finally, turning to the desired fucosyl GM1, coupling of donor 5 with a 2.0 molar excess of the acceptor 15 containing the pentenyl linker proceeded with MeOTf promotion (1.5 equivalents×2) in excellent yield (70%; see FIG. 5). Global deprotection under identical conditions as in FIG. 4, yielded the characterized hexasaccharide 1b.

Figure 6:
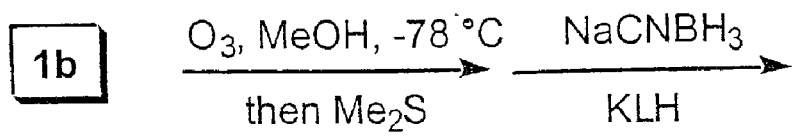
FIG. 6 depicts the synthesis of Fucosyl $GM_1$ KLH conjugate 1c.
Figure 6:
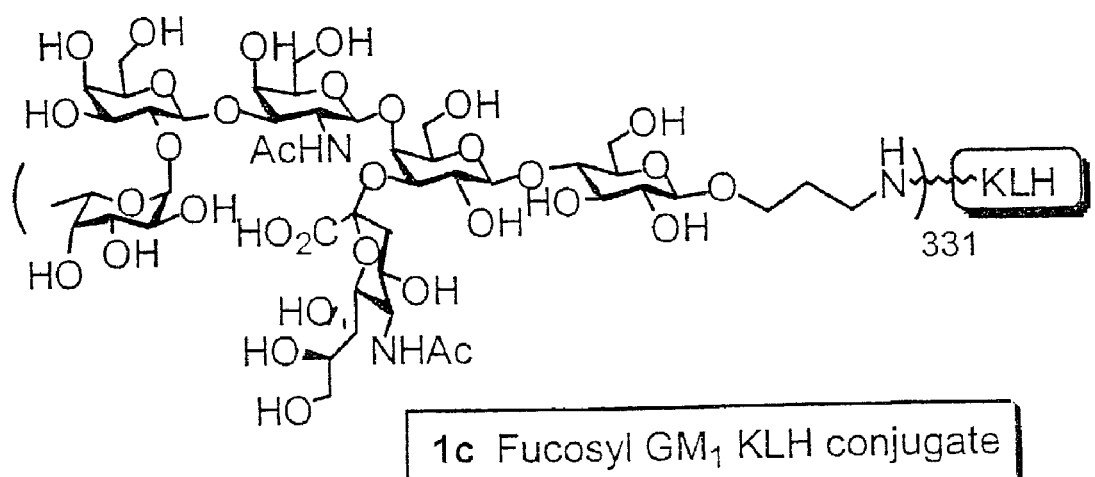

Attention was then directed to the final goal of developing a glycoconjugate. Synthetic 1b was subjected to conjugation to carrier protein KLH, as depicted in FIG. 6. The protocol started with ozonolysis, thereby producing the uncharacterized aldehyde derivative. This step was followed by coupling to KLH using reductive amination under the agency of sodium cyanoborohydride. Presumably coupling of the carbohydrate had occurred with the ε-amino group of lysine residues in the KLH. Hydrolytic carbohydrate analysis revealed approximately 331 carbohydrate residues per molecule of KLH to generate 1c.

2) Experimentals

Peracetyl pentenyl-β-D-lactoside (10). To a cooled (ice bath) suspension of lactose octaacetate (100.0 g, 147.7 mmol), glacial acetic acid (30 mL) and acetic anhydride (30 mL) was added 100 mL of 30% HBr in AcOH dropwise over a period of 60 minutes. The reaction mixture stirred for 1 hour and the ice bath was removed. Upon stirring for an additional 2 hours at room temperature, the reaction became a homogeneous yellow solution. The solution was diluted with $H_2O$ (1000 mL) and extracted with $CHCl_3$ (3×400 mL). The organic extracts were washed with $H_2O$ (2×1000 mL), satd. $NaHCO_3$ (3×500 mL), dried over $MgSO_4$ and concentrated. The α-bromo product 9 was azeotroped with anhydrous benzene and dried under high vacuum to yield 98.8 g (96%) of the lactosyl bromide which was used without further purification.

To a suspension of $Ag_2CO_3$ (100 g, 362.6 mmol), freshly activated molecular sieves (15 g) and a crystal of $I_2$ in 400 mL $CH_2Cl_2$ was added pentenyl alcohol (5.0 equiv., 73.4 mL) and then the lactosyl bromide 9 (98.8 g, 141.4 mmol) in 400 mL of $CH_2Cl_2$. After stirring in the dark at room temperature for 16 hours, the reaction was filtered through a plug of celite with additional $CH_2Cl_2$ and concentrated to a yellow oil which was purified by flash column chromatography (10% EtOAc/hexanes->50% EtOAc/hexanes) to yield 74.7 g (75%) of the pentenyl lactoside 10 as a white foam. $[\alpha]^{22}_D$ –48.9° (c 7.5, $CHCl_3$); IR (film $CHCl_3$) 2941, 1751, 1369, 1224, 1054 cm$^{-1}$; $^1$H NMR ($CDCl_3$, 400 MHz) δ 5.60 (m, 1H), 5.17 (d, 1H, J=2.7 Hz), 5.02 (m, 1H), 4.93 (dd, 1H, J=7.9, 10.3 Hz), 4.85 (d, 1H, J=1.6 Hz), 4.78 (m, 2H), 4.71 (dd, 1H, J=9.6, 7.9 Hz), 4.30 (m, 3H), 3.93 (m, 3H), 3.66 (m, 3H), 3.45 (m, 1H), 3.30 (m, 1H), 1.98 (s, 3H), 1.94 (s, 3H), 1.91 (m, 2H), 1.89 (s, 3H), 1.88 (s, 6H, 2×$CH_3$), 1.87 (s, 3H), 1.79 (s, 3H), 1.49 (m, 2H); $^{13}$C NMR ($CDCl_3$, 100 MHz) δ 170.33, 170.28, 170.09, 170.00, 169.74, 69.54, 169.01, 137.72, 115.00, 101.01, 100.51, 76.27, 72.76, 72.48, 71.64, 70.94, 70.58, 69.23, 69.01, 66.52, 61.97, 60.73, 29.75, 28.49, 20.80, 20.75, 20.64, 20.57, 20.45; HRMS (FAB) calcd. for $C_{31}H_{44}O_{18}Na$ [M+Na]$^+$ 727.2425, found 727.2418.

Pent-4-enyl 3',4'-O-acetonide-β-D-lactoside (12). Peracetylated pentenyl lactoside, 10, (18.2 g, 25.8 mmol) was dissolved in 300 mL of anhydrous MeOH and 2.0 mL of NaOMe (25% in MeOH) was added. The reaction stirred at rt for 16 hours and was neutralized with Dowex-H$^+$ (pH 5-6). The reaction was filtered with additional MeOH and concentrated to a white solid (10.6 g, quantitative) which was used without further purification. Pentenyl-β-D-lactoside 11: $^1$H NMR (D2O, 400 MHz) δ 5.81 (m, 1H), 5.00 (dd, 1H, J=17.3, 1.9 Hz), 4.92 (dd, 1H, J=8.9 Hz), 4.74 (m, 1H), 4.39 (d, 1H, J=8.0 Hz), 4.35 (d, 1H, J=7.8 Hz), 3.72-3.42 (m, 12H), 3.21 (m, 1H0, 2.06 (m, 2H), 1.63 (m, 2H); $^{13}$C NMR ($D_2O$, 100 MHz) δ 141.27, 117.31, 105.42, 104.54, 80.85, 77.84, 77.24, 76.92, 75.33, 75.00, 73.44, 72.47, 71.03, 63.52, 62.56, 31.83, 30.48.

To pentenyl lactoside 11 (10.6 g, 25.8 mmol) was added 200 mL acetone, 26 mL of dimethoxypropane and p-toluenesulfonic acid (491 mg, 0.1 equiv.). The suspension stirred at room temperature overnight at which point the reaction was homogeneous. The reaction was concentrated and purified by flash column chromatography (100% EtOAc->2% MeOH in EtOAc) to give 5.1 g (44%) of the 3,4-acetonide as a white solid and 1.27 g of the 4,6-acetonide as a white solid. 3,4-acetonide, 12: $[\alpha]^{22}_D$ 79.0° (0.96c , MeOH); IR 3422, 2980, 2933, 2870, 1242, 1073 cm$^{-1}$; $^1$H NMR (MeOH, 400 MHz) δ 5.83 (m, 1H), 5.00 (dd, 1H, J=17.1, 3.4 Hz), 4.92 (dd, 1H, J=10.2, 2.0 Hz), 4.34 (d, 1H, J=8.2 Hz), 4.25 (d, 1H, J=7.8 Hz), 4.17 (dd, 1H, J=5.5, 2.1 Hz), 4.02 (dd, 1H, J=7.2, 5.5 Hz), 3.91 (m, 3H), 3.88-3.73 (m, 5H), 3.55-3.47 (m, 3H), 3.42 (m, 1H), 3.38 (m, 1H), 3.21 (m, 1H), 2.13 (m, 2H), 1.67 (m, 2H), 1.45 (s, 3H), 1.30 (m, 3H); $^{13}$C NMR (MeOH, 100 MHz) δ 139.42, 115.20, 111.04 (O—C—O), 104.16, 104.09, 80.94, 80.77, 76.29, 76.25, 75.27, 75.00, 74.76, 74.39, 62.36, 61.82, 31.18 ($CH_3$), 30.02, 28.41, 26.51 ($CH_3$); HRMS (Fab) calcd. for $C_{20}H_{34}O_{11}Na$ [M+Na]$^+$ 473.1998, found 473.1985. 4,6-acetonide: $[\alpha]^{22}_D$ –216.0 ° (c 1.14, MeOH); IR 3364, 2926, 2870, 1380 cm$^{-1}$; $^1$H NMR (MeOH, 400 MHz) δ 5.79 (m, 1H), 4.98 (dd, 1H, J=17.0, 1.8), 4.90 (dd, 1H, J=10.2, 1.0), 4.35 (d, 1H, J-7.8 Hz), 4.24 (d, 1H, J=7.8 Hz), 4.13 (m, 2H), 3.86-3.82 (m, 3H), 3.76 (dd, 1H, J=12.9, 1.4 Hz), 3.61-3.49 (m, 5H), 3.44 (s, 1H), 3.35 (m, 1H), 3.19 (t, 1H), 2.11 (m, 2H), 1.66 (m, 2H), 1.43 (s, 3H), 1.35 (s, 3H); $^{13}$C NMR (MeOH, 100 MHz) δ 139.48, 115.20, 104.68, 104.26, 100.17

(O—C—O), 79.86, 76.40, 76.35, 74.81, 73.34, 71.46, 70.25, 69.95, 68.04, 63.67, 61.69, 31.23 ($CH_3$), 30.08, 29.56, 18.69 ($CH_3$).

Pent-4-enyl 2,3,6,2',6'-penta-O-benzyl-3',4'-O-acetonide-β-D-lactoside (13). The acetonide 12 (3.40 g, 7.54 mmol) was azeotroped with anhydrous benzene, dissolved in anhydrous DMF (60 mL, 0.12 M) and cooled to 0° C. Benzyl bromide (passed through basic alumina, 10.0 equiv. 8.97 mL), was added followed by solid NaH (95%, 7.5 equiv., 1.76 g) in one portion. The reaction was allowed to warm to room temperature overnight and then poured into ice cold $H_2O$ (500 mL) and extracted with $CHCl_3$ (200 mL, 2×100 mL). The organic extracts were washed with brine (500 mL), dried over $MgSO_4$ and concentrated to a yellow oil which was purified by flash column chromatography (5% EtOAc/hexanes->20% EtOAc/hexanes) to yield 5.70 g (84%) of the product as a viscous oil. $[\alpha]^{22}_D$ 196.0° (1.09c, $CHCl_3$); IR (film $CHCl_3$) 3062, 3029, 2868, 1367, 1093, 1055 $cm^{-1}$; $^1H$ NMR ($CDCl_3$, 400 MHz) δ 7.39-7.20 (m, 25H), 5.78 (m, 1H), 4.98 (dd, 1H, J=17.1, 3.4 Hz), 4.93 (dd, 1H, J=10.2, 2.0 Hz), 4.89 (d, 1H, J=10.6 Hz), 4.86 (d, 1H, J=10.9 Hz), 4.75 (d, 1H, J=11.7 Hz), 4.70 (d, 1H, J=10.6 Hz), 4.68 (d, 1H, J=10.8 Hz), 4.63 (d, 1H, 11.8 Hz), 4.53 (d, 1H, J=12.1 Hz), 4.46 (d, 1H, J=12.1 Hz), 4.39 (d, 1H, J=6.3 Hz), 4.36 (d, 1H, J=2.0 Hz), 4.34 (d, 1H, J=7.8 Hz), 4.28 (d, 1H, J=12.0 Hz), 4.07 (dd, 1H, J=5.5, 1.4 Hz), 3.99 (m, 1H), 3.91 (m, 2H), 3.76 (dd, 1H, J=11.9, 4.2 Hz), 3.70 (dd, 1H, J=10.8, 1.6 Hz), 3.65 (m, 2H), 3.55-3.47 (m, 3H), 3.35 (m, 2H), 3.30 (dd, 1H, J=7.9, 0.8 Hz), 2.31 (m, 2H), 1.72 (m, 2H), 1.36 (s, 3H), 1.31 (s, 3H); $^{13}C$ NMR ($CDCl_3$, 100 MHz) δ 138.92, 138.54, 138.43, 138.31, 138.19, 138.00, 128.22, 128.16, 128.08, 127.99, 127.95, 127.77, 127.63, 127.49, 127.40, 127.34, 127.20, 114.83, 109.66, 103.56, 101.76, 82.89, 81.75, 80.53, 79.26, 76.30, 75.32, 74.96, 74.91, 73.51, 73.28, 73.12, 73.08, 71.86, 69.16, 68.82, 68.18, 30.15, 28.87, 27.89, 26.34; HRMS (FAB) cald. for $[M+Na]^+ C_{55}H_{64}O_{11}Na$ 923.4346, found 923.4330.

Pent-4-enyl 2,3,6,2',6'-penta-O-benzyl-β-D-lactoside (14). The acetonide 13 (5.7 g, 6.32 mmol) was dissolved in 80% AcOH in $H_2O$ (60 mL) and heated to 75° C. for 3 hours. The reaction was cooled to rt, diluted with $H_2O$ (500 mL) and extracted with $CHCl_3$ (200 mL, 2×100 mL). The organic extracts were washed with $H_2O$ (500 mL), satd. $NaHCO_3$ (3×300 mL), dried over $MgSO_4$ and concentrated to an oil which was purified by flash column chromatography (25% EtOAc/hexanes) to yield 5.21 g (96%) of a white solid. $[\alpha]^{22}_D$ 194.1° (1.13c, $CHCl_3$); IR (film $CHCl_3$) 3444, 3028, 2868, 1091, 1058 $cm^{-1}$; $^1H$ NMR ($CDCl_3$, 400 MHz) δ 7.41-7.20 (m, 25H), 5.74 (m, 1H), 4.96-4.88 (m, 3H), 4.82 (d, 1H, J=10.9 Hz), 4.72 (d, 1H, J=11.4 Hz), 4.70 (d, 1H, J=10.9 Hz), 4.64 (d, 1H, J=10.9 Hz), 4.58 (d, 1H, J=11.6 Hz), 4.52 (d, 1H, J=10.9), 4.38-4.28 (m, 5H), 3.93-3.85 (m, 3H), 3.71 (m, 2H), 3.55-3.40 (m, 4H), 3.36 (m, 3H), 3.28 (m, 2H), 2.48 (d, OH, 1H, J=3.2 Hz), 2.40 (s, OH, 1H), 2.09 (m, 2H), 1.66 (m, 2H); $^{13}C$ NMR ($CDCl_3$, 100 MHz) δ 139.09, 138.53, 139.29, 138.17, 138.01, 137.91, 128.44, 128.35, 128.24, 127.89, 127.82, 127.77, 127.63, 127.55, 127.19, 114.86, 103.57, 102.53, 82.76, 81.71, 79.96, 76.57, 75.17, 75.02, 74.89, 74.80, 73.45, 73.40, 73.12, 72.79, 69.22, 68.71, 68.60, 68.24, 30.17, 28.88; HRMS (FAB) cald. for $C_{52}H_{60}O_{11}Na [M+Na]^+$ 883.4033, found 883.4017.

Trisaccharide 15. The phosphite donor 3 (1.0 g, 1.35 mmol) and lactosyl acceptor 14 (2.5 g, 2.90 mmol) were combined, azeotroped with anhydrous benzene and placed under high vacuum for 2 hours. The mixture was dissolved in anhydrous $CH_3CH_2CN$ (distilled from $CaH_2$), freshly activated molecular sieves were added and the reaction cooled to −40° C. A portion of TMSOTf (0.1 equiv., 27 μL) was added and the reaction was allowed to stir at −40° C. overnight. The reaction was then warmed to −30° C. and another 0.1 equivalent of TMSOTf was added. Upon stirring for an additional 2 hours at −30° C., the reaction was quenched by the addition of solid $NaHCO_3$ and was filtered through a plug of celite with the aid of EtOAc. The organic layer was washed with satd. $NaHCO_3$ (2×400 mL) and dried over $MgSO_4$. Evaporation of organic layer gave a cloudy oil which was subjected to flash column chromatography using careful gradient elution in order to recover acceptor and product trisaccharide (20% EtOAc/hexanes->75% EtOAc/hexanes). The product (1.35 g, 75%) was obtained as a white foam and 0.95 g of starting acceptor was recovered.: $[\alpha]^{22}_D$ 2.38° (c 1.30, $CHCl_3$); IR (film $CHCl_3$) 3106, 2866, 1744, 1689, 1368, 1222, 1055 $cm^{-1}$; $^1H$ NMR ($CDCl_3$, 400 MHz) δ 7.40-7.17 (m, 25H), 5.79 (m, 1H), 5.38 (m, 1H), 5.27 (dd, 1H, J=8.0, 2.0 Hz), 5.08 (d, 1H, J=10.0 Hz), 4.95 (m, 3H), 4.86 (d, 1H, J=10.9 Hz), 4.75 (d, 1H, J=5.7 Hz), 4.72 (d, 1H, J=10.8 Hz), 4.68 (d, 1H, J=11.0 Hz), 4.56 (d, 1H, J=11.9 Hz), 4.54 (d, 1H, J=7.6 Hz), 4.44 (d, 1H, J=12.2 Hz), 4.39 (m, 1H), 4.32-4.25 (m, 3H), 4.06-3.88 (m, 6H), 3.79 (m, 2H), 3.72 (s, 3H), 3.65 (m, 3H), 3.54-3.44 (m, 5H), 3.35 (m, 2H), 2.66 (d, OH, 1H, J=3.3 Hz), 2.47 (dd, 1H, J=13.0, 4.7 Hz), 2.12 (m, 2H), 2.06 (s, 3H), 2.02 (m, 1H), 1.98 (s, 3H), 1.95 (s, 3H), 1.85 (s, 3H), 1.83 (s, 3H), 1.71 (s, 3H); $^{13}C$ NMR ($CDCl_3$, 100 MHz) δ 170.77, 170.53, 170.23, 169.92, 169.87, 168.32, 139.09, 138.90, 138.61, 138.45, 138.34, 138.05, 128.27, 128.21, 137.99, 127.51, 127.42, 127.11, 114.81, 103.48, 102.29, 98.32, 82.90, 81.80, 78.37, 76.50, 76.30, 75.31, 75.01, 74.89, 74.82, 73.23, 72.97, 72.66, 72.37, 69.16, 69.03, 68.69, 68.43, 68.36, 67.81, 67.08, 62.21, 52.99, 49.17, 36.41, 30.17, 28.89, 23.11, 21.08, 20.77, 60.67, 60.47; HRMS (FAB) cald. for $C_{72}H_{87}NO_{23}Na$ $(M+Na^+)$ 1356.5566, found 1356.5557.

Hexasaccharide 7 (R=Bn). The thioethyl donor 5 (311 mg, 0.243 mmol) and acceptor 15 (627 mg, 0.487 mmol) were combined, azeotroped with anhydrous benzene (5×5 mL) and placed under high vacuum for 5 hours. The mixture was then dissolved in 1.6 mL $CH_2Cl_2$ and 3.2 mL $Et_2O$ (0.05M total), treated with freshly prepared molecular sieves and cooled to 0° C. Methyl triflate (1.5 equiv., 41 μL) was added in one portion and the reaction stirred at 0° C. overnight. In the morning, another 20 μL of MeOTf was added and the reaction was allowed to stir for an additional 2 hours at 5° C. The reaction was quenched by the addition of solid $NaHCO_3$, filtered through celite with EtOAc, concentrated and purified by flash column chromatography (gradient elution 25% EtOAc/hexanes->50%->75% EtOAc/hexanes) to give 437 mg (70%) of hexasaccharide as a white foam and 300 mg of recovered trisaccharide accpetor: $[\alpha]^{22}_D$ −29.4° (c 3.25, $CHCl_3$); IR (film CHCl3) 3285, 3028, 2940, 2865, 1794, 1749, 1690, 1220, 1090 $cm^{-1}$; $^1H$ NMR ($CDCl_3$, 400 MHz) δ 7.74 (d, 2H, J=7.5 Hz), 7.34-7.08 (m, 43H), 5.75 (m, 1H), 5.52 (d, 1H, J=4.7 Hz), 5.29 (app s, 1H), 5.23 (dd, 1H, J=9.5, 1.4 Hz), 5.15 (m, 1H), 5.02 (d, 1H, J=9.8 Hz) 4.97-4.87 (m, 5H), 4.84 (d, 1H, J=10.9 Hz), 4.81-4.70 (m, 5H), 4.63 (d, 1H, J=11.6 Hz), 4.57 (m, 3H), 4.44 (d, 1H, J=7.2 Hz), 4.40 (d, 1H, J=12.2 Hz), 4.30 (d, 1H, J=7.8 Hz), 4.10 (m, 2H), 3.98-3.81 (m, 12H), 3.82 (s, 3H), 3.78-3.68 (m, 7H), 3.64-3.45 (m, 8H), 3.27 (m, 3H), 3.17 (dd, 1H), 2.80 (d, OH, 1H, J=2.1 Hz), 2.19 (dd, 1H, J=13.0, 4.5 Hz), 2.10 (m, 3H), 2.01 (s, 3H), 1.92 (s, 3H), 1.88 (s, 3H), 1.82 (s, 3H), 1.81 (s, 3H), 1.68 (m, 2H), 1.08 (d, 3H, J=5.4 Hz), 1.00-0.92 (m, 42H); $^{13}C$ NMR ($CDCl_3$, 100 MHz) δ 170.61, 170.34, 170.26, 169.66, 167.78, 155.48, 138.95, 138.65, 138.63, 138.56, 138.42, 138.38, 138.27, 138.05, 132.17, 129.02, 128.59, 128.46, 128.18, 128.05, 127.91, 127.63, 127.51, 127.24, 127.09, 114.80, 103.42, 102.76, 102.45, 100.16, 99.58, 98.76, 82.87, 81.53, 79.06, 77.32, 77.24, 77.16, 75.12, 75.07, 74.95, 74.80, 73.92, 73.27, 73.04, 72.93, 72.19, 69.23, 69.14, 69.09, 67.89, 67.53, 61.76, 61.58, 61.12, 56.39, 53.60, 49.19, 35.36, 30.17, 28.89, 23.13, 20.97, 20.75, 20.62, 20.53, 17.85, 17.53, 17.33, 16.72, 11.80, 11.74; HRMS (FAB) calcd. for $C_{136}H_{178}N_2O_{39}SSi_2$ (M+Na$^+$) 2574.1163, found 2574.1130.

Compound 1b. To a solution of the hexasaccharide (130 mg, 0.0509 mmol) in THF (2.0 mL) was added glacial AcOH (10.0 equiv., 29 µL) and TBAF (1.0 M THF, 10.0 equiv., 0.509 mL). The reaction stirred at rt overnight, was poured into ice water and extracted with EtOAc (3×50 mL). The organic extracts were washed with satd. NaHCO$_3$ (50 mL) and brine (50 mL), dried over MgSO$_4$ and concentrated to an oil which was purified through a short plug of silica gel with EtOAc. The resulting triol was dissolved in anhydrous MeOH (2.5 mL) and sodium methoxide was added (0.250 mL of a 25% solution in MeOH). The reaction stirred at rt for 18 hours and then 0.5 mL of THF and 0.5 mL of H$_2$O were added. Stirring at rt for an additional 24 hours was followed by neutralization with Dowex-H$^+$, filtration with MeOH washings and concentration. The crude material was allowed to dry under high vacuum for 1 day. To the resulting white solid was added THF (0.5 mL) and condensed liquid NH$_3$ (~10 mL) at −78° C. Sodium (~50 mg) was added and the resulting blue solution stirred at −78° C. for 1.5 hours. The reaction was quenched with anhydrous MeOH (~5 mL), brought to rt and concentrated with a stream of dry N$_2$ to a volume of ~2 mL. The reaction was neutralized with Dowex-H$^+$, filtered with MeOH washings and concnetrated to a white solid. The white solid was dissolved in 1.0 mL pyridine and 1.0 mL CH$_2$Cl$_2$ and cooled to 0° C. A crystal of DMAP was added followed by acetic anhydride (1.0 mL). The ice bath was removed and the reaction stirred at rt overnight. Concentration followed by purification by flash column chromatography (gradient elution 75% EtOAc/hexanes->100% EtOAc -:>5% MeOH/EtOAc) gave 44 mg (46%) of 8 as a white solid: $^1$H NMR (MeOH, 400 MHz) δ 8.02 (d, 1H, J=9.9 Hz), 7.87 (d, 1H, J=9.2 Hz), 5.76 (m, 1H), 5.49 (m, 1H), 5.39 (d, 1H, J=2.9 Hz), 5.34-5.31 (m, 2H), 5.22 (d, 1H, J=3.4 Hz), 5.19 (d, 1H, J=4.1 Hz), 5.17 (d, 1H, J=3.5 Hz), 5.12-5.05 (m, 3H), 4.97 (dd, 1H, J=16.8, 1.7 Hz), 4.91 (dd, 1H, J=10.0, 1.7 Hz), 4.81-4.75 (m, 3H), 4.65-4.60 (m, 2H), 4.52 (d, 1H, J=7.9 Hz), 4.48-4.44 (m, 2H), 4.37 (dd, 1H, J=10.0, 2.5 Hz), 4.28 (dd, 1H, J=12.5, 2.4 Hz), 4.22-4.18 (m, 2H), 4.14-3.99 (m, 9H), 3.96-3.92 (m, 2H), 3.89 (d, 1H, J=2.9 Hz), 3.88-3.77 (m, 4H), 3.72-3.62 (m, 3H), 3.51-3.45 (m, 1H), 2.74 (dd, 1H, J=11.3, 4.5 Hz), 2.19 (s, 3H), 2.13 (s, 3H), 2.11 (s, 3H), 2.10 (s, 3H), 2.09 (s, 3H), 2.08 (s, 3H), 2.06 (s, 3H), 2.05 (s, 3H), 2.02 (s, 3H), 2.01 (s, 3H), 2.00 (s, 3H), 1.99 (s, 3H), 1.98 (s, 3H), 1.97 (s, 3H), 1.95 (s, 3H), 1.94 (s, 3H), 0.91 (s, 3H), 0.180 (s, 3H), 1.61 (m, 2H), 1.14 (d, 3H, J=6.4 Hz), 3 protons burried beneath acetates (2 Pn, 1 C3ax); $^{13}$C NMR (MeOH, 100 MHz) δ 174.64, 173.64, 172.98, 172.89, 172.63, 172.56, 172.48, 172.44, 172.34, 172.27, 172.04, 171.99, 171.76, 171.73, 171.62, 171.35, 171.25, 139.23, 115.47, 104.62, 103.26, 101.86, 101.63, 100.78, 97.31, 78.22, 76.53, 75.08, 74.69, 74.29, 73.91, 73.53, 72.94, 72.71, 72.56, 72.16, 72.06, 71.89, 71.74, 70.19, 69.87, 69.33, 69.11, 68.92, 65.96, 65.65, 63.68, 63.52, 62.69, 54.01, 53.09, 50.60, 40.19, 31.09, 29.96, 24.17, 24.06, 22.73, 21.76, 21.59, 21.46, 21.20, 21.06, 20.89, 20.75, 20.63, 20.55, 16.52.

The peracetate (40 mg) was dissolved in anhydrous MeOH (2.0 mL) and 150 µL of sodium methoxide was added (25% solution in MeOH). The reaction stirred at rt for 18 hours and then 0.5 mL of THF and 0.5 mL of H$_2$O was added. The reaction stirred for another 24 hours at rt. Neutralization with Dowex-H$^+$ (~pH 6-7) was followed by filtration with MeOH washings, concentration and purification using P-2 Gel (H$_2$O eluent) to yield 24 mg (96%) of a white solid: IR 3346, 2940, 2882, 1657, 1620, 1376, 1069 cm$^{-1}$; $^1$H NMR (D$_2$O, 400 MHz) δ 5.86 (m, 1H), 5.18 (d, 1H, J=4.0 Hz), 5.04 (dd, 1H, J=17.22, 1.7 Hz), 4.97 (dd, 1H, J=10.6 Hz), 4.63 (d, 1H, J=7.6 Hz), 4.57 (d, 1H, J=7.7), 4.46 (d, 1H, J=7.9 Hz), 4.43 (d, 1H, J=8.1 Hz), 4.15 (m, 1H), 4.09-4.02 (m, 3H), 3.94-3.84 (m, 5H), 3.80-3.63 (m, 18H), 3.60-3.53 (m, 6H), 3.47 (dd, 1H, J=10.3, 1.8), 3.32 (t, 1H), 3.26 (t, 2H), 2.62 (dd, 1H, J=13.4, 4.3 Hz), 2.09 (m, 2H), 1.98 (s, 6H), 1.86 (m, 1H), 1.67 (m, 2H), 1.15 (d, 3H, J=6.5 Hz) ; $^{13}$C NMR (D$_2$O, 100 MHz) δ 176.29, 175.43, 175.16, 139.97, 115.99, 104.38, 103.77, 103.30, 103.22, 102.25, 100.35, 79.67, 78.12, 77.65, 77.03, 76.06, 75.94, 75.62, 75.44, 75.24, 74.85, 74.19, 74.01, 73.45, 73.01, 71.15, 70.72, 70.32, 69.87, 69.64, 69.25, 67.93, 64.01, 62.29, 62.07, 61.63, 61.29, 52.79, 52.70, 50.04, 38.45, 30.53, 29.17, 23.89, 23.23, 16.53; HRMS (FAB) calcd. for $C_{48}H_{79}N_2O_{33}Na_2$ [M−H+2Na]$^+$ 1257.4360, found 1257.4337.

Glycal hexasaccharide 6a. The thioethyl donor 5 (120 mg, 0.0938 mmol) and acceptor 4 (122 mg, 0.108 mmol) were combined, azeotroped with anhydrous benzene (5×5 mL) and placed under high vacuum overnight. The mixture was dissloved in a 2:1 mixture of Et$_2$O:CH$_2$Cl$_2$ (2.7 mL total), molecular sieves were added and the mixture stirred at rt for 1 h. The reaction was cooled to 0° C. and 1.0 equiv. of MeOTf (0.020 mL) was added. After 4 hours at 0° C. another equivalent of MeOTf was added (0.020 mL) and the reaction continued to stir for another 4 h at 10° C. The reaction was quenched with solid NaHCO$_3$, filtered through celite with additional EtOAc (100 ml) and concentrated. The resulting mixture was purified by flash column chromatography to give 50 mg (23%) of the hexasaccharide glycal 6 and 85 mg of starting acceptor, 4: R$_f$ 0.35 (66% Etoac/Hexanes); $^1$H NMR (500 MHz, C$_6$D$_6$) δ 8.31 (d, 2H), 7.62 (d, 2H), 7.52 (m, 4H), 7.45 (d, 2H), 7.40-7.15 (m, 31H), 6.47 (d, 1H, J=6.3 Hz), 6.28 (apparent s, 1H), 6.09 (d, 1H, J=3.8 Hz), 5.72 (m, 1H), 5.55 (dd, 1H, J=9.3, 1.2 Hz), 5.51 (d, 1H, J=3.5 Hz), 5.22 (d, 1H, J=10.8 Hz), 5.15 (s, 1H), 5.13-5.06 (m, 3H), 5.05 (d, 1H, J=8.1 Hz), 5.02 (m, 1H), 4.98 (d, 1H, J=10.8 Hz), 4.85 (d, 1H, J=10.6 Hz), 4.82 (d, 1H, J=9.4 Hz), 4.73-4.66 (m, 8H), 4.55-4.34 (m, 10H), 4.38-4.32 (m, 5H), 4.30 (d, 1H), 4.18 (s, 3H), 4.21-4.12 (m, 6H), 4.06 (m, 2H), 3.99 (m, 4H), 3.85 (d, 1H), 3.74 (m, 1H), 3.61 (m, 2H), 3.52 (t, 1H), 2.63 (dd, 1H, J=13.9, 5.0), 2.48 (dd, 1H, J=13.4 Hz), 2.35 (s, 3H), 2.01 (s, 3H), 1.98 (s, 3H), 1.72 (s, 3H), 1.64 (s, 3H), 1.57 (d, 3H, J=6.3), 1.31-1.20 (m, 42H); $^{13}$C NMR (100 MHz, CDCl$_3$) δ 169.71, 169.39, 169.18, 168.70, 168.12, 166.99, 154.75, 143.47, 137.81, 137.71, 137.51, 137.42, 137.07, 131.65, 128.25, 127.52, 128.32, 127.26, 127.23, 127.19, 127.10, 126.98, 126.91, 126.83, 126.73, 126.62, 126.53, 126.36, 126.29, 101.67, 101.35, 98.69, 98.32, 98.26, 97.33, 80.48, 78.05, 77.06, 76.20, 75.50, 74.64, 74.22, 73.87, 73.49, 72.90, 72.38, 72.26, 71.93, 71.47, 71.20, 70.34, 70.17, 69.99, 69.13, 68.62, 68.10, 67.92, 67.01, 66.88, 66.68, 65.52, 60.92, 60.61, 55.51, 52.59, 48.31, 34.87, 28.68, 22.19, 19.95, 19.77, 19.68, 19.59, 16.93, 16.88, 15.79, 10.86, 10.78; HRMS (FAB) calcd. for $C_{124}H_{162}N_2O_{37}Si_2SNa$ [M+Na]$^+$ 2382.0013, found 2382.0001.

Imido-hexasaccharide 6b Performing the above reaction with 10 equiv. MeOTf added in one portion, under otherwise identical conditions yields 28% of the following compound, which is much less polar than the parent N-acetylated hexasaccharide 6a. R$_f$ 0.35 (25% EtOAc/hexanes); $^1$H NMR (500 MHz, C$_6$D$_6$) δ 8.31 (d, 2H), 7.66 (d, 2H), 7.53 (t, 4H), 7.48 (d, 2H), 7.42-7.16 (m, 31H), 6.46 (d, 1H), 6.21 (app s, 1H), 6.15 (d, 1H, J=4.3 Hz), 5.81 (d, 1H, J=9.2 Hz), 5.72 (dt, 1H, J=12.8, 2.4 Hz), 5.40 (m, 1H), 5.38 (d, 1H, J=3.5 Hz), 5.20 (d, 1H, J=10.2 Hz), 5.12 (t, 2H), 5.00 (m, 3H), 4.84 (d, 1H, J-6.2 Hz), 4.81 (d, 1H, J=4.5 Hz), 4.73 (m, 2H), 4.70 (m, 2H), 4.67 (d, 1H, J=2.6 Hz), 4.65 (m, 1H), 4.59 (m, 3H), 4.53-4.46 (m, 6H), 4.40 (m, 5H), 4.36 (d, 1H, J=3.1 Hz), 4.30 (d, 1H, J=3.4 Hz), 4.26 (m, 3H), 4.23 (app s, 1H), 4.20 (m, 3H), 4.11 (m, 2H), 4.04 (d, 1H, J=5.9 Hz), 3.99 (s, 3H), 3.92 (d, 1H, J=3.2 Hz), 3.87 (d, 1H, J=2.9 Hz), 3.82 (d, 1H, J=6.5 Hz), 3.70 (m, 1H), 3.64 (s, 3H), 3.60 (d, 1H), 3.28 (t, 1H), 2.94 (dd, 1H, J=13.7, 4.5 Hz), 2.36 (t, 1H, J=13.3 Hz), 2.14 (s, 3H), 1.91 (s, 3H), 1.83 (s, 3H), 1.81 (s, 3H), 1.60 (s, 3H), 1.53 (d, 3H, J=6.5 Hz), 1.32-1.23 (m, 42H); $^{13}$C NMR (100 MHz, CHCl$_3$) δ 170.43, 169.30, 169.20, 168.98, 168.03, 164.74, 155.82, 144.74, 139.09, 138.75, 138.52, 138.48, 138.40, 138.39, 138.25, 138.17, 132.56, 129.22, 128.85, 128.39, 128.35, 128.30, 128.25, 128.01, 127.79, 127.71, 127.60, 127.55, 127.50, 127.48, 127.34, 102.57, 102.24, 99.69, 99.11, 98.25, 81.35, 79.09, 87.22, 75.64, 75.40, 74.90, 74.60, 74.15, 73.95, 73.50, 73.33, 72.94, 72.84, 72.52, 71.37, 71.17, 70.47, 70.17, 69.66, 69.05, 68.47, 68.11, 67.96, 67.71, 67.55, 61.91, 61.54, 61.05, 57.70, 56.50, 53.65, 52.75, 31.94, 29.71, 21.70, 20.97, 20.89, 20.64, 20.46, 20.44, 17.57, 16.81, 15.38, 14.13, 11.89, 11.80; LRMS (FAB) $C_{125}H_{164}N_2O_{37}SSi_2Na$ 2373 [M+Na]$^+$.

3) Conjugation Studies:

As described herein and as shown in FIG. 6, the pentenyl group in FucGM1 was converted to an aldehyde group by ozonolysis and linked to —NH$_2$ groups of KLH by reductive amination method in the presence of sodium cyanoborohydride as described for globo H (see, Ragupathi G, Park T K, Zhang S, Kim I J, Graeber L, Adluri S, Lloyd K O, Danishefsky S J and Livingston P O. Immunization of mice with conjugates of fully synthetic hexasaccharide globo H results in antibody against human cancer cells: a combined chemical immunological approach to the fashioning of an anticancer vaccine. *Angewandte Chem. Int. Ed Engl.* 36: 125-128. 1997.). In the case of cross-linker method the aldehyde group obtained through ozonolysis was first reacted with hydrazide of MMCCH (4-(maleimidomethyl)cyclohexane-1-carboxyl hydrazide) and reacted with thiolated KLH as described in Ragupathi G, Koganty R R, Qiu D, Lloyd K O and Livingston P O. A novel and efficient method for synthetic carbohydrate conjugate vaccine preparation: Synthesis of sialyl Tn-KLH conjugate using a 4-(4-N-maleimidomethyl)cyclohexane-1-carboxyl hydrazide (MMCCH) linker arm. *Glycoconjugate J.,* 15: 217-221, 1998). For example, 4 mg of FucGM1 pentenyl glycoside in methanol was stirred at −78° C. in a dry-ice/ethanol bath and ozone gas was passed through the solution for 10 min under vigorous stirring. The excess of ozone was then displaced with nitrogen over a period of 5 min. Methyl sulfide (100 µl) was added and the reaction mixture stirred at room temperature for 2 hours and distributed equally in two vials. The solvent was removed under a stream of nitrogen. The resulting white solid was used directly in the subsequent conjugation steps.

a) Direct Conjugation of FucGM1-aldehyde with KLH:

Two mg FucGM1-aldehyde was dissolved in 1 ml of 0.1M phosphate buffered saline (PBS) pH 7.2 and 4 mg of KLH in PBS. Two mg sodium cyanoborohydride was added and the mixture incubated under gentle agitation at 37° C. for 48 h. After 16 h, an additional 1.0 mg sodium cyanoborohydride was added and the incubation continued. The unreacted FucGM1 aldehyde was removed completely with multiple washes using a Amicon Centriprep with molecular weight cut-off value 30000 dalton, with 6-7 changes of PBS at 4° C.

b) Conjugation of FucGM1-aldehyde through MMCCH to thiolated KLH:

Preparation of FucGM1-MMCCH

Two mg of FucGM1-aldehyde was dissolved in 1 ml of 0.1M sodium acetate buffer pH 5.5, and 4 mg of MMCCH in 100 µl of dimethyl sulfoxide (DMSO) was added. The reaction mixture was incubated at room temperature for 15 min with gentle stirring. At the end of 15 min 2 mg of solid sodium cyanoborohydride was added and the incubation continued at room temperature for 2 h. Unreacted MMCCH was removed in a Sephadex G10 column equilibrated previously with 0.1 M sodium phosphate buffer pH 6.0 containing 5 mM EDTA and eluted with the same buffer. The fractions positive for FucGM1 by TLC with orcinol were combined.

Addition of Sulfhydryl groups to KLH

2-Iminothiolane (2 mg) dissolved in thiolation buffer (50 mM triethanolamine, 0.15 M NaCl, 5 mM EDTA, pH 8.0) was added to 4 mg of KLH and incubated with stirring at room temperature for 2 h. Unreacted 2-iminothiolane was removed by Sephadex G15 column equilibrated previously with 0.1 M sodium phosphate buffer pH 7.2 containing 5 mM EDTA and eluted with the same buffer. Fractions positive for KLH with BioRad protein assay dye reagent were combined. A small portion was used to estimate sulfhydryl groups in the thiolated KLH using Ellman's reagents and cysteine as standard as described earlier (Riddles P W, Blackeley R L, Zerner B Ellman's reagent: 5,5'-dithiobis(2-nitrobenzoic acid)—a reexamination, *Anal Biochem* 94: 75-81, 1979). The KLH was estimated by a dye method using BioRad dye reagent according to the manufacture's instructions.

Conjugation of FucGM1-MMCCH to thiolated KLH

The FucGM1-MMCCH product and thiolated KLH were mixed and adjusted to pH 7.2 with 0.1M sodium phosphate buffer pH 8.0. The reaction mixture was then incubated at room temperature overnight. The content of the FucGM1-MMCCH-KLH reaction vial was transferred to a Centriprep concentrator 30 (Amicon: molecular cut-off 30000 Dalton) and unreacted FucGM1-MMCCH was removed completely with multiple washes. The conjugate was checked by HPTLC for the absence of unreacted FucGM1 as mentioned above. The epitope ratios of two batches of conjugate were determined by estimating protein content by BioRad dye binding protein assay and carbohydrate by a HPAEC-PAD assay. The epitope ratio of FucGM1-KLH (by direct method) and FucGM1-MMCCH-KLH was 149/1 and 1527/1 respectively.

B. Example 2

Synthesis of Globo-H and Conjugates Thereof

1) Discussion of Synthesis:

In yet another embodiment of the present invention, an improved synthesis of Globo-H is provided utilizing the novel synthetic methodology as presented herein. The previous synthesis of globo-H described by the present inventors (Park et al. *J. Am. Chem. Soc.* 1996, 118, 11488; Bilodeau et al. *J. Am. Chem. Soc.* 1995, 117, 7840; Kim et al. *J. Org. Chem.* 1995, 60, 7716) utilized all glycal building blocks (Danishefsky et al. *Angew. Chem.* 1996, 108, 1482; *Angew. Chem. Int. Ed. Engl.* 1996, 35, 1380) for the rapid construction this complex oligosaccharide. These investigations relied on a highly convergent [3+3] coupling to generate the hexasaccharide core contained in the final target. In this approach, a flexible terminal glycal was maintained throughout the hexasaccharide construction. The glycal was then used to install the ceramide side chain present en route to globo-H glycolipid 16a or its allyl glycoside 16b. The synthesis of 16a served to facilitate the proof of structure and immunocharacterization of globo-H. The allyl glycoside 16b was employed for immunoconjugation to biocarrier proteins. The previous protocols were effective in producing adequate quantities of synthetic material for proof of structure, immunocharacterization, conjugation, mouse vaccinations and phase I human clinical trials. However, improved synthetic methodologies were desired to allow for efficient bioconjugation and also to provide suitable material for clinical purposes.

Figure 7:
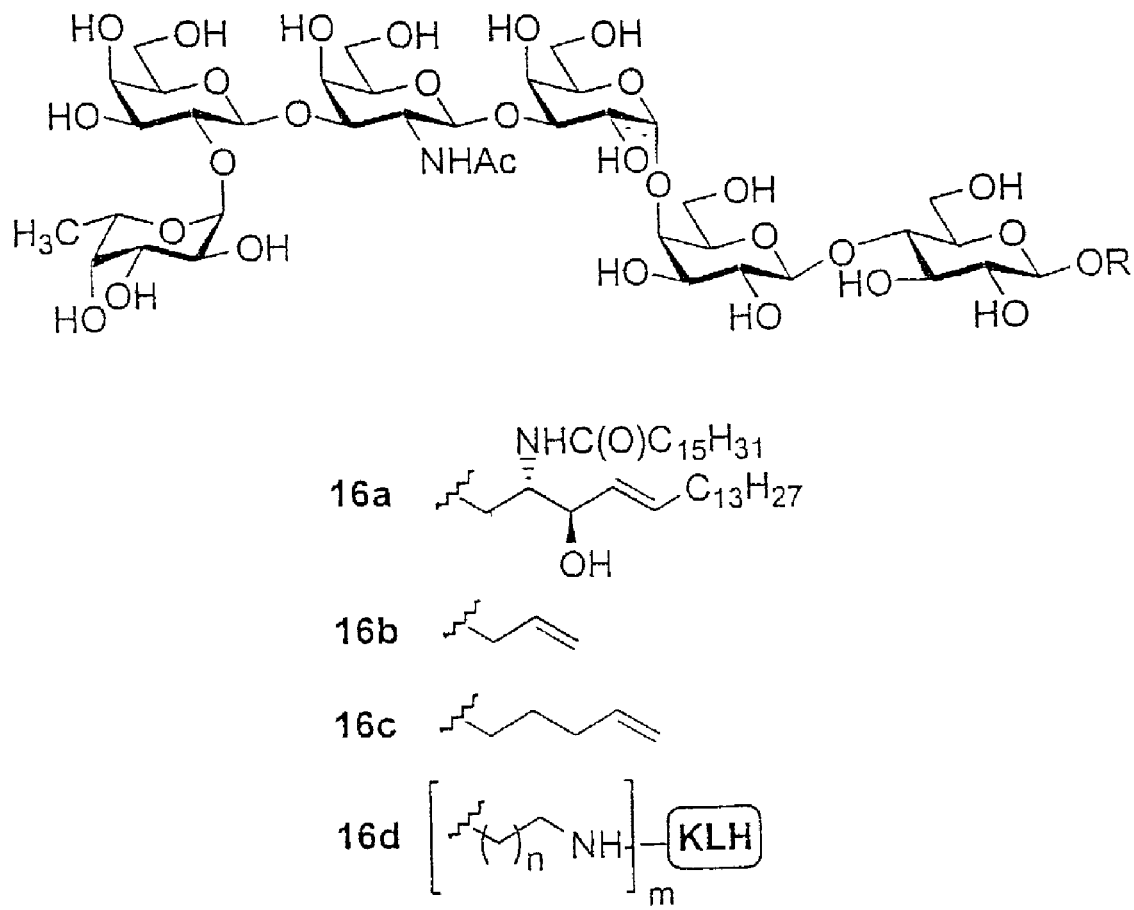
FIG. 7 depicts Globo-H, derivatives and constructs thereof.
Figure 8:
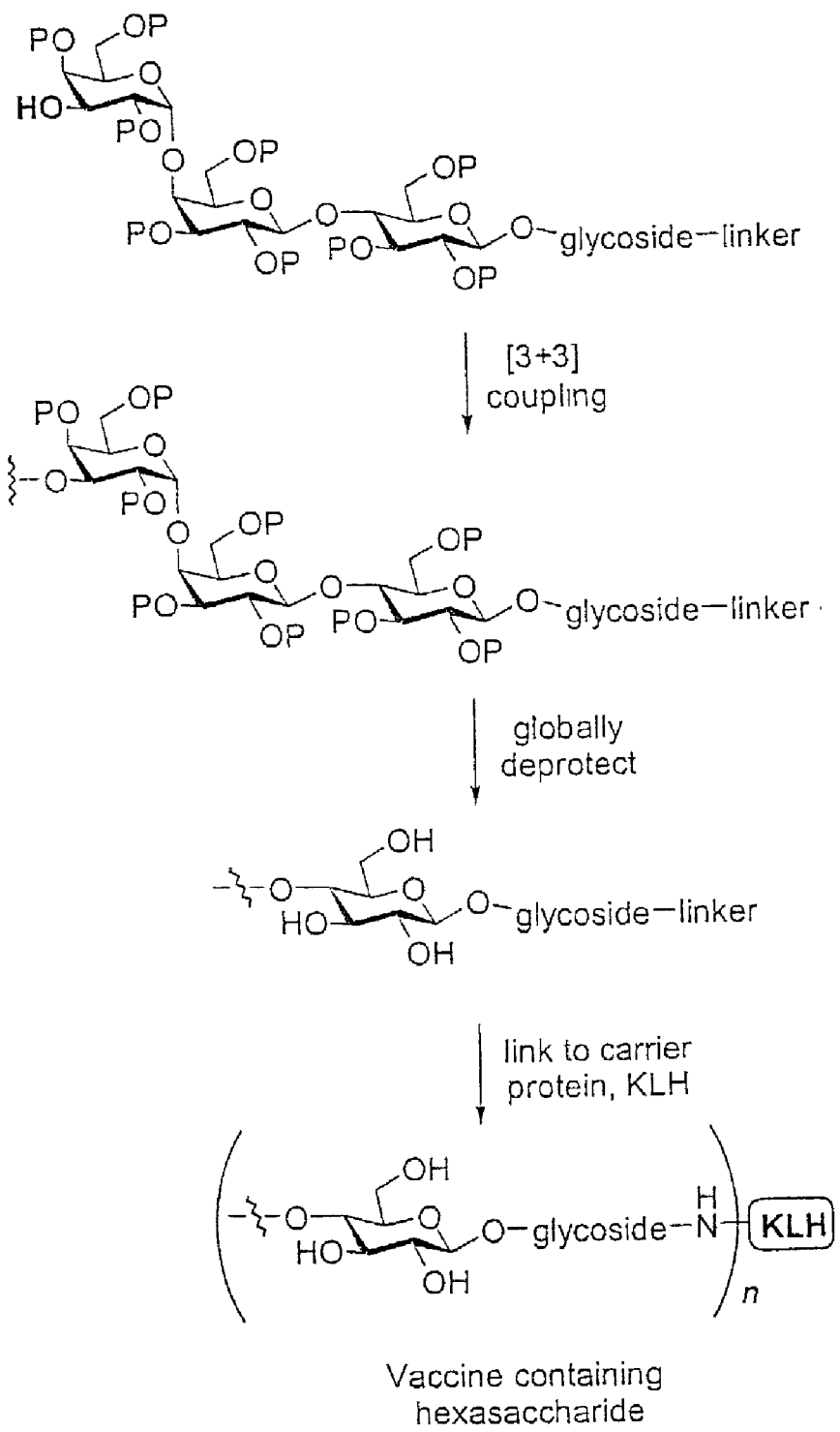
FIG. 8 depicts a synthetic scheme for a second generation synthesis of globo-H and constructs thereof.

Difficulties associated with the allyl glycoside approach invited an alternative solution which, in general terms, is described herein, and is more specifically described for fucosyl GM1 above, and additionally for Globo-H below (FIG. 7). Thus, it was conceived that a hexasaccharide could be constructed containing a glycoside that would enable linkage to carrier protein, already in place (see FIG. 8). Indeed this group would already have been incorporated at the reducing end of the acceptor in the [3+3] coupling step. For successful implementation of this significant new variation of the globo-H synthesis (and other complex tumor associated antigens), it would be preferable that 1) the trisaccharide acceptor containing the glycoside construct would be readily synthesizable; 2) the glycoside construct would be compatible with the [3+3] coupling; 3) the construct, in contrast to the allyl glycoside, would survive global deprotection; and 4) efficient conjugation would be implementable.

Figure 9:
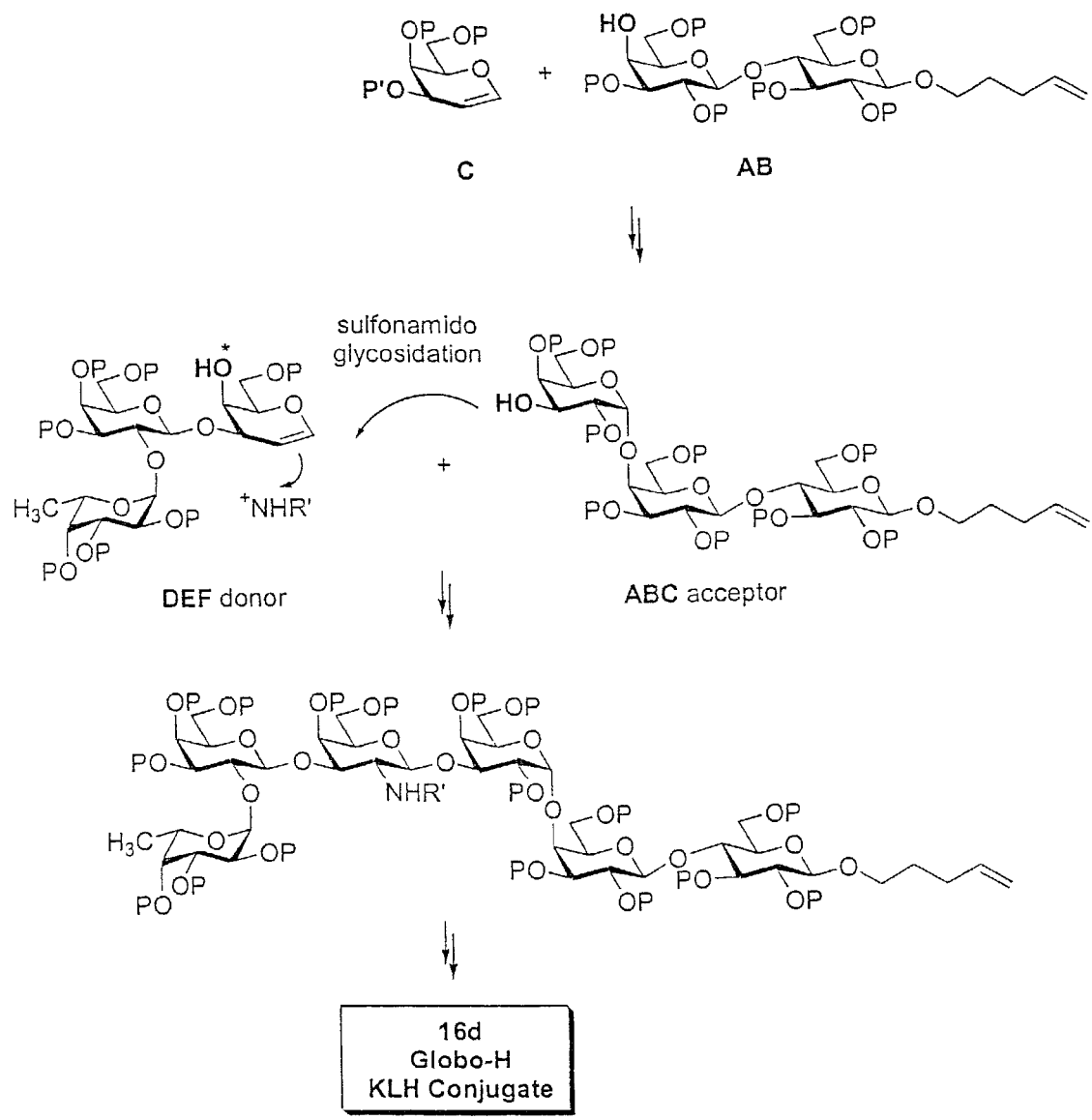
FIG. 9 depicts a retrosynthetic analysis of Globo-H and conjugates thereof.

An initial retrosynthetic analysis is shown in FIG. 9. For maximum convergency, the ABC acceptor was envisioned containing the aforediscussed pentenyl glycosidic linker. Additionally, the same DEF trisaccharide donor sector would be utilized as described previously. The hexasaccharide core would then be assembled via a convergent [3+3] ABC+DEF coupling reaction using a sulfonamido glycosidation protocol (Griffith et al. *J. Am. Chem. Soc.* 1990, 112, 5811; Griffith et al. *J. Am. Chem. Soc.* 1991, 113, 5863). Previous results had indicated that the presence of a free hydroxyl at C4 of the reducing end galactose (FIG. 9, see asterisk) in the DEF donor would be necessary to direct the formation of the required β-linkage in the sulfonamido glycosidation (Park et al. *J. Am. Chem. Soc.* 1996, 118, 11488; Kwon et al. *J. Am. Chem. Soc.* 1998, 120, 1588). The sequencing of the [3+3] coupling was expected to take place as shown, owing to the higher reactivity of the equatorial C3 hydroxyl group (see bold) in the acceptor as compared to the necessary axial C4 hydroxyl group in the donor trisaccharide. Important to the strategy described herein is that, once the hexasaccharide is assembled, only protecting group manipulations would be required to reach the pro-vaccine antigen.

In general, the synthesis of the DEF trisaccharide sector is fairly concise, requiring six transformations starting from 6-O-TIPS galactal and tri-O-benzyl fluoro fucose (Park et al. *J. Am. Chem. Soc.* 1996, 118, 11488; Bilodeau et al. *J. Am. Chem. Soc.* 1995, 117, 7840; Kim et al. *J. Org. Chem.* 1995, 60, 7716). For purposes of a second-generation approach, the acceptor trisaccharide component can be dissected into a lactose derivative containing the desired NPG bearing a differentiated hydroxyl at C4' and an appropriate C-ring donor (FIG. 9). The galactose donor monosaccharide also requires differential protection at C3, for eventual ABC+DEF coupling, and needs careful attention to efficiently allow for the required β-glycosidic linkage joining the AB+C domains.

Figure 10:
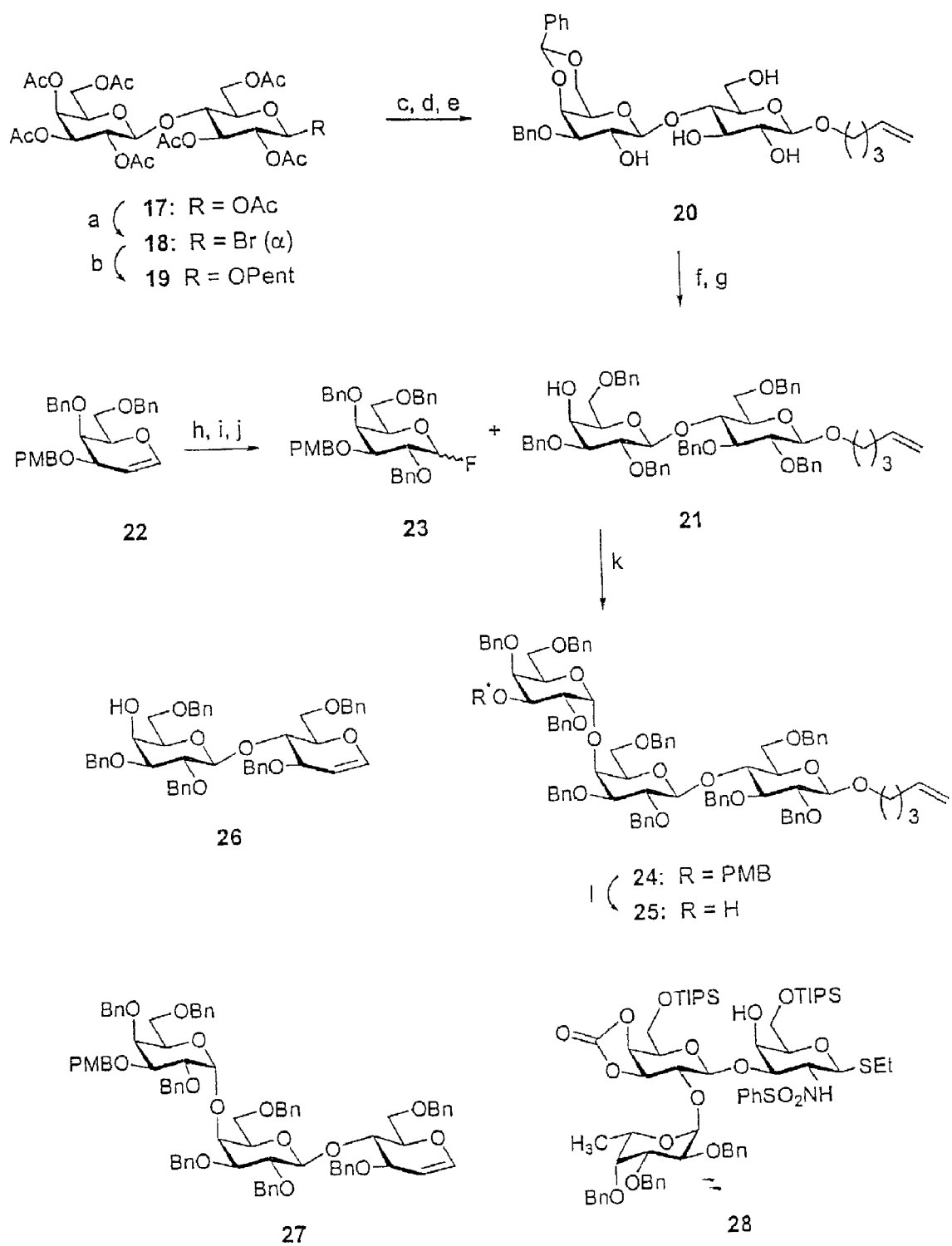
FIG. 10 depicts the synthesis of glycoside 25 and thioethyl donor 28. Reagents: (a) HBr, $Ac_2O$, AcOH, 96%; (b) PentOH, $Ag_2CO_3$, $CH_2Cl_2$, 4 Å molecular sieves, 75%; c) NaOMe, MeOH; then Dowex-$H^+$; (d) BnBr, $Bu_2SnO$, $Bu_4NI$, $C_6H_6$, 54% two steps; e) $PhCH(OMe)_2$, CSA, $CH_3CN$, 72%; (f) BnBr, NaH, DMF, $Et_4NI$, 97%; (g) $NaCNBH_3$, HCl, $Et_2O$, THF, 79%; (h) DMDO, $CH_2Cl_2$; (i) HF/pyridine, 85% two steps; (j) BnBr, NaH, DMF, 95%; (k) $Cp_2Zr(OTf)_2$, toluene/THF 5:1, 80% (α), α:β 10:1; (l) DDQ, $CH_3CN$, H2O, 84%.

As shown in FIG. 10, the synthesis of the requisite ABC acceptor was conducted taking advantage of readily available lactose octaacetate, 17. Conversion of 17 to the known α-bromo donor 18 (Reithal, Y. *J. Am. Chem. Soc.* 1952, 74, 4210; Dasgupet et al. *Carbohydr. Res.* 1994, 264, 155) was followed by silver carbonate mediated glycosylation with pentenyl alcohol as acceptor, to give 19 (Pent=$CH_2CH_2CH_2CH=CH_2$) in 75% yield on a 100 g scale (Rodriguez et al. *Aust. J. Chem.* 1990, 43, 665). Similar processing of 18 with silver triflate as promoter resulted in 17% yield of the desired product. Thus, with the formation of 19, in an early stage of the synthesis, the linker was successfully installed to be used for late stage bioconjugation.

Subsequent steps were designed to generate a free acceptor site at C4' of 19 for an eventual AB+C coupling give the ABC trisaccharide (FIG. 10). Removal of the ester protecting groups in 19 to give a pentenyl lactoside was followed by a stannane mediated monobenzylation to selectively give the C3' benzyl ether (David et al. *J. Chem. Soc. Perkin Trans. I* 1981, 1797; Maranduba et al. *Carbohydr. Res.* 1986, 151, 105). In a second step, the C4' and C6' hydroxyls were engaged as a benzylidene acetal to provide compound 20 as the only observable product (Jannson et al. *J. Org. Chem.* 1998, 53, 5629; Koeman et al. *Tetrahedron* 1993, 49, 5291; Qiu et al. *Liebigs Ann.* 1992, 217). Finally, perbenzylation of the remaining hydroxyl groups in 20 and regioselective reductive cleavage of the benzylidene with sodium cyanoborohydride and anhydrous HCl gave the C4' alcohol 21 (Garegg, P. J. *Pure Appl. Chem.* 1984, 56, 845). Thus, starting from lactose octaacetate 17, the AB pentenyl glycoside acceptor 21 was obtained in 7 steps and in 20% overall yield.

With large quantities of the protected pentenyl glycoside 21 available, attention was turned to the AB+C coupling to form the trisaccharide acceptor 24. The previous synthesis of glycal 27 (FIG. 10) required careful preparation of the highly activated β-fluoro donor 23 from glycal 22. The C3 PMB ether contained in 22 was strategically incorporated to allow for eventual ABC+DEF coupling upon selective deprotection of this group. In the course of this work, it was discovered that α-23 could be formed conveniently in high yield and on large scale. Accordingly, α-donor 23 was prepared from differentially protected glycal 22 by epoxidation, exposure to HF:pyridine to yield the cis fluoro-hydrin derivative and subsequent conversion of the resulting C2-hydroxyl to its benzyl ether. The anomeric α:β selectivity was demonstrated to be 10:1 and the overall yield in transforming 22 into 23 was 76%.

The effectiveness of the AB+C coupling using previously prepared β-23 and the newly prepared α-23 with the AB acceptor 21 was then investigated. The synthetic optimization of glycal trisaccharide 27 as a model case (see 23+26->27) was also examined because of its presumed sensitivity to overly demanding coupling promoters. In these investigations it was discovered that the reduced reactivity of α-fluoro donors could be attenuated by conducting the couplings with highly fluorophilic promoters in judiciously chosen solvents, as summarized in Table 1. The previous coupling procedure using the predominantly β-fluoro donor 23 and glycal 26 to give glycal trisaccharide 27 employed Muykiyama coupling conditions (Mukaiyama et al. *Chem. Lett.* 1981, 431; Nicolaou et al. *J. Am. Chem. Soc.* 1990, 112, 3693; Nicolaou et al. *J. Chem. Soc. Chem. Commun.* 1991, 870) and proceeded in 54% yield with modest anomeric selectivity (entry 1, Table 1). Investigations using other promoters with α-23 are shown in entries 2 and 3, but produced little satisfaction in terms of overall efficiency. However, the preparation of glycal 27 was successfully extended to include the described α-donor 23 using strongly fluorophilic $Cp_2Zr(OTf)_2$ promotion (73% yield, entry 4). Gratifyingly, these optimized glycosidation conditions for formation of 27 were successfully applied to the AB+C coupling employing pentenyl glycoside 21 to provide trisaccharide 24 in yields that rivaled the parent reaction (80% yield, entry 6). Muykiyama coupling of β-23 with 21 yielded 42% of trisaccharide 24 (entry 5). Satisfied with the events leading to smooth formation of large quantities of 24, the [3+3] coupling would be investigated. The discharge of the lone PMB group in 24 could be effected in excellent yield (92%), thus completing the assembly of the desired ABC pentenyl acceptor 25.

TABLE 1

Coupling conditions used to generate the ABC trisaccharide.

| | Acceptor AB | Donor C | Promoter, Solvent | α:β selectivity | Yield, Product |
|---|---|---|---|---|---|
| 1 | 26[a] | 23 (β)[a] | SnCl$_2$, AgClO$_4$, Et$_2$O | 3:1 | 54% (α), 18% (β) 27 |
| 2 | 26 | 23 (10α:1β) | Sn(OTf)$_2$ Toluene:THF (5:1) | 8:1 | 40% (α), 5% (β) 27 |
| 3 | 26 | 23 (10α:1β) | Cp$_2$ZrCl$_2$, AgClO$_4$, CH$_2$Cl$_2$:Et$_2$O | 2.7:1 | 55% (α) 27 |
| 4 | 26 | 23 (10α:1β) | Cp$_2$Zr(OTf)$_2$, Toluene:THF (10:1) | 10:1 | 72% (α), 8% (β) 27 |
| 5 | 21 | 23 (β) | SnCl$_2$, AgClO$_4$, Et$_2$O | 3:1 | 42% (α) 24 |
| 6 | 21 | 23 (10α:1β) | Cp$_2$Zr(OTf)$_2$, Toluene:THF (5:1) | 10:1 | 80% (α), 8% (β) 24 |

([a]see Park et al. J. Am. Chem. Soc. 1996, 118, 11488; Bilodeau et al. J. Am. Chem. Soc. 1995, 117, 7840; Kim et al. J. Org. Chem. 1995, 60, 7716).

Figure 11:
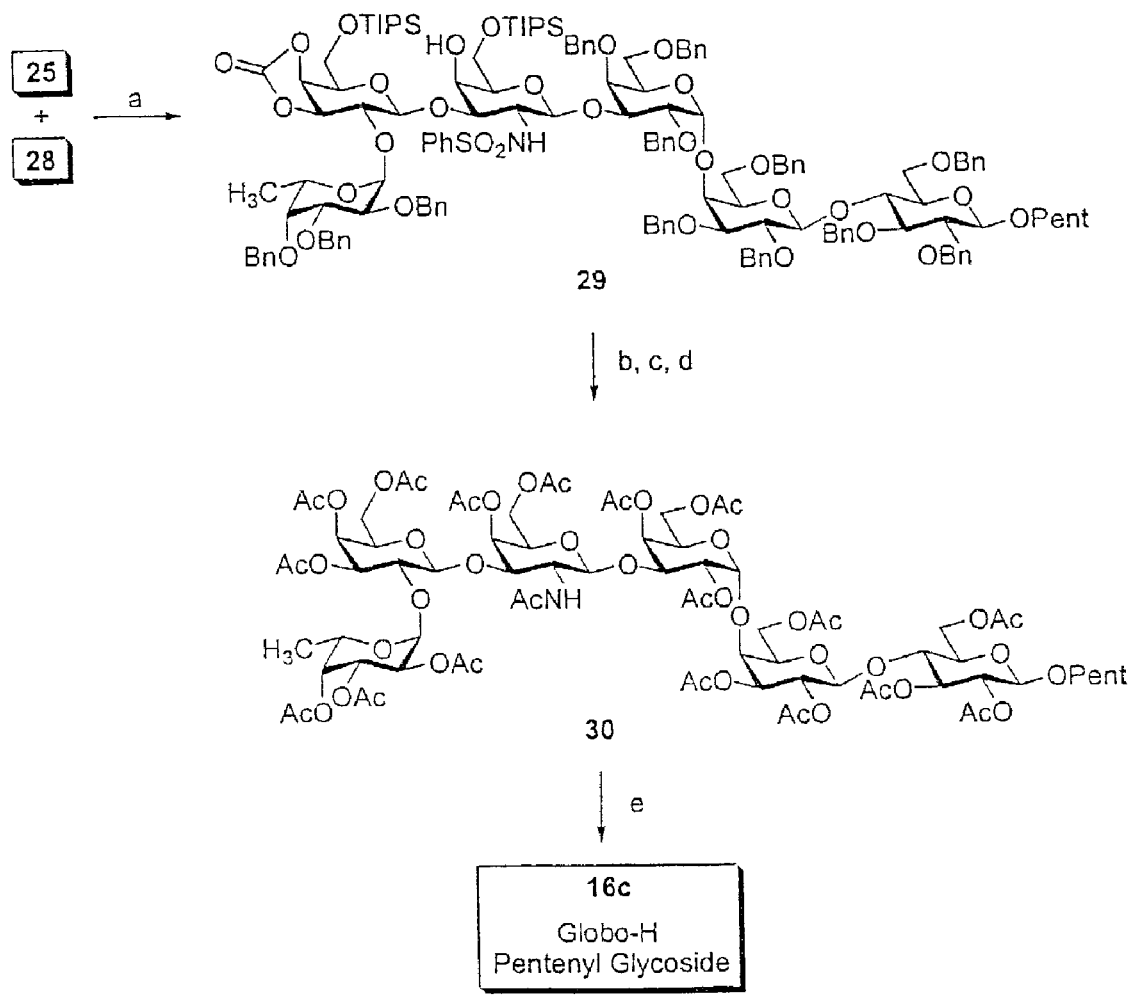
FIG. 11 depicts the synthesis of Globo-H Pentenyl Glycoside (16c).

The key step and final transformations completing the synthesis of 16c are shown in FIG. 11. Treatment of the known DEF donor 28 (see FIG. 10) with MeOTf (Lönn, H. *Carbohydr. Res.* 1985, 134, 105; Lönn, H. *J. Carbohydr. Chem.* 1987, 6, 301) In the presence of acceptor 25 smoothly provided hexasaccharide 29 in 60% yield. The configuration of the new anomeric center of 29 was confirmed to be β-configured. The [3+3] coupling yield using trisaccharide acceptor 25 was comparable to the [3+3] procedure using the glycal-based acceptor corresponding to 27. The tremendous advantage of using 15, however, is manifested in the steps which follow.

Global deprotection began with subjection of 29 to TBAF in order to remove the silyl ethers and the cyclic carbonate. The benzyl and sulfonamido protecting groups on the resulting penta-ol were then cleaved under the action of dissolving metal reduction. This protocol was followed by peracetylation to give the isolable hexasaccharide peracetate 30. As in earlier steps, the pentenyl linkage proved highly reliable under the listed deprotection conditions. It is again notable by contrast that the corresponding allyl glycoside (to ultimately yield 16b) is not stable to the reducing metal conditions required for global deprotection and therefore must be installed subsequent to deprotection. Deacetylation of 30 with methoxide yielded the fully deprotected pentenyl glycoside of globo-H, 16c, notably poised for bioconjugation. Importantly, in the second generation variation, progress toward 16d from hexasaccharide construct 29 was greatly simplified because the need for additional functionalization to allow for conjugation is eliminated.

Figure 12:
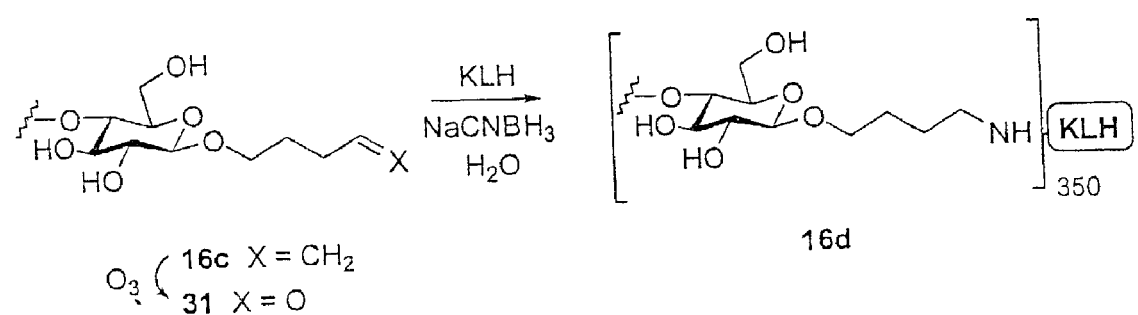
FIG. 12 depicts the conjugation of Globo-H to carrier protein KLH.

Toward the goal of facilitating clinical evaluation of synthetic globo-H, 16c has been conjugated to carrier protein KLH for purposes of creating a functional vaccine. The first step of this procedure involved ozonolysis of the pendant olefin, followed by reductive work-up, to give the uncharacterized aldehyde intermediate 31, as shown in FIG. 12. Reductive amination with KLH and sodium cyanoborohydride in phosphate buffer yielded vaccine glycoconjugate 16d (n=3). Covalent attachment of the carbohydrate to the proteins presumably occurs through the ε-amino groups on exposed lysine residues in KLH. Hydrolytic carbohydrate analysis of 16d revealed approximately 350 carbohydrate residues per molecule of carrier protein.

2) Experimentals:

Peracetyl pentenyl-β-D-lactoside (19). To a cooled (ice bath) suspension of lactose octaacetate (100.0 g, 147.7 mmol), glacial acetic acid (30 mL) and acetic anhydride (30 mL) was added 100 mL of 30% HBr in AcOH dropwise over a period of 60 minutes. The reaction mixture stirred for 1 hour and the ice bath was removed. Upon stirring for an additional 2 hours at room temperature, the mixture became a homogeneous yellow solution. The solution was diluted with H$_2$O (1000 mL) and extracted with CHCl$_3$ (3×400 mL). The organic extracts were washed with H$_2$O (2×1000 mL), satd. NaHCO$_3$ (3×500 mL), dried over MgSO$_4$ and concentrated. The product was azeotroped with anhydrous benzene and dried under high vacuum to yield 98.8 g (96%) of the lactosyl bromide which was used without further purification.

To a suspension of Ag$_2$CO$_3$ (100 g, 362.6 mmol), freshly activated molecular sieves (15 g) and a crystal of I$_2$ in 400 mL CH$_2$Cl$_2$ was added pentenyl alcohol (5.0 equiv., 73.4 mL) and then the lactosyl bromide (98.8 g, 141.4 mmol) in 400 mL of CH$_2$Cl$_2$. After stirring in the dark at room temperature for 16 hours, the reaction was filtered through a plug of Celite with additional CH$_2$Cl$_2$ and concentrated to a yellow oil which was purified by flash column chromatography (10% EtOAc/hexanes→50% EtOAc/hexanes) to yield 74.7 g (75%) of the pentenyl lactoside as a white foam. $[\alpha]_{22}^D$ −48.9° (c 7.5, CHCl$_3$); IR (film CHCl$_3$) 2941, 1751, 1369, 1224, 1054 cm$^{-1}$; $^1$H NMR (CDCl$_3$, 400 MHz) δ 5.60 (m, 1H), 5.17 (d, 1H, J=2.7 Hz), 5.02 (m, 1H), 4.93 (dd, 1H, J=7.9, 10.3 Hz), 4.85 (d, 1H, J=1.6 Hz), 4.78 (m, 2H), 4.71 (dd, 1H, J=9.6, 7.9 Hz), 4.30 (m, 3H), 3.93 (m, 3H), 3.66 (m, 3H), 3.45 (m, 1H), 3.30 (m, 1H), 1.98 (s, 3H), 1.94 (s, 3H), 1.91 (m, 2H), 1.89 (s, 3H), 1.88 (s, 6H, 2×CH3), 1.87 (s, 3H), 1.79 (s, 3H), 1.49 (m, 2H); $^{13}$C NMR (CDCl$_3$, 100 MHz) δ 170.33, 170.28, 170.09, 170.00, 169.74, 69.54, 169.01, 137.72, 115.00, 101.01, 100.51, 76.27, 72.76, 72.48, 71.64, 70.94, 70.58, 69.23, 69.01, 66.52, 61.97, 60.73, 29.75, 28.49, 20.80, 20.75, 20.64, 20.57, 20.45. FAB-HRMS calc'd for C$_{31}$H$_{44}$O$_{18}$Na$^+$; 727.2425. Found; 727.2418.

Pent-4-enyl 3'-O-benzyl-4',6'-O-benzylidenyl-β-D-lactoside (20). Peracetylated pentenyl lactoside, 8, (18.2 g, 25.8 mmol) was dissolved in 300 mL of anhydrous MeOH and 2.0 mL of NaOMe (25% in MeOH) was added. The reaction stirred at rt for 16 hours and was neutralized with Dowex-H$^+$ (pH 5-6). The reaction was filtered with additional MeOH and concentrated to a white solid, 19a, (10.6 g, quantitative) which was used without further purification: $^1$H NMR (D$_2$O, 400 MHz) δ 5.81 (m, 1H), 5.00 (dd, 1H, J=17.3, 1.9 Hz), 4.92 (dd, 1H, J=8.9 Hz), 4.74 (m, 1H), 4.39 (d, 1H, J=8.0 Hz), 4.35 (d, 1H, J=7.8 Hz), 3.72-3.42 (m, 12H), 3.21 (m, 1H0, 2.06 (m, 2H), 1.63 (m, 2H); $^{13}$C NMR (D$_2$O, 100 MHz) δ 141.27, 117.31, 105.42, 104.54, 80.85, 77.84, 77.24, 76.92, 75.33, 75.00, 73.44, 72.47, 71.03, 63.52, 62.56, 31.83, 30.48. The hepta-ol 19a (1.14 g, 2.8 mmol) and dibutyltin oxide (0.76 g, 3.1 mmol) were heated at reflux in benzene (70 mL) with azeotropic water removal for 15 h. The mixture was doubled in concentration, cooled to room temperature, and benzyl bromide (0.69 ml, 5.8 mmol) and Bu$_4$NI (1.03 g, 2.8 mmol) were added. The mixture was heated at reflux 3.5 h, cooled, silica gel was added to the flask, and the solvent was evaporated. The residue was applied to a column of silica gel, tin by-products were removed by flushing with hexanes, and elution (5% MeOH in CH$_2$Cl$_2$) gave the pure 3'-O-benzyl ether (0.76 g, 54%) as a white foam: $[\alpha]_{22}^D$ +36.7° (c 2.73, $CHCl_3$); IR (film $CHCl_3$) 3371, 2924, 2880, 1372, 1157, 1074 cm$^{-1}$; $^1$H NMR (MeOH-d$_4$, 400 MHz) δ 7.46-7.40 (m, 2H), 7.35-7.20 (m, 3H), 5.92-5.72 (m, 1H), 5.08-4.93 (m, 2H), 4.76 (d, 1H, J=11.8 Hz), 4.65 (d, 1H, J=11.8 Hz), 4.38 (d, 1H, J=7.8 Hz), 4.28 (d, 1H, J=7.8 Hz), 4.02 (d, 1H, J=2.9 Hz), 3.95-3.63 (m, 6H), 3.61-3.48 (m, 4H), 3.43-3.20 (m, 3H), 2.20-2.10 (m, 2H), 1.78-1.65 (m, 2H); $^{13}$C NMR (MeOH-d$_4$, 100 MHz) δ 139.77, 139.47, 129.29, 129.08, 128.64, 115.19, 105.02, 104.23, 82.17, 80.74, 76.88, 76.40, 76.35, 74.71, 72.55, 71.81, 70.23, 67.02, 62.44, 61.91, 31.22, 30.07. FAB-HRMS calc'd for $C_{24}H_{36}O_{11}Na^+$; 523.2155. Found; 523.2137.

The 3'-O-benzyl ether (0.6 g, 1.20 mmol) was dissolved in acetonitrile and DMF (5:2, 7 mL), and benzaldehyde dimethylacetal (0.47 mL, 3.1 mmol) and CSA (14 mg, 60 μmol) were added. After stirring 16 h at room temperature, the mixture was diluted with $CH_2Cl_2$ and washed with sat. $NaHCO_3$. The organic extracts were dried ($MgSO_4$), evaporated, and following addition of ether (100 mL) to the resulting residue, the pure 20 was recovered by filtration (0.51 g, 72%): $[\alpha]_{22}^D$ +111° (c 2.21, MeOH); IR (CHCl$_3$ film) 3440, 2872, 1368, 1163, 1109, 1048, 1005 cm$^{-1}$; $^1$H NMR (MeOH-d$_4$, 400 MHz) δ 7.55-7.11 (m, 10H), 5.82-5.69 (m, 1H), 5.45 (s, 1H), 4.98-4.83 (m, 2H), 4.64 (d, 2H, J=3.0 Hz), 4.40 (d, 1H, J=7.9 Hz), 4.23 (d, 1H, J=3.4 Hz), 4.18 (d, 1H, J=7.8 Hz), 4.15-3.98 (m, 2H), 3.87-3.66 (m, 4H), 3.55-3.10 (m, 7H), 2.20-2.10 (m, 2H), 1.65-1.53 (m, 2H); $^{13}$C NMR (MeOH-d$_4$, 100 MHz) δ 139.76, 139.49, 139.47, 129.86, 129.30, 129.07, 129.03, 128.72, 127.35, 115.19, 104.69, 104.28, 102.03, 80.63, 80.17, 76.37, 76.28, 74.77, 74.73, 72.84, 70.86, 70.25, 68.17, 61.70, 31.22, 30.07. FAB-HRMS calc'd for $C_{31}H_{40}O_{11}Na^+$; 611.2468. Found; 611.2465.

Pent-4-enyl 2,2',3,3',6,6'-hexa-O-benzyl-β-D-lactoside (21). The tetraol 20 (0.51 g, 0.87 mmol) and Et$_4$NI (0.12 g, 0.43 mmol) were dried (azeotropic distillation with benzene), dissolved in DMF (5 mL) and cooled to 0° C. Benzyl bromide (0.83 mL, 7.0 mmol) was added followed by NaH (0.22 g, 60%, 5.6 mmol) and the mixture was allowed to warm to room temperature over 14 h. The mixture was diluted with ethyl acetate, washed with water, the organic layer was dried (MgSO$_4$) and evaporated. Purification of the residue by chromatography on silica gel (4:1→2:1 hexanes:ethyl acetate) gave pure pentabenzyl lactoside as a white foam (0.80 g, 97%): $[\alpha]_{22}^D$ +129° (c 1.63, CHCl$_3$); IR (CHCl$_3$ film) 3030, 2866, 1453, 1365, 1096, 1063, 1028, 911 cm$^{-1}$; $^1$H NMR (CDCl$_3$, 400 MHz) δ 7.50-7.05 (m, 30H), 5.80-5.65 (m, 1H), 5.38 (s, 1H), 5.10 (d, 1H, J=10.6 Hz), 4.99-4.60 (m, 9H), 4.47 (d, 1H, J=12.1 Hz), 4.38 (d, 1H, J=7.8 Hz), 4.30 (d, 1H, J=7.8 Hz), 4.25 (d, 1H, J=12.1 Hz), 4.12 (d, 1H, J=13 Hz), 3.94 (d, 1H, J=3.4 Hz), 3.92-3.60 (m, 6H), 3.54 (dd, 1H, J=8.8 Hz, 9.2 Hz), 3.46 (dd, 1H, J=2.6 Hz, 7.0 Hz), 3.40-3.23 (m, 3H), 2.85 (s, 1H), 2.22-2.00 (m, 2H), 1.75-1.60 (m, 2H); $^{13}$C NMR (CDCl$_3$, 100 MHz) δ 138.92, 138.63, 138.51, 138.04, 128.80, 128.52, 128.31, 128.24, 128.17, 128.13, 128.06, 128.03, 128.00, 127.69, 127.65, 127.54, 127.49, 127.38, 127.30, 126.52, 114.84, 103.59, 102.83, 101.30, 83.01, 81.81, 79.60, 78.76, 77.65, 75.73, 75.22, 75.05, 74.97, 73.61, 72.91, 71.56, 69.27, 68.90, 68.27, 66.28, 30.18, 28.89. FAB-HRMS calc'd for $C_{59}H_{64}O_{11}Na^+$; 971.4346. Found; 971.4375.

The benzylidene (0.63 g, 0.66 mmol) was dissolved in THF (6.6 mL) and stirred with freshly activated 4 ÅMS (0.25 g) 10 min at room temperature. In one portion NaCNBH$_3$ (0.21 g, 3.3 mmol) was added followed by anhydrous HCl (2.0 M Et$_2$O), dropwise until the mixture no longer bubbled (approx. 2 mL). After stirring and additional 10 min, the mixture was passed through a plug of Celite washing with ethyl acetate, the filtrate was washed with sat. NaHCO$_3$ and brine, dried (MgSO$_4$) and the organic layers evaporated. Purification by column chromatography (9:1 hexanes:ethyl acetate) gave pure 21 as white solid (0.49 g, 79%): $[\alpha]_{22}^D$ +200° (c 1.05, CHCl$_3$); IR (CHCl$_3$ film) 3474, 3062, 3029, 2869, 1453, 1364, 1094, 1028 cm$^{-1}$; $^1$H NMR (CDCl$_3$, 400 MHz) δ 7.40-7.06 (m, 30H), 5.80-5.66 (m, 1H), 5.02-4.85 (m, 3H), 4.81 (d, 1H, J=11.0 Hz), 4.75-4.54 (m, 6H), 4.67 (d, 1H, J=12.2 Hz), 4.42-4.26 (m, 5H), 3.94 (s, 1H), 3.92-3.81 (m, 2H), 3.71 (dd, 1H, J=10.7 Hz, 4.1 Hz), 3.64 (d, 1H, J=10.6 Hz), 3.57 (dd, 1H, J=9.4 Hz, 5.5 Hz), 3.55-3.42 (m, 3H), 3.38 (dd, 1H, J=5.2 Hz, 9.6 Hz), 3.36-3.21 (m, 4H), 2.32 (s, 1H), 2.15-2.02 (m, 2H), 1.74-1.60 (m, 2H); $^{13}$C NMR (CDCl$_3$, 100 MHz) δ 139.04, 138.54, 138.52, 138.23, 138.09, 137.96, 137.81, 128.33, 128.15, 127.93, 127.66, 127.50, 114.80, 103.50, 102.43, 82.79, 81.68, 80.99, 79.27, 76.52, 75.22, 75.10, 74.99, 74.83, 73.37, 72.99, 72.67, 71.86, 69.10, 68.32, 68.16, 66.00, 30.11, 28.83. FAB-HRMS calc'd for $C_{59}H_{66}O_{11}Na^+$; 973.4503. Found; 973.4513.

α-Fluoro donor (23). A solution of 3-O-PMB-4,6-Di-O-benzyl-galactal (2.24 g, 5.02 mmol) in dry CH$_2$Cl$_2$ (5 ml) under N$_2$ at 0° C. was treated with dimethyldioxirane (0.11 M, 47 ml), and the mixture was stirred until all of the glycal was consumed (~1 h, TLC 30% EtOAc in hexane) Note: Elevated temperature and/or excess of DMDO will prompt oxidation of the PMB group and lower reaction yield. The solvents were evaporated under vacuum at 0° C. and the residue was kept under high vacuum. The flask containing galactal epoxide was charged with freshly prepared 4 Å molecular sieves (2 g), dry THF (50 ml) and cooled to 0° C. HF/Pyr complex (0.79 ml, ~5 equiv.) was added dropwise via syringe. The reaction mixture was left overnight to slowly reach room temperature and quenched with Et$_3$N (1.27 g, ~2.5 equiv.) to reach pH ~7. The mixture was filtered through a pad of anhydrous MgSO$_4$ and rinsed three times with 50 ml of EtOAc. The filtrate was washed with water (50 ml) and saturated NaHCO$_3$ solution (50 ml), dried over MgSO$_4$ and concentrated to dryness. Flash column chromatography (EtOAc/hexanes, 2/1) gave 2.06 g (85% yield) of fluorohydrin as a mixture of anomers α:β=10:1. $^{19}$F NMR (CDCl$_3$, 376 MHz, C$_6$F$_6$ as external standard) δ 9.7 (dd, α, J=54.4, 25.0 Hz) 20.0 (dd, β, J=53.9, 13.1 Hz); $^1$H NMR (CDCl$_3$, 400 MHz) δ 7.38-7.24 (m, 12H), 6.90 (d, 2H, J=8.7 Hz), 5.70 (dd, 1H, J=54.4, 2.8 Hz), 4.89 and 4.57 (two d, 2H, J=11.3 Hz), 4.70 and 4.54 (AB q, 2H, J=11.2 Hz), 4.54 and 4.46 (AB q, 2H, J=11.8 Hz), 4.17 (AMX octet, 1H, J=2.8, 10.1, 25.0 Hz), 4.13 (br t, 1H, J=6.8 Hz), 4.06 (d, 1H, J=1.5 Hz), 3.81 (s, 3H), 3.74 (dd, 1H, J=2.6, 10.1 Hz), 3.60 (m, 2H).

The above mixture (8.29 g, 17.2 mmol) was dissolved in dry DMF (100 ml) containing freshly prepared 4 Å molecular sieves (3 g) under N$_2$ at 0° C., treated with benzyl bromide (4.41 g, 25.8 mmol, 1.5 equiv.) and finally with NaH (1.24 g, 60% dispersion in oil, 30.86 mmol, 1.8 equiv.), and stirred overnight at room temperature. The reaction was quenched with glacial acetic acid (0.93 g, 0.9 equiv.) and the mixture filtered through a pad of anhydrous MgSO$_4$ with EtOAc (4×50 ml). The organic solution was washed with water (4×50 ml), dried (MgSO$_4$) and concentrated in vacuo. Flash column chromatography of the residue (hexane/EtOAc, 4/1) gave 9.36 g (95%) of the title compound as colorless liquid with the same ratio of anomers α:β=10:1 as the starting fluorohydrin. $^{19}$F NMR (CDCl$_3$, 376 MHz, C$_6$F$_6$ as external standard) δ 11.5 (dd, α, J=53.7, 25.2 Hz), 22.8 (dd, β, J=53.4, 13.0 Hz). For analytical purpose 50 mg of pure α anomer was obtained using preparative HPLC. $[\alpha]_{22}^D$ −54.5° (c 0.55, CHCl$_3$); $^1$H NMR (CDCl$_3$, 500 MHz), δ 7.38-7.24 (m, 17H), 6.88 (d, 2H, J=8.6 Hz), 5.58 (dd, 1H, J=53.7, 2.7 Hz), 4.93 (d, 2H, J=11.34 Hz), 4.56 (d, 2H, J=11.34 Hz), 4.85 (AB q, 2H, J=11.78 Hz), 4.72 (AB q, 2H, J=11.78 Hz), 4.73 (AB q, 2H, J=11.3 Hz), 4.68 (AB q, 2H, J=11.3 Hz), 4.47 (AB q, 2H, J=11.84 Hz), 4.41 (AB q, 2H, J=11.84 Hz), 4.09 (br t, 1H, J=6.5 Hz), 4.02 (AMX m, 1H, J=2.7, 10.05, 25.2 Hz), 3.98 (app s, 1H), 3.92 (dd, 1H, J=2.64, 10.05 Hz), 3.81 (s, 3H), 3.54 and 3.52 (ABX m, 2H, J=9.3, 6.05, 7.0 Hz); $^{13}$C NMR (CDCl$_3$, 125 MHz) δ 159.20, 138.35, 138.08, 137.71, 130.43, 129.18, 128.39, 128.25, 128.14, 127.92, 127.8, 127.78, 127.66, 113.81, 106.25 (d, J=229.0 Hz), 78.09, 75.65 (d, J=23.5 Hz), 74.79 (ArCH$_2$), 74.29, 73.70 (ArCH$_2$), 73.45 (ArCH$_2$), 72.71 (ArCH$_2$), 71.70 (d, J=2.7 Hz) 68.26, 55.24 (CH$_3$O); MS (NH$_3$) 586 ([M+NH$_4$]$^+$).

PMB trisaccharide (24). A mixture of lactoside (21) (402 mg, 0.423 mmol) and fluoro donor (23) (485 mg, 0.846 mmol, 2 equiv.) was azeotroped with anhydrous benzene (3×10 ml) and further dried on high vacuum for 3 h. The above mixture was dissolved in toluene (3.8 ml) and transferred via cannula to a flask containing freshly prepared 4 Å molecular sieves (0.68 g) under N$_2$, treated with 2,6-di-tert-butylpyridine (143 μl) and cooled to −20° C. (Cp)$_2$Zr(OTf)$_2$ (225 mg, 0.381 mmol, 0.9 equiv.) was suspended in THF (0.38 ml) and added via a cannula to the reaction mixture. The reaction was stirred for 72 h at 7° C. in darkness. The reaction mixture was diluted with EtOAc (10 ml) and filtered through a pad of anhydrous MgSO$_4$ with EtOAc (3×10 mL). The filtrate was washed with satd. NaHCO$_3$ solution (2×10 ml), dried over MgSO$_4$, and concentrated to dryness. Flash column chromatography (2% Et$_2$O/CH$_2$Cl$_2$) gave 509 mg (80%) of desired α-product (24) and 51 mg (8%) of β-product. [α]$_{22}^D$ +24.6° (c 3.90, CHCl$_3$); IR (CHCl$_3$ film) 3062, 3029, 2919, 2868, 1612, 1513, 1496, 1364, 1303, 1248, 1028 cm$^{-1}$; $^1$H NMR (CDCl$_3$, 400 MHz) δ 7.40-6.95 (m, 49H), 6.69 (d, 1H, J=8.5 Hz), 5.73 (m, 1H), 5.00-4.93 (m, 2H), 4.92-4.84 (m, 2H), 4.82-4.73 (m, 2H), 4.72-4.63 (m, 5H), 4.61 (d, 1H, J=13.0 Hz), 4.48-4.35 (m, 5H), 4.34-4.24 (m, 4H), 4.16 (d, 2H, J=6.8 Hz), 4.07 (dd, 1H, J=8.8 Hz), 4.02-3.80 (m, 8H), 3.78-3.60 (m, 3H), 3.68 (s, 3H), 3.60-3.35 (m, 6H), 3.35-3.18 (m, 4H), 3.12-3.04 (m, 1H), 2.06 (m, 2H), 1.65 (m, 2H); $^{13}$C NMR (CDCl$_3$, 100 MHz) δ 158.76, 139.66, 139.45, 139.26, 139.16, 139.09, 138.92, 138.57, 138.52, 131.39, 129.30, 128.95, 128.70, 128.60, 129.30, 128.08, 127.95, 115.35, 114.02, 104.05, 103.35, 101.25, 83.14, 82.17, 79.91, 79.71, 77.77, 77.04, 75.69, 75.58, 75.46, 75.33, 74.17, 73.75, 73.54, 73.48, 72.65, 72.54, 69.91, 69.71, 68.80, 68.33, 68.19, 55.11, 30.14, 28.86; FAB-HRMS calc'd for C$_{94}$H$_{102}$O$_{17}$Na$^+$; 1525.7014. Found; 1525.6996.

Trisaccharide acceptor (25). A solution of PMB trisaccharide (24) (445 mg, 0.296 mmol) in methylene chloride (10 ml) at 0° C. was treated with phosphate buffer (1.5 ml, pH=7.4) and DDQ (89 mg, 1.3 equiv.) and stirred at 0° C. for 5 h. The reaction mixture was diluted with EtOAc (50 ml), washed with satd. NaHCO$_3$ solution (2×20 ml) and water (20 ml), dried over MgSO$_4$, and concentrated to dryness. The crude material was purified by flash column chromatography (4% ether in methylene chloride) to give 344 mg (84%) of deprotected trisaccharide (25) as a colorless oil. [α]$_{22}^D$ +28.2° (c 5.70, CHCl$_3$); IR (CHCl$_3$ film) 3570, 3062, 3029, 2913, 2868, 1496, 1453, 1364, 1208, 1095 cm$^{-1}$; $^1$H NMR (CDCl$_3$, 400 MHz) δ 7.77-7.06 (m, 45H), 5.73 (m, 1H), 5.01 (dd, 1H, J=5.5, 3.3 Hz), 4.95 (dd, 1H, J=5.8, 2.6 Hz), 4.90 (m, 1H), 4.78 (d, 1H, J=10.9 Hz), 4.75 (d, 1H, J=11.4 Hz), 4.70-4.59 (6d, 6H), 4.47-4.37 (m, 5H), 4.28 (m, 3H), 4.19 (s, 2H), 4.08-3.91 (m, 6H), 3.85 (m, 2H), 3.69 (m, 5H), 3.66 (1H, d, J=11.0 Hz), 3.50-3.19 (m, 9H), 3.10 (dd, 1H), 2.07 (m, 2H), 1.79 (1H, OH), 1.65 (d, 2H); $^{13}$C NMR (CDCl$_3$, 100 MHz) δ 139.36, 138.72, 138.63, 138.52, 138.41, 138.29, 138.19, 138.07, 137.98, 128.35, 128.20, 128.06, 127.97, 127.66, 127.54, 127.08, 114.82, 103.55, 102.67, 99.58, 82.93, 81.67, 81.55, 79.32, 77.61, 76.90, 75.13, 75.02, 74.96, 74.80, 73.08, 72.99, 72.91, 72.01, 69.95, 69.22, 69.15, 68.34, 67.73, 67.57, 60.35, 30.19, 28.92; FAB-HRMS calc'd for C$_{86}$H$_{94}$O$_{16}$Na$^+$; 1405.6439. Found; 1405.6385.

Hexasaccharide (29). The thioethyl donor 28 (543 mg, 0.425 mmol) and acceptor 25 (587 mg, 0.425 mmol) were combined, azeotroped with anhydrous benzene (5×5 mL) and placed under high vacuum for 5 hours. The mixture was then dissolved in 3.5 mL CH$_2$Cl$_2$ and 7.0 mL Et$_2$O, treated with freshly prepared molecular sieves and cooled to 0° C. Methyl triflate (3.0 equiv., 144 μL) was added in one portion and the reaction stirred at 0° C. for 3 hours. Another 144 μL of MeOTf was added and the reaction was allowed to stir for an additional 2 hours at 5° C. The reaction was quenched by the addition of solid NaHCO$_3$, filtered through Celite with EtOAc, concentrated and purified by HPLC (17% EtOAc/hexanes) to give 663 mg (60%) of hexasaccharide as a white foam. [α]$_{22}^D$ −9.7° (c 1.00, CHCl$_3$); IR (CHCl$_3$ film) 3533, 3343, 3087, 3030, 2940, 2865, 1790, 1496, 1453, 133, 1095 cm$^{-1}$; $^1$H NMR (CDCl$_3$, 400 MHz) δ 7.76 (d, 2H, J=7.5 Hz), 7.45-7.00 (m, 63H), 5.84 (m, 1H), 5.20 (s, 1H), 5.11 (d, 1H, J=3.2 Hz), 5.09 (d, 1H, J=3.6 Hz), 5.05 (d, 1H, J=3.3 Hz), 5.03 (m, 1H), 4.92 (m, 2H), 4.86 (d, 1H, J=6.0 Hz), 4.82 (m, 2H), 4.78 (1H, d, J=2.2 Hz), 4.74-4.61 (m, 8H), 4.53-4.44 (4d, 4H), 4.38-4.30 (m, 4H), 4.18-3.82 (m, 20H), 3.76-3.66 (m, 5H), 3.66-3.60 (m, 2H), 3.58-3.52 (m, 2H), 3.48-3.40 (m, 2H), 3.38-3.32 (m, 2H), 3.29-3.25 (m, 3H), 3.06 (dd, 1H, J10.2 Hz), 2.86 (s, 1H), 2.74 (m, 1H), 2.16 (m, 2H), 1.74 (m, 2H), 1.23 (s, 3H, J=6.5 Hz), 1.16-1.07 (m, 42H); $^{13}$C NMR (CDCl$_3$, 100 MHz) δ 155.49, 140.71, 139.37, 138.96, 138.72, 137.70, 138.66, 138.55, 138.42, 138.37, 138.10, 138.07, 138.04, 137.88, 132.07, 128.89, 128.64, 128.50, 128.27, 128.16, 128.04, 127.86, 127.68, 127.53, 127.34, 127.20, 114.79, 103.49, 103.14, 102.61, 99.63, 99.12, 97.79, 82.26, 81.61, 81.34, 80.45, 79.36, 78.95, 78.26, 77.82, 77.64, 77.45, 77.24, 77.16, 76.83, 76.45, 75.39, 75.28, 75.12, 74.98, 74.89, 74.78, 73.94, 73.13, 72.94, 72.92, 72.52, 71.91, 71.81, 71.25, 71.11, 69.35, 69.23, 69.18, 68.18, 68.11, 68.01, 67.77, 67.54, 61.98, 61.72, 56.03, 30.16, 28.88, 18.01, 18.00, 17.95, 17.92, 11.85, 11.82; LRMS (FAB) calc'd for C$_{150}$H$_{185}$NO$_{32}$SSi$_2$Na$^+$ 2624.

Peracetate of globo-H pentenyl glycoside (30). To a solution of the hexasaccharide (585 mg, 0.224 mmol) in THF (10 mL) was added TBAF (1.0 M THF, 10 equiv., 2.24 mL). The reaction stirred at rt for 3 days, poured into ice water and extracted with EtOAc (3×50 mL). The organic extracts were washed with satd. NaHCO$_3$ (50 mL) and brine (50 mL), dried over MgSO$_4$ and concentrated to an oil which was purified through a short plug of silica gel with EtOAc. The resulting triol was dissolved in anhydrous MeOH (8 mL) and sodium methoxide was added (0.25 mL of a 25% solution in MeOH). The reaction stirred at rt for 18 hours, neutralized with Dowex-H$^+$, filtered with MeOH washings and concentrated. To the resulting white solid was added THF (2.0 mL) and condensed liquid NH$_3$ (~25 mL) at −78° C. Sodium (~500 mg) was added and the resulting blue solution stirred at −78° C. for 2 hours. The reaction was quenched with anhydrous MeOH (~10 mL), brought to rt and concentrated under a stream of dry N$_2$ to a volume of ~5 mL. The reaction was neutralized with Dowex-H$^+$, filtered with MeOH washing and concentrated to a white solid. The white solid was dissolved in 5.0 mL pyridine and 5.0 mL CH$_2$Cl$_2$ and cooled to 0° C. A crystal of DMAP was added followed by acetic anhydride (5.0 mL). The ice bath was removed and the reaction stirred at rt overnight. Concentration followed by purification by flash column chromatography (gradient elution 75% EtOAc/hexanes→100% EtOAc→5% MeOH/EtOAc) gave 168 mg (42%) of 30 as a white solid: $[\alpha]_{22}^D$ 4.37° (c 1.85, CHCl$_3$); IR (CHCl$_3$ film) 2939, 1747, 1370, 1229, 1066 cm$^{-1}$; $^1$H NMR (CDCl$_3$, 400 MHz) δ 7.66 (d, 1H, J=6.5 Hz), 5.77 (m, 1H), 5.58 (d, 1H, J=3.2 Hz), 5.47 (d, 1H, J=3.5 Hz), 5.39 (d, 1H, J=3.2 Hz), 5.29 (dd, 1H, J=10.9, 3.0 Hz), 5.24-5.06 (m, 5H), 5.04-5.02 (m, 1H), 4.99-4.85 (m, 4H), 4.74 (dd, 1H, J=10.9, 2.9 Hz), 4.53-4.40 (m, 5H), 4.36 (m, 1H), 4.26 (dd, 1H, J=10.6, 3.4 Hz), 4.18-4.03 (m, 6H), 3.99-3.96 (m, 2H), 3.87-3.81 (m, 3H), 3.77-3.74 (m, 1H), 3.51-3.45 (m, 1H), 3.03 (m, 1H), 2.16 (s, 3H), 2.15 (s, 3×3H), 2.13-2.11 (m, 2H), 2.10 (s, 3H), 2.09 (s, 3H), 2.08 (s, 2×3H), 2.08 (s, 3H), 2.07 (s, 3H), 2.05 (s, 3H), 2.04 (s, 2×3H), 2.00 (s, 3H), 1.97 (s, 2×3H), 1.89 (s, 3H), 1.65 (m, 2H), 1.62 (s, 3H), 1.14 (d, 3H, J=6.5 Hz); $^{13}$C NMR (CDCl$_3$, 100 MHz) δ 172.31, 171.55, 170.78, 170.61, 170.57, 170.48, 170.41, 170.30, 170.08, 169.75, 169.61, 169.57, 169.44, 168.96, 137.76, 115.07, 102.05, 101.29, 100.45, 99.23, 98.74, 94.29, 77.24, 77.16, 76.07, 73.68, 73.40, 73.17, 72.63, 72.34, 71.85, 71.77, 71.56, 71.34, 70.83, 70.71, 70.19, 70.08, 69.32, 69.03, 68.88, 68.09, 68.01, 67.59, 67.32, 64.48, 29.80, 28.54, 23.12, 20.90, 20.88, 20.82, 20.74, 20.73, 20.72, 20.71, 20.64, 20.62, 20.55, 20.54, 20.49, 15.91; FAB-HRMS calc'd for C$_{77}$H$_{107}$NO$_{47}$Na$^+$; 1820.5911. Found; 1820.5994.

Globo-H, pentenyl glycoside (16c). The peracetate (20 mg, 0.011 mmol) was dissolved in anhydrous MeOH (2.0 mL) and 100 μL of sodium methoxide was added (25% solution in MeOH). The reaction stirred at rt for 18 hours, was neutralized with Dowex-H$^+$ (~pH 6-7), filtered with MeOH washings, concentrated and purificated using RP silica gel (H$_2$O→1% MeOH/H$_2$O) then P-2 Gel (H$_2$O elutent) to yield 12 mg (99%) of a white solid. $[\alpha]_{22}^D$ 3.00° (c 1.00, MeOH); IR 3374, 2930, 1641, 1372, 1070 cm$^{-1}$;

$^1$H NMR (MeOH, 400 MHz) δ 5.79 (m, 1H), 5.18 (d, 1H, J=3.9 Hz), 4.98 (dm, 1H, J=7.2 Hz), 4.91 (m, 1H), 4.87 (m, 1H), 4.51 (s, 1H), 4.49 (d, 1H, J=1.4 Hz), 4.41-4.36 (m, 2H), 4.24-4.20 (m, 4H), 4.10 (d, 1H, J=2.5 Hz), 4.06-4.00 (m, 3H), 3.94 (s, 1H), 3.87-3.45 (m, 22H), 3.35-3.31 (m, 2H), 3.19 (t, 1H, J=8.8 Hz), 2.10 (m, 2H), 1.96 (s, 3H), 1.66 (m, 2H), 1.19 (d, 3H, J=6.5 Hz); $^{13}$C NMR (CDCl$_3$, 100 MHz) δ 174.53, 139.53, 115.27, 105.50, 105.44, 104.30, 103.96, 102.81, 101.07, 81.29, 80.59, 80.04, 79.16, 78.00, 76.81, 76.57, 76.49, 76.45, 76.39, 75.57, 74.89, 74.69, 73.58, 72.64, 72.49, 71.56, 70.65, 70.63, 70.38, 70.31, 69.70, 68.13, 62.63, 62.59, 61.94, 61.62, 53.11, 49.90, 31.29, 30.14, 23.55, 16.76. FAB-HRMS calc'd for C$_{43}$H$_{73}$NO$_{30}$Na$^+$; 1106.4115. Found; 1106.4105.

C. Example 3

Preparation of Glycoamino Acids And Inventive Glycopeptides-n-Pentenyl Glycoamino Acids 1) Discussion of Synthetic Methods:

a. Horner-Emmons Olefination With Protected Glycine Derived Phosphonate

Figure 13:
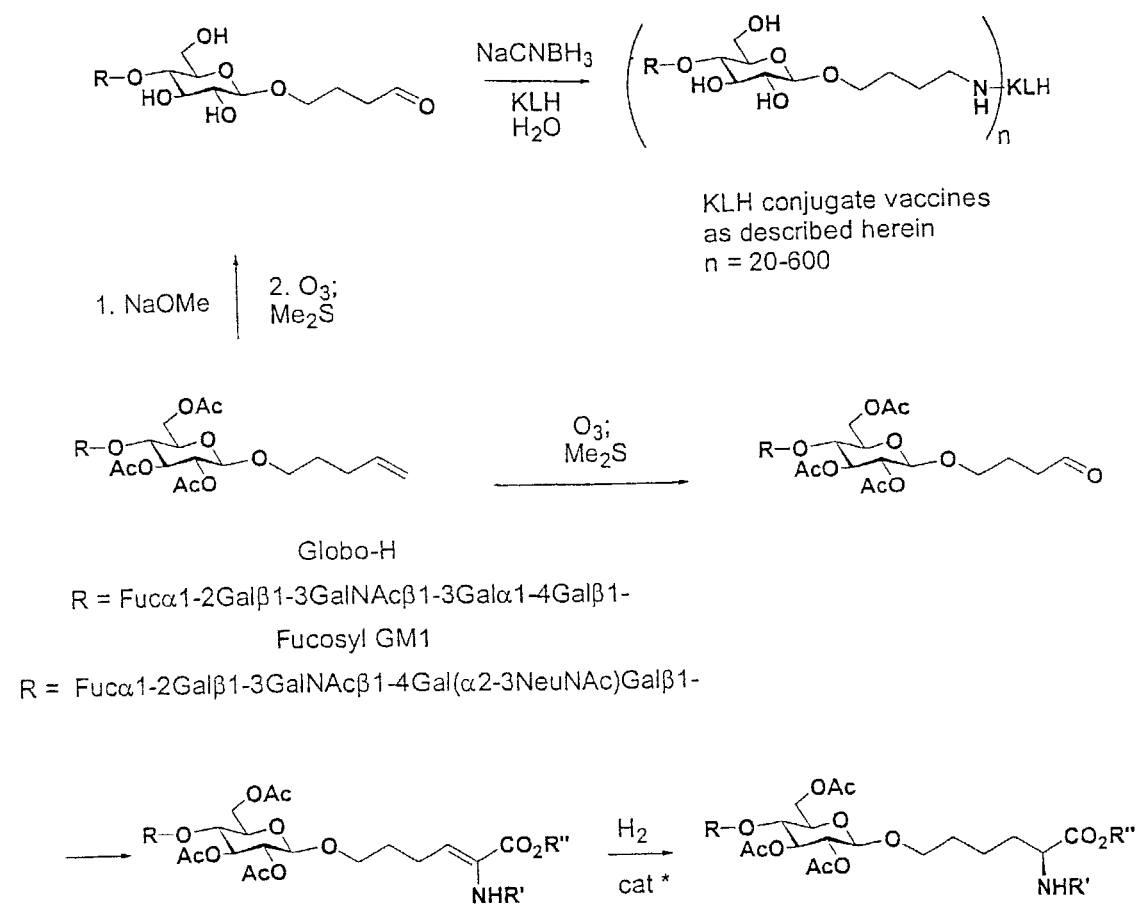
FIG. 13 depicts immunoconjugation of tumor antigens Globo-H and Fucosyl $GM_1$ and the developed glycoamino acid sequence.

In general, it was desired to incorporate the two antigens described above, fucosyl GM1 and globo-H into glycopeptides. In one embodiment, as shown in FIG. 13, a tranformation utilizing catalytic asymmetric hydrogenation of glycosylated amide esters may be used. The new approach anticipated a Horner-Emmons olefination of the protected aldehyde with a suitably protected glycine derived phosphonate to give an enamide ester. Subsequent catalytic asymmetric hydrogenation would hopefully yield diastereromerically pure glycoamino acid.

In but one example, an inventive glycoamino acid, based on a peracetylated lactose derivatives was prepared. Specifically the required lactose derived enamide ester substrate was prepared. The required lactose derived enamide ester substrate was prepared according to FIG. 14. Ozonolysis of the NPG 32 (Allen et al., *Chem. Eur. J.* 2000, 6, 1366) followed by reductive work-up gave the corresponding aldehyde derivative. The crude aldehyde was then subjected to Horner-Emmons olefination using tetramethylguanidine and phosphonate 33. Phosphonate 33, with N-Boc and 2-(trimethylsilyl)ethyl ester (TSE) protection (Schmidt et al., *Synthesis* 1984, 53; Kawai et al., *Chem. Lett.* 1990, 577) was chosen because of the need for the resulting glycoamino acids to be orthogonally suitable for peptide couplings in the presence of acetate carbohydrate protecting groups. The enamide ester 34 was obtained as a single geometric isomer in 88% yield for the 2-step procedure.

In one preferred embodiment, conditions for asymmetric hydrogenation of enamide ester 34 are detailed. The (S, S) ligand isomer of ethyl DuPHOS catalyst precursor was utilized, which has been well characterized in these types of systems to give the (S)-isomer in the amino acid product. The protected glycoamino acid was obtained in 98% yield and was determined to have been formed with a diastereomeric ratio (dr) of >20:1. Remarkably, the t-Boc protons are nearly baseline resolved and, in the asymmetric reaction, the minor isomer could not be detected. $^{13}$C analysis also supports the conclusion that the minor isomer is not formed within the limit of NMR detection. Hydrogenation of 34 with an achiral catalyst (Pd/C, MeOH) produced a 1:1 mixture of R and S configured 35, providing a comparison for diastereomeric ratio determination. This reaction also indicates that chirality transfer to yield 35 occurs from the chiral ligand and not carbohydrate derived substrate control. A final step to be performed prior to moving to synthesis and assembly of tumor antigens was that of demonstrating deprotectability of the blocking groups contained in the amino acid side chain. In the event, reaction of 35 with TBAF in THF gave acid 36, suitably prepared for peptide coupling, in 93% yield.

Figure 14:
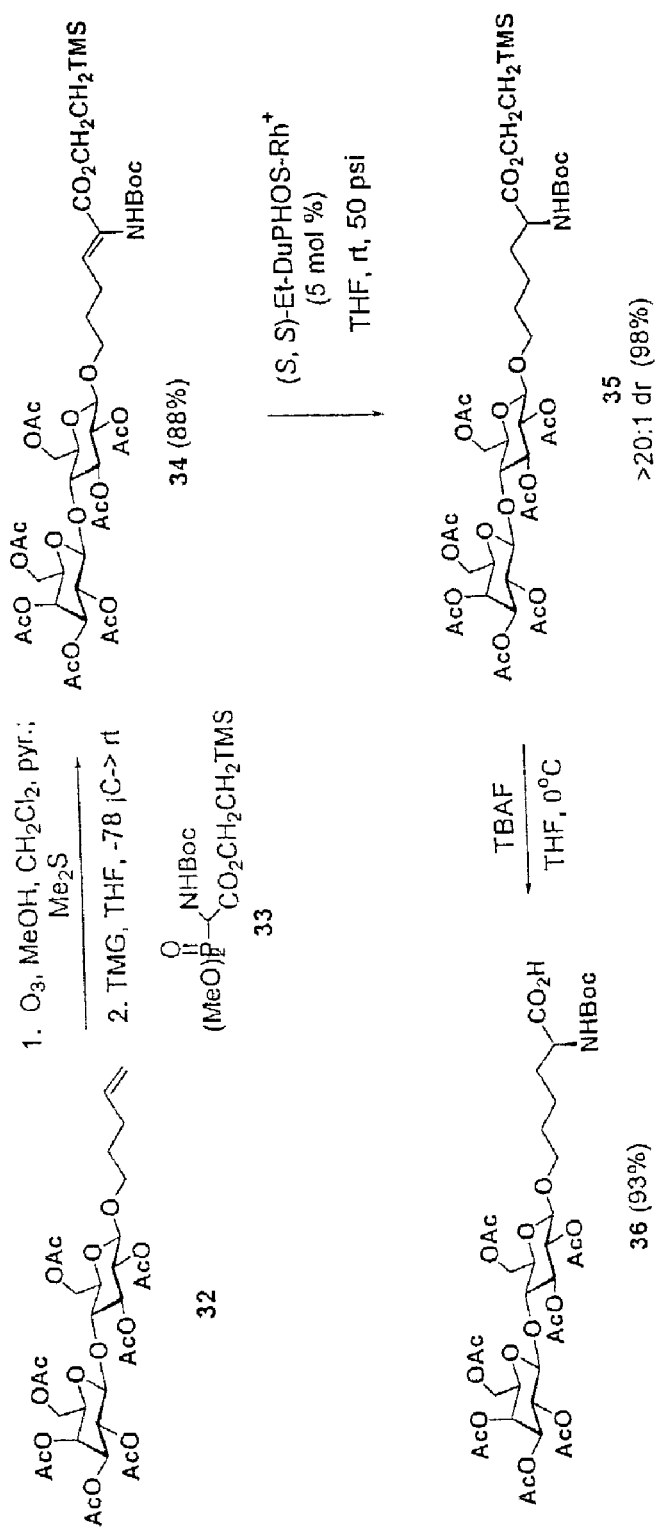
FIG. 14 depicts the synthesis of peracetylated lactose amino acid derivatives.

With the general methodology demonstrated in the lactose model, in other preferred embodiments, advanced hexasaccharides 37 and 38, as well as other antigens of interest, were investigated. As shown in Table 2, olefination of the peracetylated n-pentenyl glycoside of Globo-H, 37, under the same conditions as those used in FIG. 14, provided the corresponding enamide ester 41 in 72% yield as a single isomer and provided fucosyl GM1 hexasaccharide 16 in 10-22% yield. Notably, through use of the (S, S)-Et-DuPHOS-Rh$^+$ catalyst system, the hydrogenation of 41 and 42 proceeded in excellent yield producing 45 and 46 as single diastereomers by $^1$H NMR analysis. Compounds 45 and 46 represent the first examples of synthetic glycoamino acids containing the complex oligosaccharides Globo-H and fucosyl GM$_1$.

Similar transformations on two other clinically promising antigens to generate their corresponding glycoamino acids were also performed in certain other embodiments. As discussed previously, Lewis$^y$ (Le$^y$) oligosaccharide has been identified as an important antigen for eliciting antibodies against colon, liver, prostate and ovarian carcinomas (Lloyd et al., *Am. J. Clin. Path.* 1987, 87, 129; Lloyd et al., *Cancer Biol.* 1991, 2, 421; Yin et al., *Int. J. Cancer,* 1996, 65, 406). Previously, both a Le$^y$-KLH conjugate vaccine (Danishefsky et al. *J. Am. Chem. Soc.* 1995, 117, 5701) and a clustered Le$^y$ glycopeptide (of natural α-O-linked configuration) glycoconjugate attached to either a glycolipid or KLH have been prepared, and have initiated human clinical trials against ovarian cancer with these vaccines have been initiated (Kudryashov et al., *Cancer Immunol. Immunother.* 1998, 45, 281; Sabbatini et al., *Int. J. Cancer* 2000, 87, 79).

The results starting with both Le$^y$ n-pentenyl glycoside 39 and the α-linked n-pentenyl glycoside of the Tn antigen 40 (GalNAc) are presented in Table 2. The pentasaccharide 39 was available as an intermediate in the synthesis of Le$^y$ glycopeptide cluster and consequently illustrates the potential advantage of this strategy. Thus, if immunogenicity is retained in the artificial constructs, these NPG derived glycoamino acids offer a much shorter synthetic route to vaccine glycoconjugates than their native counterparts. As shown in Table 2, olefination of 39 and 40 was uneventful and enamide esters 43 and 44 were obtained in 85% and 75% yields respectively, again as single isomers. Asymmetric hydrogenation, as before, also produced diastereomerically pure glycoamino acids 47 and 48 in excellent yields.

TABLE 2

Horner-Emmons olefination as applied to the preparation of glycoamino acids:

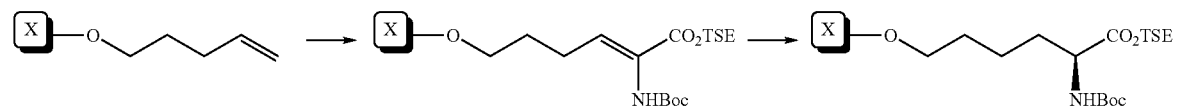

| | Conditions (1) 1. O$_3$, CH$_2$Cl$_2$, MeOH, pyr.: then Me$_2$S: (2) TMG, 33, THF, −78 jC. product, yield | Conditions (S, S)-Et-DuPHOS-Rh$^+$ H$_2$, 50 psi, THF product, yield, dr |
|---|---|---|
| 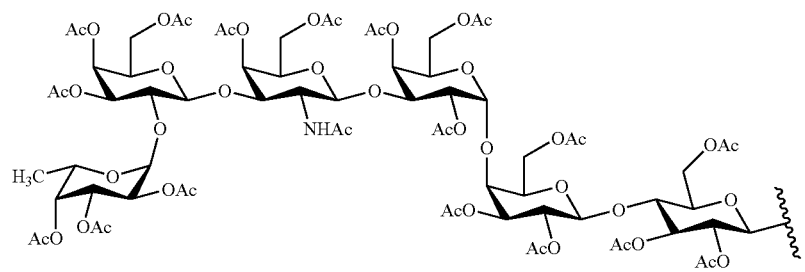 Globo-H (37) | 41, 72% | 45, 98%, >20.1 |
| 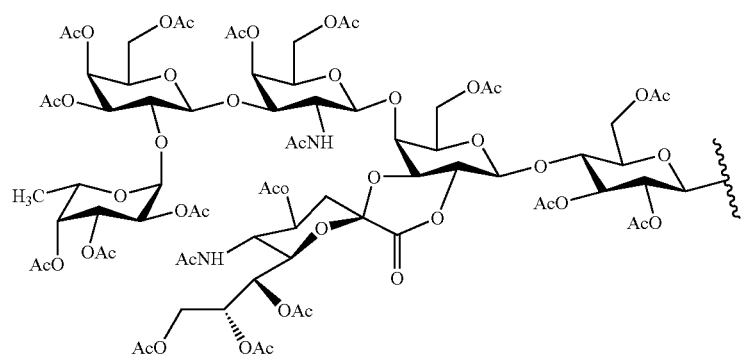 Fucosyl GM$_1$ (38) | 42, 20–22% | 46, 93%, >20.1 |

TABLE 2-continued
Horner-Emmons olefination as applied to the
preparation of glycoamino acids:
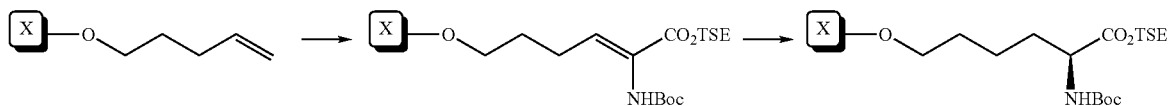
| X = | Conditions (1) 1. O$_3$, CH$_2$Cl$_2$, MeOH, pyr.: then Me$_2$S: (2) TMG, 33, THF, −78 jC. product, yield | Conditions (S, S)-Et-DuPHOS-Rh$^+$ H$_2$, 50 psi, THF product, yield, dr |
|---|---|---|
| 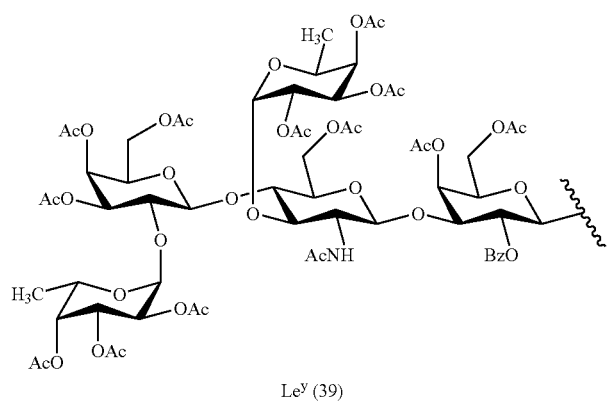<br>Le$^y$ (39) | 43, 85% | 47, 99%, >20.1 |
| 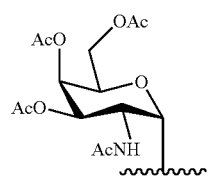<br>(40)<br>α-Tri antigen | 44, 75% | 48, 99%, >20.1 | b. Via Cross-Metathesis Reaction of a Suitable Allyl Glycoside with a Suitably Protected Allylglycine In certain other embodiments, as shown in Scheme 1 below, a tranformation utilizing a novel cross metathesis procedure may be used. The new approach involves a Ruthenium-catalyzed cross metathesis reaction of the allyl glycoside construct with a suitably protected allylglycine intermediate to give the corresponding eneamide ester adduct. Subsequent catalytic hydrogenation yields the desired diastereromerically pure glycoamino acid. R represents any carbohydrate domain described herein.

Scheme 1

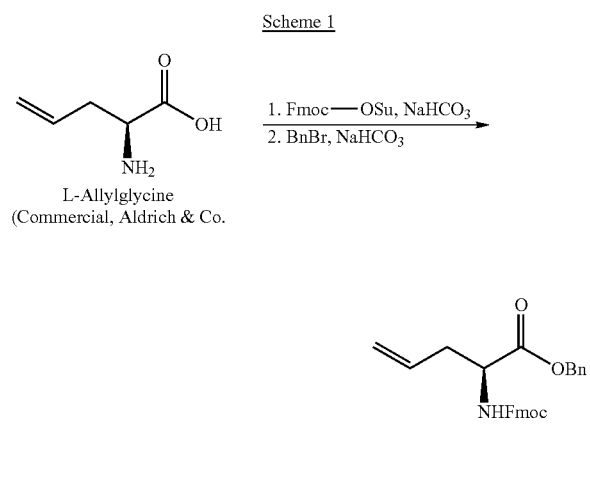

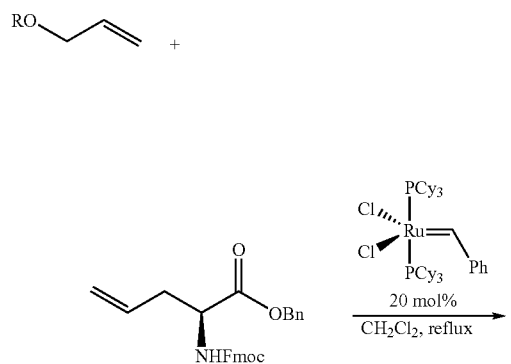

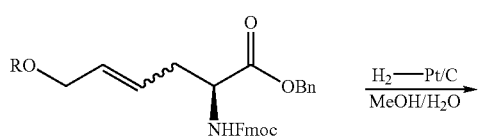

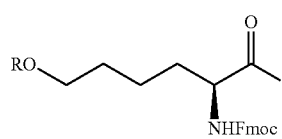

Initial studies were carried out with peracetyl α-O-allyl-D-galactose 57 and Fmoc-L-allylglycine benzyl ester 56 (see Table 3).

TABLE 3

Cross-meththesis reaction conditions.

| Entry | Equiv of 56 | Catalyst | Yield (%) |
|---|---|---|---|
| 1 | 20 | 3 | 26 |
| 2 | 20 | 4 | 45 |
| 3 | 50 | 4 | 70 |

Figure 18:
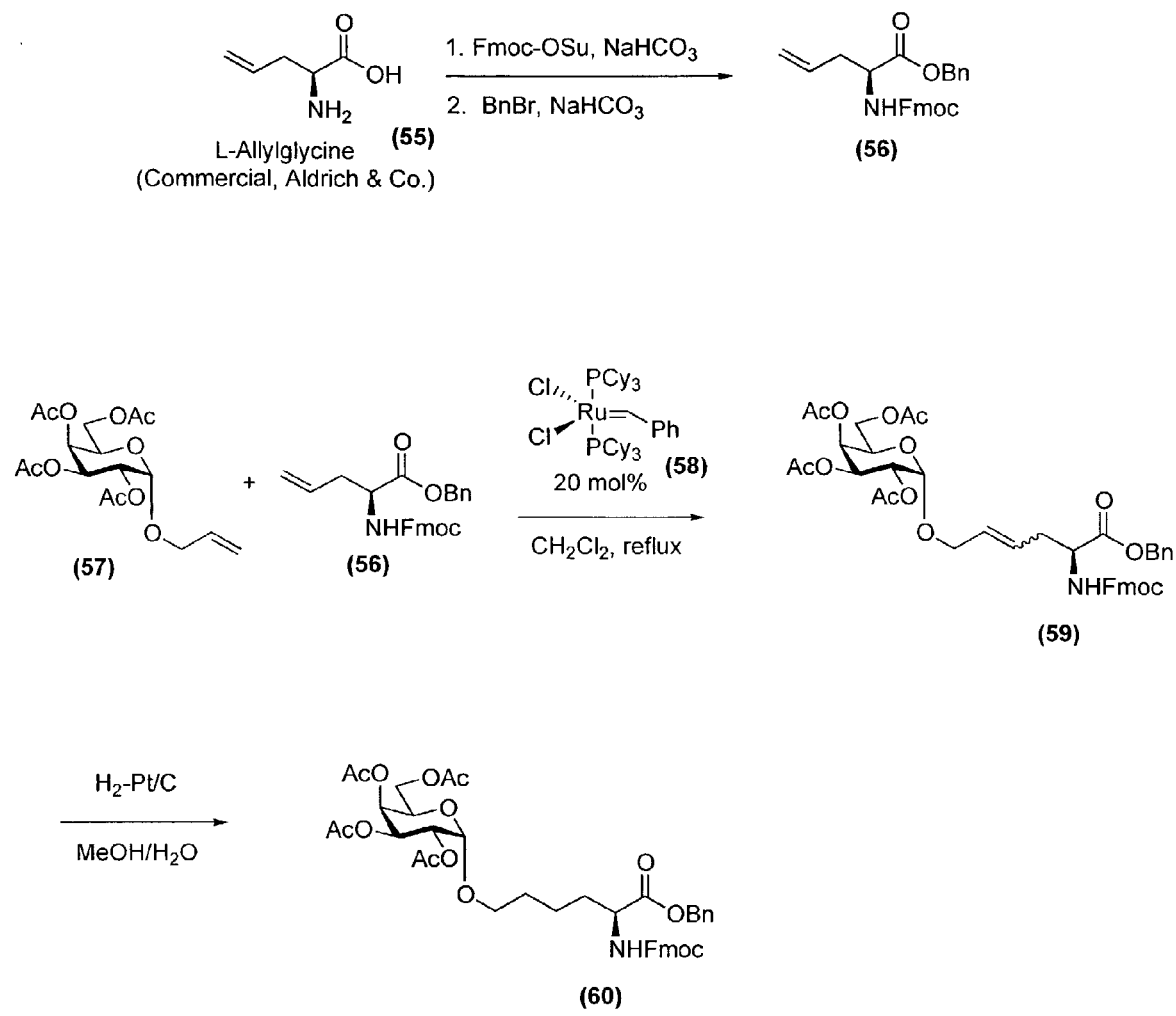
FIG. 18 depicts the synthesis of glycoamino acid 60 using a cross-metathesis reaction.
Figure 19:
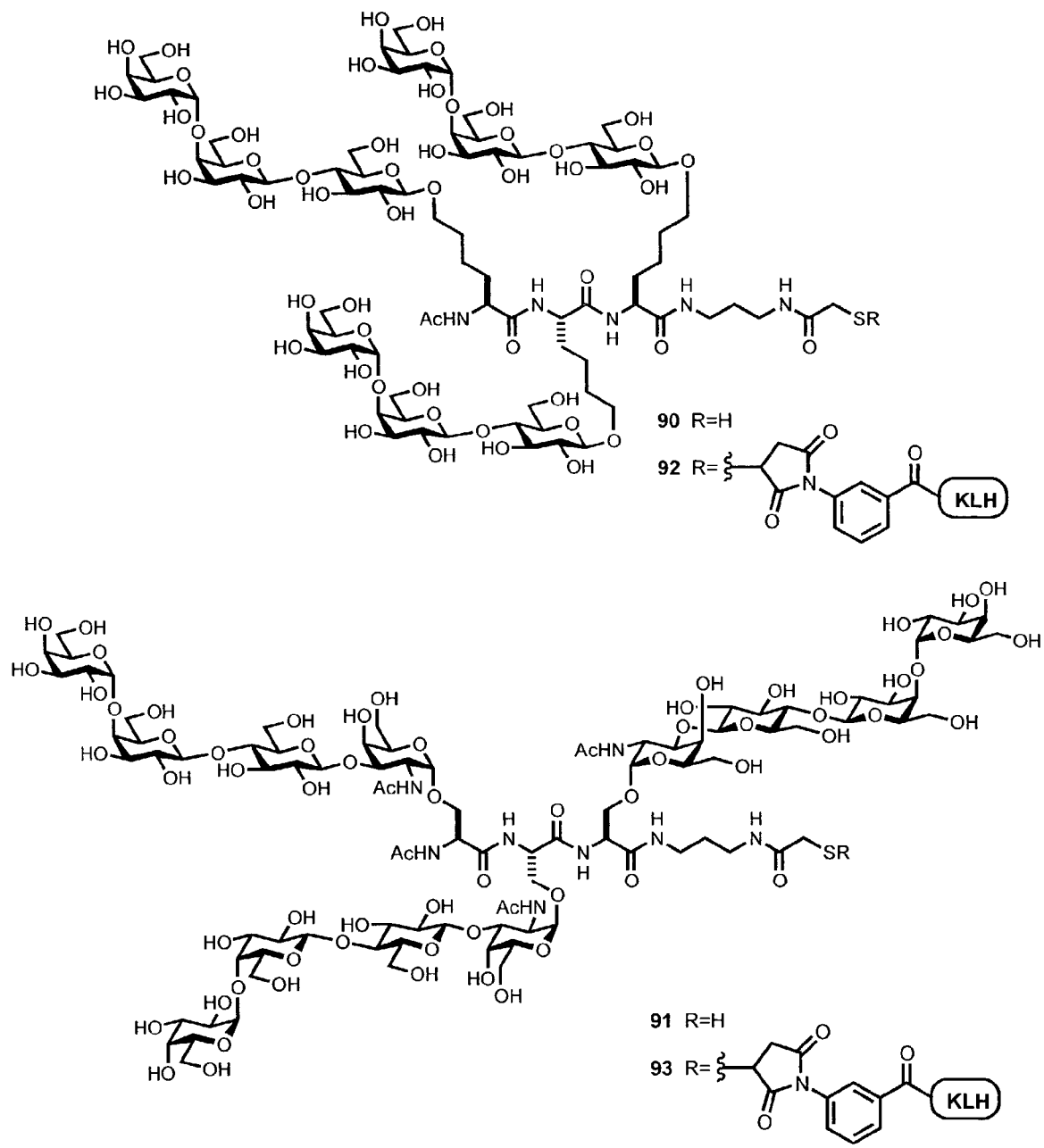
FIG. 19 depicts exemplary conjugated and non-conjugated trimeric antigenic Gb3 glycopeptides.

Fmoc-L-allylglycine benzyl ester 56 was prepared by N-Protection of commercially available L-Allylglycine 55 as its Fmoc ester, followed by protection of the carboxylic moiety as its benzyl ester (see FIG. 18). A two-fold excess of allylglycine 56, in the presence of catalyst 58b afforded the desired eneamide ester 59 in 26% yield, along with dimers of both substrates. When catalyst 58a was used, the reaction proceeded in 49% yield, which was improved to 70% yield by increasing the excess of allylglycine 56 to 5 equivalents. These conditions also led to a marked decrease in dimerization of allylglycoside 57, while increasing the yield of cross-metathesis reaction. Catalytic hydrogenation of 59 yields the desired galactose derived enamide ester substrate 60 in 87% yield as a single geometric isomer. As summarized in Table 4, the methodology was successfully applied to other glycosaccharides, including Globo-H allyl glycoside 37.

TABLE 4
Cross-metathesis reaction as applied to the preparation of glycoamino acids:
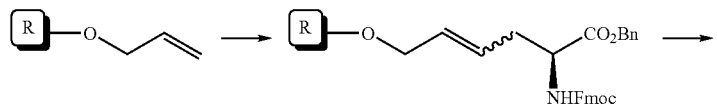
| R = | Conditions, 20 mol% 58, CH$_2$Cl$_2$ 40° C. 12 h product, yield | Conditions H$_2$, 3% Pt/C MeOH/H$_2$O, 12 h product, yield |
|---|---|---|
| (57) | 59, 70% | 60, 87% |
| (95) | 96, 66% | 97, n/d |
| (98) | 99, 70% | 100, n/d |
| Globo-H (101) | 102, 69% | 103, 90% |
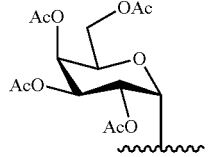
(57)
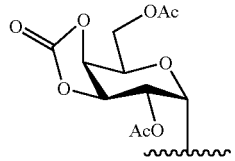
(95)
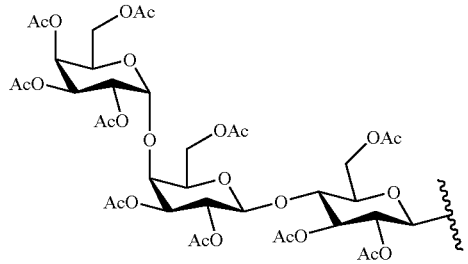
(98)
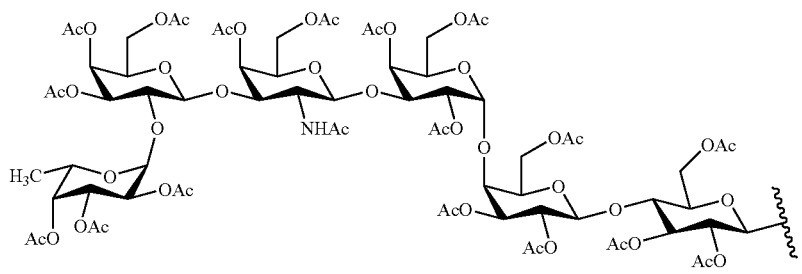
Globo-H (101)

One of ordinary skill in the art will appreciate that this general methodology may be applied to a variety of other antigens of interest. Specifically, any carbohydrate domain available (or synthesized) as an O-allyl construct may be converted to the corresponding glycoaminoacid construct via the reaction steps described above. Examples of suitable glycosaccharide constructs include, but are not limited to:

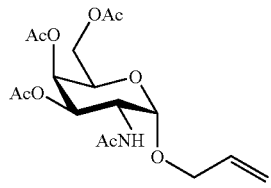

α-Tn antigen

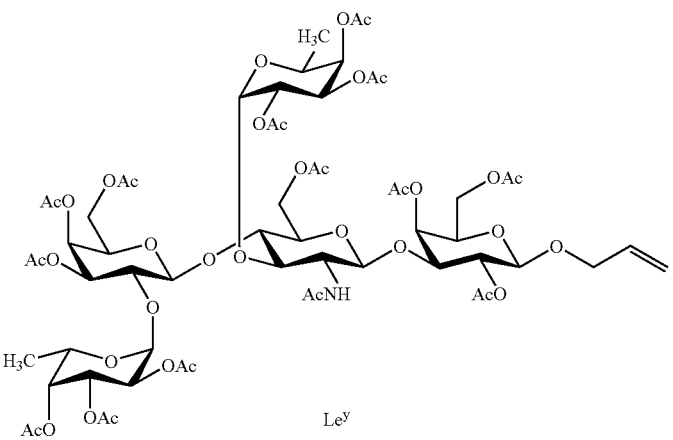

Le$^y$

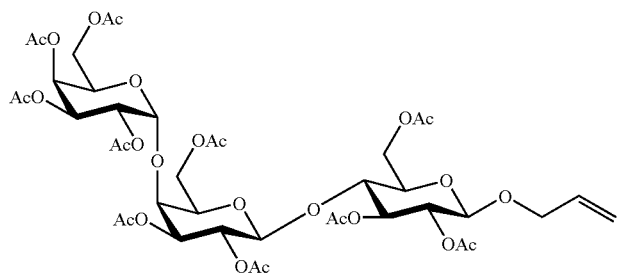

Gb3 allyl glycoside

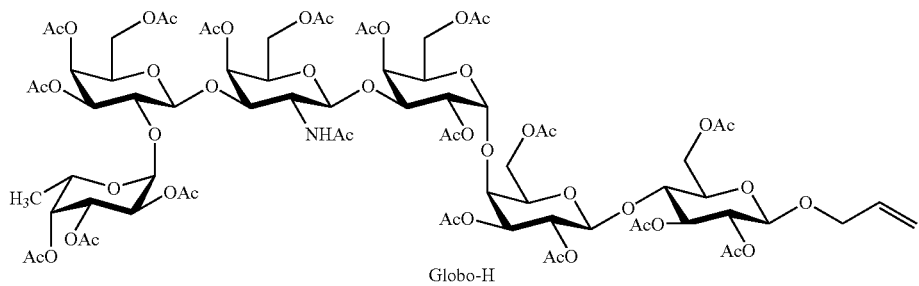

Globo-H

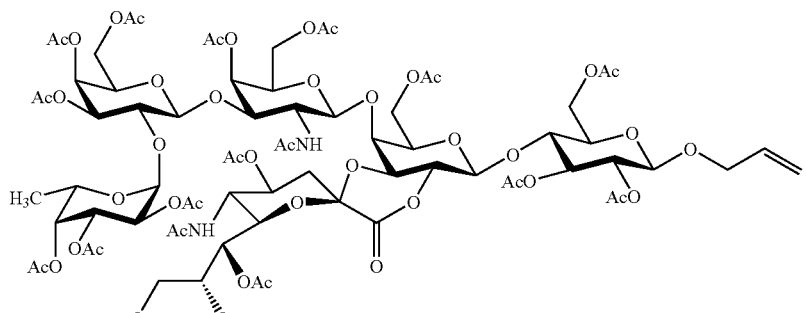

Fucosyl GM$_1$

Figure 15:
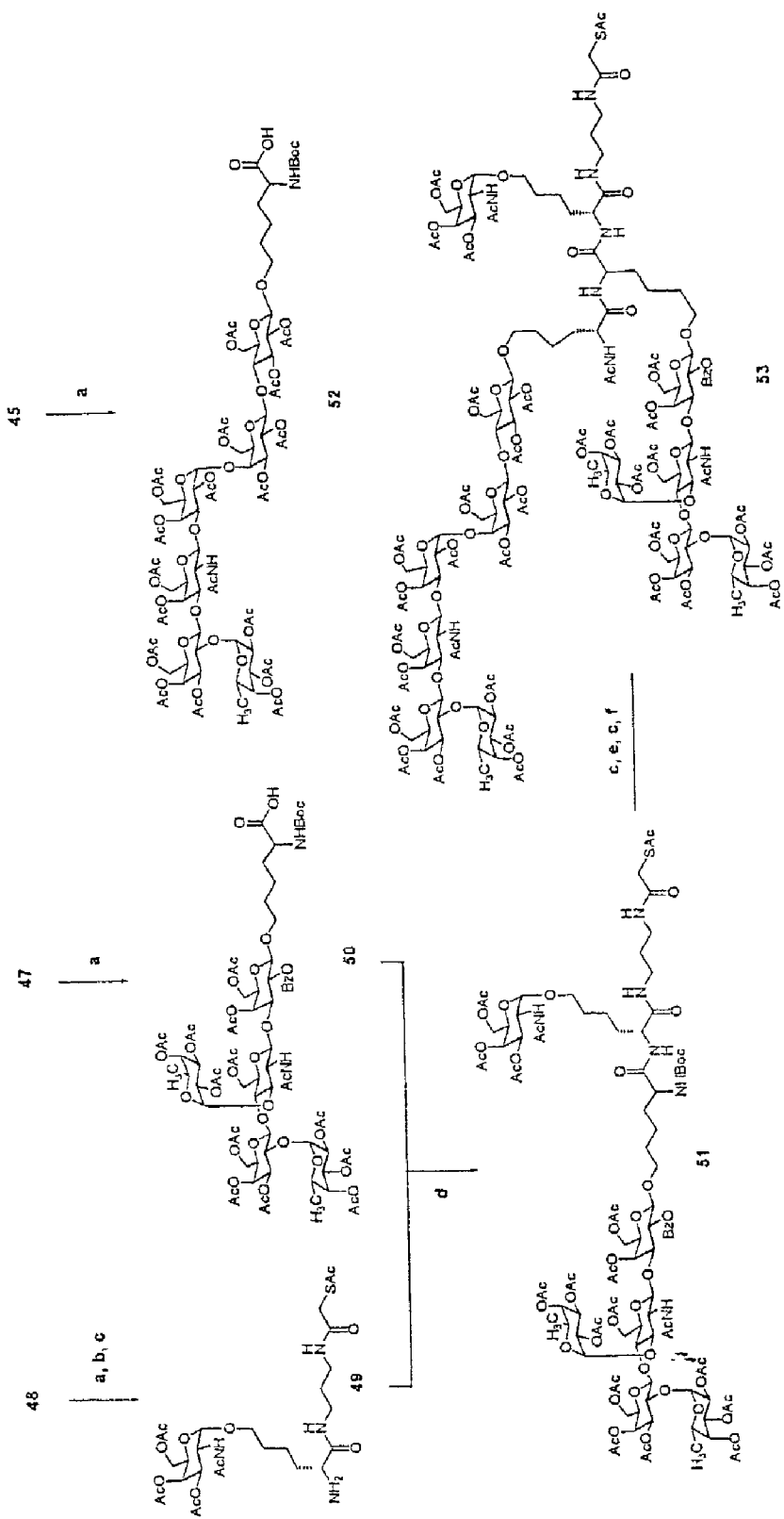
FIG. 15 depicts the synthesis of a peptide containing the Tn antigen, Lewis$^y$ antigen, and the MBr1 antigen. Reagents: (a) TBAF, THF; (b) $AcSCH_2C(O)(CH_2)_3NH_2$, BOP reagent, $iPr_2NEt$, 54%, 2 steps; (c) TFA, $CH_2Cl_2$; (d) BOP reagent, $iPr_2NEt$, 86%, 2 steps; (e) 52, BOP reagent, $iPr_2NEt$, 64%, 2 steps; (f) $Ac_2O$, $Et_3N$, cat. DMAP, 95%, 2 steps.
Figure 16:
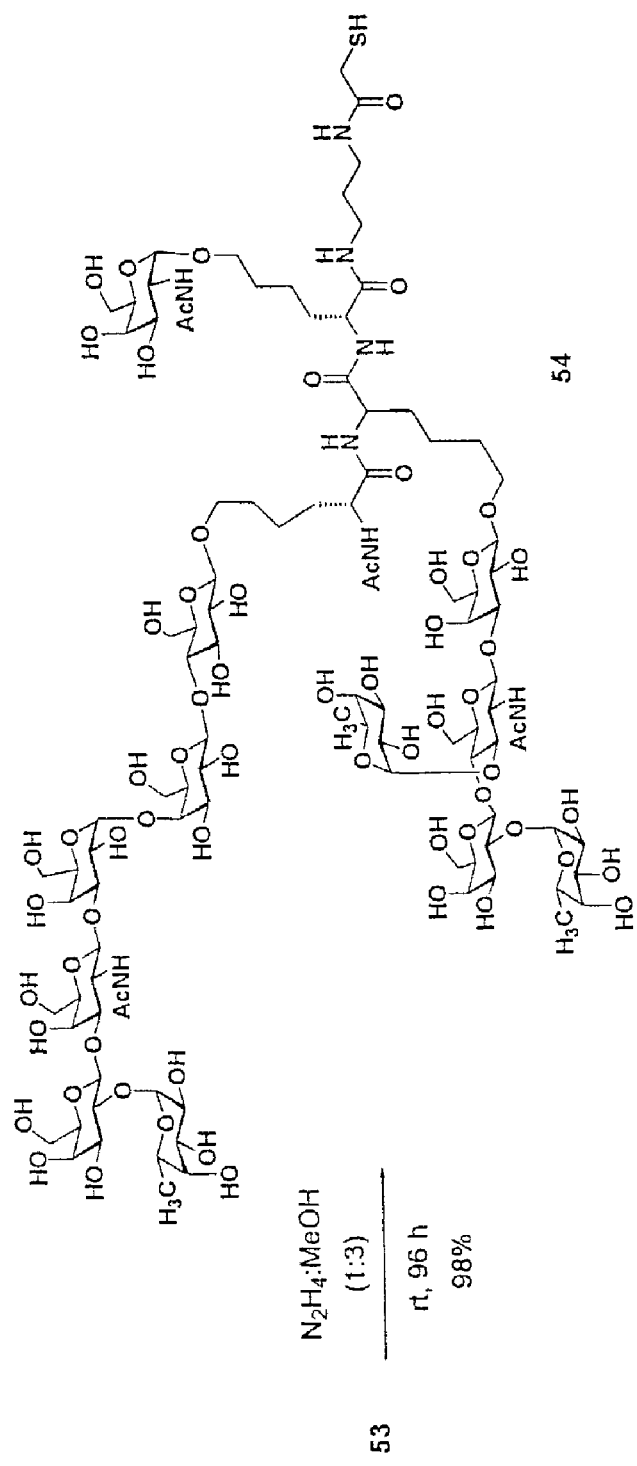
FIG. 16 depicts the preparation of fully deprotected glycopeptide 54.

With the glycoamino acids as described in a) and b) above in hand, it would thus be desirable to generate novel glycopeptides. Specifically, in one embodiment, a novel glycopeptide incorporating globo-H, Le$^y$, and Tn is provided. Specifically, the C-terminus is modified to include a conjugation handle for carrier protein KLH. The mercaptoacetamide unit has proven to be effective for this purpose. As shown in FIG. 15, the Tn glycoamino acid 48 was treated with TBAF to reveal the corresponding carboxylic acid. Coupling with a di-amino spacer terminated in a protected mercaptoacetamide ($AcSCH_2C(O)(CH_2)_3NH_2$) under the agency of the BOP reagent (benzotriazol-1-oxytris(dimethylamino)phosphonium hexafluorophosphate) gave the corresponding amide in 50% yield for the 2 steps. Removal of the N-terminal Boc group gave amine 49 as its trifluoroacetate salt. The next antigen, Le$^y$, was prepared for coupling by reaction of 47 with TBAF to give acid 50. Coupling of amine 49 with Le$^y$ acid 50, again with the BOP promoter, gave the Tn-Le$^y$ di-peptide 51 in 86% yield. Lastly, Globo-H glycoamino acid 45 was treated with TBAF to give its corresponding acid 52. Removal of the Boc protecting group in 51 followed by coupling with acid 52 gave the Tn-Le$^y$-Globo-H tri-peptide in 64% yield. Finally, the N-terminal Boc group was removed and the resulting anime capped as its acetate to give tripeptide 53 in 95% yield. With all components in place, the ester protecting groups were removed with hydrazine in degassed methanol to give the fully deprotected glycopeptide 54 (FIG. 16) in excellent yield. As discussed below, the inventive glycopeptides prepared as detailed herein can also be conjugated to a suitable carrier protein or lipid.

2) Experimental General.

DuPHOS-Rh$^+$ catalysts were purchased from Strem Chemical Co., Newburyport, Mass. All other commercial materials (purchased from Aldrich-Sigma) were used without further purification. The following solvents were obtained from a dry solvent system (passed through a column of alumina): THF, diethyl ether ($Et_2O$), $CH_2Cl_2$, toluene and benzene. All reactions were performed under an atmosphere of dry $N_2$, unless otherwise noted. NMR ($^1H$ and $^{13}C$) spectra were recorded on a Bruker AMX-400 MHz or Bruker Advance DRX-500 MHz and referenced to residual solvent unless otherwise noted. IR spectra were recorded with a Perkin-Elmer 1600 series-FTIR spectrometer and optical rotations were measured with a Jasco DIP-370 digital polarimeter using a 10-cm path length cell. Low-resolution mass spectral analysis were performed with a JOEL JMS-DX-303 HF mass spectrometer. Analytical TLC was performed on E. Merck silica gel 60 F254 plates and flash column chromatography was performed using the indicated solvents on E. Merck silica gel 60 (40-63 mm) or Sigma H-type silica gel (10-40 mm).

Figure 17:
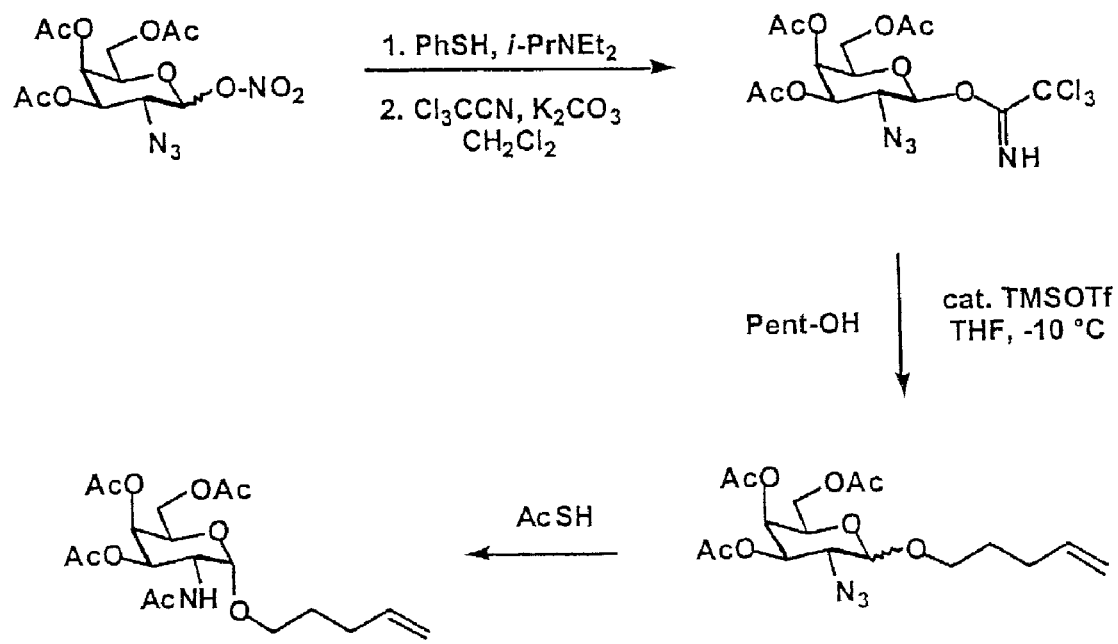
FIG. 17 depicts the synthesis of α-Tn pentenyl glycoside 40.

Procedure for the Synthesis of 40 (as shown in FIG. 17)

Trichloroacetimidate donor. The mixture of azidonitrates as shown in FIG. 17 (1.66 g, 4.41 mmol) was dissolved in $CH_3CN$ (15 mL) and cooled to 0° C. To the stirring solution was added Hunig's base (1.2 equiv., 0.925 mL) and benzene thiol (3.0 equiv., 1.35 mL). The reaction mixture was stirred at 0° C. for 1 hour and the ice bath was removed. After an additional 1 hour at room temperature, the reaction was concentrated under a stream of dry nitrogen. The resulting material was dissolved in a minimum amount of $CHCl_3$ and subjected to flash column chromatography (50% EtOAc/hexanes) to yield the hemiacetals (1.41, 97%). (Note 1: perform this flash in the hood, Note 2: isolate both anomers, which do separate on TLC/flash) The mixture of hemiacetals (1.41 g mg, 4.25 mmol) was dissolved in $CH_2Cl_2$ (8.5 mL) and trichloroacetonitrile (4.25 mL) was added, followed by $K_2CO_3$ (5.0 equiv., 2.93 g). The reaction stirred at room temperature overnight and was filtered through a plug of celite with additional methylene chloride. Concentration of the organic layer, followed by flash column chromatography (10->25% EtOAc/hexanes) gave the β-trichloroacetimidate (1.30 mg, 77%) as a yellow oil. (Note: α-anomer elutes first, then the β-anomer)

Pentenyl glycoside of α-Tn. The TCA-donor as shown in FIG. 17 (1.30 g, 2.72 mmol) was dissolved in THF (0.2M, 13.6 mL) and pentenyl alcohol (5.0 equiv., 1.2 mL) and cooled to −10° C. (acetone-ice bath). A portion of TMSOTf (0.1 equiv., 0.049 mL) was added and the reaction stirred for 1 hour. Solid $NaHCO_3$ was added and the reaction was filtered through celite, concentrated and subjected to flash column chromatography (25% EtOAc/hexanes). (Note 1: The diastereomeric anomers do not separate. Their ratio is determined by $^1H$ NMR. Note 2: The starting materials and products co-elute by TLC—gradient TLC (10% first, then 50%) can be used to visualize the progress of the reaction.) The isolated glycosides were taken up in 10 mL of AcSH and stirred at rt for 2 days. Evaporation of the solvent by a stream of dry nitrogen followed by flash column chromatography (5% acetone/toluene->10% acetone/toluene) gave 620 mg of the α-glycoside (55%) and an undertermined amount of β-glycoside. (Note: Ethyl acetate/hexanes mixtures will also separate anomers, but actone/toluene was determined to be superior.)

General procedure for olefination, 41. The preparation of enamide 41 (Globo-H) is representative of this procedure. The n-pentenyl glycoside 37 (58 mg, 0.0322 mmol) was dissolved in 10:10:1 $MeOH:CH_2Cl_2$:pyridine (3 mL, typically 0.05 M-0.01 M) and cooled to −78° C. A stream of dry ozone was passed through the reaction mixture until a pale blue color persisted. The ozone source was removed and the reaction stirred at −78° C. for an additional 15 minutes, upon which time a stream of dry nitrogen was applied to remove excess ozone. Dimethyl sulfide (50 equivs., 0.118 mL) was added to the cooled mixture, the ice bath was removed and the reaction was allowed to stir at rt for 4 hours. The reaction was diluted with $CH_2Cl_2$ (10 mL), washed with water (50 mL), and back-extracted with additional $CH_2Cl_2$ (2×10 mL). The combined organic layer was dried over anhydrous $MgSO_4$ and concentrated. The crude aldehyde was typically not purified, but was azeotroped dry with anhydrous benzene (3×3 mL) and used directly in the next step.

Phosphonate 33 (1.20 equivs., 14 mg) was dissolved in anhydrous THF (0.3 mL), cooled to −78° C. and tetramethyl guanidine (TMG) (1.25 equivs., 0.005 mL) was added dropwise. The reaction stirred at −78 for 30 minutes, followed by addition of the crude aldehyde (0.0322 mmol) in additional THF (2×0.3 mL, typically 0.1-0.01 M total reaction volume). The reaction was allowed to stir to rt overnight (10-15 h), was extracted with EtOAc (10 mL), washed with 0.05 M aqueous HCl (50 mL) and back-extracted with additional EtOAc (2×10 mL). (Note: All the TMG must be removed prior to asymmetric hydrogenation.) The combined organic layer was dried over $MgSO_4$, concentrated and purified by flash column chromatography (75% EtOAc/hexanes->100% EtOAc) to yield the desired enamide ester 41 as a single isomer. 72%, white foam; $R_f$ 0.85 (100% EtOAc); IR ($CDCl_3$ film) 3373, 2956, 2951, 1748, 1370, 1069 cm$^{-1}$; $^1H$ NMR ($CDCl_3$, 500 MHz) δ 6.65 (d, 1H, J=6.4 Hz), 6.44 (m ,1H), 6.07 (bs, 1H), 5.56 (d, 1H, J=3.1 Hz), 5.44 (d, 1H, J=3.4 Hz), 5.37 (d, 1H, J=3.3 Hz), 5.27 (dd, 1H, J=10.9, 3.0 Hz), 5.22 (d, 1H, J=2.6 Hz), 5.20-5.17 (m, 2H), 5.15 (d, 1H, J=2.1 Hz), 5.13 (d, 1H, J=4.9 Hz), 5.09 (dd, 1H, J=10.7, 7.3 Hz), 5.03 (dd, 1H, J=11.1, 3.3 Hz), 4.96 (dd, 1H, J=9.6, 3.5 Hz), 4.92 (dd, 1H, J=11.2, 3.4 Hz), 4.85 (dd, 1H, J=9.6, 8.0 Hz), 4.73 (dd, 1H, J=10.9, 2.5 Hz), 4.50-4.38 (m, 6H), 4.34 (t, 1H, J=6.2 Hz), 4.26-4.21 (m, 3H), 4.16-4.02 (m, 8H), 3.98 (d, 1H, J=2.0 Hz), 3.94 (t, 1H, J=6.4 Hz), 3.86-3.72 (m, 6H), 3.60-3.57 (m, 1H), 3.48-3.46 (m, 1H), 2.94-2.89 (m, 1H), 2.17-2.14 (m, 1H), 2.11-2.08 (m, 1H), 2.04 (s, 3H), 2.038 (s, 3H), 2.033 (s, 6H), 1.99 (s, 3H), 1.98 (s, 3H), 1.97 (s, 3H), 1.967 (s, 3H), 1.962 (s, 3H), 1.95 (s, 3H), 1.92 (s, 9H), 1.89 (s, 3H), 1.857 (s, 3H), 1.854 (s, 3H), 1.78 (s, 3H), 1.63-1.59 (m, 2H), 1.34 (s, 9H), 1.04 (d, 3H, J=6.5 Hz), 0.93-0.90 (m, 2H), −0.06 (s, 9H); $^{13}$C NMR (CDCl$_3$, 125 MHz) δ 172.20, 171.44, 170.94, 170.65, 170.52, 170.48, 170.44, 170.36, 170.29, 170.21, 170.17, 169.97, 169.63, 169.49, 169.31, 168.85, 164.78, 153.19, 134.70, 126.80, 102.35, 101.99, 101.26, 100.25, 99.12, 998.66, 94.21, 80.24, 76.88, 75.98, 73.61, 73.36, 73.08, 72.80, 72.56, 72.37, 71.81, 71.68, 71.46, 71.28, 70.78, 70.69, 70.67, 70.37, 70.06, 70.01, 68.92, 68.82, 67.99, 67.95, 67.54, 67.28, 66.94, 64.42, 62.14, 61.67, 61.29, 61.09, 60.92, 56.16, 28.12, 27.98, 24.52, 23.80, 23.03, 20.81, 20.73, 20.70, 20.68, 20.64, 20.60, 20.59, 20.54, 20.46, 20.40, 17.37, 17.24, 15.85, 15.48, 14.01, −1.58; HRMS (FAB) calcd. for C$_{88}$H$_{128}$N$_2$O$_{51}$SiNa 2079.7145, found 2079.7174.

Lactose Enamide 34. 88%, white foam; R$_f$ 0.45 (66% EtOAc/hexanes); IR (CDCl$_3$ film) 3407, 3146, 2954, 2898, 1752, 1654, 1233, 1167, 1055 cm$^{-1}$; $^1$H NMR (CDCl$_3$, 400 MHz) δ 6.34 (m, 1H), 6.03 (bs, 1H), 5.22 (d, 1H, J=3.2 Hz), 5.07 (t, 1H, J=9.4 Hz), 4.99 (dd, 1H, J=10.3, 7.9 Hz), 4.83 (dd, 1H, J=10.5, 3.3 Hz), 4.77 (t, 1H, J=9.3 Hz), 4.37-4.33 (m, 3H), 4.20-4.11 (m, 3H), 4.08-4.00 (m, 3H), 3.82-3.65 (m, 5H), 3.49-3.46 (m, 1H), 3.39-3.34 (m, 1H), 2.16-2.14 (m, 1H), 2.11-2.09 (m, 1H), 2.04 (s, 3H), 2.02 (s, 3H), 1.94 (s, 3H), 1.93 (s, 3H), 1.92 (s, 6H), 1.84 (s, 3H), 1.62-1.59 (m, 2H), 1.34 (s, 9H), 0.94-0.89 (m, 2H), 0.05 (s, 9H); $^{13}$C NMR (CDCl$_3$, 100 MHz) δ 170.29, 170.21, 170.03, 169.94, 169.66, 169.50, 168.97, 164.77, 153.20, 134.70, 100.97, 100.31, 80.23, 76.17, 72.69, 72.51, 71.56, 70.87, 70.52, 68.95, 68.83, 66.47, 63.54, 61.88, 60.66, 33.81, 28.05, 27.92, 24.47, 20.73, 20.68, 20.57, 20.51, 20.39, 17.21, −1.60; HRMS (FAB) calcd. for C$_{43}$H$_{67}$NO$_{21}$SiNa 986.4013, found 986.4029.

Lewis$^y$ enamide 43. 85%, white foam; R$_f$ 0.45 (75% EtOAc/hexanes); IR (CDCl$_3$ film) 3371, 2965, 2956, 1746, 1371, 1231, 1069 cm$^{-1}$; $^1$H NMR (CDCl$_3$, 500 MHz) δ 7.94 (d, 2H, J=7.2 Hz), 7.48 (t, 1H), 7.36 (t, 2H), 6.21 (t, 1H), 5.71 (m, 1H), 5.38 (d, 1H, J=3.2 Hz), 5.29 (dd, 1H, J=10.8, 8.8 Hz), 5.22-5.19 (m, 4H), 5.05-4.78 (m, 10H), 4.43 (dd, 1H, J=14.1, 8.0 Hz), 4.36 (dd, 1H, J=9.7, 5.1 Hz), 4.27 (m, 1H), 4.15-4.30 (m, 5H), 3.86 (dd, 1H, J=10.1, 3.3 Hz), 3.78-3.71 (m, 3H), 3.62 (dd, 1H, J=9.8, 1.7 Hz), 3.30 (d, 1H, J=9.6 Hz), 3.18-3.08 (m, 1H), 3.04 (bm, 1H), 2.08 (s, 3H), 2.04 (s, 6H), 2.01 (s, 3H), 1.99 (s, 9H), 1.98 (s, 3H), 1.94 (s, 3H), 1.89 (s, 3H), 1.88 (s, 3H), 1.86 (s, 3H), 1.83 (s, 3H), 1.55-1.52 (m, 2H), 1.32 (s, 9H), 1.01-1.00 (m, 6H), 0.91-0.88 (m, 2H), −0.07 (s, 9H); $^{13}$C NMR (CDCl$_3$, 100 MHz) δ 172.56, 172.40, 172.28, 172.11, 172.06, 172.04, 171.87, 171.77, 171.57, 171.43, 171.20, 171.06, 166.69, 166.32, 154.76, 136.48, 135.14, 131.29, 130.76, 130.19, 127.93, 102.82, 101.83, 101.72, 97.65, 97.11, 81.66, 75.40, 74.80, 74.55, 74.32, 74.01, 72.87, 72.65, 72.35, 72.28, 71.14, 70.66, 69.73, 69.28, 69.15, 69.02, 68.34, 66.43, 65.38, 64.92, 63.36, 62.05, 61.80, 59.87, 29.66, 29.62, 29.48, 25.83, 24.02, 22.51, 22.46, 22.31, 22.14, 22.12, 22.09, 22.0o3, 18.75, 17.30, 17.00, 15.63, −0.04; HRMS calcd. for C$_{79}$H$_{112}$N$_2$O$_{41}$SiNa, found x.

Tn enamide 44. 75%, white foam; R$_f$ 0.80 (100% EtOAc); IR (CDCl$_3$ film)3340, 3071, 2954, 1715, 1663, 1498, 1369, 1218, 1162, 1049 cm$^{-1}$; $^1$H NMR (CDCl$_3$, 400 MHz) δ 6.38 (bs, 1H), 6.15 (bs, 1H), 5.26 (d, 1H, J=2.7 Hz), 5.02 (dd, 1H, J=11.5, 3.2 Hz), 4.79 (s, 1H), 4.48-4.42 (m, 1H), 4.16-4.12 (m, 2H), 4.03 (m, 1H), 3.99-3.92 (m, 2H), 3.62-3.56 (m, 1H), 3.40-3.35 (m, 1H), 2.26-2.16 (m, 2H), 2.03 (s, 3H), 1.92 (s, 3H), 1.86 (s, 3H), 1.84 (s, 3H), 1.67 (s, 3H), 1.33 (s, 9H), 0.94-0.9 (m, 2H), −0.06 (s, 9H); $^{13}$C NMR (CDCl$_3$, 100 MHz) δ 170.28, 170.11, 170.06, 164.70, 134.6, 108.73, 97.26, 80.31, 67.95, 67.05, 66.35, 63.51, 61.67, 47.46, 27.87, 27.49, 22.78, 20.43, 17.05, −1.74; HRMS (FAB) calcd. for C$_{30}$H$_{51}$N$_2$O$_{13}$SiNa 675.3160, found 675.3124.

Fucosyl GM$_1$ enamide 42. 10-22%; R$_f$ 0.25 (10% MeOH/EtOAc); $^1$H NMR (MeOH, 500 MHz) δ 7.94 (d, 2H, J=7.2 Hz), 7.48 (t, 1H), 7.36 (t, 2H), 6.21 (t, 1H), 5.71 (m, 1H), 5.38 (d, 1H, J=3.2 Hz), 5.29 (dd, 1H, J=10.8, 8.8 Hz), 5.22-5.19 (m, 4H), 5.05-4.78 (m, 10H), 4.43 (dd, 1H, J=14.1, 8.0 Hz), 4.36 (dd, 1H, J=9.7, 5.1 Hz), 4.27 (m, 1H), 4.15-4.03 (m, 5H), 3.86 (dd, 1H, J=10.1, 3.3 Hz), 3.78-3.71 (m, 3H), 3.62 (dd, 1H, J=9.8, 1.7 Hz), 3.39-3.37 (m, 1H), 3.30 (bd, 1H, J=9.6 Hz), 3.18-3.08 (m, 1H), 3.04 (bm, 1H), 2.08 (s, 3H), 2.04 (s, 6H), 2.01 (s, 3H), 1.99 (s, 9H), 1.98 (s, 3H), 1.94 (s, 3H), 1.89 (s, 3H), 1.88 (s, 3H), 1.86 (s, 3H), 1.83 (s, 3H), 1.5-1.52 (m, 2H), 1.32 (s, 9H), 1.01-1.00 (m, 6H), 0.91-0.88 (m, 2H), −0.07 (s, 9H).

General procedure for asymmetric hydrogenation. Under an inert deoxygenated atmosphere, [(COD)Rh-((S, S)-Et-DuPHOS)]$^+$OTf (0.005 mmol, 5 mol %) and the desired enamide ester (0.100 mmol) were dissolved in deoxygenated anhydrous THF (10 mL, 0.01 M) in a Fischer-Porter tube. The reaction vessel was pressurized with 50 psi of H$_2$ after three vacuum/H$_2$ cycles and stirred at 25° C. for 24-36 hours, or until the reaction turned from light orange to brown in color. The vessel was depressurized, the mixture concentrated and purified through a short plug of silica gel to yield the glycoamino acid.

Lactose glycoamino acid 35. 98%; R$_f$ 0.45 (66% EtOAc/hexanes); $^1$H NMR (C$_6$D$_6$, 500 MHz) δ 5.54 (dd, 1H, J=10.4, 8.0 Hz), 5.48 (d, 1H, J=3.2 Hz), 5.39 (t, 1H, J=9.2 Hz), 5.21 (dd, 1H, J=6.2, 1.1 Hz), 5.12 (d, 1H, J=3.1 Hz), 5.09 (d, 1H, J=3.3 Hz), 4.54-4.51 (m, 2H), 4.33 (d, 1H, J=7.8 Hz), 4.19-4.06 (m, 6H), 3.74-3.58 (m, 2H), 3.49-3.40 (m, 1H), 3.38 (d, 1H, J=10.9 Hz), 3.23-3.16 (m, 2H), 1.96 (s, 3H), 1.94 (s, 3H), 1.90 (s, 3H), 1.74 (s, 3H), 1.73 (s, 3H), 1.64 (s, 3H), 1.51 (s, 3H), 1.45 (s, 9H), 0.91-0.88 (m, 2H), −0.10 (s, 9H); $^{13}$C NMR (C$_6$D$_6$, 100 MHz) δ 173.26, 170.44, 170.41, 170.18, 170.09, 169.35, 156.05, 102.98, 101.06, 79.73, 77.59, 74.13, 73.21, 72.73, 71.94, 71.19, 70.10, 69.58, 67.28, 63.76, 63.01, 61.25, 54.41, 34.76, 32.76, 28.62, 28.80, 25.75, 22.45, 21.18, 20.93, 20.84, 20.76, 20.57, 20.46, 20.15, 17.83, −1.29; HRMS (FAB) calcd. for C$_{42}$H$_{67}$NO$_{22}$SiNa 988.3870, found 988.3821.

Globo-H glycoamino acid 45. 98%; IR (CDCl$_3$ film) 3373, 2956, 2951, 1748, 1370, 1069 cm$^{-1}$; $^1$H NMR (C$_6$D$_6$, 500 MHz) δ 6.54 (d, 1H, J=6.5 Hz), 5.89 (d, 1H, J=3.5 Hz), 5.86 (d, 1H, J=3.1 Hz), 5.74-5.69 (m, 3H), 5.50-5.46 (m, 2H), 5.39-5.34 (m, 2H), 5.31 (dd, 1H, J=13.4, 0.7 Hz), 5.26-5.19 (m, 2H), 5.15 (d, 1H, J=8.1 Hz), 5.09-5.06 (m, 3H), 4.82 (dd, 1H, J=10.9, 2.5 Hz), 4.74-4.72 (m, 1H), 4.70-4.69 (m, 1H), 4.66 (t, 1H), 4.58-4.49 (m, 3H), 4.45-4.41 (m, 2H), 4.37-4.33 (m, 2H), 4.24-4.22 (m, 2H), 4.20-4.12 (m, 3H), 4.04-4.01 (m, 2H), 3.91-3.86 (m, 3H), 3.71-3.69 (m, 2H), 3.64-3.57 (m, 2H), 4.43 (t, 1H), 3.28-3.27 (m, 1H), 3.23-3.21 (m, 1H), 2.38 (s, 3H), 2.30 (s, 3H), 2.19 (s, 3H), 2.01 (s, 3H), 1.98 (s, 3H), 1.93 (s, 3H), 1.92 (s, 3H), 1.90 (s, 3H), 1.89 (s, 3H), 1.88 (s, 3H), 1.84 (s, 3H), 1.82 (s, 3H), 1.75 (s, 3H), 1.73 (s, 3H), 1.71 (s, 3H), 1.68 (s, 3H), 1.64 (s, 3H), 1.61 (s, 3H), 1.46 (s, 3H), 1.45 (s, 9H), 1.26-1.22 (m, 2H), 1.08 (d, 3H, J=6.5 Hz), 0.89 (t, 2H), −0.10 (s, 9H); $^{13}$C NMR (CDCl$_3$, 125 MHz) δ 172.87, 172.28, 171.52, 170.77, 170.61, 170.56, 170.45, 170.40, 170.29, 170.07, 169.75, 169.58, 169.44, 168.95, 155.38, 102.00, 101.29, 100.38, 99.21, 98.77, 94.31, 73.65, 73.34, 73.10, 72.61, 72.38, 71.84, 71.65, 71.58, 71.30, 70.81, 70.68, 70.17, 70.06, 69.59, 69.09, 68.85, 68.05, 67.99, 67.56, 67.30, 64.46, 63.64, 62.16, 61.74, 61.35, 61.12, 60.96, 56.11, 53.45, 32.30, 29.65, 28.96, 28.29, 28.10, 23.11, 21.69, 20.88, 20.85, 20.80, 20.76, 20.72, 20.67, 20.62, 20.55, 20.48, 17.31, 15.88, −1.55; HRMS (FAB) calcd. for C$_{88}$H$_{130}$N$_2$O$_{51}$SiNa 2081.7302, found 2081.7247.

Lewis$^y$ glycoamino acid 42. 99%; IR (CDCl$_3$ film) cm$^{-1}$; $^1$H NMR (CDCl$_3$, 400 MHz) δ 8.24 (d, 2H, J=8.4 Hz), 7.27-7.18 (m, 3H), 5.83 (dd, 1H, J=10.1, 8.0), 5.78 (d, 1H, J=3.2 Hz), 5.76 (d, 1H, J=3.0 Hz), 5.74-5.71 (m, 2H), 5.69 (d, 1H, J=3.2 Hz), 5.66 (d, 1H, J=3.3 Hz), 5.55 (d, 1H, J=3.3 Hz), 5.50 (m, 1H), 5.47 (d, 1H, J=3.8 Hz), 5.41-5.27 (m, 5H), 4.93 (d, 1H, J=7.8 Hz), 4.86 (d, 1H, J=8.6 Hz), 4.77-4.70 (m, 2H), 4.62 (d, 1H, J=7.8 Hz), 4.56-4.53 (m, 1H), 4.47-4.35 (m, 5H), 4.34-4.25 (m, 4H), 4.11-4.00 (m, 5H), 3.92-3.89 (m, 1H), 3.75-3.65 (m, 3H), 3.64-3.61 (t, 1H), 3.28-2.24 (m, 1H), 2.22 (s, 3H), 2.21 (s, 3H), 1.93 (s, 3H), 1.90 (s, 3H), 1.82 (s, 3H), 1.78 (s, 3H), 1.73 (s, 3H), 1.72 (s, 3H), 1.66 (s, 3H), 1.65 (s, 3H), 1.64 (s, 3H), 1.63 (s, 3H), 1.51 (s, 3H), 1.50 (d, 3H, J=6.5 Hz), 1.46 (s, 9H), 1.38 (d, 3H, J=6.5 Hz), 1.33-1.27 (m, 2H), 1.22-1.21 (m, 2H), 0.91-0.80 (m, 4H), −0.12 (s, 9H); $^{13}$C NMR ($C_6D_6$, 100 MHz) δ 172.86, 171.05, 170.59, 170.52, 170.46, 170.37, 170.26, 170.01, 169.97, 169.90, 165.44, 155.61, 133.24, 130.40, 101.59, 100.98, 100.71, 97.09, 96.21, 79.22, 76.42, 74.77, 74.04, 73.69, 72.03, 71.65, 71.14, 70.14, 69.20, 68.66, 68.55, 68.20, 67.99, 67.25, 65.67, 64.56, 63.23, 62.41, 61.33, 60.94, 58.23, 53.84, 39.12, 32.25, 29.30, 28.41, 22.88, 22.01, 20.93, 20.66, 20.58, 20.47, 20.40, 20.18, 20.02, 17.40, 16.36, 15.94, −1.62; HRMS (FAB) cald. for $C_{79}H_{114}N_2O_{41}SiNa$ 1797.6558, found 1797.6528.

Tn glycoamino acid 43. 99%; IR ($CDCl_3$ film) 3362, 2954, 2990, 2871, 1749, 1716, 1683, 1668, 1520, 1369, 1249, 1164, 1047 cm$^{-1}$; $^1$H NMR ($CDCl_3$, 400 MHz) δ 5.66 (d, 1H, J=9.3 Hz), 5.24 (d, 1H, J=2.8 Hz), 5.03 (dd, 1H, J=11.4, 3.3 Hz), 4.98 (d, 1H, J=8.1), 4.73 (d, 1H, J=3.3 Hz), 4.48-4.42 (m, 1H), 4.17-4.07 (m, 3H), 4.05-3.93 (m, 3H), 3.59-3.54 (m, 1H), 3.33-3.27 (m, 1H), 2.04 (s, 1H), 1.93 (s, 3H), 1.87 (s, 3H), 1.86 (s, 3H), 1.73-1.70 (m, 1H), 1.57-0.150 (m, 3H), 1.31 (s, 9H), 0.91-0.87 (m, 2H), −0.06(s, 9H); $^{13}$C NMR ($C_6D_6$, 100 MHz) δ 173.44, 171.04, 170.57, 170.35, 169.89, 156.06, 98.59, 79.82, 69.29, 68.30, 68.07, 67.43, 64.01, 62.33, 54.33, 48.63, 32.87, 29.05, 28.76, 23.24, 22.82, 20.89, 20.66, 20.47, 17.85, −1.28; HRMS (FAB) cald. for $C_{30}H_{53}N_2O_{13}SiNa$ 677.3316, found 677.3352.

General procedure for cross-metathesis reaction. The preparation of enamide 60 (galactose) is representative of this procedure.

Step 1: Protection of L-allylglycine

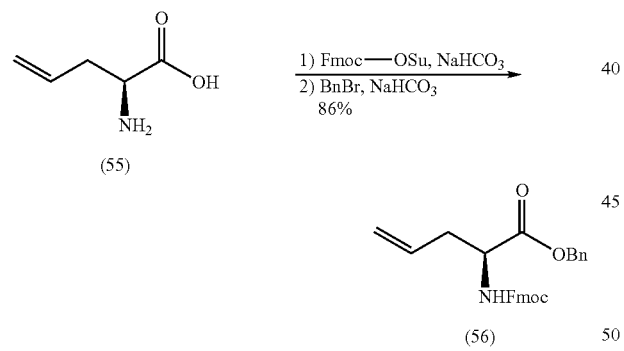

L-allylglycine (55, 2.5 g, 21.7 mmol) and Fmoc-O-succinimide (8.6 g, 25.5 mmol, 1.2 equiv) were mixed in 200 mL acetone:water (3:1) mixture and treated with solid $NaHCO_3$ (18.2 g, 217 mmol, 10.0 equiv). The reaction was stirred at rt for 24 h, diluted with EtOAc (200 mL) and washed with 1N HCl (300 mL) and brine (300 mL). The organic layer was dried ($MgSO_4$) and concentrated. The crude carbamate was dissolved in DMF (100 mL) and treated with $NaHCO_3$ (5.5 g, 65.1 mmol, 3.0 equiv) and benzyl bromide (25.4 mL, 217 mmol, 10.0 equiv). The reaction mixture was stirred at rt for 24 h, diluted with EtOAc (150 mL) and washed with water (2×200 mL) and brine (200 mL). The organic layer was dried ($MgSO_4$) and purified by silica gel chromatography (12-20% EtOAc/hexane) affording 7.9 g (86%) of 55 as a white solid:
$^1$H NMR (400 MHz) δ 7.77 (d, J=7.5 Hz, 2H), 7.59 (d, J=7.5 Hz, 2H), 7.43-7.29 (m, 9H), 5.71-5.62 (m, 1H), 5.34 (d, J=8.3 Hz, 1H), 5.20 (ABq, J=8.2 Hz, 2H), 5.15-5.08 (m, 2H), 4.56-4.53 (m, 1H), 4.39 (d, J=7.2 Hz, 2H), 4.23 (t, J=7.2 Hz, 1H), 2.62-2.50 (m, 2H); LRMS (ESI) $M_{calc.}$ 427.1 for $C_{27}H_{25}NO_4$, $(M+Na)_{found}$ 450.1.

Step 2: Cross Metathesis Reaction:

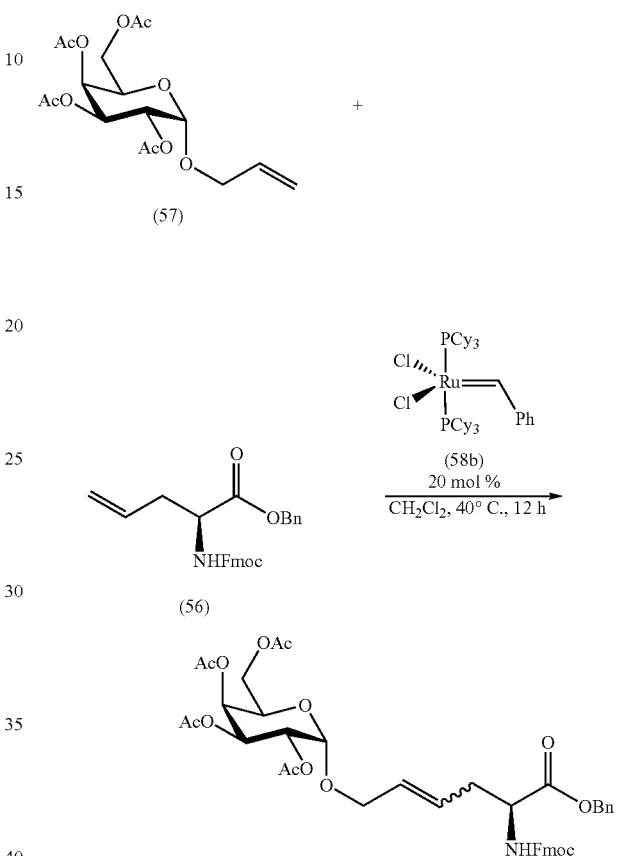

Peracetylated O-allyl-D-galactose (57, 185 mg, 0.47 mmol) was mixed with Fmoc-L-allylglycine-OBn (56, 1.01 g, 2.38 mmol, 5.0 equiv) in $CH_2Cl_2$ (3 mL) and treated with bis(tricyclohexylphosphine) ruthenium Grubbs catalyst 58 (39 mg, 0.047 mmol, 0.1 equiv). The reaction was heated to reflux. After 6 h, another 0.1 equiv of catalyst was further added. The reaction was cooled to rt after 12 h (total) and purified by silica gel chromatography (20-28-32-40% EtOAc/hexanes) to afford metathesis product 59 (250 mg, 70%), along with 392 mg (39% of 5.0 equiv) recovered 58.

Step 3: Catalytic Hydrogenation:

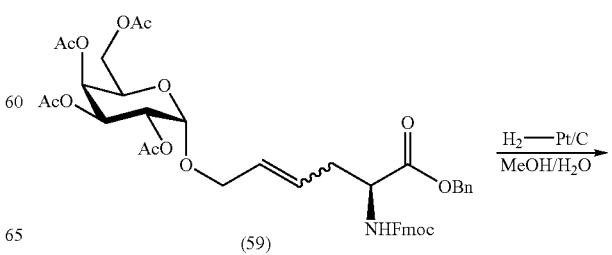

-continued

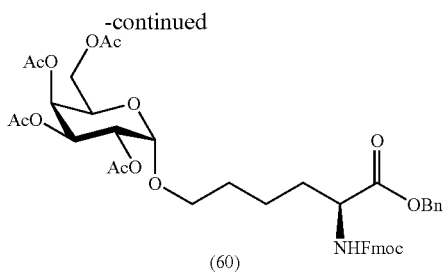

(60)

The E:Z mixture 59 (26 mg, 0.03 mmol) was dissolved in 1.1 mL methanol:water (10:1) and treated with 3% Pt/C (26 mg). The reaction flask was stirred under a hydrogen balloon for 12 h, followed by filtration to remove the solid catalyst. The filtrate was concentrated and purified by silica gel chromatography (64% EtOAc/hexane, with 1% AcOH) to afford amino acid 60 (20 mg, 87%) as a white solid:

$^1$H NMR (400 MHz) □ 7.77 (d, J=7.5 Hz, 2H), 7.61 (d, J=7.5 Hz, 2H), 7.40 (t, J=7.5 Hz, 2H), 7.31 (t, J=7.5 Hz, 2H), 5.56 (d, J=8.1 Hz, 1H), 5.45 (d, J=3.0 Hz, 1H), 5.34 (dd, J=10.0, 3.0 Hz, 1H), 5.21-5.10 (m, 2H), 4.43-4.38 (m, 3H), 4.25-4.16 (m, 3H), 4.25-4.00 (m, 1H), 3.79-3.76 (m, 1H), 3.47-3.44 (m, 1H), 2.16 (s, 3H), 2.08 (s, 3H), 2.05 (s, 3H), 2.00 (s, 3H), 1.89-1.86 (m, 2H), 1.67-1.65 (m, 2H), 1.55-1.48 (m, 2H); LRMS (ESI) $M_{calc.}$ 699.2 for $C_{35}H_{41}NO_{14}$, (M+Na)$_{found}$ 722.3.

Globo-H Glycoamino Acid 103

Peracetylated Globo-H allyl glycoside (20 mg, 0.011 mmol, Ref: Park, T. K.; Kim, I. J.; Hu, S.; Bilodeau, M. T.; Randolph, J. T.; Kwon, O.; Danishefsky, S. J. *J. Am. Chem. Soc.* 1996, 118, 11488-11500) and Fmoc-L-allylglycine benzyl ester (24 mg, 0.056 mmol, 5.0 equiv) in methylene chloride (0.05 mL) were treated bis(tricyclohexylphosphine) ruthenium Grubbs catalyst (2 mg, 0.001 mmol, 0.1 equiv). The reaction was heated to reflux. After 6 h, another 0.1 equiv of catalyst was further added. The reaction was cooled to rt after 12 h (total) and purified by silica gel chromatography (80-90% EtOAc/hexanes) to afford metathesis product (16 mg, 69%). The E:Z mixture (20 mg, 0.009 mmol) was dissolved in 0.55 mL methanol:water (10:1) and treated with 3% Pt/C (20 mg). The reaction flask was stirred under a hydrogen balloon for 12 h, followed by filtration to remove the solid catalyst. The filtrate was concentrated and purified by silica gel chromatography (EtOAc-1% AcOH/EtOAc) to afford Globo-H amino acid (17 mg, 90%) as a white solid: $^1$H NMR (400 MHz, CDCl$_3$) δ 7.77 (d, J=7.5 Hz, 2H), 7.59 (d, J=7.5 Hz, 2H), 7.40 (t, J=7.5 Hz, 2H), 7.31 (t, J=7.5 Hz, 2H), 6.77 (d, J=8.0 Hz, 1H), 5.59 (d, J=2.7 Hz, 1H), 5.54 (d, J=10.0 Hz, 1H), 5.47 (d, J=3.0 Hz, 1H), 5.40 (d, J=3.0 Hz, 1H), 5.30 (dd, J=11.0, 3.1 Hz, 1H), 5.27-5.20 (m, 3H), 5.05-4.98 (m, 2H), 4.94 (dd, J=10.5, 3.1 Hz, 1H), 4.87 (t, J=8.5 Hz, 1H), 4.76 (dd, J=10.1, 2.3 Hz, 1H), 4.60-4.34 (m, 10H), 4.35-4.23 (m, 2H), 4.20-3.94 (m, 11H), 3.93-3.72 (m, 5H), 3.69-3.62 (m, 1H), 3.58-3.52 (m, 1H), 3.21-3.06 (m, 1H), 2.19-2.14 (m, 12H), 2.12 (s, 3H), 2.11-2.02 (m, 27H), 2.01 (s, 3H), 1.99-1.95 (m, 6H), 1.93 (s, 3H), 1.82-1.68 (m, 2H), 1.67-1.56 (m, 2H), 1.53-1.40 (m, 2H), 1.15 (d, J=6.2 Hz, 3H); LRMS (ESI) $M_{calc}$ 2080.6 for $C_{93}H_{120}N_2O_{51}$, (M+H)$_{found}$ 2081.9, (M+Na)$_{found}$ 2103.7.

General procedure for N-Boc deprotection. The desired glycoamino acid (0.100 mmol) was dissolved in CH$_2$Cl$_2$ (3.0 mL) with stirring. Trifluoroacetic acid (TFA) (3.0 mL) was added dropwise and the reaction stirred at rt for 1 hour. The mixture was then concentrated with a stream of dry N$_2$ and azeotroped with anhydrous benzene (2×5 mL) to give the crude amine as its TFA salt which was typically used without further purification.

General procedure for TSE ester deprotection. The desired glycoamino acid (0.100 mmol) was dissolved in THF (1.0-3.0 mL) and cooled to 0° C. A 1.0 M solution of TBAF in THF (0.250 mmol, 2.5 equivs.) was added dropwise, the ice bath removed and the reaction stirred at rt for 1-2 hour, as judged by TLC. (Note: prolonged reaction times, i.e. >10 h, may result in deacetylation.) The reaction mixture was diluted with CH$_2$Cl$_2$ (10 mL), washed with 0.05M aqueous HCL (50 mL), and back-extracted with additional CH$_2$Cl$_2$ (2×10 mL). The combined organic layer was dried over anhydrous Mg$_2$SO$_4$ and concentrated. The crude acid was typically used without further purification. Acid 36: $^1$H NMR (CDCl$_3$, 400 MHz) δ 5.22 (d, 1H, J=2.8 Hz), 5.07 (t, 1H, J=9.3 Hz), 4.98 (dd, 1H, J=10.4, 5.9 Hz), 4.84 (dd, 1H, J=10.4, 3.5 Hz), 4.75 (dd, 1H, J=9.5, 8.0 Hz), 4.42-4.35 (m, 2H), 4.34-4.31 (m, 1H), 4.15-4.14 (m, 1H), 4.03-3.94 (m, 4H), 3.77-3.65 (m, 5H), 3.49-3.45 (m, 1H), 3.37-3.33 (m, 1H), 3.10-3.07 (m, 1H), 2.03 (s, 3H), 2.00 (s, 3H), 1.96 (s, 3H), 1.94 (s, 3H), 1.92 (s, 3H), 1.84 (s, 3H), 1.51-1.46 (m, 4H), 1.32 (s, 9H).

General procedure for BOP reagent promoted peptide coupling. The desired amine and acid (equimolar amounts) were azeotroped together with anhydrous benzene and dried under high vacuum. The mixture was dissolved in CH$_2$Cl$_2$ (0.1-0.05M), BOP reagent (1.25 equivs) was added and the solution cooled to 0° C. over 15 minutes. A dropwise addition of Hunig's base (15 equivs.) was followed by removal of the ice bath. The reaction stirred at rt for 2-4 h, as judged by TLC. Concentration of the reaction mixture was followed by purification by flash column chromatography. In cases where bi-product HMPA was difficult to remove, the peptide was subjected to sephadex purification (LH-20, MeOH).

N-Boc Tn with mercatoacetamide spacer. 54%, colorless oil; R$_f$ 0.35 (10% MeOH/EtOAc); IR (CDCl$_3$ film) 3303, 3078, 2974, 2935, 2872, 1748, 1703, 1692, 1658, 1535, 1440, 1369, 1245, 1166 cm$^{-1}$; $^1$H NMR (MeOH, 400 MHz) δ 5.40 (d, 1H, J=2.9 Hz), 5.13 (dd, 1H, J=11.6, 3.2 Hz), 4.42 (dd, 1H, J=11.5, 3.5 Hz), 4.23 (t, 1H, J=6.7 Hz), 4.14-4.05 (m, 2H), 3.96 (m, 1H), 3.74-3.69 (m, 1H), 3.60 (s, 2H), 3.49-4.44 (m, 1H), 3.26-3.13 (m, 5H), 2.36 (s, 3H), 2.12 (s, 3H), 2.02 (s, 3H), 1.94 (s, 3H), 1.93 (s, 3H), 1.67-1.59 (m, 6H), 1.43 (s, 9H); $^{13}$C NMR (CDCl$_3$, 100 MHz) δ 195.59, 172.53, 170.78, 170.54, 170.39, 170.30, 168.51, 155.62, 97.59, 79.95, 68.29, 67.96, 67.26, 66.38, 61.83, 60.28, 54.58, 47.62, 36.47, 35.97, 33.02, 31.92, 30.18, 29.14, 28.37, 28.17, 23.07, 22.35, 20.68, 20.64; HRMS (MALDI) cald. for $C_{32}H_{52}N_4O_{14}SNa$ 771.3093, found 771.3070.

Le$^y$/Tn dipeptide 51. 86%, white film; R$_f$ 0.65 (20% MeOH/EtOAc); $^1$H NMR (MeOH, 400 MHz) δ 8.06 (d, 2H, J=7.4 Hz), 7.63 (t, 1H), 7.51 (t, 2H), 5.55 (d, 1H, J=3.3 Hz), 5.40 (d, 1H, 2.7 Hz), 5.38 (d, 1H, J=2.7 Hz), 5.32 (d, 1H, J=3.3 Hz), 5.29 (d, 1H, J=4.1 Hz), 5.26 (d, 1H), 5.21-5.12 (m, 5H), 5.01 (q, 1H), 4.93 (m, 2H), 4.90 (m, 2H), 4.79 (d, 1H, J=10.8 Hz), 4.71 (d, 1H), 4.64 (d, 1H), 4.50-4.01 (m, 15H), 3.88-3.60 (m, 7H), 3.60 (s, 2H), 3.51-3.42 (m, 2H), 3.20-3.13 (m, 5H), 2.36 (s, 3H), 2.20 (s, 3H), 2.16 (s, 3H), 2.15 (s, 3H), 2.13 (s, 3H), 2.11 (s, 3H), 2.09 (s, 3H), 2.08 (s, 3H), 2.07 (s, 3H), 2.05 (s, 3H), 2.02 (s, 6H), 1.97 (s, 6H), 1.95 (s, 3H), 1.94 (s, 9H), 1.91 (s, 3H), 1.68-1.63 (m, 8H), 1.44 (s, 9H), 1.15 (d, 3H, J=6.3 Hz), 1.14 (d, 3H, J=6.3 Hz); $^{13}$C NMR (MeOH, 100 MHz) δ 196.26, 175.39, 174.30, 173.75, 173.22, 172.80, 172.72, 172.56, 172.51, 172.44, 172.39, 172.30, 172.19, 172.12, 171.85, 171.75, 171.64, 170.76, 166.77, 158.24, 134.92, 131.29, 131.10, 129.99, 103.53, 102.80, 101.77, 99.12, 97.81, 97.30, 80.90, 78.50, 75.88, 75.11, 74.65, 74.32, 73.01, 72.70, 72.56, 72.47, 72.18, 71.91, 70.86, 69.84, 69.62, 69.42, 69.09, 68.90, 67.84, 66.43, 65.43, 63.50, 63.21, 62.57, 61.68, 56.42, 55.96, 54.89, 38.21, 37.74, 37.12, 33.89, 32.72, 30.42, 30.21, 30.01, 28.92, 23.72, 23.44, 22.93, 22.73, 21.32, 21.13, 20.97, 20.86, 20.74, 20.60, 16.67, 16.29; HRMS (MALDI) cald. for $C_{101}H_{144}N_6O_{52}SiNa$ 2327.8421, found 2327.8536.

N-Boc Globo-H/Le$^y$/Tn tripeptide. 64%, white film; $R_f$ 0.45 (10% MeOH/EtOAc); $^1$H NMR (MeOH, 400 MHz) δ 8.05 (d, 2H, J=7.4 Hz), 7.63 (t, 1H), 7.50 (t, 2H), 5.64 (d, 1H, J=2.8 Hz), 5.55 (d, 1H, J=3.6 Hz), 5.43 (d, 1H, J=3.2 Hz), 5.40 (d, 1H, J=2.4 Hz), 5.37 (d, 1H, J=2.5 Hz), 5.32-5.25 (m, 7H), 5.23-5.12 (m, 10H), 5.08-5.05 (m, 2H), 5.00 (d, 1H, J=7.5 Hz), 4.96 (d, 1H, J=3.1 Hz), 4.94 (m, 2H), 4.90 (m, 2H), 4.86 (m, 2H), 4.82-4.77 (m, 3H), 4.72-4.70 (m, 3H), 4.64-4.59 (m, 3H), 4.51-4.35 (m, 9H), 4.32-3.92 (m, 31H), 3.86-3.67 (m, 13H), 3.60 (s, 2H), 3.59 (m, 1H), 3.51 (m, 1H), 3.47-3.44 (m, 2H), 3.24-3.18 (m, 5H), 2.36 (s, 3H), 2.19 (s, 3H), 2.17 (s, 3H), 2.16 (s, 3H), 2.15 (s, 3H), 2.14 (s, 3H), 2.138 (s, 3H), 2.133 (s, 3H), 2.12 (s, 3H), 2.116 (s, 3H), 2.115 (s, 3H), 2.10 (s, 3H), 2.096 (s, 3H), 2.090 (s, 3H), 2.08 (s, 3H), 2.07 (s, 31H), 2.05 (s, 6H), 2.04 (s, 3H), 2.039 (s, 3H), 2.031 (s, 9H), 2.02 (s, 6H), 2.00 (s, 3H), 1.97 (s, 3H), 1.96 (s, 3H), 1.94 (s, 18H), 1.93 (s, 3H), 1.91 (s, 3H), 1.86 (s, 3H), 1.67-1.52 (m, 16H), 1.43 (s, 9H), 1.32 (d, 3H), 1.16-1.13 (m, 6H).

N-Ac capped Globo-H/Le$^y$/Tn tripeptide 53. 95%, white film; $R_f$ 0.35 (10% MeOH/EtOAc); $^1$H NMR (CDCl$_3$, 500 MHz) δ 8.00 (d, 2H, J=7.3 Hz), 7.59 (t, 1H), 7.47 (t, 2H), 6.70 (d, 1H, J=6.3 Hz), 6.61 (d, 1H, J=9.8 Hz), 5.56 (d, 1H, J=2.9 Hz), 5.47 (d, 1H, J=2.1 Hz), 5.44 (d, 1H, J=3.4 Hz), 5.37 (d, 1H, J=3.2 Hz), 5.34 (d, 1H, J=2.7 Hz), 5.32-5.28 (m, 7H), 5.28 (d, 1H), 5.22-5.19 (m, 3H), 5.15-5.10 (m, 6H), 5.08 (m, 1H), 5.06 (m, 1H), 5.01-4.87 (m, 13H), 4.85-4.82 (m, 1H), 4.55-4.35 (m, 15H), 4.26-4.23 (m, 4H), 4.15-4.02 (m, 20H), 3.98-3.93 (m, 5H), 3.88-3.72 (m, 12H), 3.66 (m, 1H), 3.59-3.58 (m, 1H), 3.52 (s, 2H), 3.49-3.38 (m, 5H), 3.20 (m, 6H), 3.02-2.98 (m, 1H), 2.37 (s, 3H), 2.17 (s, 3H), 2.139 (s, 6H), 2.133 (s, 6H), 2.12 (s, 6H), 2.11 (s, 3H), 2.10 (s, 3H), 2.08 (s, 12H), 2.07 (s, 3H), 2.06 (s, 12H), 2.05 (s, 3H), 2.046 (s, 3H), 2.041 (s, 3H), 2.03 (s, 3H), 2.019 (s, 3H), 2.015 (s, 9H), 1.98 (s, 3H), 1.97 (s, 6H), 1.955 (s, 3H), 1.951 (s, 3H), 1.94 (s, 3H), 1.92 (s, 3H), 1.88 (s, 3H), 1.76-1.57 (m, 10H), 1.44-1.41 (m, 4H), 1.38-1.30 (m, 4H), 1.23-1.20 (m, 2H), 1.13-1.09 (m, 9H).

Fully Deprotected Globo-H/Le$^y$/Tn tripeptide 54. 98%, white film; $^1$H NMR (D$_2$O, 500 MHz) δ 5.30 (s, 1H, J=2.8 Hz), 5.25 (d, 1H, J=3.7 Hz), 5.13 (d, 1H, J=3.5 Hz), 4.91-4.87 (m, 3H), 4.75-4.74 (m, 1H), 4.63 (d, 1H, J=7.4 Hz), 4.57-4.48 (m, 3H), 4.41-4.38 (m, 2H), 4.31 (m, 1H), 4.29-4.24 (m, 6H), 4.18-4.12 (m, 3H), 4.05-3.56 (m, 58H), 3.50-3.46 (m, 3H), 3.32-3.24 (m, 5H), 2.06 (s, 3H), 2.05 (s, 3H), 2.04 (s, 6H), 1.82-1.65 (m, 14H), 1.47-1.42 (m, 6H), 1.29 (d, 3H, J=6.5 Hz), 1.25 (d, 3H, J=7.4 Hz), 1.23 (d, 3H, J=7.0 Hz); $^{13}$C NMR (D$_2$O, 125 MHz) δ 175.11, 174.85, 174.81, 174.68, 174.44, 174.25, 174.13, 171.64, 164.59, 104.37, 103.71, 103.25, 102.78, 102.39, 102.44, 100.83, 100.59, 99.80, 99.67, 98.96, 97.34, 82.76, 79.18, 78.65, 77.55, 76.74, 76.50, 75.88, 75.78, 75.45, 75.24, 75.18, 75.00, 74.90, 73.96, 73.47, 73.35, 72.50, 72.32, 72.24, 72.09, 71.31, 71.24, 70.53, 70.44, 70.40, 70.16, 70.11, 69.90, 69.57, 69.50, 69.12, 68.93, 68.87, 68.66, 68.42, 68.22, 68.12, 68.08, 67.29, 67.17, 61.85, 61.68, 61.37, 61.34, 61.20, 60.74, 60.48, 60.19, 56.57, 54.02, 52.02, 50.41, 41.31, 37.09, 31.07, 30.79, 28.69, 28.64, 28.36, 22.72, 22.64, 22.40, 22.36, 22.25, 22.05, 22.01, 21.97, 21.93, 21.87, 21.84, 15.84, 15.70.

3) Preparation of Polycarbohydrate (Globo H, Le$^y$, Tn) Cluster-KLH Conjugate Using Bifunctional Cross Linker Method:

Polycarbohydrate (globo H, Le$^y$, Tn) cluster is conjugated as described below using maleimidobenzoyl-N-hydroxysuccinimide ester (MBS) which is a heterobifunctional reagant. At neutral pH it crosslinks amino groups with succinimide and then with thiol groups with maleimide. The thiol group is provided by the cysteine residue of peptide backbone of cluster and the amino groups by the N-terminal and lysine side-chain of the KLH. After linkage MBS to KLH the unreacted MBS is purified by column and cross-linked to cysteine on the synthetic polycarbohydrate cluster. The unbound antigen is removed by passage of the reaction mixture through a CentriPrep 30 filter with a 30,000 molecular weight cut-off. The epitope ratio is then calculated by estimation of protein content by standard method and carbohydrate by high-pH anion-exchange chromatography with pulsed amperometric detection (HPAEC-PAD) method.

4) Preparation of Polycarbohydrate (TF, Le$^y$, Tn) Cluster-KLH Conjugate Using Bifunctional Cross Linker Method:

Polycarbohydrate (TF, Le$^y$, Tn) cluster is prepared in a similar fashion as that described in 3) above.

D. Example 4

Synthesis of N-alkylene Gb3 and Conjugates Thereof

1) Discussion of Synthesis:

As discussed above, in one aspect of the invention, the synthesis of Gb3 pentenyl glycoside 80 is provided (See Scheme 2). In one embodiment of the present invention, the synthesis of the disaccharide 73 starting from the known monosaccharides 68 and 70, was first undertaken. Saccharide 68 was protected as its dioxolopyranone 69. Selective protection of 70 gave bibenzyl ether 71. Coupling of 70 and 71 under suitable conditions gives the desired disaccharide 72, which, upon reaction with BnBr in the presence of NaH, yields disccharide 73. Partial deprotection of 73, followed by reprotection the primary and equatorial hydroxyl groups as their benzyl ethers gives intermediate 75, which, upon reaction with fluoro monosaccharide donor 76 under suitable conditions, gives trisaccharide construct 77.

Scheme 2

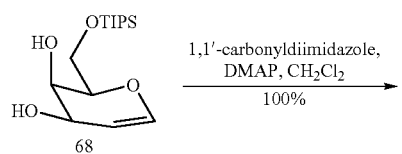

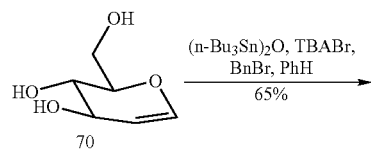

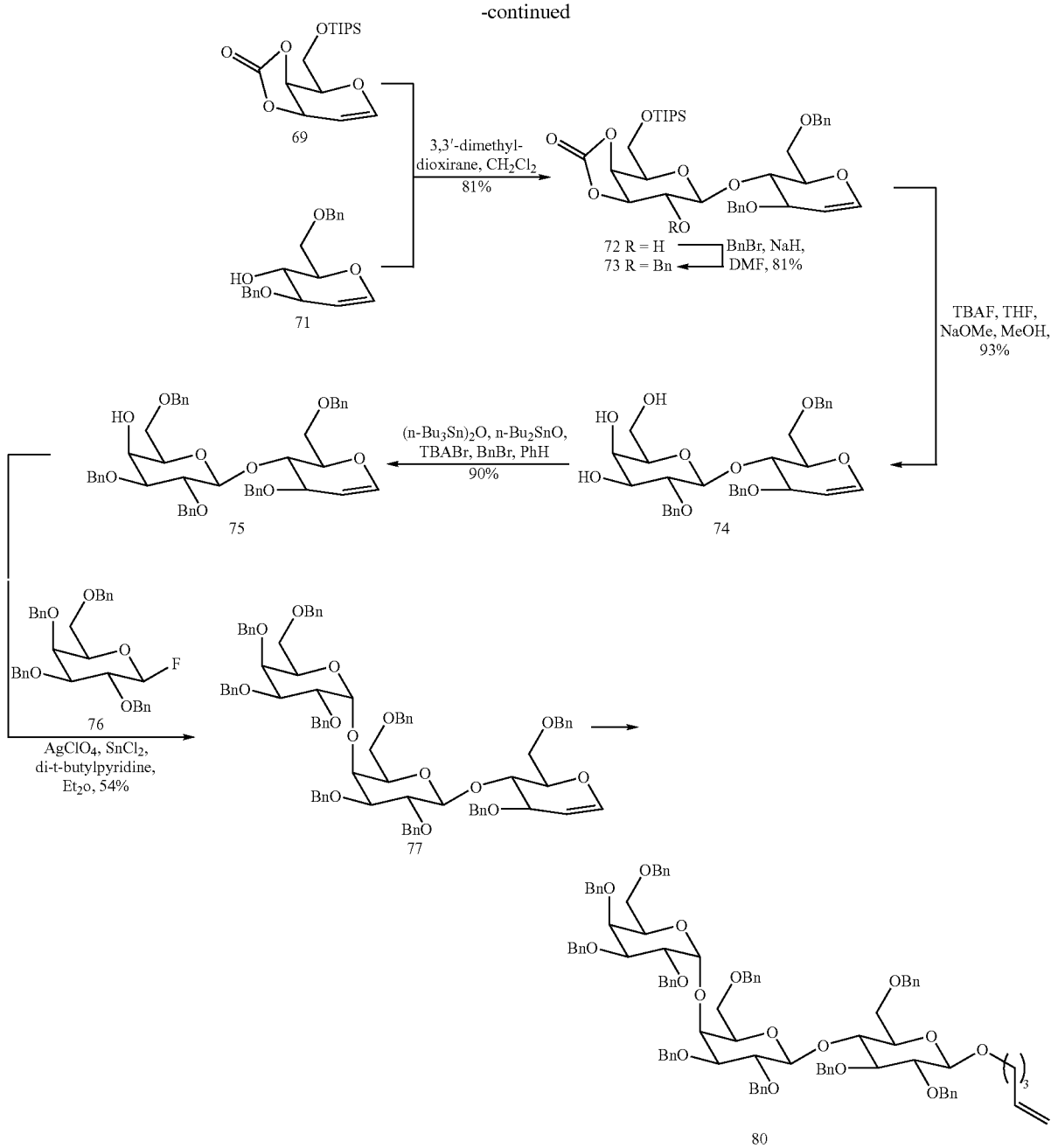

In but one example, the use of a n-pentenyl glycoside was considered (For a review of n-pentenyl glycosides, see Fraser-Reid et al., *Synlett*, 1992, 927; Udodong et al. *J. Am. Chem. Soc.* 1993, 115, 7886; Merritt et al. *J. Am. Chem. Soc.* 1994, 116, 8334; Fraser-Reid et al. 1990, 55, 6068; Mootoo et al. *J. Am. Chem. Soc.* 1988, 110, 2662; Mootoo et al. *J. Am. Chem. Soc.* 1989, 111, 8540 and references therein). N-pentenyl glycosides are stable to a range of reaction conditions and reagents, but are readily activated for glycosidation reactions by treatment with a halogen oxidant. As a result of their stability and the neutral conditions required for their activation, pentenyl glycosides have been demonstrated to be valuable linkages for mechanistic and synthetic studies. Additionally, a terminal pentenyl group, or more generally a terminal alkenyl group, could also provide a handle for bioconjugation. Thus, in one embodiment, trisaccharide 77 may be reacted with pentenyl alcohol and anhydrous zinc chloride (Gordon et al. *Carbohydrate Res.* 1990, 206, 361) to afford the desired Gb3 n-pentenyl glycoside 80. Indeed, with the pentenyl glycoside in place, global deprotection of 80 is possible.

In certain embodiments, a Gb3 glycoconjugate may be prepared. Ozonolysis of intermediate 80, thereby producing the corresponding aldehyde derivative, followed by coupling to KLH using reductive amination under the agency of sodium cyanoborohydride and global deprotection yields the desired Gb3-KLH glycoconjugate.

2) Experimentals
N-pentenyl Gb3-KLH glycoconjugate:

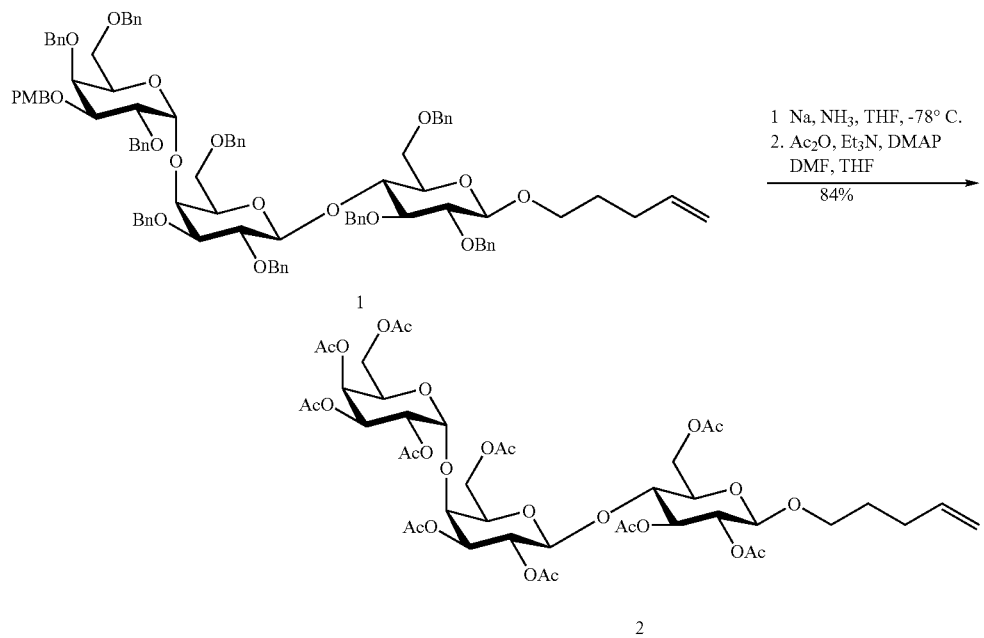

Sodium (38 mg, 1.69 mmol, 60.0 equiv) was added to condensed liquid ammonia (25 mL) at −78° C. Pentenyl trisaccharide 1 (37 mg, 0.024 mmol; Ref: Allen, J. R.; Allen, J. G.; Zhang, X. F.; Williams, L. J.; Zatorski, A.; Ragupathi, G.; Livingston, P. O.; Danishefsky, S. J. *Chem. Eur. J.* 2000, 6, 1366-1375) in THF (0.5 mL) was added to the resulting blue solution, and the reaction was stirred at −78° C. for 45 min. MeOH (2 mL) was added to quench the reaction, followed by warming to rt to evaporate the condensed ammonia. Solid NH$_4$Cl (100 mg) was added, followed by filtration of the solids. The filtrate was concentrated, and the crude sugar was dissolved in 1:1:1 DMF:THF:Et$_3$N (1.5 mL), followed by DMAP (1 mg) and Ac$_2$O (0.14 mL, 1.48 mmol, 53.0 equiv). The reaction was stirred at rt for 15 h, diluted with EtOAc (5 mL) and washed with water (5 mL). The aqueous layer was extracted with EtOAc (2×5 mL). The combined organic layers were dried (MgSO$_4$), filtered, concentrated and purified by silica gel chromatography (72% EtOAc/hexanes) to afford peracetate 2 (20 mg, 84%) as a colorless oil.

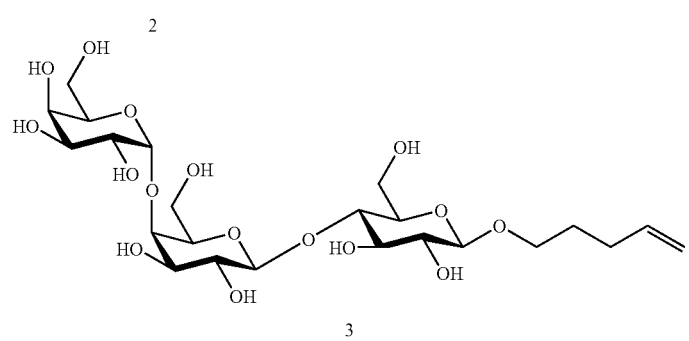

Peracetate 2 (18 mg, 0.018 mmol) in MeOH (1 mL) was treated with solid NaOMe (24 mg, 0.45 mmol, 25.0 equiv) and stirred at rt for 24 h. The reaction was quenched with Amberlite IR-120 acidic resin (20 mg), filtered, concentrated and purified by reverse phase chromatography (RP-18 silica gel, 20% MeOH/H$_2$O) to afford Gb3 trisaccharide 3 (11 mg, 99%) as a white solid: $^1$H NMR (400 MHz, D$_2$O) □ 5.89 (ddt, J=17.1, 10.4, 6.8 Hz, 1H), 5.07 (d, J=17.4 Hz, 1H), 5.00 (d, J=10.2 Hz, 1H), 4.92 (d, J=3.7 Hz, 1H), 4.50-4.45 (m, 2H), 4.34 (t, J=6.4 Hz, 1H), 4.01 (m, 2H), 3.96 (d, J 11.0 Hz, 1H), 3.95-3.87 (m, 3H), 3.84-3.79 (m, 3H), 3.78-3.73 (m, 2H), 3.73-3.66 (m, 3H), 3.64-3.61 (m, 2H), 3.58-3.53 (m, 2H), 3.27 (t, J=8.4 Hz, 1H), 2.15-2.03 (m, 2H), 1.74-1.67 (m, 2H); $^{13}$C NMR (100 MHz, D$_2$O) δ 140.0, 116.0, 104.5, 103.2, 101.5, 79.9, 78.6, 76.7, 76.0, 75.7, 74.2, 73.4, 72.1, 70.4, 70.1, 69.8, 61.7, 61.6, 61.3, 30.6, 29.2; LRMS (ESI) M$_{calc}$ 572.2 for C$_{23}$H$_{40}$O$_{16}$, (M+Na)$_{found}$ 595.2.

E. Example 5

Preparation of Gb3-glycoside-glycoamino Acids and Trimeric Gb3 Glycopeptides 90 and 92

Figure 20A:
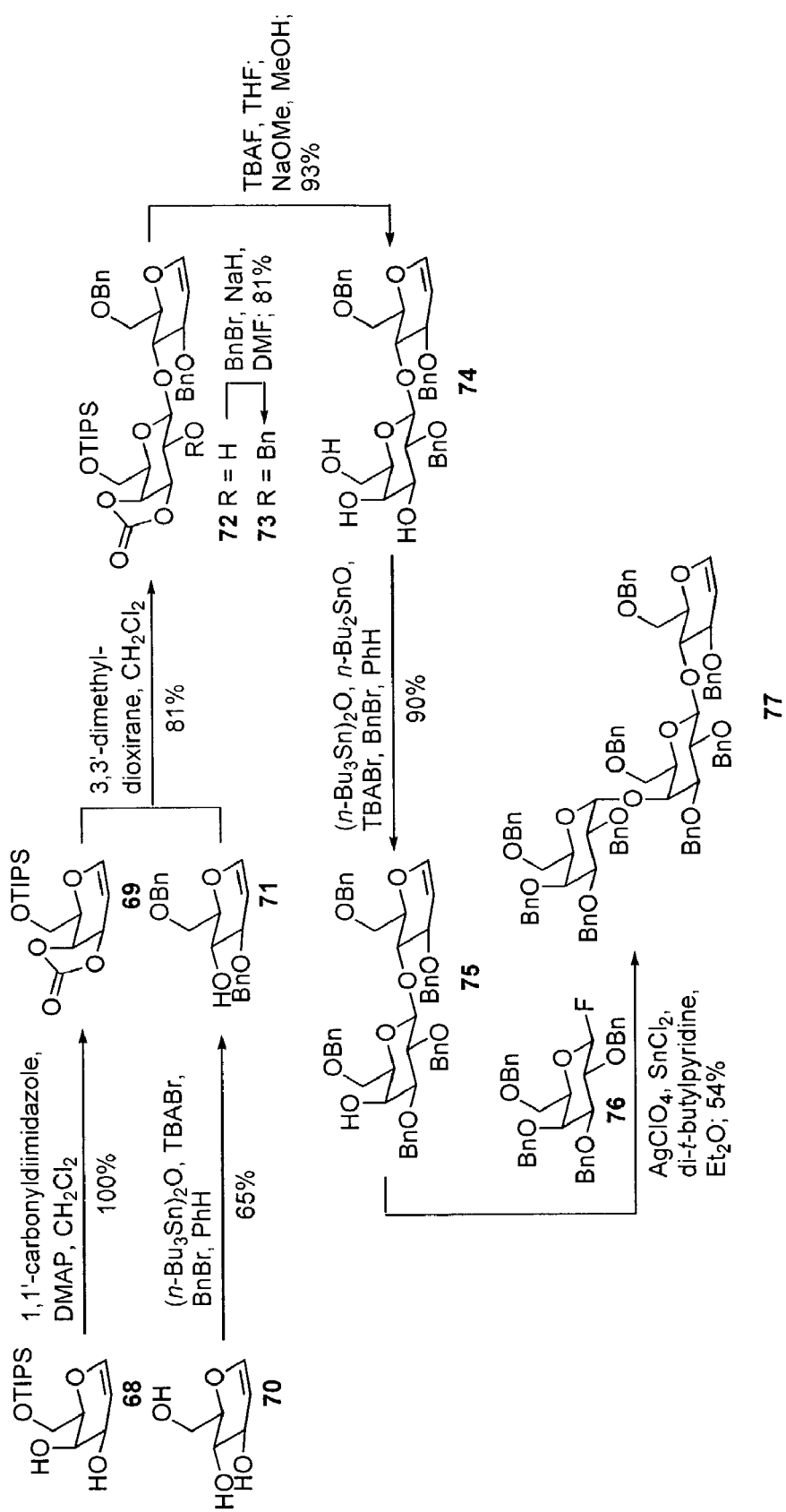
FIGS. 20 A and 20B depict an exemplary synthesis of trimeric antigenic Gb3 glycopeptides 90 and 92.
Figure 20B:
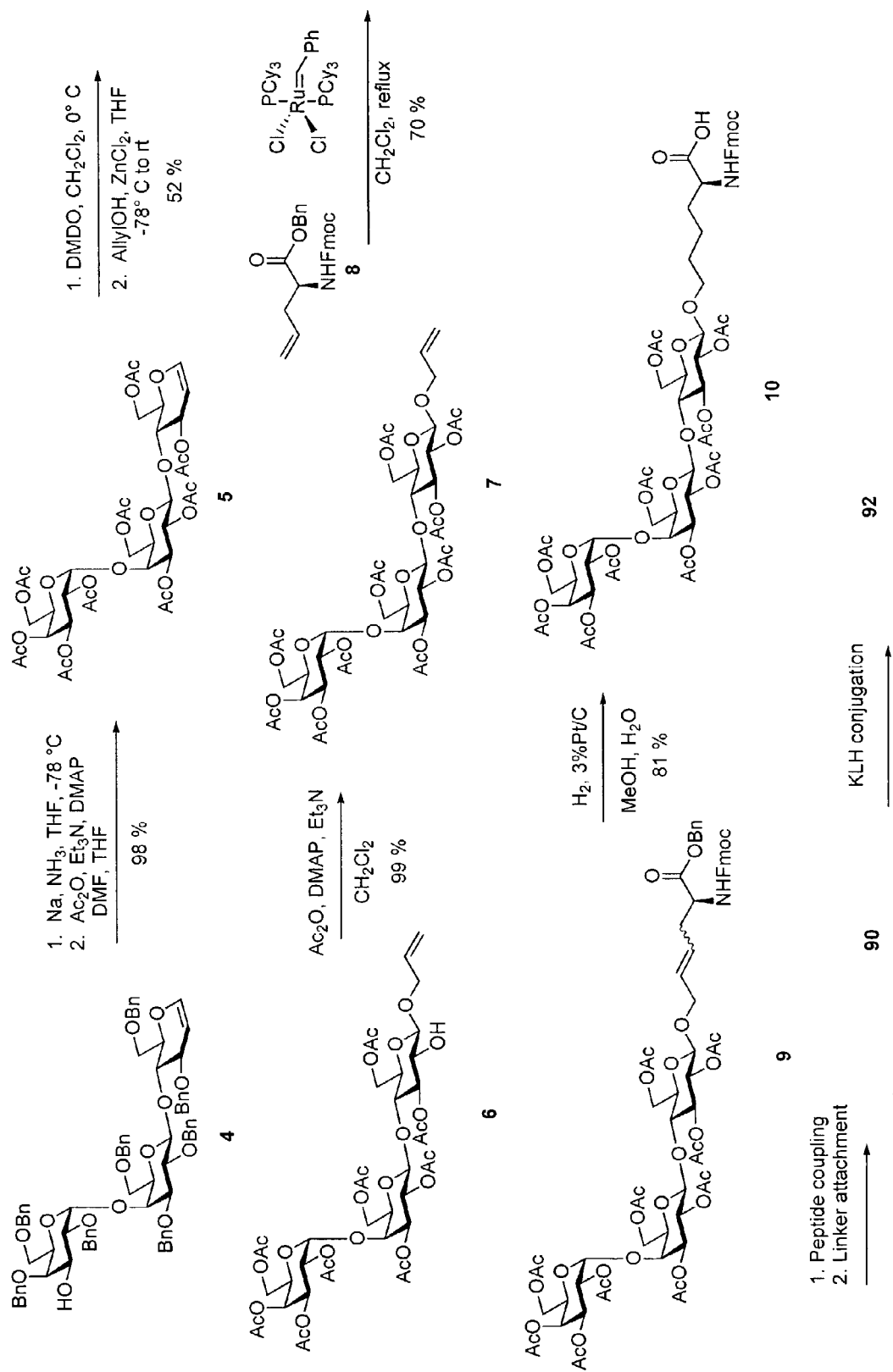

1) Synthesis of Gb3 glycoamino acid 10 (FIG. 20B)

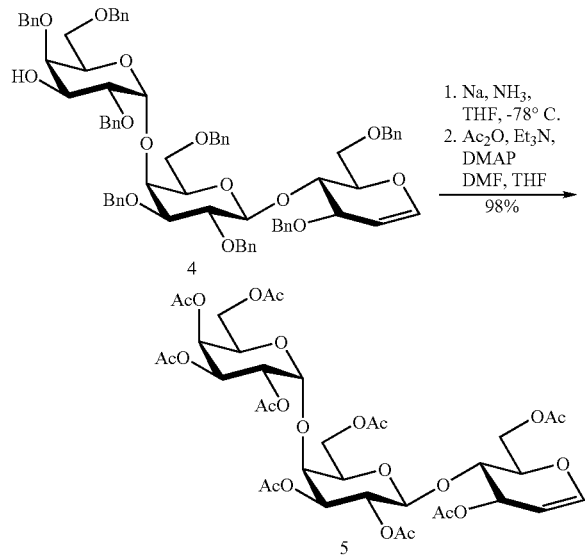

Sodium (193 mg, 8.41 mmol, 60.0 equiv) was added to condensed liquid ammonia (30 mL) at −78° C. Glycal 4 (162 mg, 0.14 mmol; Ref: Park, T. K.; Kim, I. J.; Hu, S.; Bilodeau, M. T.; Randolph, J. T.; Kwon, O.; Danishefsky, S. J. *J. Am. Chem. Soc.* 1996, 118, 11488-11500) in THF (2.0 mL) was added to the resulting blue solution, and the reaction was stirred at −78° C. for 45 min. MeOH (5 mL) was added to quench the reaction, followed by warming to rt to evaporate the condensed ammonia. Solid NH$_4$Cl (445 mg, 8.41 mmol, 60.0 equiv) was added, followed by filtration of the solids. The filtrate was concentrated, and the crude sugar was dissolved in 1:1:1 DMF:THF:Et$_3$N (6.9 mL), followed by DMAP (10 mg) and Ac$_2$O (0.7 mL, 7.42 mmol, 53.0 equiv). The reaction was stirred at rt for 15 h, diluted with EtOAc (25 mL) and washed with water (25 mL). The aqueous layer was extracted with EtOAc (2×25 mL). The combined organic layers were dried (MgSO$_4$), filtered, concentrated and purified by silica gel chromatography (90% EtOAc/hexanes) to afford peracetate 5 (112 mg, 98%) as a white foam: $^1$H NMR (400 MHz, CDCl$_3$) □ 6.36 (d, J=6.0 Hz, 1H), 5.53 (d, J=2.2 Hz, 1H), 5.38-5.32 (m, 2H), 5.15-5.10 (m, 2H), 4.95 (d, J=3.3 Hz, 1H), 4.80 (dd, J=5.9, 3.1 Hz, 1H), 4.74 (dd, J=9.8, 2.1 Hz, 1H), 4.63 (d, J=7.8 Hz, 1H), 4.47 (t, J=6.8 Hz, 1H), 4.41-4.34 (m, 2H), 4.18-4.02 (m, 5H), 3.97-3.94 (m, 2H), 3.75 (t, J=6.6 Hz, 1H), 2.08 (s, 3H), 2.06 (s, 6H), 2.03-2.01 (m, 12H), 1.99 (s, 3H), 1.94 (s, 3H); $^{13}$C NMR (100 MHz, CDCl$_3$) □ 170.5, 170.4, 170.3, 170.3, 170.2, 169.9, 169.8, 169.6, 168.8, 145.2, 100.8, 99.3, 99.0, 77.2, 74.5, 74.0, 72.4, 71.5, 69.1, 68.5, 68.4, 67.6, 67.1, 66.9, 61.8, 61.2, 60.2, 20.9, 20.7, 20.6, 20.5, 20.4, 20.3; LRMS (ESI) M$_{calc}$ 848.2 for C$_{36}$H$_{48}$O$_{23}$, (M+Na)$_{found}$ 871.3.

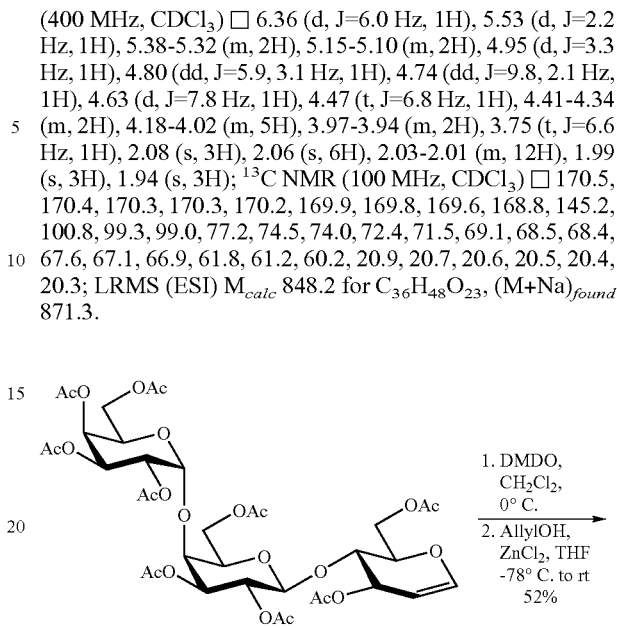

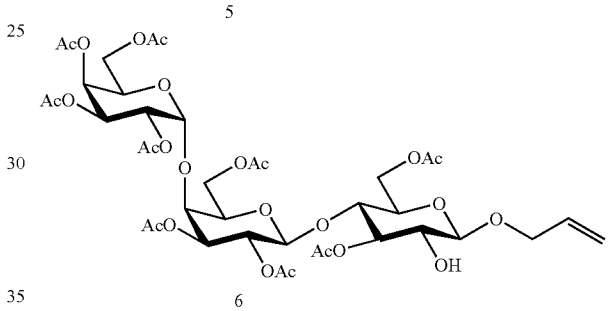

A solution of glycal 5 (181 mg, 0.213 mmol) in methylene chloride (1 mL) was cooled to 0° C. and treated with 2,2′-dimethyldioxirane (7 mL of a 0.06 M solution in acetone, 2.0 equiv). The reaction mixture was concentrated under vacuum after 45 min, and further dried by the addition of methylene chloride (1 mL) and subsequent evaporation, while maintaining the temperature at 0° C. The crude glycal epoxide was dissolved in a 1:1 THF:allyl alcohol mixture (4 mL), cooled to −78° C. and was treated with ZnCl$_2$ (0.26 mL of a 1.0 M solution in diethyl ether, 1.2 equiv). The reaction was allowed to warm to rt slowly, and was maintained at that temperature for 15 h. EtOAc (20 mL) was added, and the solution was washed with a saturated solution of NaHCO$_3$ (20 mL), brine (20 mL), dried (MgSO$_4$), filtered, concentrated and purified by silica gel chromatography (60-76% EtOAc/hexanes) to afford allyl glycoside 6 (99 mg, 52%) as a colorless oil, along with 64 mg (34%) of the corresponding □-manno diastereomer: $^1$H NMR (400 MHz, CDCl$_3$) □ 5.89 (ddt, J=16.8, 11.4, 6.2 Hz, 1H), 5.55 (d, J=2.2 Hz, 1H), 5.34 (dd, J=11.0, 3.2 Hz, 1H), 5.29 (d, J=17.2 Hz, 1H), 5.20 (d, J=10.5 Hz, 1H), 5.15 (dd, J=11.0, 3.4 Hz, 1H), 5.10-5.05 (m, 2H), 4.96 (d, J=3.4 Hz, 1H), 4.71 (dd, J=10.8, 2.2 Hz, 1H), 4.56-4.30 (m, 6H), 4.16-4.05 (m, 5H), 3.99 (s, 1H), 3.82-3.68 (m, 2H), 3.61-3.58 (m, 2H), 3.47 (t, J=8.5 Hz, 1H), 2.72 (bs, 1H), 2.19 (s, 3H), 2.10 (s, 3H), 2.08 (s, 3H), 2.05-2.02 (m, 15H), 1.96 (s, 3H); $^{13}$C NMR (100 MHz, CDCl$_3$) □ 170.6, 170.5, 170.4, 170.3, 169.9, 169.4, 168.7, 133.3, 118.2, 101.3, 100.8, 99.5, 76.8, 76.2, 74.9, 74.7, 72.7, 72.6, 72.5, 71.7, 70.3, 68.8, 68.7, 67.8, 67.0, 66.9, 62.3, 61.3, 60.2, 20.8, 20.7, 20.6, 20.6, 20.5, 20.5, 20.4; LRMS (ESI) M$_{calc}$ 922.3 for C$_{39}$H$_{54}$O$_{25}$, (M+H)$_{found}$ 923.3, (M+Na)$_{found}$ 945.3.

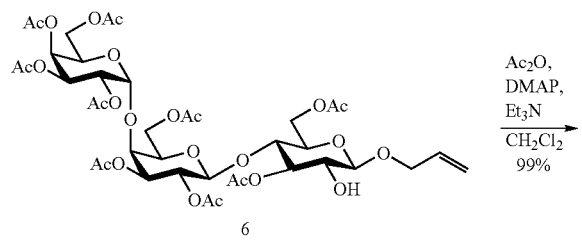

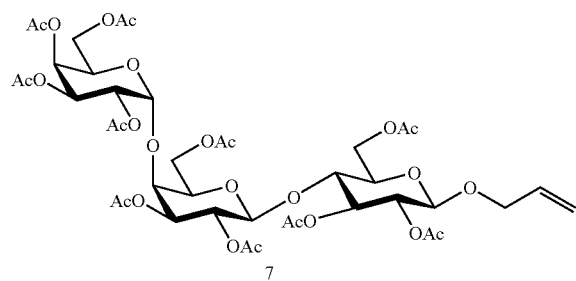

A solution of alcohol 6 (80 mg, 0.086 mmol) in methylene chloride (2.5 mL) was treated with Et$_3$N (0.06 mL, 0.43 mmol, 5.0 equiv), DMAP (10 mg, 0.086 mmol, 1.0 equiv) and acetic anhydride (0.035 mL, 0.346 mmol, 4.0 equiv) and stirred at rt. After 5 h, the reaction mixture was poured into a saturated solution of NaHCO$_3$ (10 mL) and extracted with EtOAc (3×10 mL). The combined organic layers were dried (MgSO$_4$), filtered, concentrated and purified by silica gel chromatography (60-68% EtOAc/hexanes) to afford peracetate 7 (81 mg, 99%) as a colorless foam: $^1$H NMR (400 MHz, CDCl$_3$) □ 5.82 (ddt, J=16.8, 10.7, 5.8 Hz, 1H), 5.57 (d, J=2.3 Hz, 1H), 5.37 (dd, J=11.0, 3.2 Hz, 1H), 5.27 (d, J=2.2 Hz, 1H), 5.22-5.14 (m, 3H), 5.08 (dd, J=10.8, 7.8 Hz, 1H), 4.96 (d, J=3.5 Hz, 1H), 4.91 (t, J=8.6 Hz, 1H), 4.71 (dd, J=10.8, 2.2 Hz, 1H), 4.58-4.39 (m, 5H), 4.29 (dd, J=13.2, 4.8 Hz, 1H), 4.17-4.04 (m, 5H), 3.95 (s, 1H), 3.81-3.73 (m, 2H), 3.63-3.59 (m, 1H), 2.11 (s, 3H), 2.10 (s, 3H), 2.06 (s, 6H), 2.05 (s, 3H), 2.05 (s, 3H), 2.04 (s, 3H), 2.03 (s, 6H), 1.97 (s, 3H); $^{13}$C NMR (100 MHz, CDCl$_3$) □ 170.6, 170.4, 170.0, 169.6, 169.6, 169.4, 168.8, 133.3, 117.5, 101.0, 99.5, 99.2, 76.8, 76.4, 73.0, 72.7, 72.4, 71.7, 71.6, 69.9, 68.9, 68.7, 67.8, 67.0, 67.0, 62.1, 61.2, 60.2, 20.8, 20.8, 20.6, 20.6, 20.5, 20.5, 20.4; LRMS (ESI) M$_{calc}$ 964.3 for C$_{41}$H$_{56}$O$_{26}$, (M+H)$_{found}$ 965.2, (M+Na)$_{found}$ 987.3.

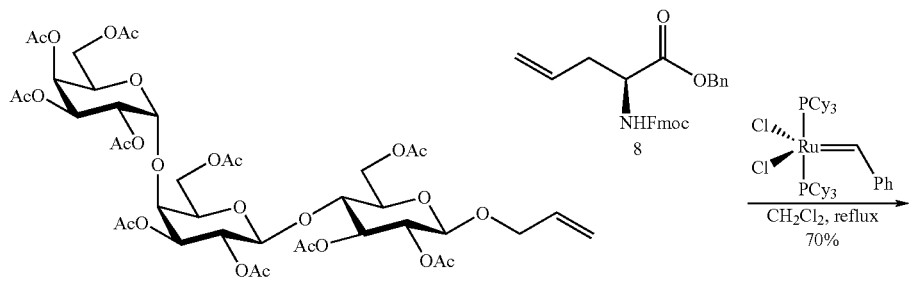

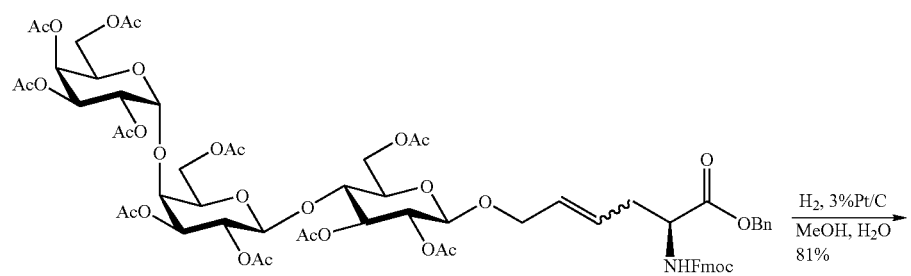

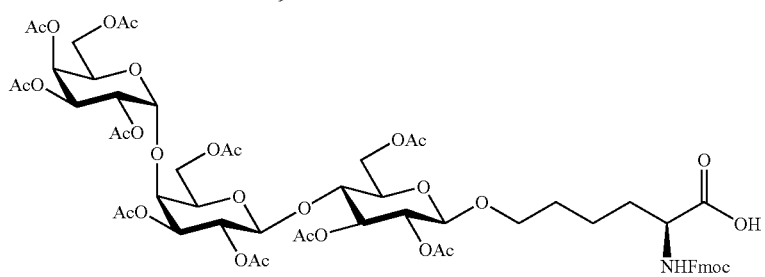

Peracetylated Gb3 allyl glycoside 7 (10 mg, 0.01 mmol) and Fmoc-L-allylglycine benzyl ester 8 (25 mg, 0.05 mmol, 5.0 equiv) in methylene chloride (0.05 mL) were treated bis(tricyclohexylphosphine) ruthenium Grubbs catalyst (1 mg, 0.001 mmol, 0.1 equiv). The reaction was heated to reflux. After 6 h, another 0.1 equiv of catalyst was further added. The reaction was cooled to rt after 12 h (total) and purified by silica gel chromatography (40% acetone/hexanes) to afford metathesis product 9 (9 mg, 70%). The E:Z mixture 9 (78 mg, 0.057 mmol) was dissolved in 0.55 mL methanol:water (10:1) and treated with 3% Pt/C (70 mg). The reaction flask was stirred under a hydrogen balloon for 12 h, followed by filtration to remove the solid catalyst. The filtrate was concentrated and purified by silica gel chromatography (EtOAc-1% AcOH/EtOAc) to afford Gb3 amino acid 10 (58 mg, 81%) as a white solid: $^1$H NMR (400 MHz, CDCl$_3$) δ 7.76 (d, J=7.5 Hz, 2H), 7.60 (d, J=7.5 Hz, 2H), 7.40 (t, J=7.5 Hz, 2H), 7.31 (t, J=7.5 Hz, 2H), 5.59 (d, J=2.6 Hz, 1H), 5.50 (d, J=7.9 Hz, 1H), 5.39 (dd, J=11.0, 3.0 Hz, 1H), 5.22-5.16 (m, 2H), 5.09 (dd, J=10.4, 8.0 Hz, 1H), 5.01 (s, 1H), 4.98 (d, J=3.2 Hz, 1H), 4.87 (t, J=8.5 Hz, 1H), 4.75-4.71 (m, 1H), 4.53-4.38 (m, 6H), 4.23 (t, J=6.9 Hz, 1H), 4.19-4.08 (m, 4H), 4.00 (s, 1H), 3.81-3.73 (m, 3H), 3.64-3.61 (m, 1H), 3.48-3.46 (m, 1H), 2.13 (s, 3H), 2.10 (s, 3H), 2.06 (s, 9H), 2.05 (s, 6H), 2.03 (s, 3H), 2.02 (s, 3H), 1.98 (s, 3H), 1.92-1.89 (m, 1H), 1.83-1.81 (m, 1H), 1.60-1.54 (m, 2H), 1.30-1.24 (m, 2H); $^{13}$C NMR (100 MHz, CDCl$_3$) □ 175.1, 170.7, 170.6, 170.5, 170.4, 170.0, 169.9, 169.6, 169.5, 168.8, 156.0, 143.7, 141.2, 134.4, 129.7, 128.9, 128.5, 127.7, 127.0, 125.0, 119.9, 101.0, 100.4, 99.5, 79.1, 77.2, 76.3, 73.0, 72.7, 72.5, 71.8, 69.3, 68.9, 68.8, 67.8, 67.0, 62.1, 60.2, 53.6, 47.1, 31.6, 28.8, 21.5, 20.9, 20.8, 20.6, 20.6, 20.5, 20.4; LRMS (ESI) M$_{calc.}$ 1275.4 for C$_{59}$H$_{73}$NO$_{30}$, (M+H)$_{found}$ 1276.3, (M+Na)$_{found}$ 1298.4.

2) Synthesis of trimeric Gb3 glycopeptides 90 and 92

As depicted below, peptide coupling of intermediate 10, followed by attachement of the resulting trimeric peptide to a suitable linker and global deprotection yields the desired trimeric glycopeptide 90. Conjugation to KLH under suitable conditions affords trimeric glycopeptide 92.

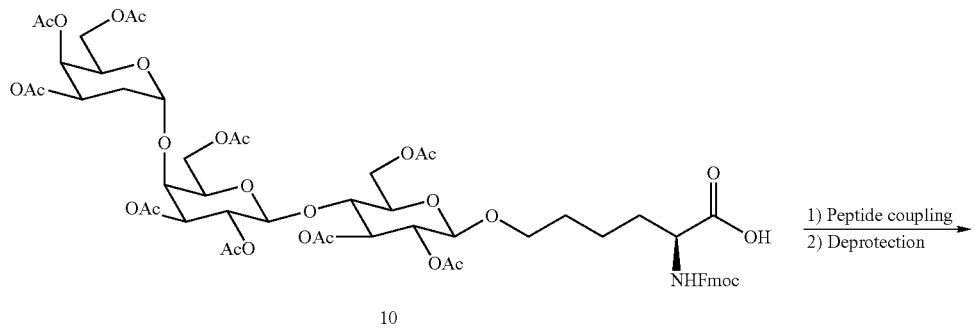

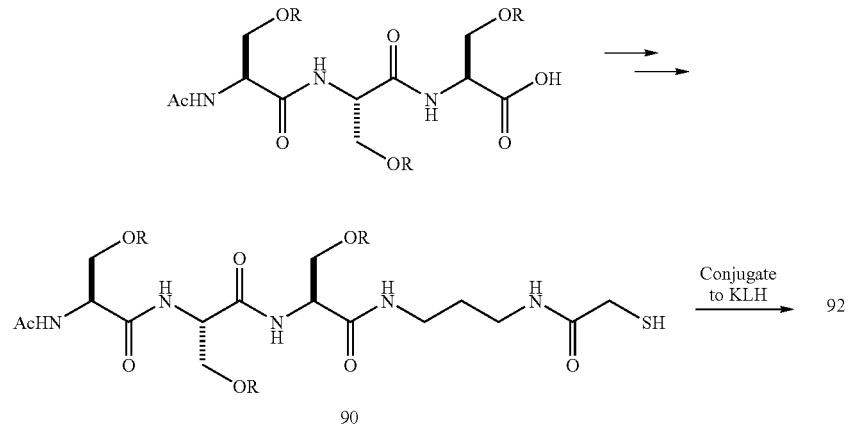

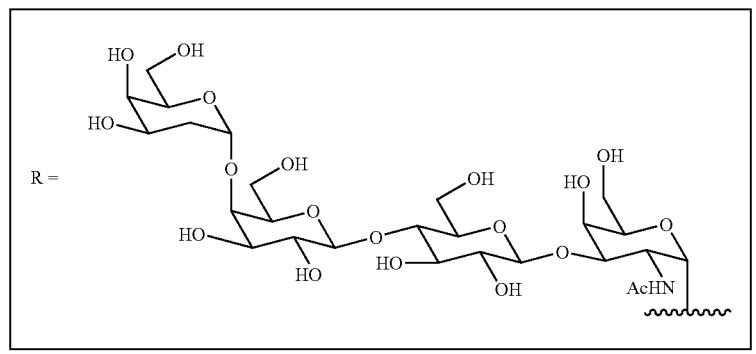

Figure 21:
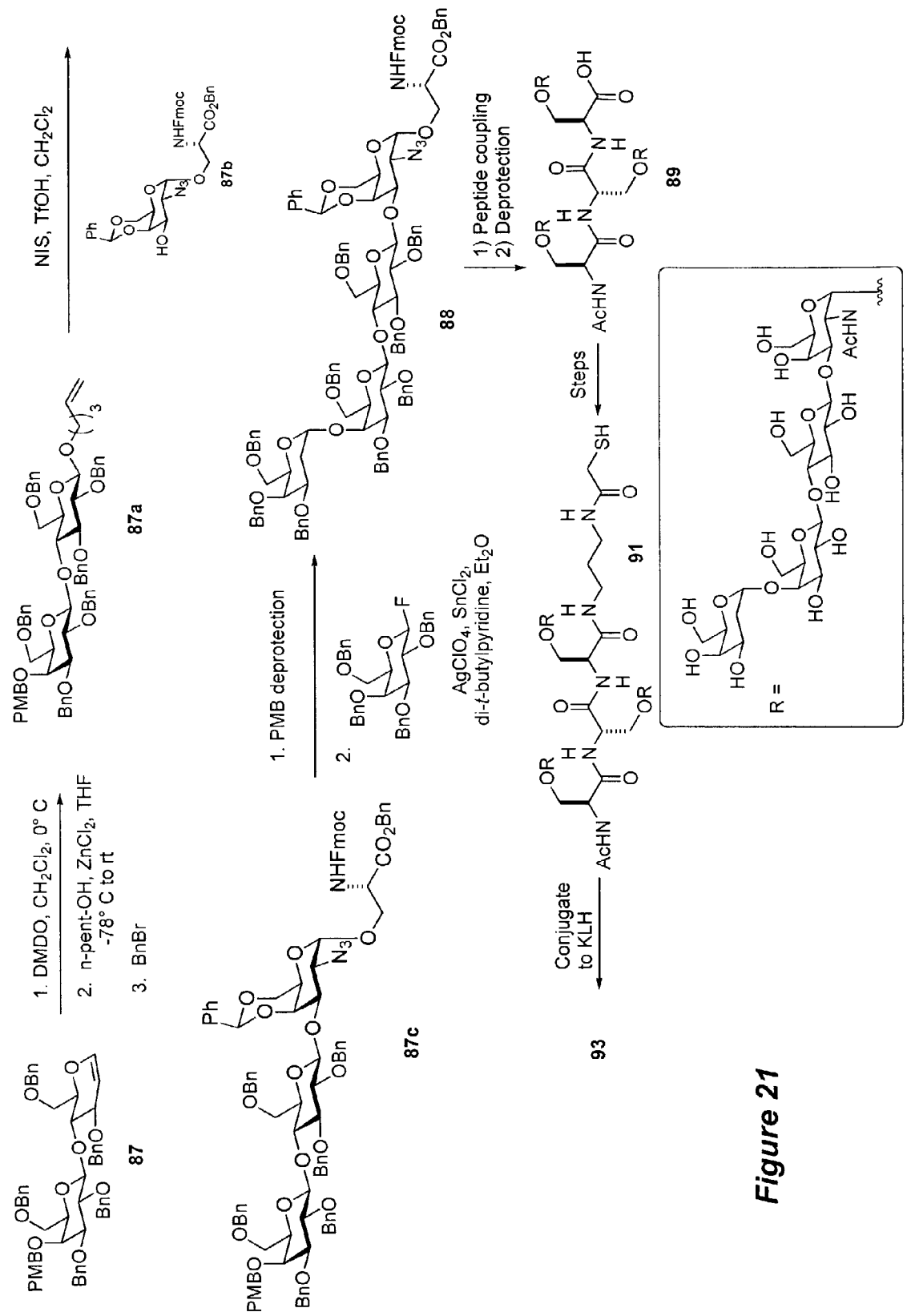
FIG. 21 depicts an exemplary synthesis of trimeric antigenic Gb3 glycopeptides 91 and 93.
Figure 22:
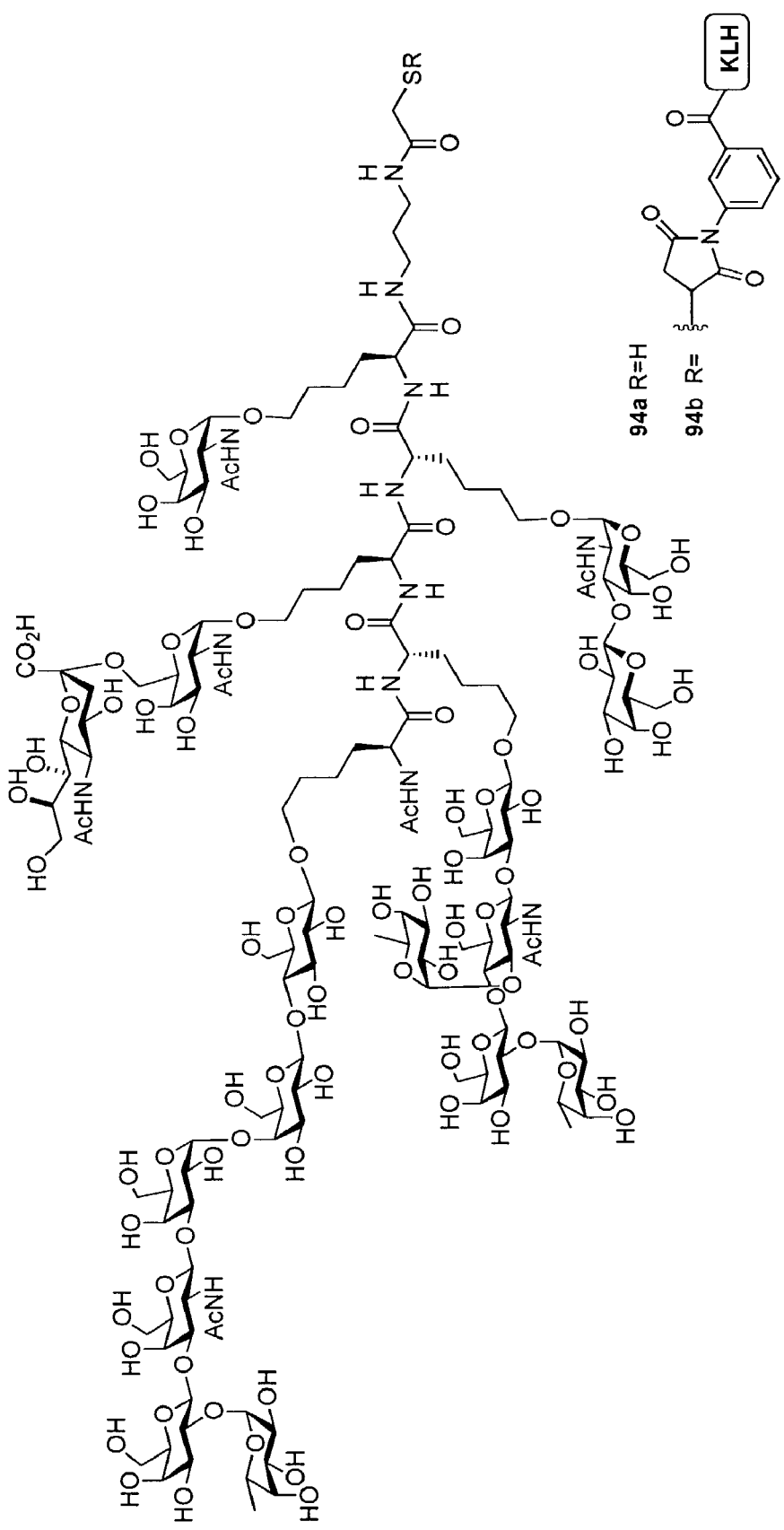
FIG. 22 depicts a pentameric antigenic glycopeptide containing Globo-H, Le$^y$, STn, TF and Tn antigens.

2) Synthesis of trimeric Gb3 glycopeptides 91 and 93 (FIG. 21)—Discussion of Synthetic Methods:

As described above, Gb3 glycoamino acids may be prepared. In certain embodiments, Gb3 glycoamino acid constructs are provided comprising a Gb3 epitope linked to an aliphatic amino acid moiety through a monosaccharide moiety. The synthetic route that we have been investigating towards this end relies on the initial synthesis of a suitably protected Gb3 glycal (77), which was carried out as detailed herein (FIGS. 20A and B). With the glycal in hand, we began an investigation into incorporating monosaccharide amino acid 82 acceptor at the reducing end. Despite the use of several different donor types (78, 79, 80, 81), efforts directed at coupling the Gb3 trisaccharide and the acceptor 82 were unsuccessful (Scheme 2).

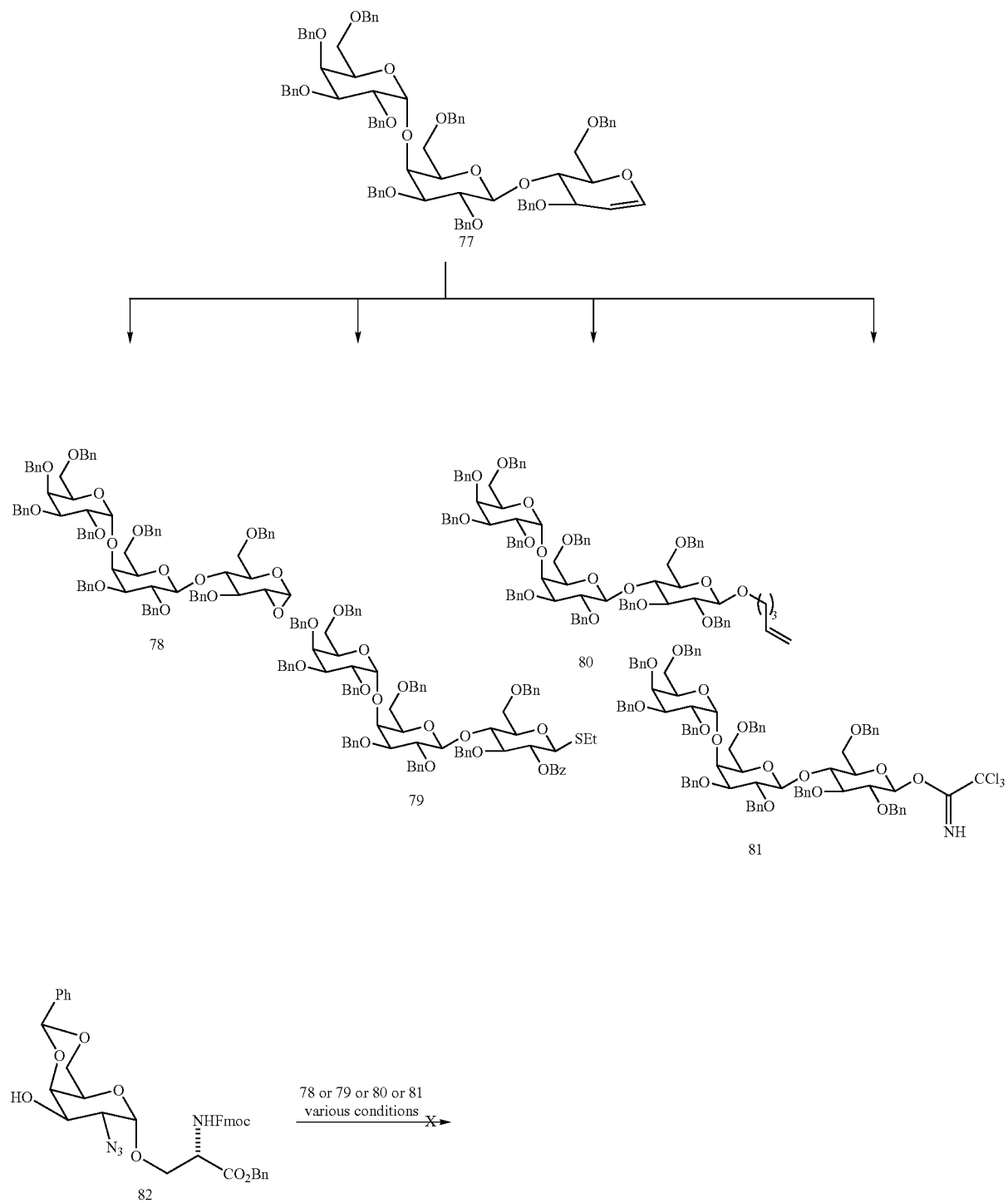

-continued

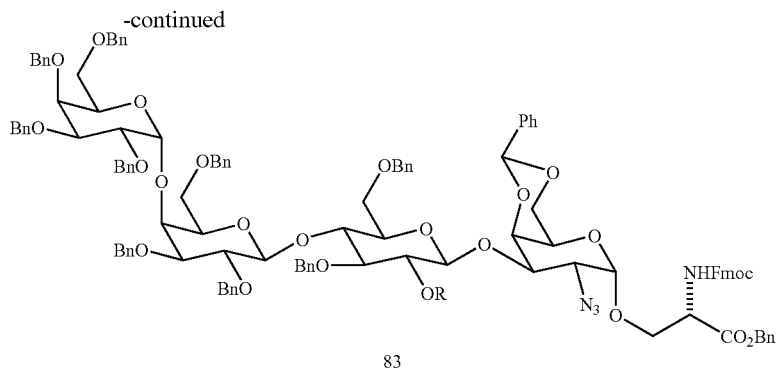

83

We have, thus, been led to investigate an alternative approach, in which monosaccharide amino acid acceptor 82 is coupled to the AB disaccharide portion of Gb3, and then the resulting adduct is coupled with the C residue, thereby generating the required Gb3-GalNAc glycoamino acid. Initial experiments in this vein have shown that the coupling is, indeed, possible using the peracylated lactose donor 84 (Scheme 3).

Scheme 3

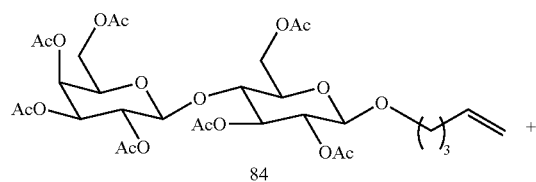
84

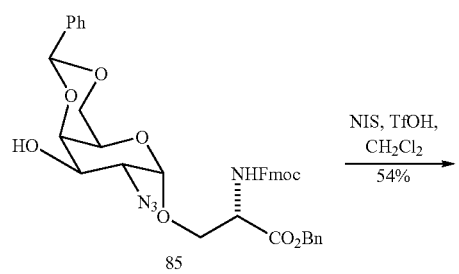
85

NIS, TfOH, CH$_2$Cl$_2$
54%

-continued

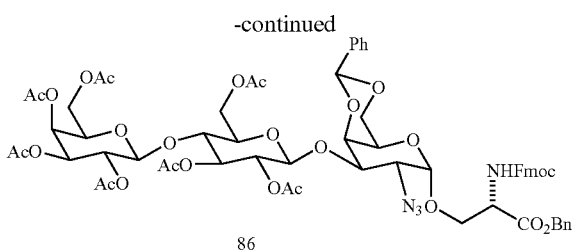
86

Consequently, the orthogonally protected lactal residue 87 has been prepared (Scheme 4) for introduction of monosaccharide amino acid acceptor 82 into this piece. As depicted in Scheme 4 (and in more details in FIG. 21), conversion of 87 to the corresponding donor, followed by coupling with monosaccharide amino acid acceptor 82, removal of the PMB group and capping with a suitable galactose donor generates the desired glycoamino acid 88. Hence, in certain embodiments, clustered variants of Gb3 are provided. Given the structural similarity of Gb3 to the reducing end of Globo-H, the approach developed to synthesize the Gb3-GalNAc glycoamino acid will potentially be applicable to the synthesis of the corresponding glycoamino acid derived from Globo-H.

Scheme 4

Convert to donor
Couple to cassette,
Remove PMB group,
Cap with suitable
galactose donor
→

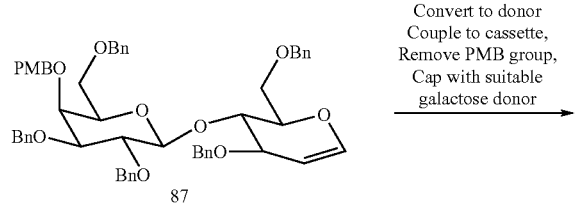
87

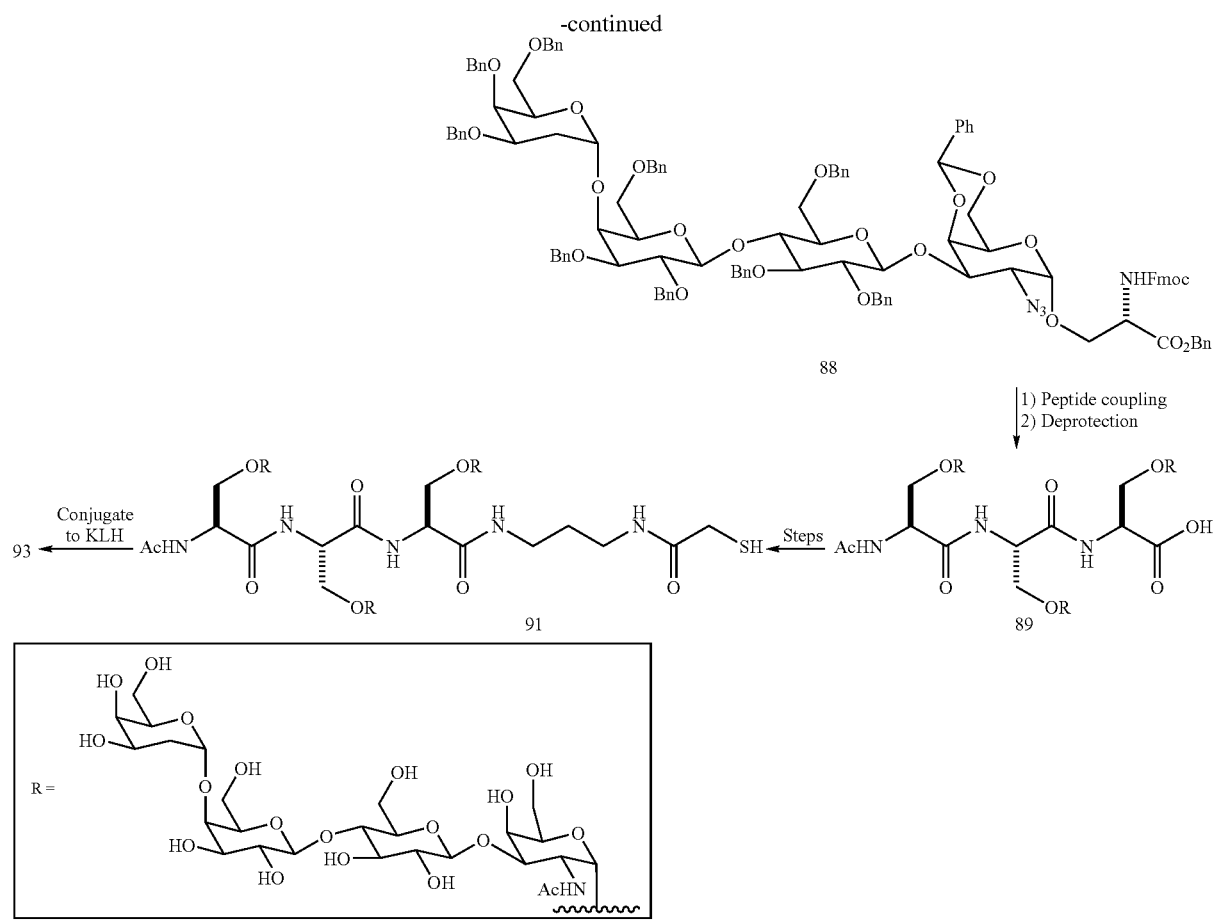

F. Example 6

Immunological Studies

It will be appreciated that the inventive glycoconjugates and glycopeptides, as provided herein, are useful for the treatment of cancer and are useful for inducing an antibody response in a subject. Typical protocols for the use of such glycoconjugates and glycopeptides are described in more detail below, and are also detailed in certain references incorporated herein.

1) Preparation of Vaccine

Figure 23:
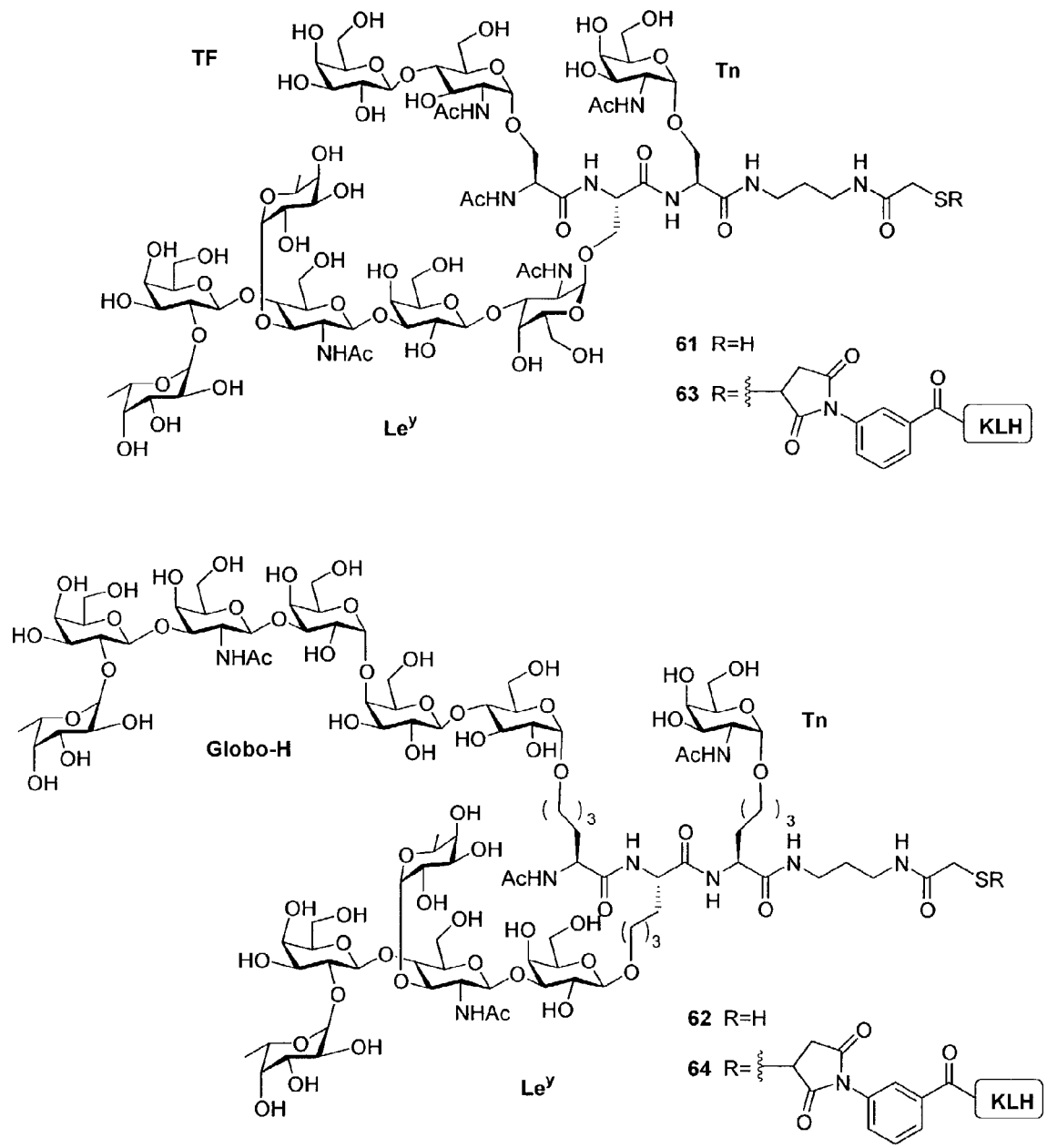
FIG. 23 depicts the multi-antigenic constructs used in the vaccination studies.
Figure 24:
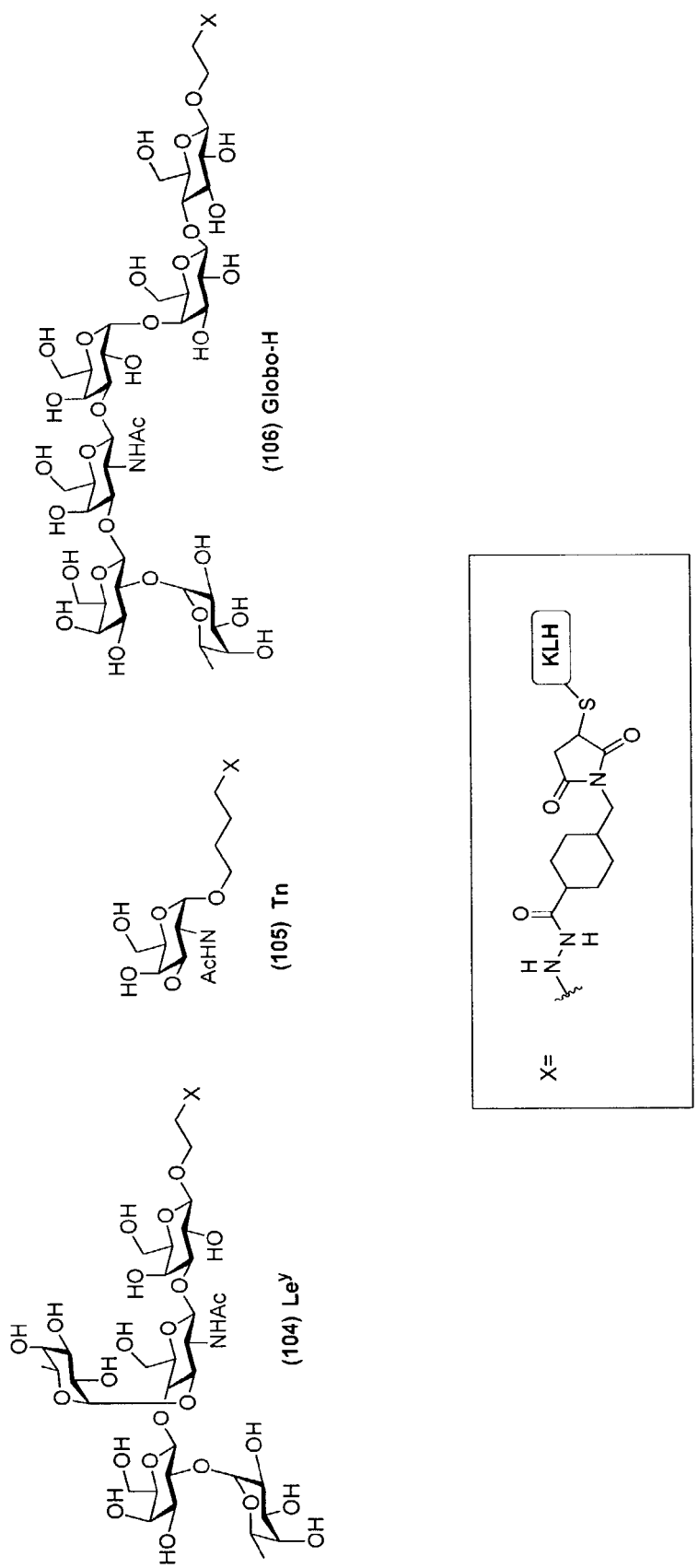
FIG. 24 depicts the monomeric controls used in the vaccination studies.

Conjugate vaccines 63 and 64 (FIG. 23) were prepared as follows. KLH (Sigma Chemical Co, MO, MW $8.6 \times 10^6$) was modified using m-malemidobenzoyl-N-hydroxysuccinimide ester (MBS) (Pierce Co., Rockford, Ill.) as described (Zhang, S., Graeber, L. A., Helling, F., Ragupathi, G., Adluri, S., Lloyd, K. O. & Livingston, P. O. (1996) *Cancer Research* 56, 3315-3319). Construct 61, containing TF, Le$^y$, and Tn, and construct 62, containing Globo-H, Le$^y$, and Tn, were prepared by total synthesis using solution phase peptide synthesis from the appropriately protected constituent glycoamino acids (Williams, L. J., Harris, C. R., Glunz, P. W. & Danishefsky, S. J. (2000) *Tetrahedron Lett.* 41, 9505-9508. Allen, J. R., Harris, C. A. & Danishefsky, S. J. (2001) *J. Am. Chem. Soc.* 123, 1890-1897). The sulfhydryl function was incorporated to facilitate attachment to KLH. Global deprotection of the synthetic material revealed compounds 61 and 62. Addition of construct 61 or 62 to the maleimide-derivatized KLH was achieved by incubating the mixture at room temperature for 3 hours, followed by removal of the unreacted synthetic glycopeptide peptide using a 30,000 molecular cut-off Centriprep filter (Zhang, S., Graeber, L. A., Helling, F., Ragupathi, G., Adluri, S., Lloyd, K. O. & Livingston, P. O. (1996) *Cancer Research* 56, 3315-3319).

2) Immunization of Mice

Groups of five mice (C57BL; Female, 6 weeks of age, from Jackson Laboratory, Bar Harbor, Me.) are immunized subcutaneously as follows: Group 1—immunized with construct 62 (10 μg), plus QS-21(10 μg) (Antigenic Inc., NY, N.Y.); Group 2—immunized with 62 (10 μg), plus KLH (not conjugated to 62), plus QS-21 (10 μg); Group 3—immunized with 4 (3 μg), plus QS-21 (10 μg); Group 4—immunized with 64 (3 μg), plus GPI-0100 (100 μg) (Galenica Pharmaceuticals Inc., Birmingham, Ala.); Group 5—immunized with a mixture containing 104, 105 and 106 (3 μg each), plus QS-21 (10 μg). Mice were immunized on days 1, 7, and 14, and bled 10 days after third vaccination. The presence of antibody is assayed by an enzyme linked immunosorbent assay (ELISA) as described previously (Ragupathi et al. *Angew. Chem. Int. Ed. Engl.* 1997, 36, 125) using the appropriate target antigen (e.g., globo H-ceramide, Le$^y$ ceramide and/or Tn(c)-pamcys as target antigen). The cell surface reactivity can then be tested, for example, the cell surface reactivity of anti-globo H, Le$^y$, and Tn antibodies are tested on globo H, Le$^y$, Tn positive cell-lines by flow cytometry assays (FACS).

3) Serological Analyses

Enzyme-Linked Immunosorbent Assay (ELISA). ELISAs were performed as previously described (Ragupathi, G., Park, T. K., Zhang, S., Kim, I. J., Graber, L., Adluri, S., Lloyd, K.

O., Danishefsky, S. J. & Livingston, P. O. (1997) *Angew. Chem. Int. Ed. Engl.* 36, 125-128). Briefly, ELISA plates were coated with either synthetic Globo-H-ceramide, or Le$^y$ and Le$^b$ expressing mucin purified from ovarian cyst fluid (Lloyd, K. O., Kabat, E. A., Layug, E. J. & Gruezo, F. (1966) *Biochemistry* 5, 1489-1501), or Tn-HAS, or Globo-H-Le$^y$-Tn-HSA in 0.1 M carbonate buffer (pH 11), at 0.3 µg/well for glycolipids and 0.2 µg/well for glycoproteins. Serially diluted antiserum was added to each well, and alkaline phosphatase-conjugated goat anti-mouse IgM or anti-mouse IgG was added at a dilution of 1:200 (Southern Biotechnology Associates, Inc, Birmingham, Ala.). Absorbance was measured at 414 nm. ELISA titers are defined as the highest dilution yielding an absorbance of 0.1 or greater over that of normal control mouse sera.

4) Cell Surface Reactivity Determined by FACS.

The cell surface reactivity of immune sera was tested on human cell lines as previously described (Ragupathi, G., Park, T. K., Zhang, S., Kim, I. J., Graber, L., Adluri, S., Lloyd, K. O., Danishefsky, S. J. & Livingston, P. O. (1997) *Angew. Chem. Int. Ed. Engl.* 36, 125-128). Briefly, reactivity was assessed using anti-Globo-H, anti-Le$^y$, and anti-Tn antibodies tested on MCF-7 (Globo-H and Le$^y$ positive) and LS-C (Tn and Le$^y$ positive) cells (provided by Dr. S. H. Itzkowitz, (Mt. Sinai Hospital, NY)) (Ogata, S., Chen, A. & Itzkowitz, S. H. (1994) *Cancer Res.* 54, 4036-4044). Single cell suspensions of $2\times10^5$ cells/tube were washed in PBS with 3% fetal calf serum (FCS) and 0.01M NaN$_3$ and incubated with 20 µl of 1:20 diluted antisera or monoclonal antibodies for 30 min on ice. The positive control mAbs were VK-9 against synthetic Globo-H (Kudryashov, V., Ragupathi, G., Kim, I. J., Breimer, M. E., Danishefsky, S. J., Livingston, P. O. & Lloyd, K. O. (1998) *Glycoconjugate Journal* 15, 243-249), 3S193 against Le$^y$ (Hellstrom, I., Garrigues, H. J., Garrigues, U. & Hellstrom, K. E. (1990) *Cancer Res.* 50, 2183-2190), and αTn against Tn (DAKO Corporation, Carpinteria, Calif.). After two washes with 3% FCS in PBS, 20 µl of 1:15 diluted goat anti-mouse IgM or IgG-labeled with fluorescein-thiocyanate (FITC) was added, and the mixture incubated for 30 min. After a final wash, the positive population and mean fluorescence intensity of stained cells were differentiated using FACScan (Becton & Dickinson, Calif.).

5) Discussion of Immunological Studies

As discussed above, in one aspect of the invention, multiantigenic glycopeptides are provided. In certain exemplary embodiments, the inventive multiantigenic glycopeptides are trimeric constructs and comprise three different carbohydrate domains found on tumor cell surfaces. In one embodiment, as shown on FIG. 23, the inventive glycopeptides comprise a TF, a Tn and an Le$^y$ epitope (construct 61). In another embodiment, the inventive glycopeptides comprise a Globo-H, a Tn and an Le$^y$ epitope (construct 63).

Figure 25:
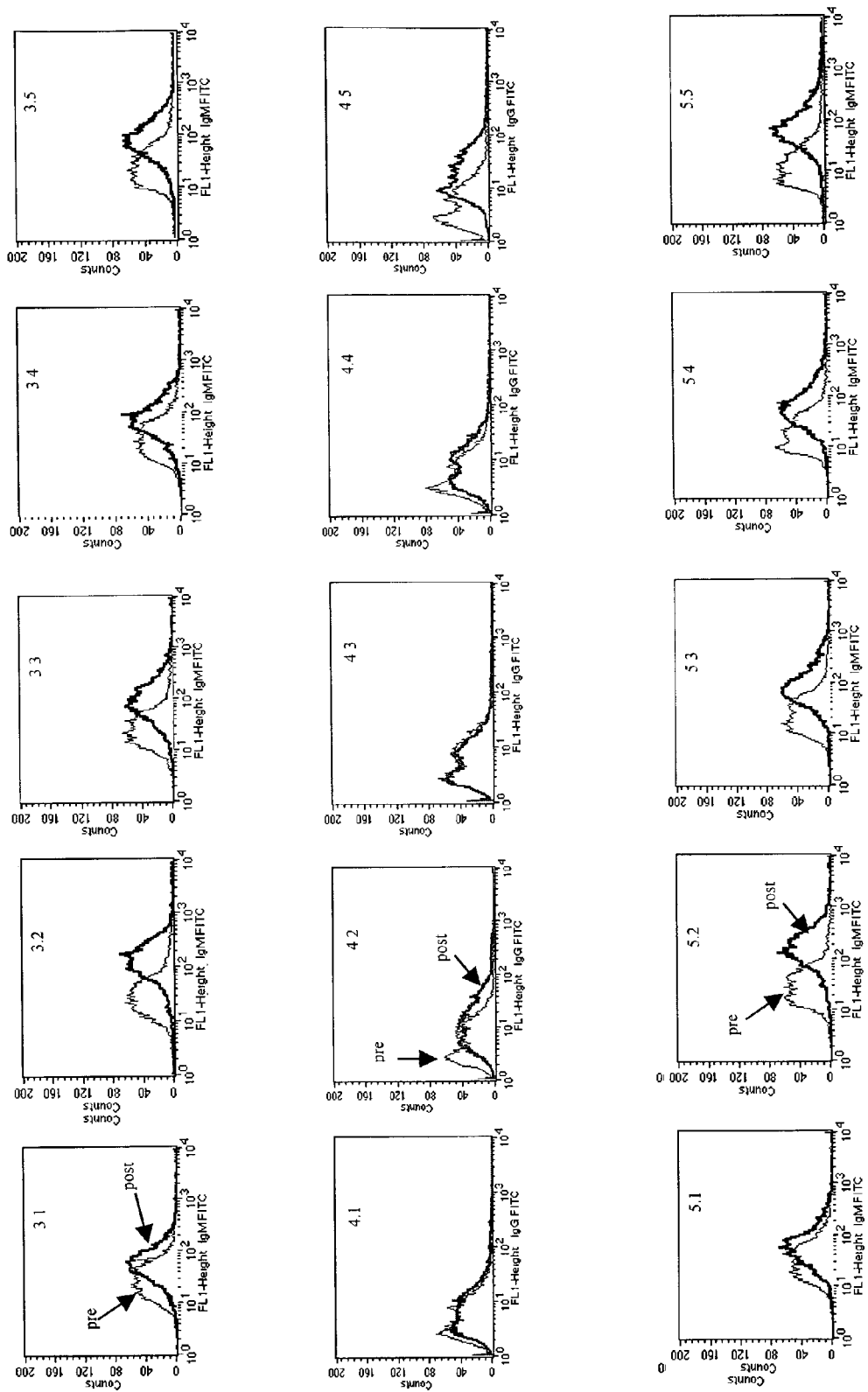
FIG. 25 depicts FACS histograms corresponding to the analysis of cell surface reactivity of IgM and IgG antibodies in sera from mice immunized with construct 64 against MCF-7.

In the study described herein, the immunological properties of 64 when administered in the presence of QS-21 (Kensil, C. R., Patel, U., Lennick, M. & Marciani, D. (1991) *J. Immunol.* 146, 431-437) were examined, or, for comparison purposes, when administered in the presense of the related, but less toxic adjuvant GPI-0100 (Marciani, D. J., Press, J. B., Reynolds, R. C., Pathak, A. K., Pathak, V., Gundy, L. E., farmer, J. T., Koratich, M. S. & May, R. D. (2000) *Vaccine* 18, 3141-3151). As controls, the immunogenicity of the nonconjugated compound 62 was evaluated, and a concurrent investigation on a mixture containing each of the monomeric antigens conjugated to KLH (104, 105 and 106, FIG. 25) was conducted. The later experiment was conducted for the purposes of comparing the response by a single mouse to each of the individual antigens, in response to vaccination with the polyvalent construct versus the mixture of monomers. In order to address issues relating to vaccine formulation, the level of immune response directed against each antigen, within the construct was determined. Furthermore, in anticipation of clinical trials, the ability of antibodies, so generated, to react in vitro with human cell lines known to express the individual antigens was assessed.

In certain other embodiments, the inventive glycopeptides are conjugated to a suitable carrier either directly, or indirectly through a linker or linker-crosslinker moiety. As discussed above, the carrier may be a protein, polypeptide or a lipid. In certain exemplary embodiments, the inventive glycopeptides are conjugated to the highly immunogenic protein carrier KLH. Vaccine candidates 63 and 64 were prepared by conjugating the totally synthetic glycopeptides 61 and 62, respectively, to the highly immunogenic protein carrier KLH. QS-21, or the related compound GPI-0100, was used as an adjuvant in order to enhance the immune response against the tumor-associated antigens present in the constructs. Initial ELISA investigations (data not shown) of the two potential conjugate vaccines indicated that construct 64 was superior to 63 from an immunological standpoint, and, consequently, construct 64 was thoroughly investigated. Remarkably, antibodies raised in response to 64 were not only able to identify the individual antigens in ELISAs but, as determined by FACS analysis, they also reacted strongly with tumor cells known to selectively express each tumor-associated antigen.

Numerous factors could influence the magnitude of the antibody response against individual antigens when more than one antigen is administered during vaccination. The combination of separate pathogen vaccines, such as diphtheria, tetanus, acellular pertussis, hepatitis A, haemophilus influenzae, type b-tetanus toxoid conjugate, and inactivated poliomyelitis, generally results in similar antibody responses against the individual components, whether they are administered separately, simultaneously, or sequentially (Jones, I. G., Tyrrell, H., Hill, A., Horobin, J. M. & Taylors, B. (1988) *Vaccine* 16, 113; Usonis, V., Bakasenas, V., Williams, P. & Clemens, R. (2000) *Vaccine* 18, 947-954; and Kanra, G., Silier, T., Yurdakok, K., Yavuz, T., Baskan, S., Ulukol, B., Ceyhan, M., Ozmert, E., Turday, F. & Pehlivan, T. (1999) *Vaccine* 18, 947-954). Similarly, combining purified bacterial capsular polysaccharides does not seem to reduce the immunogenicity of the individual polysaccharide components. By contrast, for conjugate vaccines, several factors could potentially negatively impact the antibody response to individual antigens, especially when monomeric conjugate vaccines are combined and administered using a cocktail-like approach (See, for example, Anderson, P. (1983) *Infection & Immunity* 39, 233-238; Kurika, S. (1996) *Vaccine* 14, 1239-1242; Barington, T., Gyhrs, A., Kristensen, K. & Heilmann, C. (1994) *Infection & Immunity* 62, 9-14; Peters, C. C., Tenbergen-Meeks, A. M., Poolman, J. T., Beurret, M., Zegers, B. J. M. & Rijkers, G. T. (1974) *Infect. Immun.* 59, 3504-3510; Sarvas, H., Makela, O., Toivanen, P. & Toivanen, A. (1974) *Scand. J. Immunol.* 3, 455-460; Fattom, A., Cho, Y. H., Chu, C., Fuller, S., Fries, L. & Naso, R. (1999) *Vaccine* 17, 126-133; Barington, T., Skettrup, M., Juul, L. & Heilman, C. (1993) *Infect. Immun.* 61, 432-438; Cross, A. M., Artenstein, A., Qu, J. & et al. (1994) *Journal of Infectious Diseases* 170, 834-840; Sarnaik, S., Kaplan, J., Schiffman, G., Bryla, D., Robbins, J. B. & Schneerson, R. (1990) *Pediatric Infectious Disease* 9, 181-186; and Molrine, D. C., Tarbell, G. S. & et al. (1995) *Annals of International Medicine* 123, 828-834).

In some instances, exposure to a carrier appears to produce an amplified response upon subsequent challenge, thereby resulting in increased antibody production against antigens conjugated to the same carrier protein (see, Anderson, P. (1983) *Infection & Immunity* 39, 233-238; Kurika, S. (1996) *Vaccine* 14, 1239-1242). In other cases, prior exposure to a carrier results in increased antibody levels only against the carrier and not to the conjugated antigens (See, Barington, T., Gyhrs, A., Kristensen, K. & Heilmann, C. (1994) *Infection &*

*Immunity* 62, 9-14; Peters, C. C., Tenbergen-Meeks, A. M., Poolman, J. T., Beurret, M., Zegers, B. J. M. & Rijkers, G. T. (1974) *Infect. Immun.* 59, 3504-3510; Sarvas, H., Makela, O., Toivanen, P. & Toivanen, A. (1974) *Scand. J. Immunol.* 3, 455-460). Combining conjugate vaccines containing the same carrier, or simultaneous administration of the carrier in non-conjugated form, may result in a decreased antibody response against the target antigens (See, Fattom, A., Cho, Y. H., Chu, C., Fuller, S., Fries, L. & Naso, R. (1999) *Vaccine* 17, 126-133; Barington, T., Skettrup, M., Juul, L. & Heilman, C. (1993) *Infect. Immun.* 61, 432-438; Cross, A. M., Artenstein, A., Qu, J. & et al. (1994) *Journal of Infectious Diseases* 170, 834-840; Sarnaik, S., Kaplan, J., Schiffman, G., Bryla, D., Robbins, J. B. & Schneerson, R. (1990) *Pediatric Infectious Disease* 9, 181-186; and Molrine, D. C., Tarbell, G. S. & et al. (1995) *Annals of International Medicine* 123, 828-834). Without wishing to be bound to any particular theory, Applicant proposes that these complications could be avoided through combination of the various antigens on the same conjugate vaccine. There was a possibility that, upon combining several antigens within the same construct, the immune response against one or more of the members of that set could be suppressed. Additionally, cross-reactivity involving more than one antigen might be observed, which would be expected to result in a portion of the antibody population produced having reduced affinity to particular antigens displayed on the cell surface. With that in mind, the effect of the administration of a glycopeptide bearing different antigens on the imminus response in subject was investigated. Significantly, the studies with compound 64 revealed that there was no substantial decrease in antibody titers over the course of immunizations with 64. Furthermore, no indication of an impaired antibody response against the individual antigens within the construct was apparent, as assessed by ELISA and FACS analysis. In fact, the antibody response for each individual antigen within the clustered construct was similar to that observed when the mixture of individual monomers was administered. What is even more significant from a potential therapeutic point of view is that, compared to the mixture of monomers, antibodies raised to the multivalent construct exhibited equal or higher reactivity with human cell lines expressing the native antigens, as determined by FACS analysis. Interestingly, although relatively high ELISA-based antibody titers were observed when sera resulting form vaccination with the polyvalent construct were screened against the polyvalent construct itself (see Table 5), FACS-based analyses (see Table 6) showed that that sera reacted just as well as sera derived form the monomers. The ELISA-based data in this case would seem to suggest that there was, indeed, cross-reactivity of antibodies between the antigens in the multivalent construct. However, the FACS data clearly indicate that this cross-reactivity does not negatively impact recognition of the antigens on the cell surface.

Antibody Response against Globo-H-Le$^y$-Tn construct (62). ELISA antibody titers against Globo-H-Le$^y$-Tn in sera from mice immunized with 64 was determined and results are summarized in Table 5. Relatively strong IgM and IgG titers were detected in mice vaccinated with 64, compared to pre-vaccination sera which showed no IgG and IgM titers. Construct 64 induced both IgM and IgG antibodies, with the GPI-0100 group inducing significantly higher titers compared to the QS-21 group. Group 5 induced very low IgM and IgG titers against the multivalent construct (see Table 5), when compared with groups 3 and 4.

Antibody Response against Globo-H ceramide. ELISA antibody titers against Globo-H-ceramide in sera from mice immunized with 64 were determined. As summarized in Table 5, weak IgM titers were detected in pre-vaccination sera, while sera obtained after vaccination with 64 showed increased IgM and IgG titers. No difference in IgM titers between groups 3 and 4 was detected. However, the group receiving QS-2 1 induced IgG antibodies against Globo-H, whereas the group receiving GPI-0100 failed to do so. Sera obtained from group 5 reacted strongly with Globo-H, relative to all other groups.

Antibody Response against Le$^y$. ELISA antibody titers against Le$^y$ in sera from mice immunized with 64 were tested and the results are summarized in Table 5. With the exception of group 1, no detectable anti-Le$^y$ antibodies were present in pre-vaccination sera. In general, sera obtained following vaccination with 64, or a mixture of three vaccines, reacted relatively strongly with Le$^y$ by ELISA. Construct 64 induced both IgM and IgG antibodies against Le$^y$. No difference in antibody production was observed between groups 3 and 4, having received QS-21 and GPI-0100, respectively. No difference in antibody titers was observed between mice immunized with construct 62, or with a mixture containing monomeric constructs 104, 105, and 106.

Antibody Response against Tn antigen. ELISA antibody titers against Tn-HSA in sera from mice immunized with 64 and mixture of constructs 104, 105, and 106 were determined. As summarized in Table 5, no IgM or IgG activity was detected in pre-vaccination sera. Groups 3 and 4 induced both IgM and IgG titers against Tn, but the adjuvant GPI-0100 induced one fold higher titer than adjuvant QS-21. Group 5 also showed high IgG titers against Tn antigen.

Cell surface reactivities. Cell surface reactivity of the sera was tested by flow cytometry using MCF-7 (Globo-H, Le$^y$ and Tn positive) and LS-C (Tn and Le$^y$ positive) cell lines. The results are summarized in Table 6, and the histograms of FACS against MCF-7 for groups 3, 4 and 5 are presented in FIG. 25. Sera obtained from all pre-vaccinated mice showed minimal reactivity (<10% positive cells). Following vaccination, groups 3, 4 and 5 showed significant IgM reactivity and low IgG reactivity against MCF-7 cells. No significant difference in cell surface reactivity against MCF-7 was observed with sera obtained after vaccination with construct 64 (group 3) or a mixture of constructs 104, 105, and 106 (group 5). There also did not appear to be a difference in cell surface reactivity between the adjuvants QS-21 (group 3) and GPI-0100 (group 5).

Without wishing to be bound to any particular theory, Applicant proposes that the lack of suppression of the antibody response against these multiantigenic vaccines may be due to the KLH/adjuvant combination (See, for example, Helling, F., Shang, A., Calves, M., Zhang, S., Ren, S., Yu, R. K., Oettgen, H. F. & Livingston, P. O. (1994) *Cancer Research* 54, 197-203; Kim, S. K., Ragupathi, G., Musselli, C., Choi, S. J., Park, Y. S. & Livingston, P. O. (2000) *Vaccine* 18, 597-603; and Kim, S., Ragupathi, G., Cappello, S., Kagan, E. & Livingston, P. O. (2000) *Vaccine* 19, 530-537). The use of KLH as carrier and QS-21 as adjuvant has been shown to result in a potent helper T cell type-1 response (See Helling, F., Shang, A., Calves, M., Zhang, S., Ren, S., Yu, R. K., Oettgen, H. F. & Livingston, P. O. (1994) *Cancer Research* 54, 197-203). This is likely the case for GPI-0100 as well, given its close structural relationship to QS-21. It has been reported that KLH is more effective as an immunogenic carrier than are a variety of other standard proteins. It has also been demonstrated that for GD3-KLH and MUC1-KLH conjugates, adjuvants such as QS-21 induce a 1000-100,000 fold augmentation of antibody responses in the mouse, compared to the use of the conjugates alone (See Kim, S. K., Ragupathi, G., Musselli, C., Choi, S. J., Park, Y. S. & Livingston, P. O. (2000) *Vaccine* 18, 597-603; and Kim, S., Ragupathi, G., Cappello, S., Kagan, E. & Livingston, P. O. (2000) *Vaccine* 19, 530-537). However, since our goal in the present study was primarily that of determining whether a multivalent conjugate vaccine could be administered without clear loss of immunogenicity against the individual components, we did not attempt to saturate the system.

Several other observations are noteworthy. Since GPI-0100 is less toxic than QS-21, greater quantities of GPI-0100 could be safely administered to the mice, and this resulted in a commensurate increase in antibody production. Also regarding antibody production, in general, construct 63 produced lower titers than 64. The structural differences between 63 and 64 may account for the immunological variance observed for these vaccines. Compound 63 is a more accurate mimic of mucin glycoproteins. Clustered glycoamino acids containing the mucin α-O-linked GalNAc core are highly rigidified, even in the case of very short glycopeptides, as a result of specific interactions between the glycan and peptide backbone (Don M. Coltart, Ajay K. Royyuru, Lawrence J. Williams, Peter W. Glunz, Dalibor Sames, Scott D. Kuduk, Jacob B. Schwarz, Xiao-Tao Chen, Samuel J. Danishefsky, David H. Live *J. Am. Chem. Soc.* In press). Thus, as a result of such structurally-based interactions, use of a mucin mimic that is faithful to the known architectural features of the cell surface molecule might impede the identification of the individual constituent antigens displayed on the peptide backbone during the immune response. In addition, the close resemblance of the structural core of the mucin-based vaccine construct (63) to self antigens within the mice, might make it more difficult to break tolerance.

In summary, single vaccine constructs bearing several different carbohydrate antigens such as those described herein, have the potential to stimulate a multifaceted immune response, necessary for optimal targeting of the heterogenous population of cells associated with a particular cancer type. Thus, since Globo-H, Le$^y$, and Tn are each over-expressed on prostate cancer, vaccination with 64 could potentially induce a broader range of antibodies, which will have a greater likelihood of accomplishing immunosurveillance against a greater range of aberrant cells. One of ordinary skill in the art will apreciate that the methods disclosed herein for the preparation of these constructs disclosed herein, as well as methods disclosed elsewhere (see, for example, Williams, L. J., Harris, C. R., Glunz, P. W. & Danishefsky, S. J. (2000) *Tetrahedron Lett.* 41, 9505-9508; Allen, J. R., Harris, C. A. & Danishefsky, S. J. (2001) *J. Am. Chem. Soc.* 123, 1890-1897 and U.S. patent application Ser. Nos. 09/083,776 and 09/276,595) are readily adaptable to the inclusion of more complex patterns of glycosylation and more elaborate peptide motifs, which might activate other elements of the immune system.

TABLE 5

Vaccination-induced ELISA-based antibody titers

| (Group) Vaccine Formulation | Mouse* | Against Multivalent construct | | | | Against Globo-H | | | |
|---|---|---|---|---|---|---|---|---|---|
| | | Pre-vaccination | | 10 days post 3$^{rd}$ vaccination | | Pre-vaccination | | 10 days post 3$^{rd}$ vaccination | |
| | | IgM | IgG | IgM | IgG | IgM | IgG | IgM | IgG |
| (1) 10 μg Globo-H-Le$^y$-Tn + 10 μg QS-21 | 1.1 | 0 | 0 | 0 | 0 | 320 | 40 | 0 | 0 |
| | 1.2 | 0 | 0 | 0 | 0 | 640 | 0 | 320 | 0 |
| | 1.3 | 0 | 0 | 0 | 0 | 0 | 0 | 40 | 0 |
| | 1.4 | 0 | 0 | 0 | 0 | 40 | 0 | 0 | 40 |
| | 1.5 | 0 | 0 | 0 | 0 | 320 | 160 | 80 | 40 |
| | Median | 0 | 0 | 0 | 0 | 320 | 0 | 40 | 0 |
| (2) 10 μg Globo-H-Le$^y$-Tn + KLH (nonconjugated) + 10 μg QS-21 | 2.1 | 0 | 0 | 320 | 320 | 0 | 0 | 40 | 40 |
| | 2.2 | 0 | 0 | 160 | 640 | 0 | 80 | 320 | 0 |
| | 2.3 | 0 | 0 | 0 | 320 | 0 | 40 | 0 | 0 |
| | 2.4 | 0 | 0 | 160 | 320 | 160 | 0 | 320 | 40 |
| | 2.5 | 0 | 0 | 160 | 320 | 80 | 0 | 160 | 40 |
| | Median | 0 | 0 | 160 | 320 | 0 | 0 | 160 | 0 |
| (3) 3 μg Globo-H-Le$^y$-Tn-KLH + 10 μg QS-21 | 3.1 | 0 | 0 | 160 | 5120 | 160 | 0 | 80 | 0 |
| | 3.2 | 0 | 0 | 640 | 10240 | 0 | 40 | 0 | 0 |
| | 3.3 | 0 | 0 | 1280 | 10240 | 0 | 0 | 80 | 40 |
| | 3.4 | 0 | 0 | 640 | 2560 | 0 | 0 | 40 | 40 |
| | 3.5 | 0 | 0 | 320 | 10240 | 0 | 0 | 40 | 40 |
| | Median | 0 | 0 | 640 | 10240 | 0 | 0 | 40 | 40 |
| (4) 3 μg Globo-H-Le$^y$-Tn-KLH + 100 μg GPI-0100 | 4.1 | 0 | 0 | 640 | 40960 | 80 | 0 | 40 | 0 |
| | 4.2 | 0 | 0 | 160 | 20480 | 0 | 0 | 160 | 0 |
| | 4.3 | 0 | 0 | 2560 | 40960 | 0 | 0 | 0 | 0 |
| | 4.4 | 0 | 0 | 2560 | 20480 | 0 | 0 | 40 | 0 |
| | 4.5 | 0 | 0 | 1280 | 40960 | 0 | 0 | 0 | 0 |
| | Median | 0 | 0 | 1280 | 40960 | 0 | 0 | 40 | 0 |
| (5) 3 μg Globo-H-KLH, 3 μg Le$^y$-KLH, 3 μg Tn-KLH + 10 μg QS-21 | 5.1 | 0 | 0 | 80 | 640 | 0 | 0 | 160 | 40 |
| | 5.2 | 0 | 0 | 640 | 320 | 0 | 0 | 320 | 160 |
| | 5.3 | 80 | 0 | 0 | 0 | 0 | 0 | 160 | 40 |
| | 5.4 | 0 | 0 | 1280 | 640 | 160 | 0 | 160 | 0 |
| | 5.4 | 0 | 0 | 2560 | 1280 | 160 | 0 | 320 | 80 |
| | Median | 0 | 0 | 640 | 640 | 0 | 0 | 160 | 40 |

| (Group) Vaccine Formulation | Mouse* | Against Le$^y$ | | | | Against Tn | | | |
|---|---|---|---|---|---|---|---|---|---|
| | | Pre-vaccination | | 10 days post 3$^{rd}$ vaccination | | Pre-vaccination | | 10 days post 3$^{rd}$ vaccination | |
| | | IgM | IgG | IgM | IgG | IgM | IgG | IgM | IgG |
| (1) 10 μg Globo-H-Le$^y$-Tn + 10 μg QS-21 | 1.1 | 0 | 80 | 0 | 0 | 0 | 0 | 0 | 0 |
| | 1.2 | 0 | 160 | 0 | 0 | 0 | 0 | 0 | 0 |
| | 1.3 | 0 | 40 | 0 | 0 | 0 | 0 | 0 | 0 |

TABLE 5-continued

Vaccination-induced ELISA-based antibody titers

|  |  |  |  |  |  |  |  |  |  |
|---|---|---|---|---|---|---|---|---|---|
|  | 1.4 | 0 | 160 | 0 | 0 | 0 | 0 | 40 | 0 |
|  | 1.5 | 0 | 160 | 0 | 0 | 0 | 0 | 80 | 0 |
|  | Median | 0 | 160 | 0 | 0 | 0 | 0 | 0 | 0 |
| (2) | 2.1 | 0 | 0 | 80 | 40 | 0 | 0 | 80 | 0 |
| 10 µg Globo-H-Le$^y$- | 2.2 | 0 | 0 | 0 | 40 | 0 | 0 | 160 | 320 |
| Tn + KLH | 2.3 | 0 | 0 | 0 | 80 | 0 | 0 | 0 | 320 |
| (nonconjugated) + | 2.4 | 0 | 0 | 40 | 0 | 0 | 0 | 80 | 160 |
| 10 µg QS-21 | 2.5 | 0 | 0 | 80 | 40 | 0 | 0 | 40 | 160 |
|  | Median | 0 | 0 | 40 | 40 | 0 | 0 | 80 | 160 |
| (3) | 3.1 | 0 | 0 | 40 | 40 | 0 | 0 | 80 | 320 |
| 3 µg Globo-H-Le$^y$- | 3.2 | 0 | 0 | 320 | 80 | 0 | 0 | 80 | 0 |
| Tn-KLH + | 3.3 | 0 | 0 | 160 | 80 | 0 | 0 | 320 | 80 |
| 10 µg QS-21 | 3.4 | 0 | 0 | 40 | 80 | 0 | 0 | 320 | 320 |
|  | 3.5 | 0 | 0 | 80 | 80 | 0 | 0 | 160 | 80 |
|  | Median | 0 | 0 | 80 | 80 | 0 | 0 | 160 | 160 |
| (4) | 4.1 | 0 | 0 | 80 | 40 | 0 | 0 | 160 | 160 |
| 3 µg Globo-H-Le$^y$- | 4.2 | 0 | 0 | 160 | 40 | 0 | 0 | 320 | 160 |
| Tn-KLH + | 4.3 | 0 | 0 | 80 | 40 | 0 | 0 | 320 | 640 |
| 100 µg GPI-0100 | 4.4 | 0 | 0 | 640 | 320 | 0 | 0 | 320 | 640 |
|  | 4.5 | 0 | 0 | 80 | 0 | 0 | 0 | 1280 | 1280 |
|  | Median | 0 | 0 | 80 | 40 | 0 | 0 | 320 | 640 |
| (5) | 5.1 | 0 | 0 | 40 | 80 | 0 | 0 | 1280 | 81920 |
| 3 µg Globo-H-KLH, | 5.2 | 0 | 0 | 160 | 320 | 0 | 0 | 80 | 10240 |
| 3 µg Le$^y$-KLH, | 5.3 | 0 | 0 | 160 | 80 | 0 | 0 | 5120 | 81920 |
| 3 µg Tn-KLH + | 5.4 | 0 | 0 | 80 | 160 | 0 | 0 | 1280 | 163840 |
| 10 µg QS-21 | 5.4 | 0 | 0 | 160 | 80 | 0 | 0 | 1280 | 40960 |
|  | Median | 0 | 0 | 160 | 80 | 0 | 0 | 1280 | 81920 |

*Each number corresponds to an individual mouse.

TABLE 6

FACS assay on MF7 and LSC cell lines with immune sera obtained pre- and post-immunization

| | | % Positive cells by FACS (MFI)* | | | | | | | |
|---|---|---|---|---|---|---|---|---|---|
| | | MCF-7 human breast cell line | | | | LSC human colon cell line | | | |
| | | Pre-serum | | Post-serum | | Pre-serum | | Post-serum | |
| (Group) Vaccine Formulation | Mouse* | IgM | IgG | IgM | IgG | IgM | IgG | IgM | IgG |
| (1) | 1.1 | 10 (21) | 11 (12) | 5 (18) | 11 (11) | 10 (31) | 10 (12) | 12 (36) | 12 (14) |
| 10 µg Globo-H-Le$^y$-Tn + | 1.2 | 9 (13) | 9 (12) | 31 (18) | 8 (9) | 11 (30) | 10 (17) | 11 (31) | 11 (15) |
| 10 µg QS-21 | 1.3 | 10 (15) | 11 (10) | 15 (17) | 9 (11) | 10 (52) | 10 (12) | 10 (50) | 11 (12) |
|  | 1.4 | 10 (5) | 11 (9) | 28 (11) | 16 (11) | 11 (28) | 10 (10) | 7 (22) | 15 (14) |
|  | 1.5 | 10 (14) | 10 (5) | 29 (20) | 15 (26) | 10 (32) | 11 (11) | 10 (32) | 14 (14) |
|  | Median | 10 (14) | 11 (10) | 28 (18) | 11 (11) | 10 (31) | 10 (12) | 10 (32) | 12 (14) |
| (2) | 2.1 | 10 (51) | 10 (12) | 31 (65) | 11 (11) | 10 (20) | 11 (13) | 15 (21) | 18 (17) |
| 10 µg Globo-H-Le$^y$-Tn + | 2.2 | 11 (44) | 10 (10) | 43 (79) | 18 (16) | 11 (19) | 11 (13) | 24 (29) | 29 (19) |
| KLH (nonconjugated) + | 2.3 | 11 (41) | 9 (9) | 68 (99) | 13 (15) | 10 (34) | 11 (11) | 22 (50) | 14 (12) |
| 10 µg QS-21 | 2.4 | 11 (38) | 10 (7) | 82 (127) | 20 (16) | 11 (54) | 11 (17) | 12 (61) | 23 (37) |
|  | 2.5 | 10 (44) | 10 (10) | 51 (86) | 20 (16) | 10 (20) | 11 (11) | 45 (67) | 21 (19) |
|  | Median | 11 (44) | 10 (10) | 51 (86) | 18 (16) | 10 (20) | 10 (13) | 22 (50) | 21 (19) |
| (3) | 3.1 | 10 (42) | 11 (8) | 46 (62) | 20 (11) | 10 (14) | 11 (22) | 20 (18) | 7 (17) |
| 3 µg Globo-H-Le$^y$-Tn- | 3.2 | 11 (34) | 10 (5) | 93 (144) | 48 (18) | 10 (13) | 10 (5) | 70 (32) | 68 (24) |
| KLH + 10 µg QS-21 | 3.3 | 11 (36) | 11 (10) | 76 (109) | 26 (16) | 10 (64) | 10 (25) | 18 (94) | 30 (68) |
|  | 3.4 | 11 (43) | 11 (7) | 53 (89) | 23 (12) | 10 (70) | 11 (52) | 20 (107) | 14 (60) |
|  | 3.5 | 11 (33) | 11 (7) | 77 (95) | 39 (15) | 10 (62) | 10 (20) | 24 (95) | 38 (53) |
|  | Median | 11 (36) | 11 (7) | 76 (95) | 26 (15) | 10 (62) | 10 (22) | 20 (94) | 30 (53) |
| (4) | 4.1 | 11 (33) | 10 (8) | 47 (65) | 17 (10) | 11 (13) | 10 (8) | 23 (18) | 25 (13) |
| 3 µg Globo-H-Le$^y$-Tn- | 4.2 | 12 (39) | 10 (8) | 66 (102) | 36 (25) | 10 (16) | 10 (10) | 31 (26) | 43 (17) |
| KLH + | 4.3 | 10 (37) | 10 (11) | 73 (100) | 8 (11) | 11 (71) | 10 (28) | 18 (122) | 19 (50) |
| 100 µg GPI-0100 | 4.4 | 12 (41) | 10 (7) | 87 (167) | 23 (12) | 11 (63) | 9 (23) | 72 (251) | 36 (67) |
|  | 4.5 | 11 (34) | 10 (8) | 55 (76) | 57 (26) | 10 (58) | 10 (22) | 13 (66) | 29 (54) |
|  | Median | 11 (37) | 10 (8) | 66 (100) | 23 (12) | 11 (58) | 10 (22) | 23 (66) | 29 (50) |
| (5) | 5.1 | 12 (47) | 11 (10) | 41 (69) | 14 (11) | 10 (14) | 10 (13) | 14 (17) | 16 (24) |
| 3 µg Globo-H-KLH, 3 µg | 5.2 | 12 (35) | 10 (8) | 96 (175) | 16 (10) | 9 (21) | 10 (10) | 32 (44) | 22 (12) |
| Le$^y$-KLH, 3 µg Tn- | 5.3 | 10 (34) | 10 (9) | 77 (105) | 23 (12) | 10 (17) | 11 (27) | 78 (131) | 29 (53) |
| KLH + 10 µg QS-21 | 5.4 | 11 (31) | 10 (7) | 69 (75) | 30 (16) | 11 (91) | 10 (23) | 7 (73) | 22 (36) |
|  | 5.4 | 12 (17) | 9 (7) | 96 (89) | 25 (11) | 10 (69) | 10 (27) | 18 (110) | 52 (70) |
|  | Median | 12 (34) | 10 (8) | 77 (89) | 23 (11) | 10 (21) | 10 (23) | 18 (73) | 22 (36) |

*Mean fluorescence intensity. Monoclonal antibody 3S193 (IgG) showed 99%, VK-9 showed 42% on MCF-7.
3S193 (IgG) showed 78%, HB-Tn-1 showed 91% on LSC.

The invention claimed is:

1. A glycopeptide or glycoconjugate comprising a peptidic backbone made up of two or more amino acids, wherein one or more of said amino acids is/are independently:

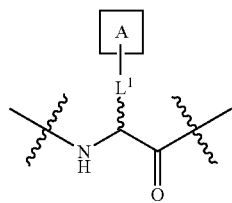

wherein each occurrence of $L^1$ is independently a substituted or unsubstituted aliphatic or heteroaliphatic moiety; wherein $L^1$ is not —O—(CHMe)- or —O—CH$_2$—;
each occurrence of A is independently a carbohydrate determinant having the structure:

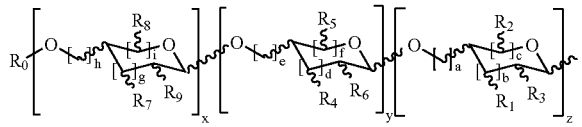

wherein a, b, c, d, e, f, g, h, i, x, y and z are independently 0, 1, 2 or 3, with the proviso that the x, y and z bracketed structures represent pyranose moieties and the sum of b and c is 2, the sum of d and f is 2, and the sum of g and i is 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, OR$^i$, NHR$^i$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

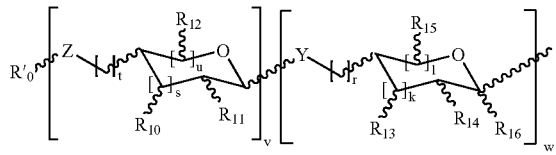

wherein Y and Z are independently NH or O; wherein k, l, r, s, t, u, v and w are each independently 0, 1 or 2; with the proviso that the v and w bracketed structures represent pyranose moieties and the sum of l and k is 2, and the sum of s and u is 2, and with the proviso that v and w are not simultaneously 0; wherein R'$_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, OR$^{iii}$, NHR$^{iii}$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, COOR$^{ii}$, CONHR$^{ii}$, a substituted or unsubstituted linear or branched chain alkyl or aryl group; wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group;
wherein at least one occurrence of A is Gb3.

2. The glycoconjugate of claim 1 wherein the glycoconjugate is covalently linked to an immunogenic carrier protein, peptide or lipid.

3. The glycoconjugate of claim 2, wherein the immunogenic carrier is bovine serum albumin, polylysine, keyhole limpet hemocyanin or tripalmitoyl-S-glycerylcysteinylserine.

4. The glycopeptide or glycoconjugate of claim 1, wherein said glycopeptide or glycoconjugate is a construct having the structure:

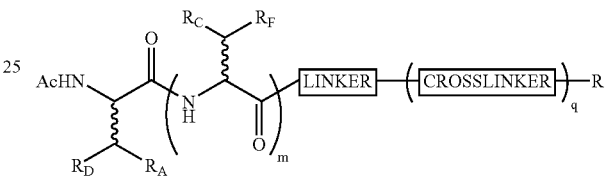

wherein
m is an integer from 1-20;
q is 0 or 1;
R is hydrogen or an immunogenic carrier;
the crosslinker is a moiety derived from a crosslinking reagent capable of conjugating a surface amine of the carrier and a thiol of the linker; and
the linker is either —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester.

5. The glycopeptide or glycoconjugate of claim 4 wherein, in the glycopeptide or glycoconjugate, the linker is —O—, —NR$_G$—, —NR$_G$(aliphatic)NR$_J$—, —NR$_G$(heteroaliphatic)NR$_J$—, -(aliphatic)NR$_J$—, -heteroaliphatic)NR$_J$—, —O(aliphatic)NR$_J$—, —O(heteroaliphatic)NR$_J$—, —NR$_G$(aliphatic)NR$_J$(C=O)(CR$_H$R$_I$)$_k$S—, —NR$_G$(heteroaliphatic)NR$_J$(C=O)(CR$_H$R$_I$)$_k$S—, —O(aliphatic)NR$_J$(C=O)(CR$_H$R$_I$)$_k$S—, —(heteroaliphatic)NR$_J$(C=O)(CR$_H$R$_I$)$_k$S—, —O(aliphatic)NR$_J$(C=O)(CR$_H$R$_I$)$_k$S—, —O(heteroaliphatic)NR$_J$(C=O)(CR$_H$R$_I$)$_k$S—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5; wherein each occurrence of R$_G$, R$_H$, R$_I$ or R$_J$ is independently hydrogen, a linear or branched, substituted or unsubstituted, cyclic or acyclic moiety, or a substituted or unsubstituted aryl moiety, and wherein each aliphatic or heteroaliphatic moiety is independently substituted or unsubstituted, linear or branched, cyclic or acyclic.

6. The glycopeptide or glycoconjugate of claim 4 wherein the linker is —O—, —NR$_G$(CR$_H$R$_I$)$_k$NR$_J$—, —NR$_G$(CR$_H$R$_I$)$_k$NR$_J$(C=O)(CR$_H$R$_I$)$_k$S—, —NR$_G$—, —(CR$_H$R$_I$)$_k$NR$_J$—, —O(CR$_H$R$_I$)$_k$NR$_J$—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5, wherein each occurrence of R$_G$, R$_H$, R$_I$ or R$_J$ is independently hydrogen, a linear or branched, substituted or unsubstituted, cyclic or acyclic moiety, or a substituted or unsubstituted aryl moiety.

7. The glycopeptide or glycoconjugate of claim 1 or 4 wherein at least one occurrence of L$^1$ is —O—(CH$_2$)$_n$—, wherein n is an integer from 2-9.

8. The glycopeptide or glycoconjugate of claim 7 wherein n is 4.

9. The glycopeptide or glycoconjugate of claim 1 or 4 wherein at least one occurrence of L$^1$ comprises a glycoside moiety.

10. The glycopeptide or glycoconjugate of claim 9 wherein the glycoside moiety is a monosaccharide.

11. The glycopeptide or glycoconjugate of claim 9 wherein the monosaccharide is a moiety having the structure:

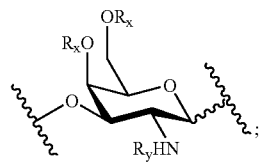

wherein each occurrence of R$_x$ is independently hydrogen or a protecting group, and R$_y$ is a nitrogen protecting group.

12. The glycopeptide or glycoconjugate of claim 4 wherein each occurrence of A is independently Globo-H, fucosyl GM1, KH-1, glycophorin, Le$^y$, N3, Tn, STN, 2,6-STn, (2,3) ST, Gb3, TF, or a carbohydrate domain having the structure:

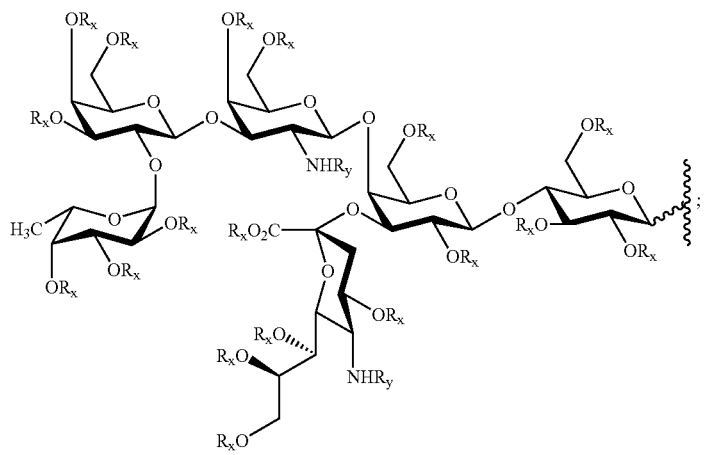

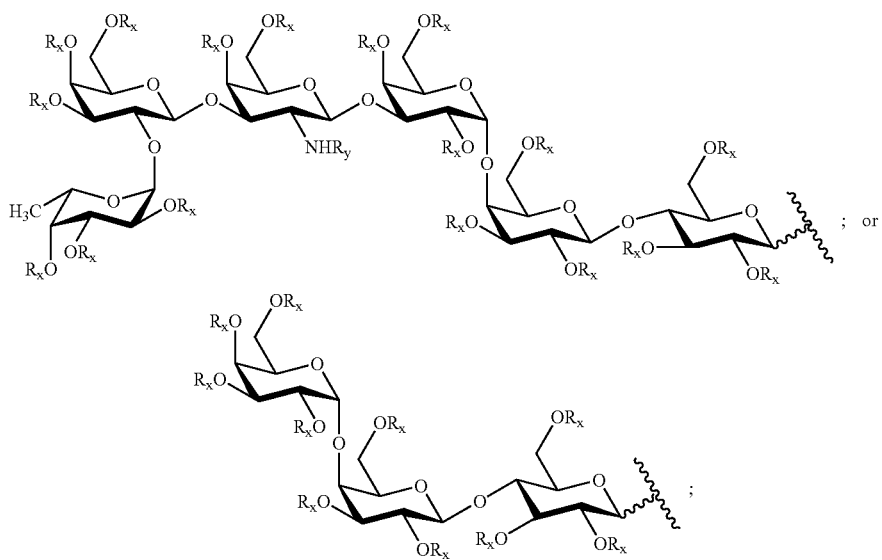

wherein each occurrence of $R_x$ is independently hydrogen or a protecting group; and wherein each occurrence of $R_y$ is independently hydrogen or a nitrogen protecting group.

13. The glycopeptide of claim 1, wherein the glycopeptide glycoamino acid residues are prepared by a method comprises steps of:

a. providing an alkenyl glycoside;
b. providing a protected alkenylamino acid;
c. reacting said alkenyl glycoside with the alkenylamino acid in the presence of a catalyst to generate a glycoenamide ester; and
d. reducing the glycoenamide ester to generate a glycoamino acid;

wherein, in the method:

the alkenyl glycoside of step (a) has the structure:

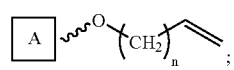

wherein n is 1-8;

A is a carbohydrate domain having the structure:

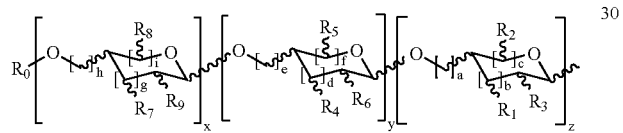

wherein a, b, c, d, e, f, g, h, i, x, y and z are independently 0, 1, 2 or 3, with the proviso that the x, y and z bracketed structures represent pyranose moieties and the sum of b and c is 2, the sum of d and f is 2, and the sum of g and i is 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

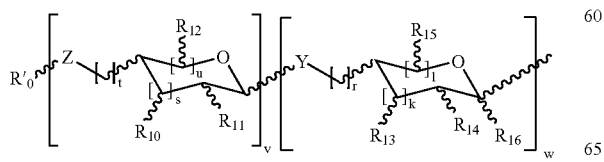

wherein Y and Z are independently NH or O; wherein k, l, r, s, t, u, v and w are each independently 0, 1 or 2; with the proviso that the v and w bracketed structures represent pyranose moieties and the sum of l and k is 2, and the sum of s and u is 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;

the alkenylamino acid of step (b) is an alkenylglycine having the structure:

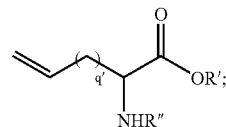

wherein R' and R" are each independently hydrogen or a protecting group and q' is an integer from 0-8;

the glycoenamide ester generated in step (c) has the structure:

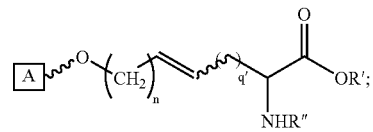

wherein R' and R" are each independently hydrogen or a protecting group, n is an integer from 1-8, and q' is an integer from 0-8; and the glycoamino acid generated in step (d) has the structure:

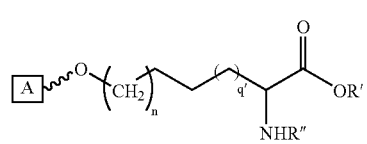

wherein R' and R" are each independently hydrogen or a protecting group, n is an integer from 1-8, and q' is an integer from 0-8;

wherein the catalyst of step (c) is selected from the group consisting of:

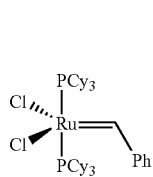
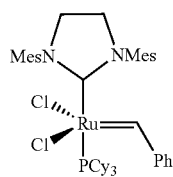
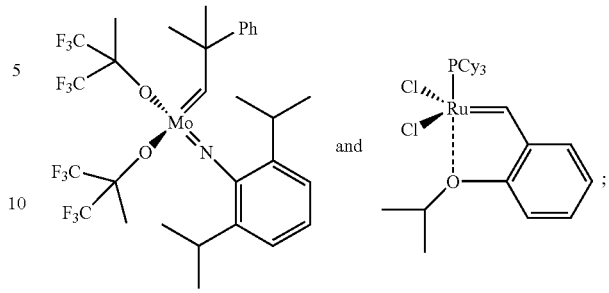

wherein Cy represents a cyclohexyl moiety.

14. The glycopeptide of claim 13 wherein, in the method, A is selected from the group consisting of Globo-H, fucosyl GM1, KH-1, glycophorin, STN, (2,3)ST, Le$^y$, N3, Tn, STn, 2,6-STn, Gb3, TF, or a carbohydrate domain having the structure:

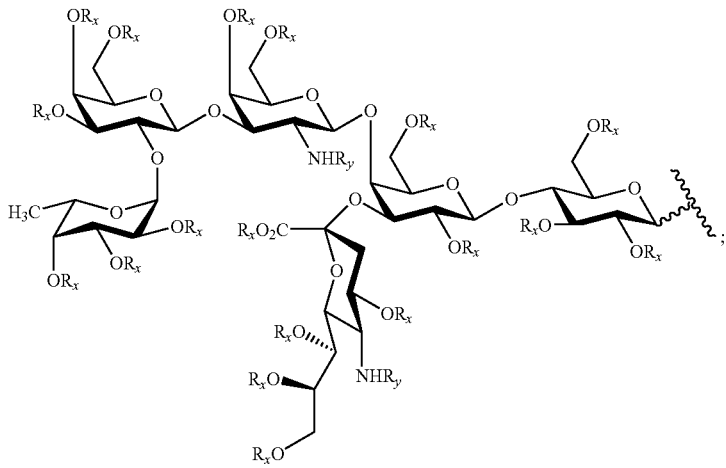

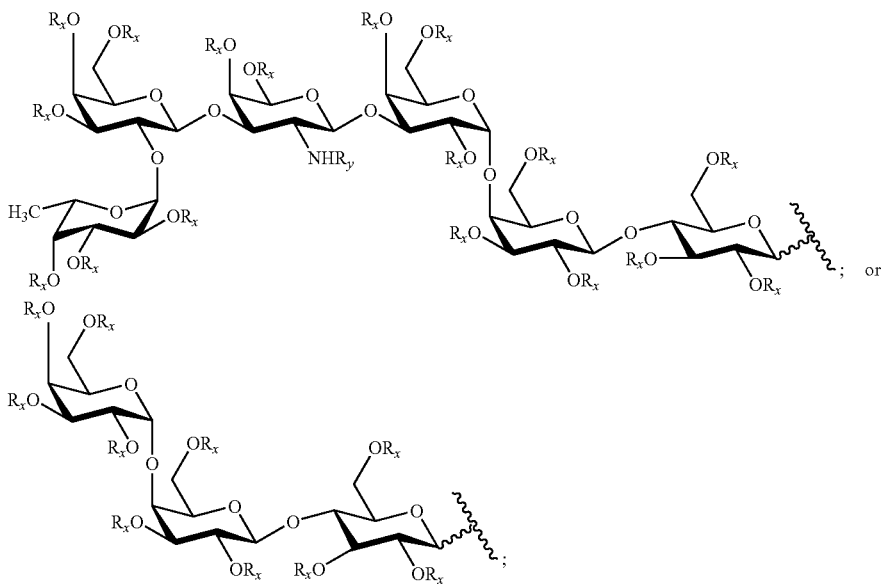

wherein each occurrence of $R^x$ is independently hydrogen or a protecting group; and wherein each occurrence of $R^y$ is independently hydrogen or a nitrogen protecting group.

15. The glycopeptide of claim 13 wherein, in the method, the catalyst of step (c) has the structure:

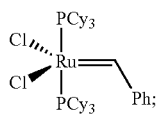

wherein Cy represents a cyclohexyl moiety.

16. The glycopeptide of claim 13 wherein, in the method, the step of reducing said glycoenamide ester to generate a glycoamino acid comprises reacting said enamide ester under hydrogenation conditions and subsequent reaction under deprotection conditions to generate a glycoamino acid.

17. The glycopeptide or glycoconjugate of claim 1, wherein at least one occurrence of A-L$^1$- is derived from a compound having the structure:

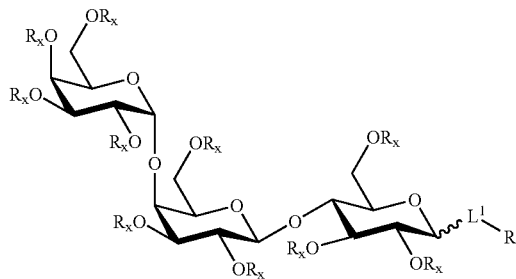

wherein L$^1$ is a substituted or unsubstituted, linear or branched, cyclic or acyclic, saturated or unsaturated aliphatic or heteroaliphatic moiety;

each occurrence of $R^x$ is independently hydrogen or a protecting group;

wherein R is hydrogen; substituted or unsubstituted alkyl; alkenyl; aryl;

—CH$_2$CH(CO$_2$R')(NHR"), wherein R' or R" are each independently hydrogen, protecting group, substituted or unsubstituted alkyl, aryl, peptide or protein.

18. The glycopeptide or glycoconjugate of claim 17 wherein L$^1$ is —O—(CH$_2$)$_n$— wherein n is an integer from 2-9.

19. The glycopeptide or glycoconjugate of claim 17, wherein L$^1$ comprises a glycoside moiety.

20. The glycopeptide or glycoconjugate of claim 19, wherein the glycoside moiety is a monosaccharide.

21. The glycopeptide or glycoconjugate of claim 20, wherein the monosaccharide is a moiety having the structure:

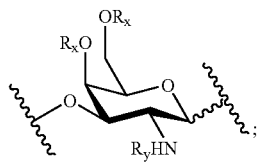

wherein each occurrence of $R_x$ is independently hydrogen or a protecting group, and $R_y$ is a nitrogen protecting group.

22. The glycopeptide of claim 17, wherein R is —CH$_2$CH(CO$_2$R')(NHR")— and the compound has the structure:

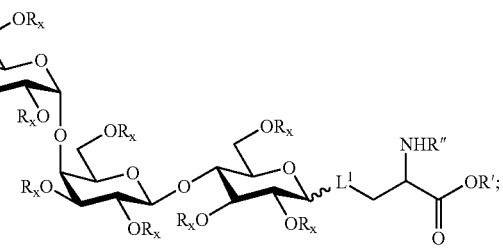

wherein R' and R" are each independently hydrogen or a protecting group, and $R_x$ and L$^1$ are as defined in claim 17.

23. The glycopeptide of claim 22, wherein L$^1$ is —O(CH$_2$)$_n$— and the compound has the structure:

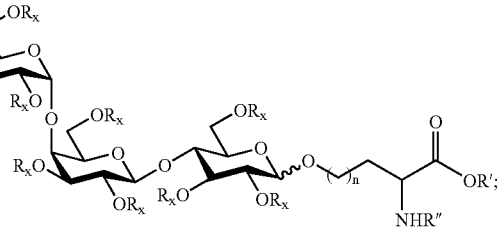

wherein n is an integer from 1-8 and R' and R" are each independently hydrogen or a protecting group.

24. The glycopeptide of claim 22 or 23, wherein R' and R" are each protecting groups independently selected from the group consisting of Fmoc, acetyl, Benzyl, Boc, t-butyl, Cbz and TSE.

25. The glycopeptide of claim 23, wherein n is 3.

26. The glycopeptide or glycoconjugate of claim 1, wherein at least one occurrence of A is Globo-H, fucosyl GM1, KH-1, glycophorin, STN, Le$^y$, N3, Tn, 2,6-STn, (2,3) ST, TF, or a carbohydrate domain having the structure:

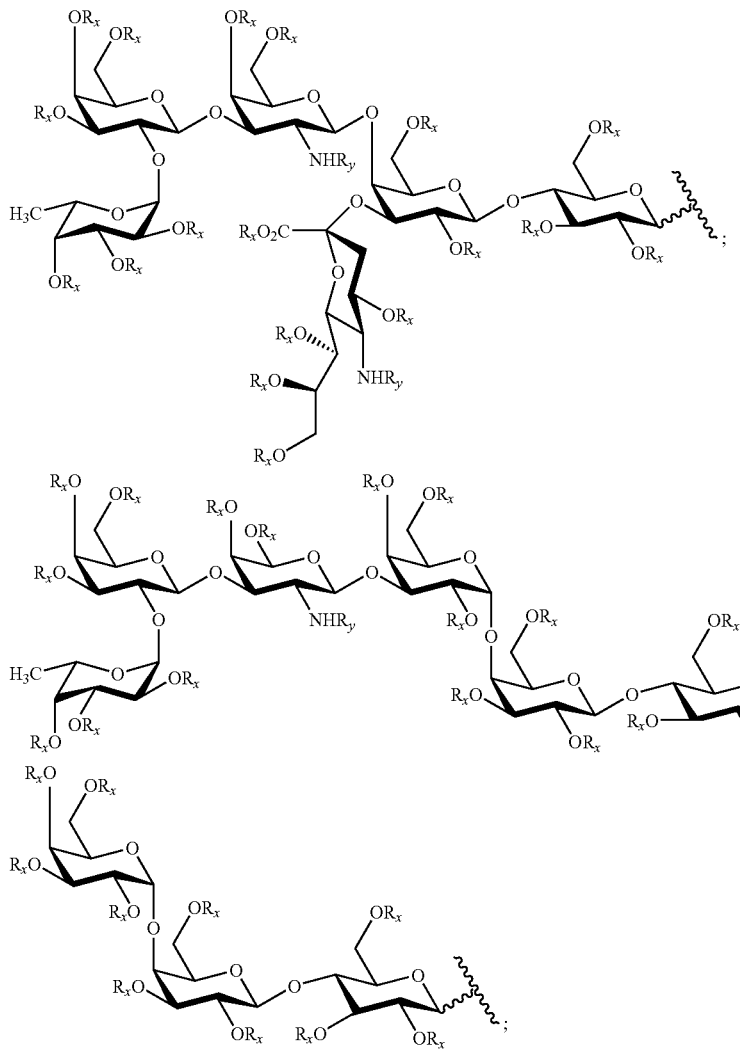

wherein each occurrence of $R_x$ is independently hydrogen or a protecting group; and wherein each occurrence of $R_y$ is independently hydrogen or a nitrogen protecting group.

27. A glycopeptide or glycoconjugate comprising a peptidic backbone made up of two or more amino acids, wherein one or more of said amino acids is/are independently:

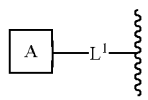

wherein each occurrence of $L^1$ is independently a substituted or unsubstituted aliphatic or heteroaliphatic moiety; wherein $L^1$ is not —O-(CHMe)- or —O—CH$_2$—; each occurrence of A is independently a carbohydrate determinant having the structure:

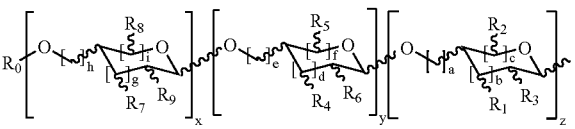

wherein a, b, c, d, e, f, g, h, i, x, y and z are independently 0, 1, 2 or 3, with the proviso that the x, y and z bracketed structures represent pyranose moieties and the sum of b and c is 2, the sum of d and f is 2, and the sum of g and i is 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, OR$'$, NHR$'$, NHCOR$'$, F, CH$_2$OH, CH$_2$OR$'$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$'$ is independently hydrogen, CHO, COOR$''$, or a substituted or unsubstituted linear or branched chain alkyl, acyl, arylalkyl or aryl group or a saccharide moiety having the structure:

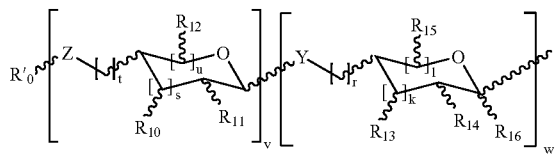

wherein Y and Z are independently NH or O; wherein k, l, r, s, t, u, v and w are each independently 0, 1 or 2; with the proviso that the v and w bracketed structures represent pyranose moieties and the sum of l and k is 2, and the sum of s and u is 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R16 is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;

wherein at least one occurrence of A is a carbohydrate domain having the structure:

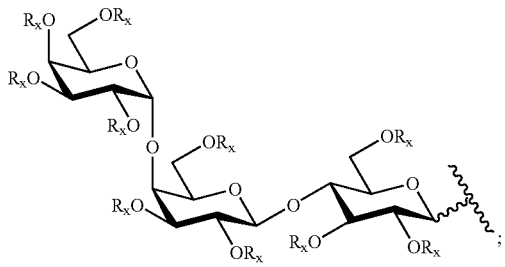

wherein each occurrence of $R_x$ is independently hydrogen or a protecting group.

28. A glycopeptide or glycoconjugate comprising a peptidic backbone made up of two or more amino acids, wherein one or more of said amino acids is/are independently substituted with a glycosidic moiety having the structure:

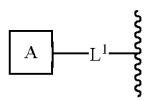

wherein each occurrence of $L^1$ is independently a substituted or unsubstituted aliphatic or heteroaliphatic moiety;

wherein said glycopeptide or glycoconjugate is a construct having the structure:

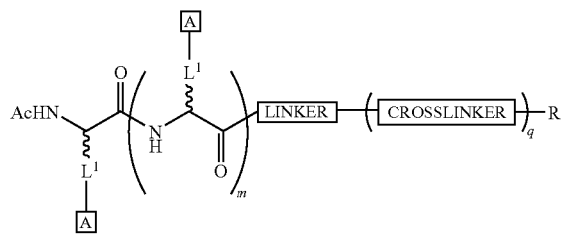

wherein m is 2;

q is 0 or 1;

R is hydrogen or an immunogenic carrier;

the linker is either —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester; and wherein at least one occurrence of $L^1$ is —O(CH$_2$)$_n$—, wherein n is an integer from 2-9; wherein $L^1$ is not —O-(CHMe)- or —O—CH$_2$—;

the crosslinker is a moiety derived from a crosslinking reagent capable of conjugating a surface amine of the carrier and a thiol of the linker;

and each occurrence of A is independently a carbohydrate domain having the structure:

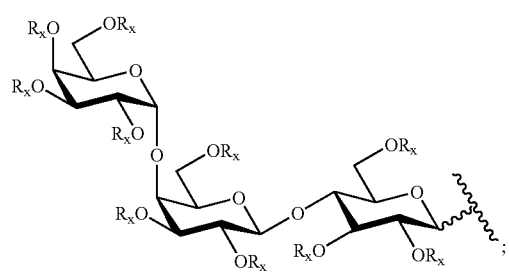

wherein each occurrence of $R_x$ is independently hydrogen or a protecting group.

29. A glycopeptide or glycoconjugate comprising a peptidic backbone made up of two or more amino acids, wherein one or more of said amino acids is/are independently substituted with a glycosidic moiety having the structure:

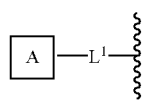

wherein each occurrence of $L^1$ is independently a substituted or unsubstituted aliphatic or heteroaliphatic moiety; wherein $L^1$ is not —O-(CHMe)- or —O—CH$_2$—;

wherein said glycopeptide or glycoconjugate is a construct having the structure:

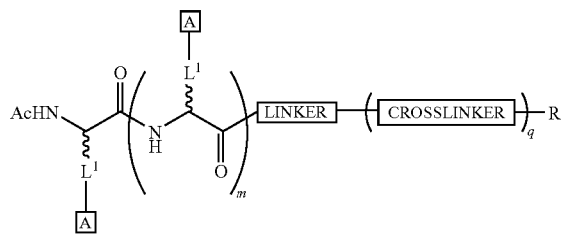

wherein m is 2;

q is 0 or 1;

R is hydrogen or an immunogenic carrier;

the linker is either —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;

the crosslinker is a moiety derived from a crosslinking reagent capable of conjugating a surface amine of the carrier and a thiol of the linker; and wherein at least one occurrence of $L^1$ comprises a glycoside moiety, and each occurrence of A is independently a carbohydrate domain having the structure:

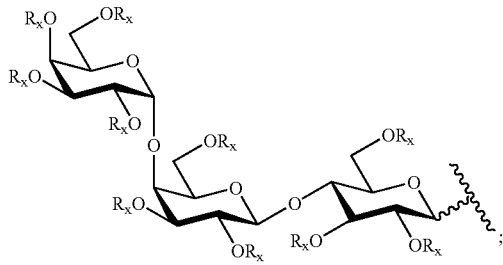

wherein each occurrence of $R_x$ is independently hydrogen or a protecting group.

30. The glycopeptide or glycoconjugate of claim 29 wherein the glycoside is a monosaccharide.

31. The glycopeptide or glycoconjugate of claim 30 wherein the monosaccharide is a moiety having the structure:

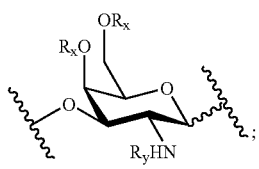

wherein each occurrence of $R_x$ is independently hydrogen or a protecting group, and $R_y$ is a nitrogen protecting group.

32. A glycopeptide or glycoconjugate having the structure:

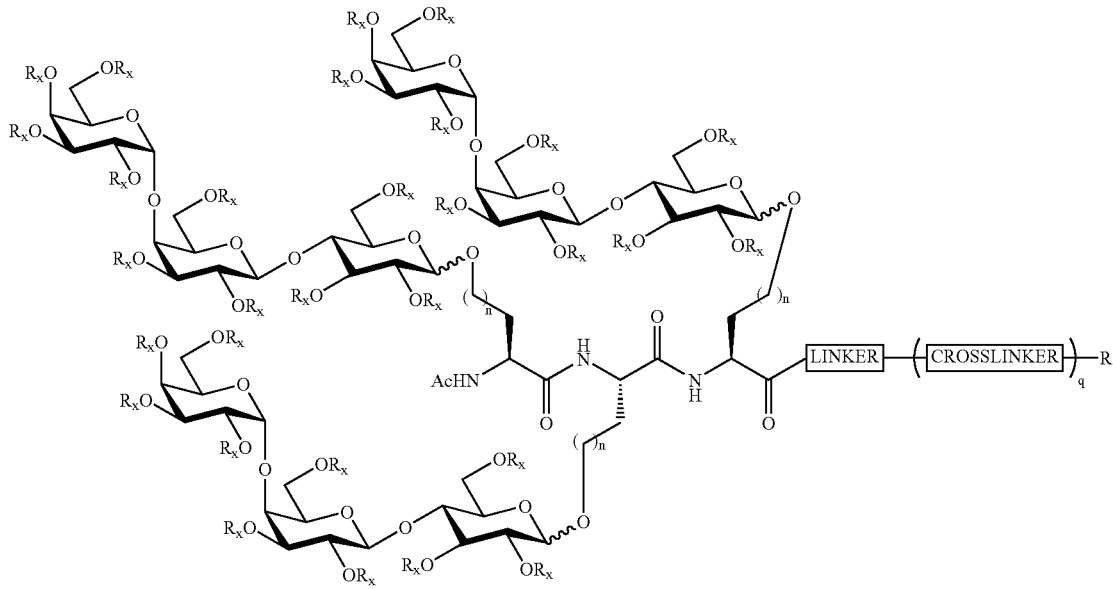

wherein
q is 0 or 1;
R is hydrogen or an immunogenic carrier;
the linker is either —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;
the crosslinker is a moiety derived from a crosslinking reagent capable of conjugating a surface amine of the carrier and a thiol of the linker;
each occurrence of n is independently an integer from 1-9; and
each occurrence of $R_x$ is independently hydrogen or a protecting group.

33. A glycopeptide or glycoconjugate having the structure:

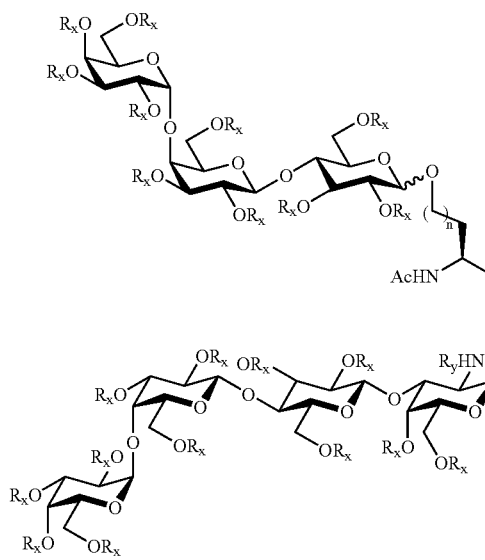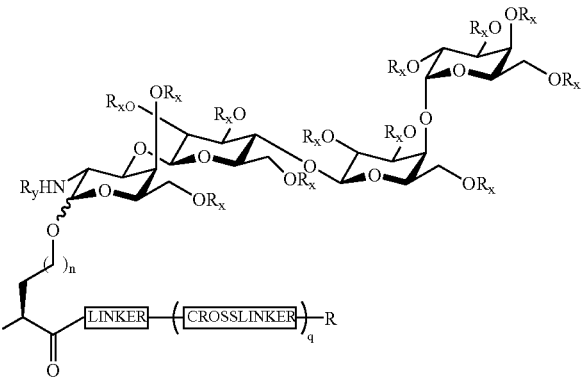

wherein
q is 0 or 1;
R is hydrogen or an immunogenic carrier;
the linker is either —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;
the crosslinker is a moiety derived from a crosslinking reagent capable of conjugating a surface amine of the carrier and a thiol of the linker;
each occurrence of n is independently an integer from 1-9;
each occurrence of $R_x$ is independently hydrogen or a protecting group, and
$R_y$ is a nitrogen protecting group.

34. The glycopeptide or glycoconjugate of claim 32 wherein each occurrence of n is 3.

35. The glycopeptide or glycoconjugate of claim 32 or 33 wherein the linker is a moiety having the structure —NH(CH$_2$)$_t$NHC(=O)(CH$_2$)$_v$S—; wherein t and v are each independently integers from 1-6.

36. The glycopeptide or glycoconjugate of claim 32 or 33 wherein each occurrence of $R_x$ is hydrogen.

37. The glycopeptide or glycoconjugate of claim 33 wherein each occurrence of $R_y$ is Ac.

38. The glycopeptide or glycoconjugate of claim 33 wherein n is 3-5, and the linker is a moiety having the structure —NH(CH$_2$)$_t$NHC(=O)(CH$_2$)$_v$S— wherein t and v are each independently integers from 1-6.

39. The glycopeptide or glycoconjugate of claim 32 wherein n is 3, and the linker is a moiety having the structure —NH(CH$_2$)$_t$NHC(=O)(CH$_2$)$_v$S— wherein t and v are each independently integers from 1-6.

40. The glycopeptide or glycoconjugate of claim 32 or 33 wherein t is 3 and v is 1.

41. A glycopeptide or glycoconjugate comprising a peptidic backbone made up of two or more amino acids, wherein one or more of said amino acids is/are independently:

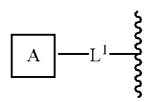

wherein said glycopeptide or glycoconjugate is a construct having the structure:

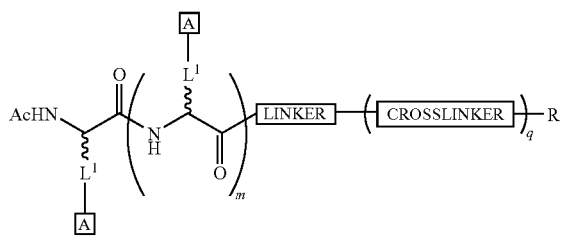

wherein
m is an integer from 1-20;
q is 0 or 1;
R is hydrogen or an immunogenic carrier;
the linker is either —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester;
the crosslinker is a moiety derived from a crosslinking reagent capable of conjugating a surface amine of the carrier and a thiol of the linker;
wherein each occurrence of $L^1$ is independently a substituted or unsubstituted aliphatic or heteroaliphatic moiety; wherein $L^1$ is not —O-(CHMe)- or —O—CH$_2$—;
and wherein each occurrence of A is independently a carbohydrate determinant having the structure:

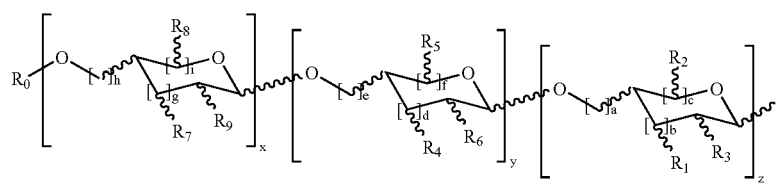

wherein a, b, c, d, e, f, g, h, i, x, y and z are independently 0, 1, 2 or 3, with the proviso that the x, y and z bracketed structures represent pyranose moieties and the sum of b and c is 2, the sum of d and f is 2, and the sum of g and i is 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, COOR$^{ii}$, or a substituted or unsubstituted linear or branched chain alkyl, acyl, arylalkyl or aryl group or a saccharide moiety having the structure:

wherein Y and Z are independently NH or O; wherein k, l, r, s, t, u, v and w are each independently 0, 1 or 2; with the proviso that the v and w bracketed structures represent pyranose moieties and the sum of l and k is 2, and the sum of s and u is 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, COOR$^{ii}$, CONHR$^{ii}$, a substituted or unsubstituted linear or branched chain alkyl or aryl group; wherein each occurrence of $R^{iii}$ is hydrogen, CHO, COOR$^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group;
wherein, in the glycopeptide or glycoconjugate, at least one occurrence of A is a carbohydrate domain having the structure:

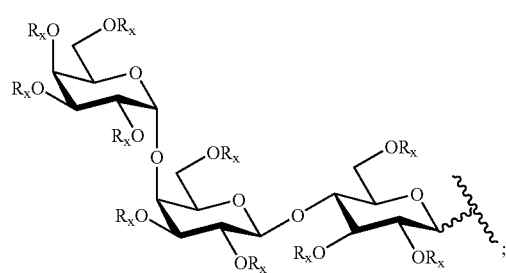

wherein each occurrence of $R_x$ is independently hydrogen or a protecting group.

42. A pharmaceutical composition comprising a glycopeptide or glycoconjugate of any one of claims 1, 27-29, 32-33, or 41, and a pharmaceutically acceptable excipient.

43. The pharmaceutical composition of claim 1, further comprising one or more immunological adjuvants.

44. The pharmaceutical composition of claim 43, wherein at least one of said one or more immunological adjuvants is a saponin adjuvant.

45. The pharmaceutical composition of claim 44, wherein the saponin adjuvant is GPI-0100.

46. The pharmaceutical composition of claim 43, wherein at least one of said one or more immunological adjuvants is bacteria or liposomes.

47. The pharmaceutical composition of claim 43, wherein the immunological adjuvant is Salmonella minnesota cells, bacille Calmette-Guerin or QS21.

48. A method of treating cancer in a subject suffering therefrom comprising:
    administering to a subject a therapeutically effective amount of a composition comprising a glycoconjugate of claim 1;
    one or more immunological adjuvants; and
    a pharmaceutically acceptable carrier.

49. The method of claim 48, wherein the cancer is a solid tumor.

50. The method of claim 48, wherein the subject is in clinical remission, or where the subject has been treated by surgery, has limited unresected disease.

51. A method of inducing antibodies in a subject, wherein the antibodies are capable of specifically binding with tumor cells, which comprises administering to the subject an amount of a composition effective to induce the antibodies, wherein the composition comprises:
    a pharmaceutically acceptable carrier;
    an immunogenic carrier; and
    a glycopeptide comprising a peptidic backbone made up of two or more amino acids, wherein one or more of said amino acids is/are independently:

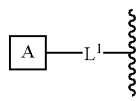

wherein each occurrence of $L^1$ is independently a substituted or unsubstituted aliphatic or heteroaliphatic moiety; wherein $L^1$ is not —O-(CHMe)- or —O—CH$_2$—;
each occurrence of A is independently a carbohydrate determinant having the structure:

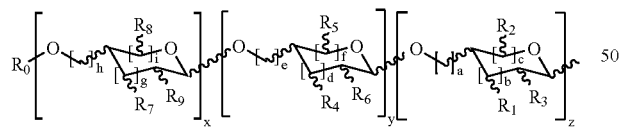

wherein a, b, c, d, e, f, g, h, i, x, y and z are independently 0, 1, 2 or 3, with the proviso that the x, y and z bracketed structures represent pyranose moieties and the sum of b and c is 2, the sum of d and f is 2, and the sum of g and i is 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, OR$^i$, NHR$^i$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

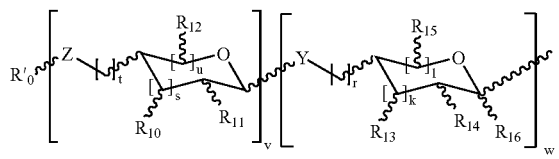

wherein Y and Z are independently NH or O; wherein k, l, r, s, t, u, v and w are each independently 0, 1 or 2; with the proviso that the v and w bracketed structures represent pyranose moieties and the sum of l and k is 2, and the sum of s and u is 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, OR$^{iii}$, NHR$^{iii}$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, COOR$^{ii}$, CONHR$^{ii}$, a substituted or unsubstituted linear or branched chain alkyl or aryl group;

wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group;

wherein the glycopeptide has three occurrences of A, each of which is selected from Tn, TF or Le$^y$ and the antibodies induced are those that recognize Tn, TF and/or Le$^y$ antigens;

the glycopeptide has five occurrences of A, each of which is selected from Globo-H, Le$^y$, STn, TF or Tn, and the antibodies induced are those that recognize Globo-H, Le$^y$, STn, TF and/or Tn antigens; or at least once occurrence of A is Gb3, or a carbohydrate domain having the structure:

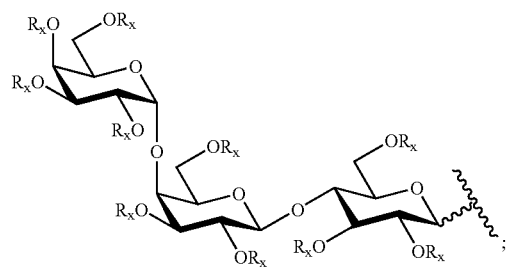

wherein each occurrence of $R_x$ is independently hydrogen or a protecting group; and each occurrence of $R_y$ is independently hydrogen or a nitrogen protecting group.

52. The method of claim 51, wherein the composition comprises the structure:

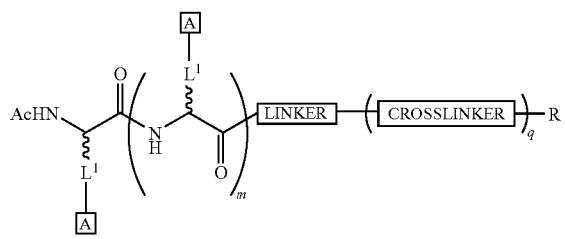

wherein m is an integer from 1-20;

q is 0 or 1;

R is hydrogen or an immunogenic carrier;

the linker is either —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester; and the crosslinker is a moiety derived from a crosslinking reagent capable of conjugating a surface amine of the carrier and a thiol of the linker.

53. The method of claim 51 or 52, wherein at least one occurrence of $L^1$ is —O—$(CH_2)_n$—, wherein n is an integer from 2-9.

54. The method of claim 53, wherein n is 4.

55. The method of claim 51 or 52, wherein at least one occurrence of $L^1$ comprises a glycoside moiety.

56. The method of claim 55, wherein the glycoside moiety is a monosaccharide.

57. The method of claim 56, wherein the monosaccharide is a moiety having the structure:

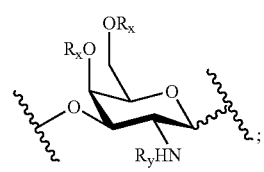

wherein each occurrence of $R_x$ is independently hydrogen or a protecting group, and $R_y$ is a nitrogen protecting group.

58. The method of claim 51 or 52, wherein in the glycopeptide, each occurrence of A is independently a carbohydrate domain selected from the group consisting of Globo-H, fucosyl GM1, KH-1, glycophorin, STN, $Le^y$, N3, Tn, 2,6-STn, (2,3)ST, Gb3, TF, a carbohydrate domain having the structure:

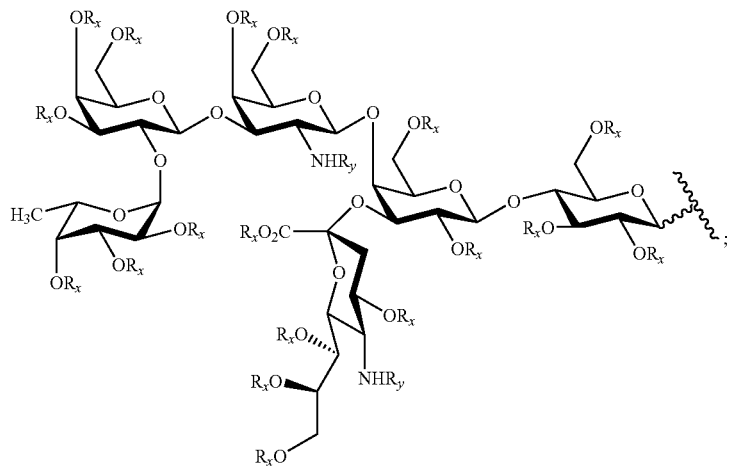

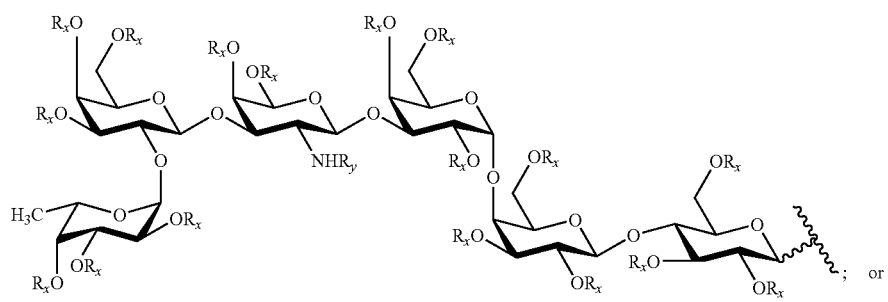

; or

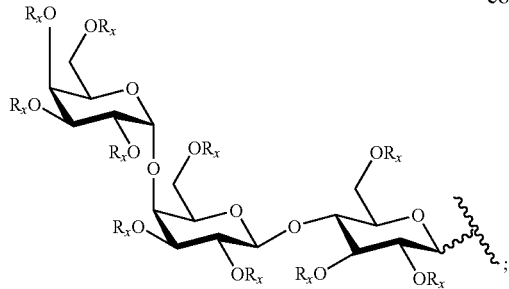

wherein each occurrence of $R_x$ is independently hydrogen or a protecting group; and wherein each occurrence of $R_y$ is independently hydrogen or a nitrogen protecting group.

59. The method of claim 51 or 52, wherein the glycopeptide comprises at least two different carbohydrate antigens, and the antibodies induced recognize said carbohydrate antigens present on the peptidic backbone.

60. The method of claim 59, wherein the carbohydrate antigens present on the peptidic backbone independently comprise a carbohydrate domain or elongated version thereof, that is present on tumor cells.

61. The method of claim 51 or 52, wherein the glycopeptide has three occurrences of A, each of which is selected from Tn, TF or Le$^y$ and the antibodies induced are those that recognize Tn, TF and/or Le$^y$ antigens.

62. The method of claim 61, wherein the glycopeptide has the structure:

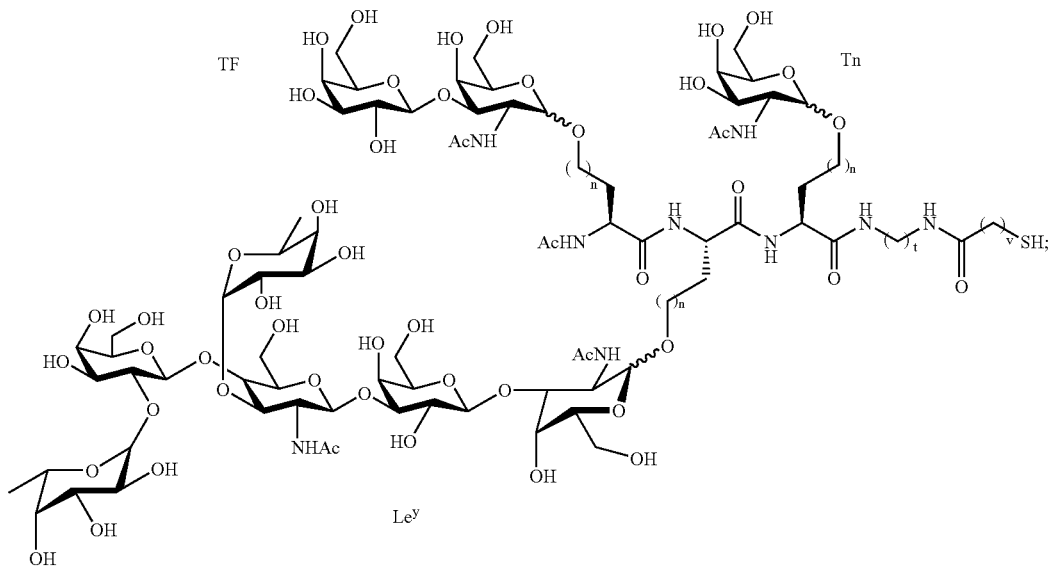

wherein n is an integer from 1-9, and t and v are each independently integers from 0-6.

63. The method of claim 51 or 52, wherein the glycopeptide has five occurrences of A, each of which is selected from Globo-H, Le$^y$, STn TF or Tn, and the antibodies induced are those that recognize Globo-H, Le$^y$, STn, TF and/or Tn antigens.

64. The method of claim 63, wherein the glycopeptide has the structure:

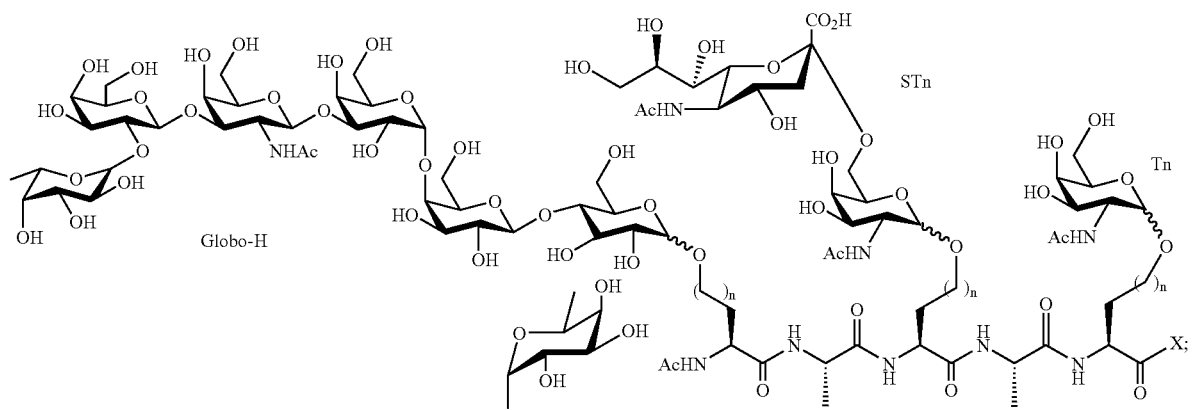

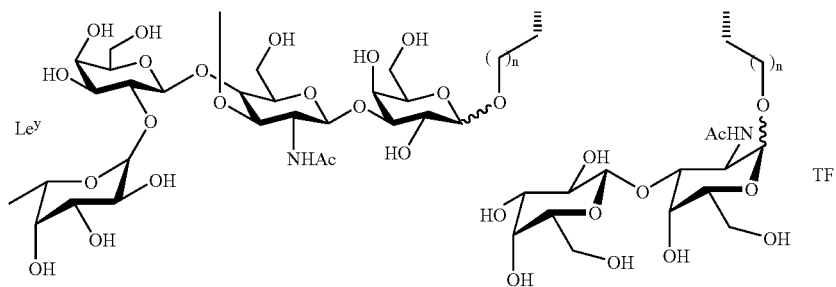

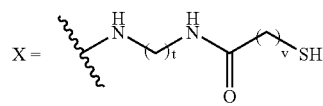

wherein n is an integer from 1-9, and t and v are each independently integers from 0-6.

65. The method of claim 51 or 52, further comprising co-administering one or more immunological adjuvants.

66. The method of claim 65, wherein at least one of said one or more immunological adjuvants is a saponin adjuvant.

67. The method of claim 66, wherein said saponin adjuvant is GPI-0100.

68. The method of claim 65, wherein at least one of said one or more immunological adjuvants is bacteria or liposomes.

69. The method of claim 68, wherein the immunological adjuvant is *Salmonella minnesota* cells, bacille Calmette-Guerin or QS21.

70. The method of claim 51 or 52, wherein the immunogenic carrier is a protein, peptide or lipid.

71. The method of claim 70, wherein the carrier is KLH, BSA or polylysine.

72. The method of claim 70, the immunogenic carrier is a lipid having the structure:

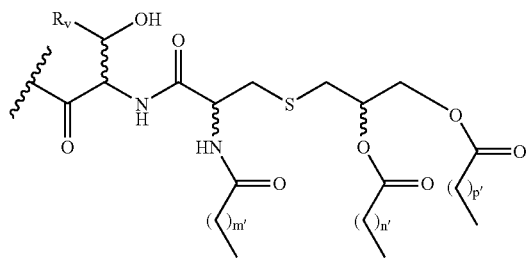

wherein m', n' and p' are each independently integers between about 8 and 20; and $R_v$ is hydrogen, substituted or unsubstituted linear or branched chain lower alkyl or substituted or unsubstituted phenyl.

73. The method of claim 72, wherein m', n' and p' are each 14 and the lipid is tripalmitoyl-S-glycerylcysteinylserine.

74. The method of claim 51 or 52, wherein at least one occurrence of A is Gb3.

75. The glycopeptide or glycoconjugate of any one of claims 4, 28, 29, 32, 33, 52, or 41, wherein the crosslinker is a fragment having the structure:

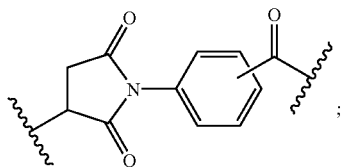

whereby said structure is generated upon conjugation of a maleimidobenzoic acid N-hydroxy succinimide ester with a linker.

76. The method of claim 48, wherein the cancer is ovarian.

* * * * *

UNITED STATES PATENT AND TRADEMARK OFFICE
CERTIFICATE OF CORRECTION

PATENT NO. : 7,854,934 B2  
APPLICATION NO. : 10/209618  
DATED : December 21, 2010  
INVENTOR(S) : Danishefsky et al.

Page 1 of 5

It is certified that error appears in the above-identified patent and that said Letters Patent is hereby corrected as shown below:

In claim 4, column 146, beginning at line 22 and ending at line 30, please delete the structure:

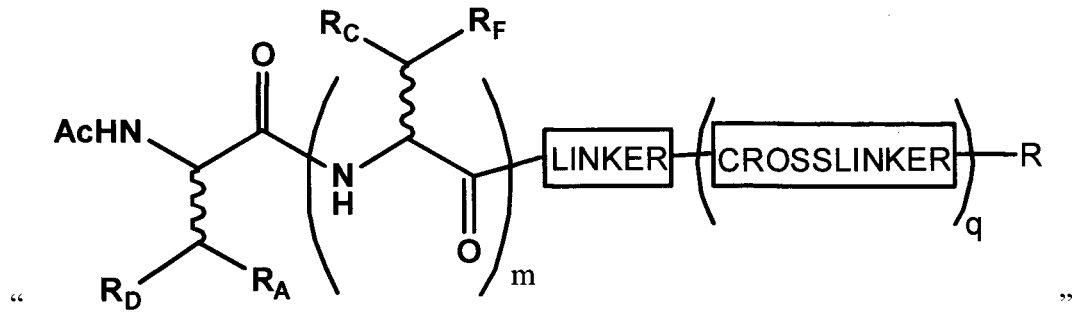

and insert the structure:

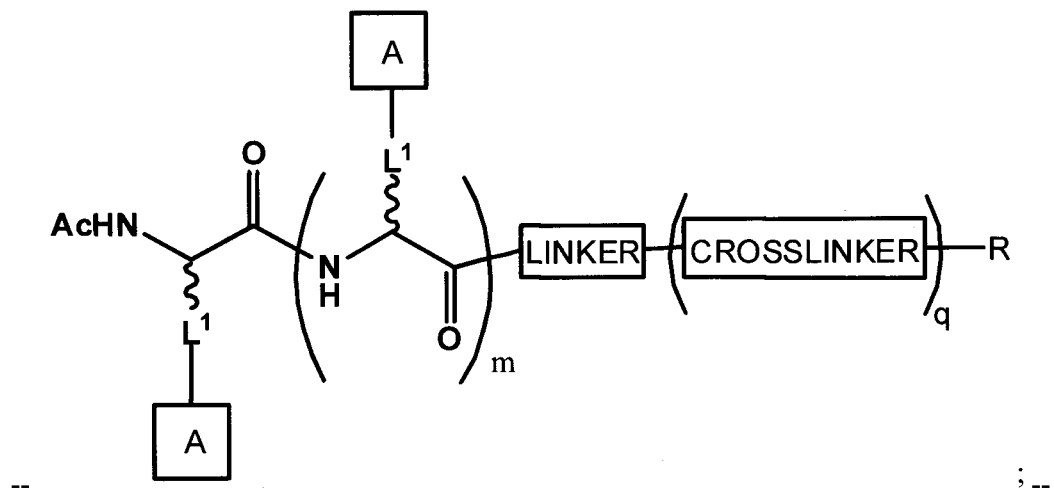

Signed and Sealed this
Twenty-eighth Day of August, 2012

David J. Kappos
*Director of the United States Patent and Trademark Office*

CERTIFICATE OF CORRECTION (continued)
U.S. Pat. No. 7,854,934 B2

In claim 27, column 155, beginning at line 53 and ending at line 62, please delete the structure:

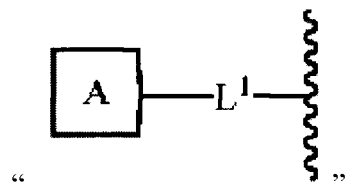

" "

and insert the structure:

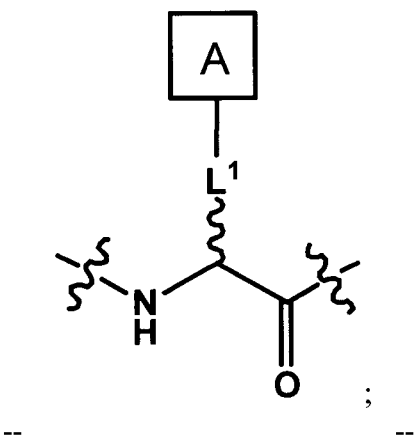

-- ; --

In claim 33, columns 161 and 162, beginning at line 23 and ending at line 50, please delete the structure:

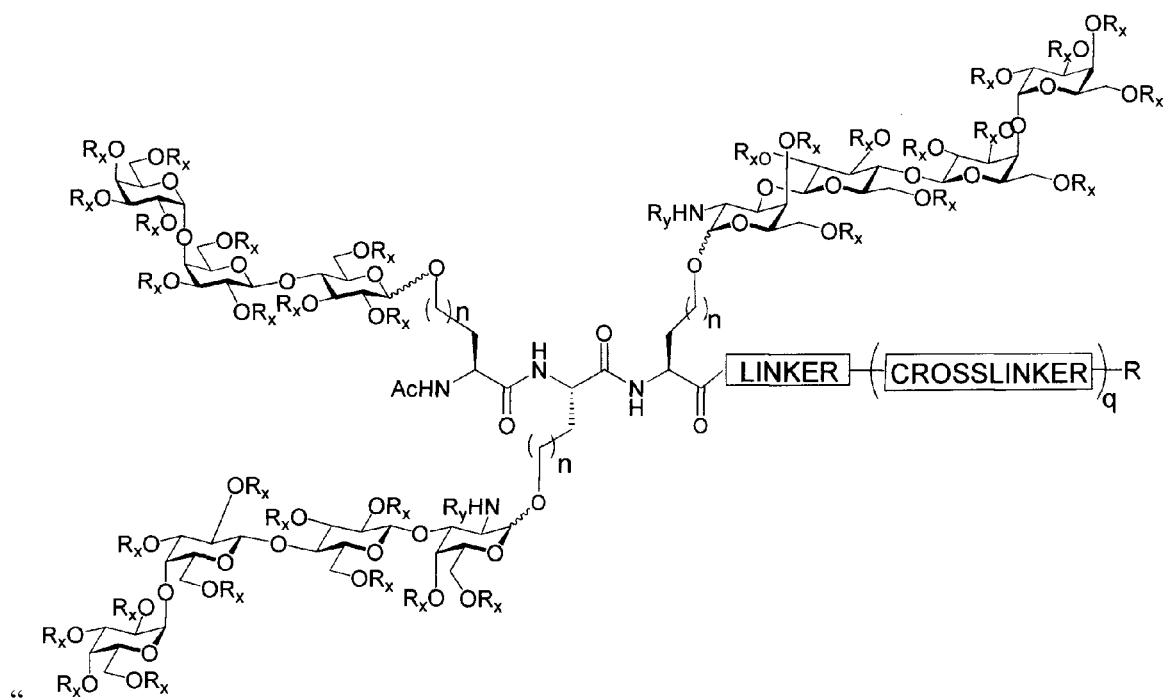

" "

and insert the structure:
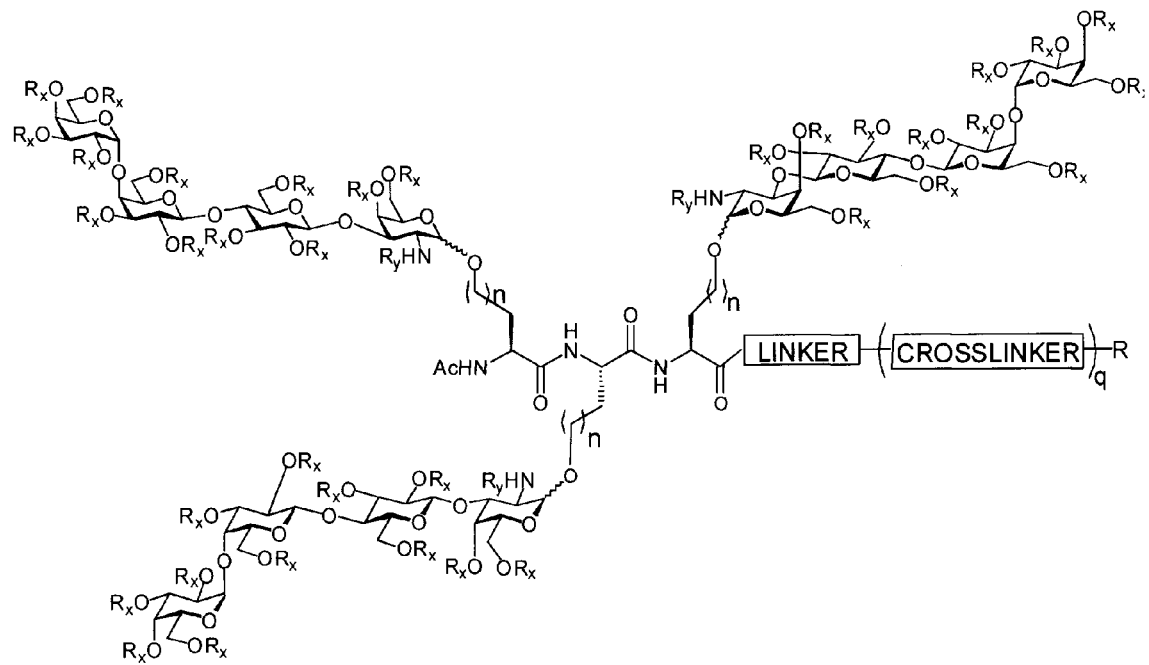
--                                                                                                              --
In claim 40, column 162, beginning at line 51 and ending at line 52, please delete:
"40. The glycopeptide or glycoconjugate of claim 32 or 33 wherein t is 3 and v is 1."
and insert:
--40. The glycopeptide or glycoconjugate of claim 38 or 39 wherein t is 3 and v is 1.--
In claim 41, column 162, beginning at line 58 and ending at line 65, please delete the structure:
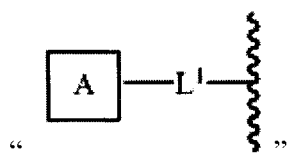

CERTIFICATE OF CORRECTION (continued)
U.S. Pat. No. 7,854,934 B2

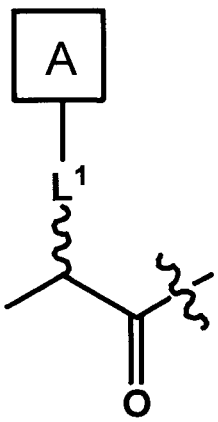

and insert the structure       --                                    --

In claim 51, column 165, beginning at line 35 and ending at line 40, please delete the structure:

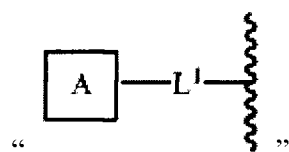

" "

and insert the structure:

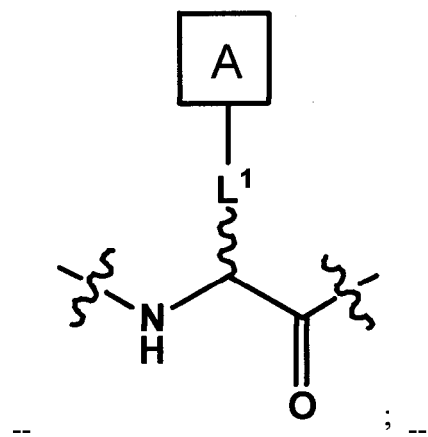

--                                    ; --

CERTIFICATE OF CORRECTION (continued)
U.S. Pat. No. 7,854,934 B2

In claim 64, columns 171 and 172, beginning at line 6, please delete the structure:

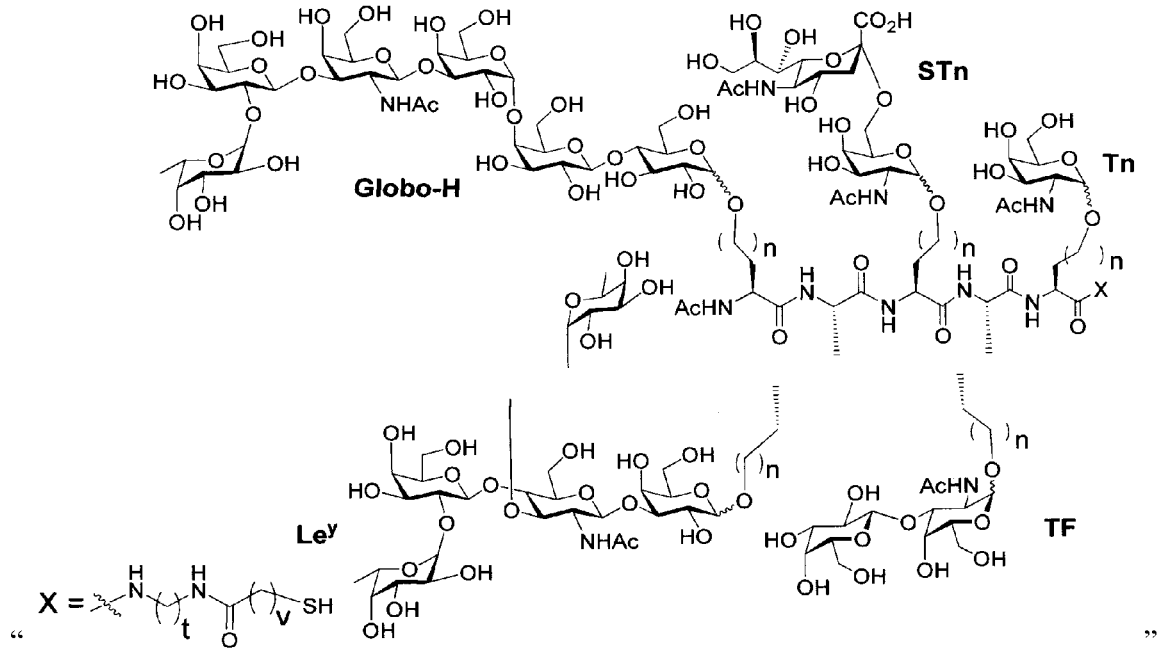

"

"

and insert the structure:

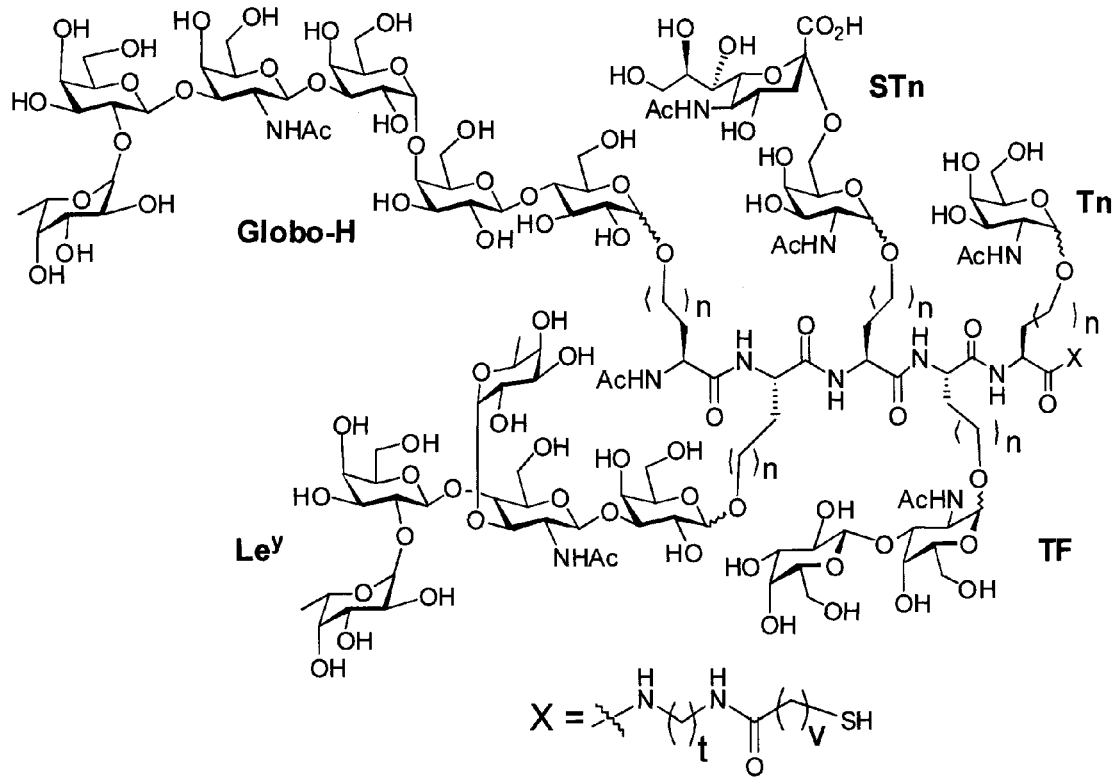

--  --